United States Patent
Hillebrand et al.

(10) Patent No.: US 9,717,243 B2
(45) Date of Patent: Aug. 1, 2017

(54) PIPERIDINECARBOXYLIC ACID DERIVATIVES AS FUNGICIDES

(71) Applicant: BAYER CROPSCIENCE AKTIENGESELLSCHAFT, Monheim am Rhein (DE)

(72) Inventors: Stefan Hillebrand, Neuss (DE); Matthias Riedrich, Cologne (DE); Sebastian Hoffmann, Neuss (DE); Mark James Ford, Schmitten (DE); Joachim Telser, Wuppertal (DE); Mazen Es-Sayed, Langenfeld (DE); Guenter Hoemberger, Eppstein (DE); Pierre Wasnaire, Duesseldorf (DE); Ulrike Wachendorff-Neumann, Neuwied (DE); Tomoki Tsuchiya, Lyons (FR)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 14/899,709

(22) PCT Filed: Jun. 20, 2014

(86) PCT No.: PCT/EP2014/063073
§ 371 (c)(1),
(2) Date: Dec. 18, 2015

(87) PCT Pub. No.: WO2014/206896
PCT Pub. Date: Dec. 31, 2014

(65) Prior Publication Data
US 2016/0135461 A1    May 19, 2016

(30) Foreign Application Priority Data
Jun. 24, 2013 (EP) .................... 13173353

(51) Int. Cl.
*A01N 43/80* (2006.01)
*C07D 417/14* (2006.01)

(52) U.S. Cl.
CPC .......... *A01N 43/80* (2013.01); *C07D 417/14* (2013.01)

(58) Field of Classification Search
None
See application file for complete search history.

(56) References Cited

U.S. PATENT DOCUMENTS

| | | | |
|---|---|---|---|
| 7,943,774 B2 | 5/2011 | Cristau et al. | |
| 8,449,898 B2* | 5/2013 | Gregory | A01N 43/40 424/405 |
| 8,524,743 B2 | 9/2013 | Cristau et al. | |
| 8,569,509 B2 | 10/2013 | Cristau et al. | |
| 8,759,527 B2 | 6/2014 | Tsuchiya et al. | |
| 8,822,693 B2 | 9/2014 | Hoffmann et al. | |
| 9,006,266 B2 | 4/2015 | Tsuchiya et al. | |
| 9,029,549 B2 | 5/2015 | Cristau et al. | |
| 9,150,565 B2 | 10/2015 | Tsuchiya et al. | |
| 9,167,821 B2 | 10/2015 | Cristau et al. | |
| 2012/0122928 A1 | 5/2012 | Tsuchiya et al. | |
| 2014/0005224 A1 | 1/2014 | Hillebrand et al. | |
| 2014/0303210 A1 | 10/2014 | Hoffmann et al. | |
| 2015/0065541 A1 | 3/2015 | Cristau et al. | |
| 2015/0175598 A1 | 6/2015 | Tsuchiya et al. | |
| 2015/0218152 A1 | 8/2015 | Hillebrand et al. | |
| 2015/0237859 A1 | 8/2015 | Cristau et al. | |

FOREIGN PATENT DOCUMENTS

| | | |
|---|---|---|
| WO | 2007014290 A2 | 2/2007 |
| WO | 2008013622 A2 | 1/2008 |
| WO | 2008013925 A2 | 1/2008 |
| WO | 2008091580 A2 | 7/2008 |
| WO | 2008091594 A2 | 7/2008 |
| WO | 2009055514 A2 | 4/2009 |
| WO | 2009094407 A2 | 7/2009 |
| WO | 2009094445 A2 | 7/2009 |
| WO | 2009132785 A1 | 11/2009 |
| WO | 2010037479 A1 | 4/2010 |
| WO | 2010065579 A2 | 6/2010 |

(Continued)

OTHER PUBLICATIONS

Pozharskii et. al. Heterocycles in Life and Society Wiley, 1997, pp. 1-6.*

(Continued)

*Primary Examiner* — David K O'Dell
(74) *Attorney, Agent, or Firm* — McBee Moore Woodward Vanik LLC; Susan McBee; David Woodward

(57) ABSTRACT

Piperidinecarboxylic acidderivatives of the formula (I)

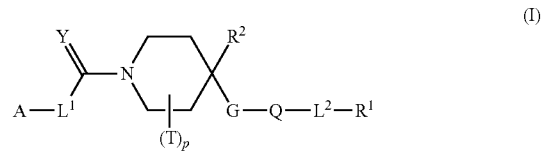

in which the symbols A, $L^1$, $L^2$, G, p, Q, $R^1$, $R^2$, T and Y are each as defined in the description, and salts, metal complexes and N-oxides of the compounds of the formula (I), and the use thereof for controlling phytopathogenic harmful fungi and processes for preparing compounds of the formula (I).

15 Claims, No Drawings

(56) References Cited

FOREIGN PATENT DOCUMENTS

| WO | 2011018401 A1 | 2/2011 |
| WO | 2011018415 A2 | 2/2011 |
| WO | 2011076510 A1 | 6/2011 |
| WO | 2011076699 A1 | 6/2011 |
| WO | 2011146182 A1 | 11/2011 |
| WO | 2012020060 A1 | 2/2012 |
| WO | 2012025557 A1 | 3/2012 |
| WO | 2012055837 A1 | 5/2012 |
| WO | 2012082580 A2 | 6/2012 |
| WO | 2012104273 A1 | 8/2012 |
| WO | 2013037768 A1 | 3/2013 |
| WO | 2013098229 A2 | 7/2013 |
| WO | 2013127784 A1 | 9/2013 |
| WO | 2013127789 A1 | 9/2013 |
| WO | 2013127808 A1 | 9/2013 |

OTHER PUBLICATIONS

Pitt "Heteroaromatic Rings of the Future" J. Med. Chem. 2009, 52, 2952-2963.*
Pasteris "Discovery of oxathiapiprolin, a new oomycete fungicide that targets an oxysterol binding protein" Bioorganic & Medicinal Chemistry 24 (2016) 354-361.*
International Search Report from corresponding PCT/EP2014/063073, mailed Jul. 21, 2014.

* cited by examiner

PIPERIDINECARBOXYLIC ACID DERIVATIVES AS FUNGICIDES

CROSS REFERENCE TO RELATED APPLICATIONS

This application is a §371 National Stage Application of PCT/EP2014/063073, filed 20 Jun. 2014 which claims priority to EP 13173353.7, filed 24 Jun. 2013.

BACKGROUND

Field of the Invention

The invention relates to piperidinecarboxylic acid derivatives, to agrochemically active salts thereof, to use thereof and to methods and compositions for controlling phytopathogenic harmful fungi in and/or on plants or in and/or on seed of plants, to processes for producing such compositions and treated seed, and to use thereof for controlling phytopathogenic harmful fungi in agriculture, horticulture and forestry, in animal health, in the protection of materials and in the domestic and hygiene sector. The present invention further relates to a process for preparing piperidinecarboxylic acid derivatives.

Description of Related Art

It is already known that particular heterocyclically substituted thiazoles can be used as fungicidal crop protection compositions (see WO 07/014290, WO 08/013925, WO 08/013622, WO 08/091594, WO 08/091580, WO 09/055514, WO 09/094407, WO 09/094445, WO 09/132785, WO 10/037479, WO 10/065579, WO 11/076510, WO 11/018415, WO 11/018401, WO 11/076699, WO 11/146182, WO 12/055837, WO 12/025557, WO 12/082580, WO2012104273, WO2012020060, WO2013127808, WO2013127789, WO2013127784, WO2013037768, WO2013098229). However, specifically at relatively low application rates, the fungicidal efficacy of these compounds is not always adequate.

Since the ecological and economical demands made on modern crop protection agents are increasing constantly, for example with respect to activity spectrum, toxicity, selectivity, application rate, formation of residues and favourable manufacture, and there can furthermore be problems, for example, with resistances, there is a constant need to develop novel crop protection compositions, in particular fungicides, which, at least in some areas, have advantages over the known ones.

It has now been found that, surprisingly, the present piperidinecarboxylic acid derivatives achieve at least some aspects of the objects mentioned and are suitable for use as crop protection compositions, especially as fungicides.

SUMMARY

The invention provides compounds of the formula (I)

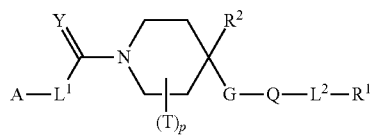

(I)

in which the radicals are each defined as follows:

A is phenyl which may contain up to five substituents, where the substituents are each independently selected from $Z^{A-1}$, or A is an optionally benzofused, unsubstituted or substituted 5- or 6-membered heteroaryl which may contain up to four substituents, where the substituents on carbon are each independently selected from $Z^{A-2}$ and the substituents on nitrogen are each independently selected from $Z^{A-3}$, $Z^{A-1}$ are the same or different and are each independently hydrogen, halogen, hydroxyl, thiol, nitro, cyano, —C(=O)H, —C(=O)OH, alkyl, alkenyl, alkynyl, haloalkyl, haloalkenyl, haloalkynyl, cycloalkyl, cycloalkenyl, halocycloalkyl, halocycloalkenyl, hydroxyalkyl, cyanoalkyl, formylalkyl, alkoxyalkyl, haloalkoxyalkyl, cycloalkoxyalkyl, alkynyloxyalkyl, alkylthioalkyl, alkylsulphinylalkyl, alkylaminoalkyl, haloalkylaminoalkyl, cycloalkylamino alkyl, dialkylaminoalkyl, alkylcarbonylalkyl, alkylsulphonylalkyl, alkylcycloalkyl, alkylcycloalkenyl, alkoxy, alkylcycloalkylalkyl, halocycloalkoxy, alkylthio, haloalkylthio, cycloalkylthio, alkynylthio, alkenyloxy, alkynyloxy, haloalkoxy, haloalkenyloxy, haloalkynyloxy, cycloalkoxy, alkoxyalkoxy, cycloalkylalkoxy, alkylcarbonyloxy, haloalkylcarbonyloxy, cycloalkylcarbonyloxy, cycloalkylamino, alkylcarbonylamino, cycloalkylcarbonylamino, alkoxycarbonylamino, alkylsulphonylamino, haloalkylsulphonylamino, phenylsulphonylamino, cycloalkylalkyl, halocycloalkylalkyl, cycloalkylcycloalkyl, alkoxyalkoxyalkyl, alkylaminocarbonyloxy, alkylcarbonylalkoxy, cyclo alkyl aminocarbonyl, cycloalkylalkoxycarbonyl, alkylsulphinyl, haloalkylsulphinyl, alkylsulphonyl, haloalkylsulphonyl, cycloalkylsulphonyl, alkylcarbonyl, haloalkylcarbonyl, cycloalkylcarbonyl, alkoxycarbonyl, cycloalkoxycarbonyl, trialkylsilyl, —SF$_5$, phenyl, —C(=O)NR$^3$R$^4$ or —NR$^3$R$^4$, $Z^{A-2}$ and R$^{G1}$ are the same or different and are each independently hydrogen, halogen, hydroxyl, thiol, nitro, cyano, —C(=O)H, —C(=O)OH, alkyl, alkenyl, alkynyl, haloalkyl, haloalkenyl, haloalkynyl, cycloalkyl, halocycloalkyl, hydroxyalkyl, formylalkyl, alkoxyalkyl, alkylcarbonylalkyl, alkylcycloalkyl, alkoxy, alkylcycloalkylalkyl, alkylthio, haloalkylthio, alkynylthio, alkenyloxy, alkynyloxy, haloalkoxy, alkoxyalkoxy, alkylcarbonyloxy, haloalkylcarbonyloxy, cycloalkylcarbonylamino, alkylsulphonylamino, haloalkylsulphonylamino, phenylsulphonylamino, cycloalkylalkyl, halocycloalkylalkyl, cycloalkylcycloalkyl, alkoxycarbonyloxy, alkylcarbonylthio, alkylsulphinyl, haloalkylsulphinyl, alkylsulphonyl, haloalkylsulphonyl, alkylcarbonyl, haloalkylcarbonyl, alkoxycarbonyl, alkylaminocarbonyloxy, —C(=O)NR$^3$R$^4$ or —NR$^3$R$^4$, $Z^{A-3}$ are the same or different and are each independently hydrogen, —C(=O)H, —C(=O)NR$^3$R$^4$, alkyl, alkenyl, alkynyl, haloalkyl, haloalkenyl, haloalkynyl, cycloalkyl, halocycloalkyl, alkylcycloalkyl, cycloalkylalkyl, alkoxyalkyl, alkylsulphonyl, haloalkylsulphonyl, cycloalkylsulphonyl, phenylsulphonyl, alkylcarbonyl, haloalkylcarbonyl, alkoxycarbonyl, haloalkoxycarbonyl, cycloalkoxycarbonyl, phenyl or benzyl, G is

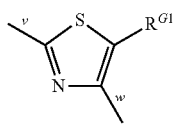

where the bond identified by "v" is bonded directly to dihydropyridine ring and where the bond identified by "w" is bonded directly to Q, $L^1$ is $NR^{L12}$ or $C(R^{L11})_2$, $R^{L11}$ is the same or different and is independently hydrogen, halogen, hydroxyl, cyano, —C(=O)H, —C(=O)OH, alkyl, alkenyl, alkynyl, haloalkyl, haloalkenyl, haloalkynyl, alkoxyalkyl, alkylthioalkyl, alkylaminoalkyl, dialkylaminoalkyl, alkoxy, alkylthio, haloalkylthio, haloalkoxy, alkylcarbonyloxy, alkylcarbonylamino, alkylcarbonylthio, alkylsulphonyl, haloalkylsulphonyl, alkylcarbonyl, haloalkylcarbonyl, alkoxycarbonyl, trialkylsilyloxy, —$NR^3R^4$ or —C(=O)$NR^3R^4$, or the two $R^{L11}$ radicals, together with the carbon atom to which they are bonded, form a cyclopropyl ring, or the two $R^{L11}$ radicals are =$CH_2$, =CH($OR^6$), =$NOR^3$ or =CHN($R^6$)$_2$, $R^{L12}$ is hydrogen, —C(=O)H, alkyl, alkenyl, alkynyl, haloalkyl, haloalkenyl, haloalkynyl, cycloalkyl, halocycloalkyl, alkylcycloalkyl, cycloalkylalkyl, alkoxy, alkylamino, cycloalkylaminocarbonyl, halo alkylaminocarbonyl, alkylsulphonyl, haloalkylsulphonyl, cycloalkylsulphonyl, alkylcarbonyl, haloalkylcarbonyl, alkoxycarbonyl, haloalkoxycarbonyl, cycloalkoxycarbonyl, alkylaminocarbonyl, dialkylaminocarbonyl, phenyl or benzyl, $L^2$ is a direct bond or —$CH_2O$—, $L^3$ is a direct bond, —C(=O)—, oxygen, —$NR^{21}$—, —C(=S)—, —S(=O)$_m$—, —$CHR^{20}$—, —$CHR^{20}$—$CHR^{20}$—, —$CR^{20}$=$CR^{20}$—, —$OCHR^{20}$—, —$CHR^{20}$O—, —C(=O)O—, —C(=O)$NR^3$—, —OC(=O)—, —$NR^3$C(=O)—, —$OCH_2$C≡C— or —$OCH_2$CH=CH—, $L^4$ is —O—, —C(=O)—, S(=O)$_m$ or $CHR^{20}$, m is 0, 1 or 2, p is 0, 1 or 2, Q is saturated or partly or fully unsaturated 5-membered heterocyclyl which is substituted by $L^2$-R' and may otherwise be unsubstituted or substituted, where the substituents are each independently selected from $R^5$, $R^1$ is phenyl, benzyl, naphthalenyl, an optionally benzo-fused, substituted 5- or 6-membered heteroaryl which may be unsubstituted or substituted with one, two, or three substituents, where the substituents are each independently selected from $Z^4$ and from $Z^1$, or $R^1$ is a 5- to 8-membered nonaromatic (saturated or partially saturated) carbocyclic ring, a 5-, 6- or 7-membered nonaromatic heterocyclyl radical or an 8- to 11-membered carbocyclic or heterocyclic bicyclic ring, each of which may be unsubstituted or substituted with one, two, or three substituents, where the substituents are each independently selected from oxo, thioxo, $Z^4$ or $Z^1$, $R^2$ is —$COOR^O$, —CON($R^N$)$_2$, —C(=S)N($R^N$)$_2$, —CON($R^N$)$OR^O$, $R^O$ is hydrogen, alkyl, cycloalkyl, alkenyl, alkynyl, phenyl, benzyl or a 5- or 6-membered heterocyclic ring containing one to three heteroatoms independently selected from O, S and N, providing that the heterocycle does not contain adjacent oxygen atoms, adjacent sulphur atoms, or adjacent sulfur and oxygen atoms, wherein alkyl, cycloalkyl, alkenyl and alkynyl are optionally substituted by one or more groups independently selected from halogen, CN, $NH_2$, $NO_2$, OH, =O, =S, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfanyl, $C_1$-$C_4$-haloalkysulfanyl, $C_1$-$C_4$-alkyl-$C_1$-$C_4$-alkoxy and $C_1$-$C_4$-alkoxy -$C_1$-$C_4$-alkyl, and wherein phenyl, benzyl and the heterocyclic ring are optionally substituted by one or more groups independently selected from halogen, CN, $NH_2$, $NO_2$, OH, $C_1$-$C_4$-alkyl, $C_1$-$C_4$-haloalkyl, $C_1$-$C_4$-alkoxy, $C_1$-$C_4$-alkylsulfanyl, $C_1$-$C_4$-haloalkysulfanyl, $C_1$-$C_4$-haloalkoxy, and $C_1$-$C_4$-alkoxy-$C_1$-$C_4$-alkyl, $R^N$ is the same or different and is independently hydrogen, OH, alkyl, alkoxy, alkoxyalkyl, alkenyl, alkynyl, or $COR^C$, wherein the alkyl, alkoxy, alkenyl and alkynyl are optionally substituted by one or more halogen; wherein when two radicals $R^N$ are attached to the same nitrogen atom, these radicals can be identical or different; wherein when two radicals $R^N$ are attached to the same nitrogen atom, both of these radicals cannot be OH, alkoxy or haloalkoxy; and wherein when two radicals $R^N$ are attached to the same nitrogen atom, these two radicals together with the nitrogen atom to which they are attached may form a saturated or partially saturated 5-, 6-, 7- or 8-membered $C_5$-$C_8$-heterocyclic ring containing one to three heteroatoms independently selected from O, S and N, $R^C$ is hydrogen, alkyl, cycloalkyl, alkenyl, alkynyl, phenyl or benzyl wherein alkyl, cycloalkyl, alkenyl and alkynyl are optionally substituted by one or more groups independently selected from halogen, CN, $NH_2$, $NO_2$, OH, =O, =S, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfanyl, $C_1$-$C_4$-haloalkysulfanyl, and wherein phenyl and benzyl are optionally substituted by one or more groups independently selected from halogen, CN, $NH_2$, $NO_2$, OH, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfanyl, $C_1$-$C_4$-haloalkysulfanyl, $R^3$ and $R^4$ are the same or different and are each independently hydrogen, alkyl, alkenyl, alkynyl, haloalkyl, cycloalkyl, benzyl or phenyl, $R^5$ is the same or different and is independently:
bonded to carbon of the 5-membered heterocyclyl of Q: oxo, thioxo, hydrogen, halogen, cyano, hydroxyl, nitro, amino, —CHO, —C(=O)OH, —C(=O)$NH_2$, —$NR^7R^8$, alkyl, alkenyl, alkynyl, haloalkyl, haloalkenyl, haloalkynyl, cycloalkyl, halocycloalkyl, alkylcycloalkyl, cycloalkylalkyl, cycloalkylcycloalkyl, halocycloalkylalkyl, alkylcycloalkylalkyl, cycloalkenyl, halocycloalkenyl, alkoxyalkyl, cycloalkoxyalkyl, alkoxyalkoxyalkyl, alkylthioalkyl, alkylsulphinylalkyl, alkylsulphonylalkyl, alkylaminoalkyl, dialkylaminoalkyl, haloalkylaminoalkyl, cycloalkylaminoalkyl, alkylcarbonyl, haloalkylcarbonyl, cycloalkylcarbonyl, alkoxycarbonyl, cycloalkoxycarbonyl, cycloalkylalkoxycarbonyl, alkylaminocarbonyl, dialkylaminocarbonyl, cycloalkylaminocarbonyl, haloalkoxyalkyl, hydroxyalkyl, alkoxy, haloalkoxy, cycloalkoxy, halocycloalkoxy, cycloalkylalkoxy, alkenyloxy, haloalkenyloxy, alkynyloxy, haloalkynyloxy, alkoxyalkoxy, alkylcarbonyloxy, haloalkylcarbonyloxy, cycloalkylcarbonyloxy, alkylcarbonylalkoxy, alkylthio, haloalkylthio, cycloalkylthio, alkylsulphinyl, haloalkylsulphinyl, alkylsulphonyl, haloalkylsulphonyl, cycloalkylsulphonyl, trialkylsilyl, alkylsulphonylamino, haloalkylsulphonylamino,
bonded to nitrogen of the 5-membered heterocyclyl of Q:
hydrogen, alkyl, alkenyl, alkynyl, haloalkyl, haloalkenyl, haloalkynyl, cycloalkyl, halocycloalkyl, alkylcycloalkyl, cycloalkylalkyl, phenyl, benzyl, alkylsulphonyl, —C(=O)H, alkoxycarbonyl or alkylcarbonyl, $R^6$ is alkyl, alkenyl, alkynyl, haloalkyl, cycloalkyl, benzyl or phenyl, $R^7$ is hydrogen, alkyl, haloalkyl, cycloalkyl, alkylcarbonyl, haloalkylcarbonyl, alkoxycarbonyl or haloalkoxycarbonyl, $R^8$ is alkyl, haloalkyl, cycloalkyl, alkylcarbonyl, haloalkylcarbonyl, alkoxycarbonyl, haloalkoxycarbonyl or -$L^4R^1$, $R^9$ is hydrogen, alkyl, haloalkyl, benzyl or $Z^3$, $R^{10}$ is hydrogen, alkyl, haloalkyl, cycloalkylalkyl, cycloalkyl, alkylcycloalkyl, haloalkylcycloalkyl, alkoxylalkyl, haloalkoxyalkyl, benzyl or phenyl, $R^{11}$ and $R^{12}$ are the same or different and are each independently hydrogen, alkyl, alkenyl, alkynyl, haloalkyl, cycloalkyl, alkoxyalkyl, cyanoalkyl, formyl, haloalkyl, phenyl, alkylcarbonyl, cycloalkoxycarbonyl, alkoxycarbonyl, alkenyloxycarbonyl, alkynyloxycarbonyl, haloalkylcarbonyl, halocycloalkylcarbonyl, cycloalkoxycarbonyl, cycloalkylcarbonyl, dialkylaminocarbonyl, dialkylaminothiocarbonyl, benzyl or phenyl, $R^{20}$ is hydrogen, alkyl or haloalkyl, $R^{21}$ is hydrogen, alkyl, haloalkyl, cycloalkyl, alkylcarbonyl, haloalkylcarbonyl, alkoxycarbonyl or haloalkoxycarbonyl, T is attached to any carbon of the piperidine ring except for the position that is substituted by $R^2$, T is the same or different and is independently hydrogen, —COOR$^O$, —CON(R$^N$)$_2$, alkyl, alkenyl, alkynyl, haloalkyl, alkoxy, halogen, cyano or hydroxyl, Y is sulphur or oxygen, $Z^1$ is
bonded to carbon of R$^1$:
hydrogen, halogen, hydroxyl, amino, nitro, amino, cyano, alkyl, alkenyl, alkynyl, haloalkyl, haloalkenyl, haloalkynyl, cycloalkyl, halocycloalkyl, hydroxy alkyl, alkoxyalkyl, alkylcycloalkyl, alkoxy, alkylcycloalkylalkyl, alkylthio, haloalkylthio, haloalkoxy, alkylcarbonyloxy, alkylamino, dialkylamino, cycloalkylalkyl, cycloalkylcycloalkyl, alkylcarbonylthio, alkylsulphinyl, haloalkylsulphinyl, alkylsulphonyl, haloalkylsulphonyl, alkylcarbonyl, alkoxycarbonyl, alkylaminocarbonyl, dialkylaminocarbonyl, trialkylsilyl, and cycloalkylamino, cycloalkenyl, halocycloalkenyl, cycloalkoxy alkyl, halocycloalkoxy, cycloalkylthio, cycloalkoxy, cycloalkylalkoxy, cycloalkylamino, halocycloalkylalkyl, cycloalkylcarbonyl, cycloalkylsulphonyl, or -$L^3Z^3$,
bonded to nitrogen of R':
alkyl, alkylcarbonyl, alkoxycarbonyl or alkoxy, $Z^3$ is a phenyl radical, naphthalenyl radical or a 5- or 6-membered heteroaryl radical, each of which may contain 0, 1, 2 or 3 substituents, where the substituents are each independently selected from the following list:
substituents on carbon: halogen, cyano, nitro, hydroxyl, amino, —SH, alkyl, alkenyl, alkynyl, haloalkyl, haloalkenyl, haloalkynyl, cycloalkyl, halocycloalkyl, alkoxyalkyl, alkylcarbonyl, haloalkylcarbonyl, alkoxycarbonyl, alkoxy, haloalkoxy, cycloalkoxy, halocycloalkoxy, alkenyloxy, alkynyloxy, alkoxyalkoxy, alkylamino, dialkylamino, alkylthio, haloalkylthio, alkylsulphinyl, haloalkylsulphinyl, alkylsulphonyl, haloalkylsulphonyl, trisilylalkyl or phenyl,
substituents on nitrogen: hydrogen, —C(=O)H, alkyl, alkenyl, alkynyl, haloalkyl, haloalkenyl, haloalkynyl, cycloalkyl, halocycloalkyl, alkylcycloalkyl, cycloalkylalkyl, alkoxyalkyl, alkylsulphonyl, haloalkylsulphonyl, cycloalkylsulphonyl, phenylsulphonyl, alkylcarbonyl, haloalkylcarbonyl, alkoxycarbonyl, haloalkoxycarbonyl, cycloalkoxycarbonyl, —C(=O)NR$^{11}$R$^{12}$, phenyl or benzyl, $Z^4$ is —SH, —C(=O)H, haloalkoxyalkyl, alkylthioalkyl, alkylsulphinylalkyl, alkylaminoalkyl, haloalkylaminoalkyl, cycloalkylaminoalkyl, dialkylaminoalkyl, alkylsulphonylalkyl, alkenyloxy, alkynyloxy, haloalkenyloxy, haloalkynyloxy, alkoxyalkoxy, haloalkylcarbonyloxy, cycloalkylcarbonyloxy, alkylsulphonylamino, haloalkylsulphonyl amino, alkoxy alkoxyalkyl, alkylcarbonylalkoxy, cycloalkylaminocarbonyl, cycloalkylalkoxycarbonyl, haloalkylcarbonyl, cycloalkoxycarbonyl, $C_4$-$C_6$-alkylcarbonyl, $C_5$-$C_6$-alkoxy, $C_5$-$C_6$-haloalkoxy, $C_5$-$C_6$-alkylthio, $C_5$-$C_6$-haloalkylthio, $C_5$-$C_6$-haloalkylsulphinyl, $C_5$-$C_6$-haloalkylsulphonyl, cyanoalkyl, alkenylcarbonyloxy, alkoxyalkylthio, haloalkenylcarbonyloxy, alkoxycarbonylalkyl, alkoxyalkynyl, alkynylthio, halocycloalkylcarbonyloxy, alkenylamino, alkynylamino, haloalkylamino, cycloalkylalkylamino, alkoxyamino, haloalkoxyamino, alkylcarbonylamino, haloalkylcarbonylamino, alkoxycarbonylamino, alkylcarbonyl(alkyl)amino, haloalkylcarbonyl(alkyl)amino, alkoxycarbonyl(alkyl)amino, alkenylthio, haloalkoxycarbonyl, alkoxyalkylcarbonyl, —SF$_5$, haloalkoxycarbonylamino, di(haloalkyl)aminoalkyl, halocycloalkenyloxyalkyl, alkoxy(alkyl)aminocarbonyl, haloalkylsulphonylaminocarbonyl, alkoxycarbonylalkoxy, alkylaminothiocarbonylamino, cycloalkylalkylaminoalkyl, alkylthiocarbonyl, cycloalkenyloxyalkyl, alkoxyalkoxycarbonyl, dialkylaminothiocarbonylamino, alkylsulphonylaminocarbonyl, haloalkoxyhaloalkoxy, halocycloalkoxyalkyl, dialkylaminocarbonylamino, alkoxyalkenyl, alkoxyhaloalkoxy, alkylthiocarbonyloxy, haloalkoxyalkoxy, haloalkylsulphonyloxy, alkylsulphonyloxy, alkoxyhaloalkyl, di(haloalkyl)amino, dialkoxyalkyl, alkylaminocarbonylamino, haloalkoxyhaloalkyl, alkylaminocarbonylalkylamino, trialkylsilylalkynyloxy, trialkylsilyloxy, trialkylsilylalkynyl, cyano(alkoxy)alkyl, dialkylthioalkyl, alkoxysulphonyl, cycloalkylsulphinyl, halocycloalkoxycarbonyl, alkylcycloalkylcarbonyl, halocycloalkylcarbonyl, alkenyloxycarbonyl, alkynyloxycarbonyl, cyanoalkoxycarbonyl, alkylthioalkoxycarbonyl, alkynylcarbonyloxy, haloalkynylcarbonyloxy, cyanocarbonyloxy, cyanoalkylcarbonyloxy, cycloalkylsulphonyloxy, cycloalkylalkylsulphonyloxy, halocycloalkylsulphonyloxy, alkenylsulphonyloxy, alkynylsulphonyloxy, cyanoalkylsulphonyloxy, haloalkenylsulphonyloxy, haloalkynylsulphonyloxy, alkynylcycloalkyloxy, cyanoalkenyloxy, cyanoalkynyloxy, alkoxycarbonyloxy, alkenyloxycarbonyloxy, alkynyloxycarbonyloxy, alkoxyalkylcarbonyloxy, —O(C=O)H, —SCN, —NHC(=O)H, —C(=NOR$^9$)R$^{10}$, —NR$^{12}$SO$_2$Z$^3$, —O(C=S)NR$^{11}$R$^{12}$, —O(C=S)SR$^6$, —N=C(R$^6$)$_2$, —OSO$_2$Z$^3$, —NHCN, —SO$_2$NHCN, —C(=O)OH, —C(=O)NH$_2$, —C(=S)NR$^{11}$R$^{12}$, —C(=O)NHCN, —OC(=O)NR$^{11}$R$^{12}$, —NR$^{11}$R$^{12}$, —C(=O)NR$^{11}$R$^{12}$, —SO$_2$NR$^{11}$R$^{12}$ or -$L^3Z^3$, or $Z^4$ is alkyl which contains 1 or 2 substituents, where the substituents are each independently selected from the following list:

cyano, alkoxycarbonyl, —C(=N—R$^6$)R$^{10}$, —C(=N—NR$^3$R$^4$)R$^{10}$, alkylcarbonylamino, haloalkylcarbonylamino, dialkylcarbonylamino, alkylcarbonyloxy, —C(=O)H, benzyloxy, benzoyloxy, —C(=O)OH, alkenyloxy, alkynyloxy, haloalkenyloxy, haloalkynyloxy, halocycloalkoxy, alkoxyamino, alkenylthio, alkynylthio, cycloalkylthio, haloalkoxyamino, haloalkylthio, alkenylsulphinyl, alkynylsulphinyl, cycloalkylsulphinyl, haloalkylsulphinyl, alkenylsulphonyl, alkynylsulphonyl, cycloalkylsulphonyl, haloalkylsulphonyl, alkoxycarbonyloxy, alkylcarbonyloxy, cycloalkylcarbonyloxy, haloalkylcarbonyloxy, haloalkenylcarbonyloxy, —SCN, alkylaminocarbonyloxy, alkylcarbonyl(alkyl)amino, alkoxycarbonyl(alkyl)amino, alkylaminocarbonylamino, alkylsulphonyloxy, haloalkoxycarbonylamino, haloalkylcarbonyl(alkyl)amino, haloalkylsulphonyloxy, alkylsulphonylamino, haloalkylsulphonylamino, alkylthiocarbonyloxy, cyanoalkoxy, cycloalkylalkoxy, benzyloxyalkoxy, alkoxyhaloalkoxy, alkoxyalkylthio, alkoxyalkylsulphinyl, alkoxyalkylsulphonyl, alkoxyalkylcarbonyloxy, cycloalkoxyalkoxy, haloalkoxyalkoxy, haloalkoxyhaloalkoxy, alkoxycarbonylalkoxy, alkylcarbonylalkoxy, alkylthioalkoxy, dialkylaminocarbonylamino, alkoxyalkoxyalkoxy, trialkylsilyloxy, trialkylsilylalkynyloxy, alkynylcycloalkyloxy, cycloalkylalkynyloxy, alkoxycarbonylalkynyloxy, arylalkynyloxy, alkylaminocarbonylalkynyloxy, dialkylaminocarbonylalkynyloxy, alkenylcarbonyloxy, alkynylcarbonyloxy, haloalkynylcarbonyloxy, cyanoalkylcarbonyloxy, cycloalkylsulphonyloxy, cycloalkylalkylsulphonyloxy, halocycloalkylsulphonyloxy, alkenylsulphonyloxy, alkynylsulphonyloxy, cyanoalkylsulphonyloxy, haloalkenylsulphonyloxy, haloalkynylsulphonyloxy, dialkylaminocarbonyloxy, haloalkylaminocarbonyloxy, N-alkyl-N-haloalkylaminocarbonyloxy, alkenyloxycarbonyl, alkynyloxycarbonyl, haloalkynyloxycarbonyl, cyanoalkyloxycarbonyl, alkenyloxysulphonyl, alkynyloxysulphonyl, or Z$^4$ is alkenyl which contains 1 or 2 substituents, where the substituents are each independently selected from the following list: trialkylsilyl, cycloalkyl, cyclopropylidenyl, alkoxy, trialkylsilyloxy, alkylcarbonyloxy or Z$^4$ is alkynyl which contains 1 or 2 substituents, where the substituents are each independently selected from the following list: cycloalkyl, cyclopropylidenyl, or Z$^4$ is alkoxy which contains 1 or 2 substituents, where the substituents are each independently selected from the following list: alkoxycarbonyl, cycloalkoxy, alkylcarbonyloxy, —O(C=O)H, alkylthio, hydroxyalkyl, trialkylsilyl, cycloalkylsulphonyl, haloalkylsulphonyl, benzyloxy, alkoxyalkoxy, alkylsulphonyl, cyano, or Z$^4$ is alkenyloxy which contains 1 or 2 substituents, where the substituents are each independently selected from the following list: cycloalkyl, hydroxyl, alkoxy, alkenyloxy, alkynyloxy, haloalkoxy, haloalkenyloxy, haloalkynyloxy, cycloalkoxy, cyclohaloalkoxy, alkoxycarbonyl, haloalkoxycarbonyl, cycloalkoxycarbonyl, alkenyloxycarbonyl, haloalkenyloxycarbonyl, alkynyloxycarbonyl, haloalkynyloxycarbonyl, alkylcarbonyl, haloalkylcarbonyl, cycloalkylcarbonyl, cyclohaloalkylcarbonyl, alkenylcarbonyl, haloalkenylcarbonyl, alkynylcarbonyl, haloalkynylcarbonyl, or Z$^4$ is alkynyloxy which contains 1 or 2 substituents, where the substituents are each independently selected from the following list: cycloalkyl, alkoxycarbonyl, —Z$^3$, alkylaminocarbonyl, dialkylaminocarbonyl, and salts, metal complexes and N-oxides of the compounds of the formula (I).

The invention further provides for the use of the compounds of the formula (I) as fungicides.

Inventive piperidinecarboxylic acid derivatives of the formula (I) and the salts, metal complexes and N-oxides thereof are very suitable for controlling phytopathogenic harmful fungi. The aforementioned inventive compounds exhibit, in particular, potent fungicidal activity and can be used in crop protection, in the domestic and hygiene sector and in the protection of materials.

DETAILED DESCRIPTION OF A PREFERRED EMBODIMENT

The compounds of the formula (I) may be present either in pure form or as mixtures of different possible isomeric forms, especially of stereoisomers, such as E and Z, threo and erythro, and also optical isomers, such as R and S isomers or atropisomers, and, if appropriate, also of tautomers. Both the E and Z isomers, and the threo and erythro isomers, and also the optical isomers, any desired mixtures of these isomers, and the possible tautomeric forms are claimed.

The radical definitions of the inventive compounds of the formula (I) preferably, more preferably and most preferably have the following definitions:

A is preferably phenyl which may contain up to two substituents, where the substituents are each independently selected from the following list:
  halogen, cyano, hydroxyl, —NR$^3$R$^4$, —C(=O)NR$^3$R$^4$, nitro, $C_1$-$C_6$-alkyl, $C_2$-$C_6$-alkenyl, $C_2$-$C_6$-alkynyl, $C_3$-$C_8$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, $C_1$-$C_4$-alkoxy, $C_1$-$C_4$-haloalkoxy, $C_1$-$C_4$-alkenyloxy, $C_1$-$C_4$-alkynyloxy, $C_1$-$C_4$-alkylthio, $C_1$-$C_4$-alkylsulphonyl, $C_1$-$C_4$-haloalkylthio, $C_1$-$C_4$-haloalkylsulphonyl, $C_1$-$C_4$-alkoxy-$C_1$-$C_6$-alkyl, hydroxy-$C_1$-$C_4$-alkyl, $C_1$-$C_6$-alkylcarbonyl, $C_1$-$C_6$-alkoxycarbonyl, $C_1$-$C_6$-alkylcarbonyloxy or —C(=O)H, or A is preferably a heteroaromatic radical selected from the following group: furan-2-yl, furan-3-yl, thiophen-2-yl, thiophen-3-yl, isoxazol-3-yl, isoxazol-4-yl, isoxazol-5-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, pyrazol-5-yl, imidazol-1-yl, imidazol-2-yl, imidazol-4-yl, 1,2,3-triazol-1-yl, 1,2,4-triazol-1-yl, pyridin-2-yl, pyridin-3-yl, pyridin-4-yl, pyridazin-3-yl, pyridazin-4-yl, pyrazin-2-yl, pyrazin-3-yl, pyrimidin-2-yl, pyrimidin-4-yl or pyrimidin-5-yl which may contain up to two substituents, where the substituents are each independently selected from the following list:
  substituents on carbon:
  halogen, cyano, hydroxyl, nitro, —NR$^3$R$^4$, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, $C_1$-$C_4$-alkoxy, $C_1$-$C_4$-haloalkoxy, $C_1$-$C_4$-alkylthio, $C_1$-$C_4$-alkylsulphonyl, $C_1$-$C_4$-haloalkylthio, $C_1$-$C_4$-haloalkylsulphonyl, $C_1$-$C_4$-alkoxy-$C_1$-$C_4$-alkyl, hydroxy-$C_1$-$C_4$-alkyl, $C_1$-$C_6$-alkylcarbonyl, $C_1$-$C_6$-alkoxycarbonyl, $C_1$-$C_6$-alkylcarbonyloxy or phenyl,
  substituents on nitrogen:
  $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_{10}$-cycloalkyl-$C_1$-$C_6$-alkyl, $C_1$-$C_6$-haloalkylcarbonyl, phenyl, benzyl, $C_1$-$C_4$-alkylsulphonyl, $C_1$-$C_4$-haloalkylsulphonyl, phenylsulphonyl, —C(=O)H, or $C_1$-$C_6$-alkylcarbonyl, A is more preferably phenyl which may contain up to two substituents, where the substituents are each independently selected from the following list:

fluorine, bromine, iodine, chlorine, cyano, nitro, methyl, ethyl, n-propyl, 1-methylethyl, 1,1-dimethylethyl, chlorofluoromethyl, dichloromethyl, dichlorofluoromethyl, difluoromethyl, trichloromethyl, trifluoromethyl, cyclopropyl, ethoxy, 1-methylethoxy, n-propoxy, methoxy, trifluoromethoxy, difluoromethoxy, 1-methylethylthio, methylthio, ethylthio, n-propylthio, difluoromethylthio or trifluoromethylthio, or A is more preferably a heteroaromatic radical selected from the following group: furan-2-yl, furan-3-yl, thiophen-2-yl, thiophen-3-yl, isoxazol-3-yl, isoxazol-4-yl, isoxazol-5-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, pyrazol-1-yl, pyrazol-3-yl, pyrazol-5-yl, imidazol-1-yl, imidazol-2-yl, imidazol-4-yl, 1,2,3-triazol-1-yl, 1,2,4-triazol-1-yl, pyridin-2-yl, pyridin-3-yl, pyridin-4-yl, pyridazin-3-yl, pyridazin-4-yl, pyrimidin-2-yl, pyrimidin-4-yl or pyrimidin-5-yl, which may contain up to two substituents, where the substituents are the same or different and are each independently selected from the following list:

substituents on carbon:

fluorine, chlorine, bromine, iodine, cyano, nitro, methyl, ethyl, n-propyl, 1-methylethyl, 1,1-dimethylethyl, chlorofluoromethyl, dichloromethyl, dichlorofluoromethyl, difluoromethyl, trichloromethyl, trifluoromethyl, cyclopropyl, ethoxy, 1-methylethoxy, n-propoxy, methoxy, trifluoromethoxy, difluoromethoxy, 1-methylethylthio, methylthio, ethylthio, n-propylthio, difluoromethylthio, trifluoromethylthio or phenyl, substituents on nitrogen:

methyl, ethyl, n-propyl, 1-methylethyl, methylsulphonyl, trifluoromethylsulphonyl, methylcarbonyl, trifluoromethylcarbonyl, chloromethylcarbonyl, 2,2-trifluoroethyl, 2,2-difluoroethyl, 2,2-dichloro-2-fluoroethyl, 2-chloro-2-difluoroethyl or 2-chloro-2-fluoroethyl.

A is most preferably phenyl which may contain up to two substituents, where the substituents are each independently selected from the following list:

methyl, ethyl, iodine, chlorine, bromine, fluorine, methoxy, ethoxy, difluoromethyl or trifluoromethyl, trifluoromethoxy, cyano or A is most preferably pyrazol-1-yl, pyrazol-4-yl or pyrazole-5-yl each one of which may contain up to two substituents, where the substituents are each independently selected from the following list:

methyl, ethyl, chlorine, chloromethyl, dichlorometyhy, bromine, fluorine, fluoromethyl, difluoromethyl or trifluoromethyl, $R^{G1}$ is preferably hydrogen, $C_1$-$C_3$-alkoxycarbonyl, —C(=O)OH or halogen and more preferably hydrogen, $L^1$ is preferably $C(R^{L11})_2$ or $NR^{L12}$, more preferably $CHR^{L11}$ or $NR^{L12}$, and most preferably $CH_2$ or NH, $R^{L11}$ is preferably hydrogen, alkyl, $C_1$-$C_4$-haloalkyl, $C_1$-$C_4$-alkylcarbonyl, $C_1$-$C_4$-haloalkylcarbonyl, $C_1$-$C_4$-alkoxycarbonoyl, $C_1$-$C_4$-haloalkoxycarbonyl, $R^{L11}$ is more preferably hydrogen, methyl, methoxycarbonyl or ethoxycarbonyl, $R^{L12}$ is preferably hydrogen, $C_1$-$C_4$-alkyl, $C_1$-$C_4$-haloalkyl, $C_3$-$C_8$-cycloalkyl, $C_1$-$C_4$-alkylsulphonyl, $C_1$-$C_4$-alkoxycarbonyl, and more preferably hydrogen, methyl, methoxycarbonyl or ethoxycarbonyl, $L^2$ is preferably a direct bond, $L^3$ is preferably a direct bond, —$CH_2$—, sulphur, oxygen, —(S=O)$_2$— —C(=O)O—, —C(=O)NH—, —OC(=O)—, —NHC(=O)— or —OCH$_2$C≡C— and more preferably a direct bond, —OCH$_2$C≡C— or —C(=O)O—, $L^4$ is preferably a direct bond, —C(=O)— or S(=O)$_2$, p is preferably 0 to 1, and more preferably 0, Q is preferably

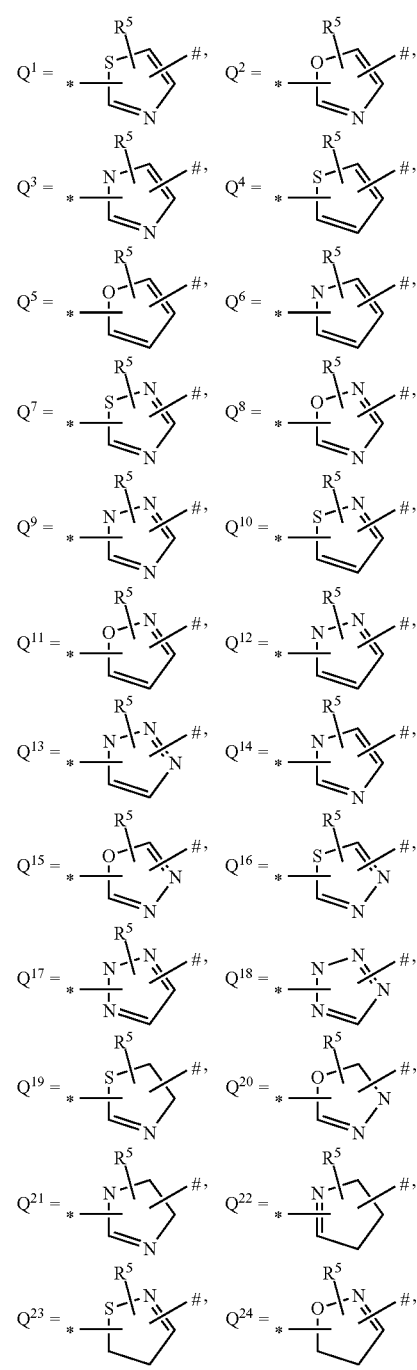

-continued

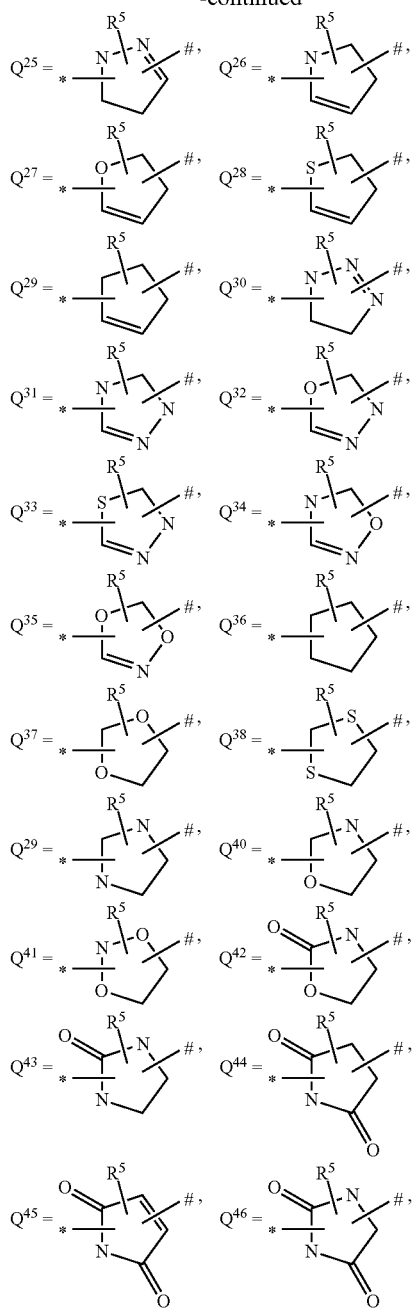

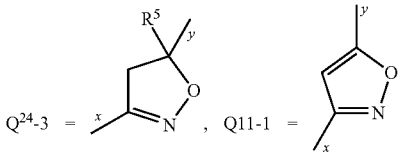

where the bond identified by "*" is bonded directly to G or L², and where the bond identified by "#" is bonded directly to L² or G, or where the bond identified by "*" is bonded directly to L², and the bond identified by "#" is at the same time bonded directly to G, Q is more preferably $Q^{11}$ and $Q^{24}$, Q is most preferably

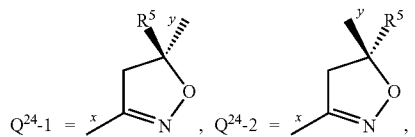

where the bond identified by "x" is bonded directly to G, and where the bond identified by "y" is bonded directly to L², $R^1$ is preferably $C_5$-$C_6$-cycloalkenyl or $C_3$-$C_8$-cycloalkyl which may be unsubstituted or substituted, where the substituents are each independently selected from $Z^4$ and from $Z^{1-1}$, and more preferably substituted or unsubstituted cyclopentenyl, cyclohexenyl, cyclopentyl, cyclohexyl or cycloheptyl, each of which may contain 1 or 2 substituents, where the substituents are each independently selected from $Z^4$ and optionally from the following list: methyl, ethyl, methoxy, ethoxy, trifluoromethoxy, ethynyl, methylcarbonyloxy, ethylcarbonyloxy, methylthio, ethylthio or trifluoromethylthio, or $R^1$ is preferably phenyl which may contain 0, 1, 2, 3, or 4 substituents, where the substituents are each independently selected from $Z^4$ and from $Z^{1-2}$, and more preferably phenyl which may contain 0, 1, 2 or 3 substituents, where the substituents are each independently selected from $Z^4$ and from the following list: fluorine, chlorine, bromine, iodine, cyano, nitro, hydroxyl, amino, methyl, ethyl, n-propyl, 1-methylethyl, n-butyl, 1,1-dimethylethyl, 1,2-dimethylethyl, ethenyl, ethynyl, trifluoromethyl, difluoromethyl, trichloromethyl, dichloromethyl, cyclopropyl, methoxy, ethoxy, n-propoxy, 1-methylethoxy, 1,1-dimethylethoxy, methylcarbonyl, ethylcarbonyl, methoxycarbonyl, ethoxycarbonyl, n-propoxycarbonyl, 1-methylethoxycarbonyl, 1,1-dimethylethoxycarbonyl, 1-methylcarbonyloxy, methylthio, ethylthio, methylsulphonyl or -$L^3R^3$, and most preferably phenyl which contains 0, 1, 2 or 3 substituents, where the substituents are each independently selected from the following list:

formyl, methoxymethoxy, 2-methoxyethoxy, allyloxy, 2-fluoroprop-2-en-1-yloxy, 2-chloroprop-2-en-1-yloxy, 3-chloroprop-2-en-1-yloxy, 2-bromoprop-2-en-1-yloxy, 2-methylprop-2-en-1-yloxy, 3,3-dichloroprop-2-en-1-yloxy, 3,3-dichloro-2-fluoroprop-2-en-1-yloxy, but-2-en-1-yloxy, but-3-en-2-yloxy, but-3-en-1-yloxy, 3-chlorobut-2-en-1-yloxy, 3-methylbut-2-en-1-yloxy, 4,4,4-trifluorobut-2-en-1-yloxy, prop-2-yn-1-yloxy, 3-chloroprop-2-yn-1-yloxy, 3-bromoprop-2-yn-1-yloxy, but-2-yn-1-yloxy, pent-2-yn-1-yloxy, 2-fluoro-2-methylpropanoyloxy, 3,3,3-trifluoropropanoyloxy, cyclopropylcarbonyloxy, cyclohexylcarbonyloxy, (1-chlorocyclopropyl)carbonyloxy, but-2-enoyloxy, acryloyloxy, benzoyloxy, 2-fluorobenzoyloxy, 3-fluorobenzoyloxy, 4-fluorobenzoyloxy, cyanomethoxy, methylsulphonyloxy, ethylsulphonyloxy, trifluoromethylsulphonyloxy, cyclopropylsulphonyloxy, 2-methoxyethoxymethyl, allyloxymethyl, prop-2-yn-1-yloxymethyl, methylsulphonylmethyl, methylcarbonylaminomethyl, methylsulphonylaminomethyl, —C(=NOH)H, —C(=NOCH₃)H, —C(=NOCH₂CH₃)H, —C(=NOCH(CH₃)CH₃)H, —C(=NOH)CH₃, —C(=NOCH₃)CH₃, —C(=NOCH₂CH₃)CH₃, —C(=NOCH(CH₃)CH₃)CH₃, dimethylaminosulphonyl, C(=O)NH₂, ethylaminosulphonyl, trimethylsilylethynyl, diethylaminosulphonyl, methylaminosulphonyl, trimethylsilyloxy, trimethylsilylprop-2-yn-1-yloxy, trifluoromethylamino, dimethylaminocarbonylamino, —C(=O)OH, 1,1-dimethylethylcarbonyl amino, chloromethylcarbonylamino, trifluoromethylcarbonylamino, 1,1-dimethylethoxycarbonylamino, ethylcarbonylamino, 1-methylethoxycarbonylamino, trifluoromethylcarbonylamino, methylcarbonylamino, methoxycarbonylamino, ethoxycarbonylamino, iso-propoxycarbonylamino, 1-methylethylcarbonylamino, methylsulphonylamino or phenylsulphonylamino, 3-bromoprop-2-en-1-yloxy, fluorine, chlorine, methyl, trifluoromethyl, methoxy, or $R^1$ is preferably naphthalen-1-yl, naphthalen-2-yl, 1,2,3,4-tetrahydronaphthalen-1-yl, 1,2,3,4-tetrahydronaphthalen-2-yl, 5,6,7,8-tetrahydronaphthalen-1-yl, 5,6,7,8-tetrahydronaphthalen-2-yl, decalin-1-yl, decalin-2-yl, 1H-inden-1-yl, 2,3-dihydro-1H-inden-1-yl, 1H-inden-2-yl, 1H-inden-3-yl, 1H-inden-4-yl, 1H-inden-5-yl, 1H-inden-6-yl, 1H-inden-7-yl, indan-1-yl, indan-2-yl, indan-3-yl, indan-4-yl or indan-5-yl, where these are unsubstituted or each substituted with 1 or 2 substituents by substituents from $Z^4$ and $Z^{1-3}$, $R^1$ is more preferably naphthalen-1-yl, naphthalen-2-yl, 1,2,3,4-tetrahydronaphthalen-1-yl, 1,2,3,4-tetrahydronaphthalen-2-yl, 5,6,7,8-tetrahydronaphthalen-1-yl, 5,6,7,8-tetrahydronaphthalen-2-yl, decalin-1-yl, decalin-2-yl, 1H-inden-1-yl, 2,3-dihydro-1H-inden-1-yl, 1H-inden-2-yl, 1H-inden-3-yl, 1H-inden-4-yl, 1H-inden-5-yl, 1H-inden-6-yl, 1H-inden-7-yl, indan-1-yl, indan-2-yl, indan-3-yl, indan-4-yl or indan-5-yl, where these may each be unsubstituted or substituted with 1, 2 or 3 substituents selected from $Z^4$ and from the group consisting of methyl, methoxy, cyano, fluorine, chlorine, bromine and iodine, or $R^1$ is preferably a 5- or 6-membered heteroaryl radical which is unsubstituted or substituted with 1 or 2 substituents, where the substituents are each independently selected from $Z^4$ and $Z^{1-4}$, and the substituents on nitrogen are each independently selected from $Z^2$, $R^1$ is more preferably furan-2-yl, furan-3-yl, thiophen-2-yl, thiophen-3-yl, isoxazol-3-yl, isoxazol-4-yl, isoxazol-5-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,4-oxadiazol-3-yl, 1,2,4-oxadiazol-5-yl, 1,3,4-oxadiazol-2-yl, 1,2,4-thiadiazol-3-yl, 1,2,4-thiadiazol-5-yl, 1,3,4-thiadiazol-2-yl, 1,2,3-triazol-1-yl, 1,2,3-triazol-2-yl, 1,2,3-triazol-4-yl, 1,2,4-triazol-1-yl, 1,2,4-triazol-3-yl, 1,2,4-triazol-4-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl or pyrazin-2-yl, each of which may contain 0, 1 or 2 substituents, where the substituents are each independently selected from $Z^4$ and from the following list:

substituents on carbon: fluorine, chlorine, bromine, iodine, cyano, nitro, hydroxyl, amino, methyl, ethyl, n-propyl, 1-methylethyl, n-butyl, 1,1-dimethylethyl, 1,2-dimethylethyl, ethenyl, ethynyl, trifluoromethyl, difluoromethyl, trichloromethyl, dichloromethyl, cyclopropyl, methoxy, ethoxy, n-propoxy, 1-methylethoxy, 1,1-dimethylethoxy, methylcarbonyl, ethylcarbonyl, methoxycarbonyl, ethoxycarbonyl, n-propoxycarbonyl, 1-methylethoxycarbonyl, 1,1-dimethylethoxycarbonyl, methylcarbonyloxy, methylthio, ethylthio or methylsulphonyl, substituents on nitrogen: methyl, ethyl, n-propyl, —C(=O)H, methylcarbonyl, trifluoromethylcarbonyl, chloromethylcarbonyl, methylsulphonyl, trifluoromethylsulphonyl, phenylsulphonyl, phenyl or 2-propynyl, or $R^1$ is preferably benzofused substituted 5- or 6-membered heteroaryl which is unsubstituted or substituted with 1 or 2 substituents, where substituents are selected from $Z^4$ and the substituents on carbon are each independently selected from $Z^{1-5}$, and the substituents on nitrogen are each independently selected from $Z^2$, and more preferably indol-1-yl, indol-2-yl, indol-3-yl, indol-4-yl, indol-5-yl, indol-6-yl, indol-7-yl, benzimidazol-1-yl, benzimidazol-2-yl, benzimidazol-4-yl, benzimidazol-5-yl, indazol-1-yl, indazol-3-yl, indazol-4-yl, indazol-5-yl, indazol-6-yl, indazol-7-yl, indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,3-benzoxazol-2-yl, 1,3-benzoxazol-4-yl, 1,3-benzoxazol-5-yl, 1,3-benzoxazol-6-yl, 1,3-benzoxazol-7-yl, quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl or isoquinolin-8-yl, each of which may contain up to two substituents, where the substituents are each independently selected from the following list:

substituents on carbon: fluorine, chlorine, bromine, iodine, methyl, methoxy, substituents on nitrogen: methyl, ethyl, n-propyl, —C(=O)H, methylcarbonyl, trifluoromethylcarbonyl, chloromethylcarbonyl, methylsulphonyl, trifluoromethylsulphonyl, phenylsulphonyl, phenyl or 2-propynyl, or $R^1$ is preferably $C_5$-$C_{15}$-heterocyclyl which is unsubstituted or substituted with 1 or 2 substituents, where substituents on carbon are selected from $Z^4$ and $Z^{1-6}$ and the substituents on nitrogen are each independently selected from $Z^2$, $R^1$ is more preferably piperidin-1-yl, piperidin-2-yl, piperidin-3-yl, piperidin-4-yl, piperazin-1-yl, piperazin-2-yl, piperazin-3-yl, morpholin-1-yl, morpholin-2-yl, morpholin-3-yl, tetrahydropyran-2-yl, tetrahydropyran-3-yl, tetrahydropyran-4-yl, 1,2,3,4-tetrahydroquinolin-1-yl, 1,2,3,4-tetrahydroisoquinolin-2-yl, 1,2,3,4-tetrahydroquinoxalin-1-yl, indolin-1-yl, isoindolin-2-yl, decahydroquinolin-1-yl oder decahydroisoquinolin-2-yl, each of which may contain 1 or 2 substituents, where the substituents are each independently selected at least once from $Z^4$ and optionally from the following list:

substituents on carbon: fluorine, chlorine, bromine, iodine, methyl, methoxy, substituents on nitrogen: methyl, ethyl, n-propyl, —C(=O)H, methylcarbonyl, trifluoromethylcarbonyl, chloromethylcarbonyl, methylsulphonyl, trifluoromethylsulphonyl, phenylsulphonyl, phenyl or 2-propynyl, $R^2$ is preferably —COOR$^O$, —CON(R$^N$)$_2$ or —CON(R$^N$)OR$^O$, and more preferably —COOR$^O$, $C_1$-$C_4$-alkylaminocarbonyl or $C_3$-$C_4$-alkenylaminocarbonyl and most preferably —COOH, (tetrahydrofuran-3-yloxy)carbonyl, methoxycarbonyl, ethoxycarbonyl, iso-propoxycarbonyl, tert-butoxycarbonyl, n-butoxycarbonyl, phenoxycarbonyl, 2,6-dimethylphenoxycarbonyl, 2,6-diisopropylphenoxycarbonyl, 2,6-di-tert-butylphenoxycarbonyl, benzyloxycarbonyl, 4-methoxybenzyloxycarbonyl, 3,4 dimethoxybenzyloxy-carbonyl, prop-2-enyloxycarbonyl, but-2-en-1-yloxycarbonyl, prop-2-ynyloxycarbonyl, methoxyethoxycarbonyl, methoxyethoxycarbonyl, methylsulfanylethoxycarbonyl, or methylaminocarbonyl, ethylaminocarbonyl, propylaminocarbonyl, iso-propylcarbonyl, butylcarbonyl, sec-butylcarbonyl or tert-butylcarbonyl, $R^3$ and $R^4$ are preferably the same or different and are each independently hydrogen, $C_1$-$C_6$-alkyl, $C_2$-$C_6$-alkenyl, $C_2$-$C_6$-alkynyl, $C_1$-$C_6$-haloalkyl, $C_3$-$C_8$-cycloalkyl, benzyl or phenyl, and more preferably hydrogen, methyl, ethyl, n-propyl, 1-methylethyl, n-butyl or 1,1-dimethylethyl, $R^5$ is preferably the same or different and is independently
bonded to carbon of the 5-membered heterocyclyl of Q: hydrogen, halogen, cyano, —$NR^3R^4$, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_8$-cycloalkyl, $C_3$-$C_8$-halocycloalkyl, $C_3$-$C_8$-halocycloalkyl, $C_1$-$C_4$-alkyl-$C_3$-$C_8$-cycloalkyl, $C_3$-$C_8$-cycloalkyl-$C_1$-$C_4$-alkyl, $C_1$-$C_4$-alkoxy-$C_1$-$C_4$-alkyl, $C_3$-$C_8$-cycloalkoxy-$C_1$-$C_4$-alkyl, $C_1$-$C_4$-alkoxy-$C_1$-$C_4$-alkoxy-$C_1$-$C_4$-alkyl, $C_1$-$C_4$-alkylthio-$C_1$-$C_4$-alkyl, $C_1$-$C_6$-alkoxy, $C_1$-$C_6$-haloalkoxy, $C_3$-$C_8$-cycloalkoxy, $C_3$-$C_8$-halocycloalkoxy, $C_3$-$C_8$-cycloalkyl-$C_1$-$C_4$-alkoxy, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkoxy-$C_1$-$C_4$-alkoxy, $C_1$-$C_6$-alkylcarbonyloxy, $C_1$-$C_6$-haloalkylcarbonyloxy, $C_3$-$C_8$-cycloalkylcarbonyloxy, $C_1$-$C_6$-alkylcarbonyl-$C_1$-$C_6$-alkoxy, $C_1$-$C_6$-alkylthio, $C_1$-$C_6$-haloalkylthio, $C_3$-$C_8$-cycloalkylthio, tri($C_1$-$C_4$-alkyl)silyl,
bonded to nitrogen of the 5-membered heterocyclyl of Q: hydrogen, —C(=O)H, $C_1$-$C_3$-alkyl, $C_1$-$C_6$-alkylcarbonyl, $C_1$-$C_6$-alkoxycarbonyl or benzyl, $R^5$ is more preferably hydrogen, cyano, methyl, trifluoromethyl, difluoromethyl or methoxymethyl, or $R^5$ is most preferably hydrogen, $R^7$ is preferably hydrogen, $C_1$-$C_6$-alkyl, $C_1$-$C_6$-haloalkyl, $C_3$-$C_8$-cycloalkyl, $C_1$-$C_4$-alkylcarbonyl, $C_1$-$C_4$-haloalkylcarbonyl, $C_1$-$C_4$-alkoxycarbonyl or $C_1$-$C_4$-haloalkoxycarbonyl, $R^8$ is preferably $C_1$-$C_3$-alkyl or -$L^4R^1$, $R^9$ is preferably hydrogen, $C_1$-$C_6$-alkyl, $C_1$-$C_6$-haloalkyl, benzyl or $Z^3$, more preferably hydrogen, methyl, ethyl, n-propyl, 1-methylethyl, n-butyl, 1,1-dimethylethyl or 2-methylpropyl, $R^{10}$ is preferably hydrogen, $C_1$-$C_6$-alkyl, $C_1$-$C_6$-haloalkyl, $C_3$-$C_8$-cycloalkyl-$C_1$-$C_4$-alkyl, $C_3$-$C_8$-cycloalkyl, $C_1$-$C_4$-alkyl-$C_3$-$C_8$-cycloalkyl, $C_1$-$C_4$-haloalkyl-$C_3$-$C_8$-cycloalkyl, $C_1$-$C_4$-alkoxy-$C_1$-$C_4$-alkyl, $C_1$-$C_4$-haloalkoxy-$C_1$-$C_4$-alkyl, benzyl or phenyl, more preferably hydrogen, methyl, ethyl, n-propyl, 1-methylethyl, n-butyl, 1,1-dimethylethyl or 2-methylpropyl, $R^{11}$ and $R^{12}$ are preferably the same or different and are preferably each independently hydrogen, $C_1$-$C_3$-alkyl, $C_3$-$C_4$-alkenyl, $C_3$-$C_4$-alkynyl, cyano-$C_1$-$C_3$-alkyl, formyl, $C_1$-$C_3$-haloalkyl, benzyl, phenyl, $C_1$-$C_3$-alkylcarbonyl, $C_3$-$C_8$-cycloalkoxycarbonyl, $C_1$-$C_3$-alkoxycarbonyl, $C_3$-$C_4$-alkenyloxycarbonyl, $C_3$-$C_4$-alkynyloxycarbonyl, $C_1$-$C_3$-haloalkylcarbonyl, $C_3$-$C_8$-halocycloalkylcarbonyl, $C_3$-$C_8$-cycloalkoxycarbonyl, $C_3$-$C_8$-cycloalkylcarbonyl, di($C_1$-$C_3$-alkyl)aminocarbonyl, $R^O$ is preferably hydrogen, $C_1$-$C_8$-alkyl, $C_3$-$C_8$-cycloalkyl, $C_2$-$C_8$-alkenyl, $C_2$-$C_8$-alkynyl, phenyl, benzyl, tetrahydrofuran, wherein alkyl, cycloalkyl, alkenyl and alkynyl, are optionally substituted by one or more groups independently selected from halogen, CN, $NH_2$, $NO_2$, OH, =O, =S, $C_1$-$C_4$-alkyl, $C_1$-$C_4$-haloalkyl, $C_1$-$C_4$-alkoxy, $C_1$-$C_4$-haloalkoxy, $C_1$-$C_4$-alkysulfanyl, $C_1$-$C_4$-haloalkysulfanyl, $C_1$-$C_4$-alkyl-$C_1$-$C_4$-alkoxy and $C_1$-$C_4$-alkoxy-$C_1$-$C_4$-alkyl, and wherein phenyl and benzyl are optionally substituted by one or more groups independently selected from halogen, CN, $NH_2$, $NO_2$, OH, $C_1$-$C_4$-alkyl, $C_1$-$C_4$-haloalkyl, $C_1$-$C_4$-alkoxy, $C_1$-$C_4$-haloalkoxy, $C_1$-$C_4$-alkysulfanyl, $C_1$-$C_4$-haloalkysulfanyl, $C_1$-$C_4$-alkyl-$C_1$-$C_4$-alkoxy and $C_1$-$C_4$-alkoxy-$C_1$-$C_4$-alkyl, $R^O$ is more preferably hydrogen, methyl, ethyl, n-propyl, iso-propyl, n-butyl, iso-butyl, tert-butyl, n-octyl, 2-ethylhexyl, cyclopropyl, cyclobutyl, cyclopentyl, cyclohexyl, prop-2-enyl, 3-methylbut-2-enyl, prop-2-ynyl, phenyl, 2,6-dimethylphenyl, 2,6-diisopropylphenyl, 2,6-di-tert-butylphenyl, benzyl, 4-methoxybenzyl, 3,4-dimethoxybenzyl, tetrahydrofuran, methoxyethyl, ethoxyethyl, methylsulfanylethyl, ethylsulfanylethyl, cyclopropylmethyl, cyanomethyl, cyanoethyl, $R^N$ is preferably hydrogen, OH, $C_1$-$C_8$-alkyl, $C_1$-$C_8$-alkoxy, $C_1$-$C_8$-alkoxy-$C_1$-$C_8$-alkyl, $C_2$-$C_8$-alkenyl, $C_2$-$C_8$-alkynyl, wherein the alkyl, alkoxy, alkenyl and alkynyl are optionally substituted by one or more halogen; wherein when two radicals $R^N$ are attached to the same nitrogen atom, these radicals can be identical or different; wherein when two radicals $R^N$ are attached to the same nitrogen atom, both of these radicals cannot be OH, alkoxy or haloalkoxy; and wherein when two radicals $R^N$ are attached to the same nitrogen atom, these two radicals together with the nitrogen atom to which they are attached may form piperidine or morpholine, $R^C$ is preferably hydrogen, $C_1$-$C_8$-alkyl, $C_3$-$C_8$-cycloalkyl, $C_2$-$C_8$-alkenyl, $C_1$-$C_8$-alkynyl, phenyl or benzyl wherein the alkyl, cycloalkyl, alkenyl and alkynyl are optionally substituted by one or more groups independently selected from halogen, CN, $NH_2$, $NO_2$, OH, =O, =S, $C_1$-$C_4$-alkyl, $C_1$-$C_4$-haloalkyl, $C_1$-$C_4$-alkoxy, $C_1$-$C_4$-haloalkoxy, $C_1$-$C_4$-alkysulfanyl and $C_1$-$C_4$-haloalkysulfanyl, and wherein phenyl and benzyl are optionally substituted by one or more groups independently selected from halogen, CN, $NH_2$, $NO_2$, OH, $C_1$-$C_4$-alkyl, $C_1$-$C_4$-haloalkyl, $C_1$-$C_4$-alkoxy, $C_1$-$C_4$-haloalkoxy, $C_1$-$C_4$-alkysulfanyl and $C_1$-$C_4$-haloalkysulfanyl;

T is preferably the same or different and is independently hydrogen, $C_1$-$C_4$-alkyl or $C_1$-$C_2$-haloalkyl, and more preferably hydrogen, Y is preferably sulphur or oxygen, and more preferably oxygen, $Z^{1-1}$ is preferably and are the same or different and are each independently hydrogen, cyano, halogen, $C_1$-$C_6$-alkyl, $C_1$-$C_6$-haloalkyl, $C_3$-$C_6$-cycloalkyl, $C_2$-$C_6$-alkenyl, $C_2$-$C_6$-haloalkenyl, $C_2$-$C_6$-alkynyl, $C_2$-$C_6$-haloalkynyl, hydroxyl, $C_1$-$C_6$-alkoxy, $C_1$-$C_6$-haloalkoxy, $C_1$-$C_6$-alkylcarbonyloxy, $C_1$-$C_6$-alkylthio or $C_1$-$C_6$-haloalkylthio, $Z^{1-2}$ is preferably hydrogen, halogen, cyano, hydroxyl, amino, nitro, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_8$-cycloalkyl, $C_3$-$C_8$-halocycloalkyl, $C_3$-$C_8$-cycloalkenyl, $C_3$-$C_8$-halocycloalkenyl, $C_1$-$C_6$-alkoxy-$C_1$-$C_6$-alkyl, $C_1$-$C_6$-alkylcarbonyl, $C_3$-$C_8$-cycloalkylcarbonyl, $C_1$-$C_6$-alkoxycarbonyl, $C_1$-$C_6$-alkoxy, $C_1$-$C_6$-haloalkoxy, $C_3$-$C_8$-cycloalkoxy, $C_3$-$C_8$-halocycloalkoxy, $C_1$-$C_6$-alkylcarbonyloxy, $C_1$-$C_6$-alkylthio, $C_1$-$C_6$-haloalkylthio, $C_3$-$C_6$-cycloalkylthio, $C_1$-$C_6$-alkylsulphonyl, $C_1$-$C_6$-haloalkylsulphonyl, $C_3$-$C_8$-cycloalkylsulphonyl, tri($C_1$-$C_4$-alkyl)silyl, or -$L^3Z^3$, $Z^{1-3}$ and $Z^{1-5}$ is preferably and are the same or different and are each independently hydrogen, halogen, cyano, nitro, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_1$-$C_4$-alkoxy-$C_1$-$C_4$-alkyl, $C_1$-$C_6$-alkylcarbonyl, $C_1$-$C_6$-alkoxycarbonyl, $C_1$-$C_4$-alkoxy, $C_1$-$C_4$-haloalkoxy, $C_1$-$C_6$-alkylcarbonyloxy, $C_1$-$C_6$-alkylcarbonylthio, $C_1$-$C_4$-alkylthio, $C_1$-$C_4$-haloalkylthio, $C_1$-$C_4$-alkylsulphonyl or $C_1$-$C_4$-haloalkylsulphonyl, $Z^{1-4}$ is preferably hydrogen, halogen, cyano, hydroxyl, amino, nitro, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_8$-cycloalkyl, $C_3$-$C_8$-halocycloalkyl, $C_3$-$C_8$-cycloalkenyl, $C_3$-$C_8$-halocycloalkenyl, $C_1$-$C_6$-alkoxy-$C_1$-$C_6$-alkyl, $C_1$-$C_6$-alkylcarbonyl, $C_3$-$C_8$-cycloalkylcarbonyl, $C_1$-$C_6$-alkoxycarbonyl, $C_1$-$C_6$-alkoxy, $C_1$-$C_6$-haloalkoxy, $C_3$-$C_8$-cycloalkoxy, $C_3$-$C_8$-halocycloalkoxy, $C_1$-$C_6$-alkylcarbonyloxy, $C_1$-$C_6$-alkylthio, $C_1$-$C_6$-haloalkylthio, $C_3$-$C_6$-cycloalkylthio, $C_1$-$C_6$-alkylsulphonyl, $C_1$-$C_6$-haloalkylsulphonyl or $C_3$-$C_8$-cycloalkylsulphonyl, $Z^{1-6}$ is preferably and are the same or different and are each independently hydrogen, cyano, halogen, $C_1$-$C_6$-alkyl, $C_1$-$C_6$-haloalkyl, $C_3$-$C_6$-cycloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_6$-alkylthio, $C_1$-$C_6$-alkylcarbonyl, $C_1$-$C_6$-alkoxycarbonyl, $C_1$-$C_6$-alkylcarbonyloxy, $C_1$-$C_6$-haloalkylthio or phenyl, $Z^2$ is preferably the same or different and is independently hydrogen, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_1$-$C_4$-alkoxy-$C_1$-$C_4$-alkyl, phenyl, benzyl, $C_1$-$C_4$-haloalkylsulphonyl, $C_1$-$C_6$-alkoxycarbonyl, $C_1$-$C_6$-haloalkoxycarbonyl, phenylsulphonyl, $C_1$-$C_4$-alkylsulphonyl, —C(=O)H, $C_1$-$C_3$-haloalkylcarbonyl or $C_1$-$C_3$-alkylcarbonyl, $Z^3$ is preferably a phenyl radical, naphthalenyl or a 5- or 6-membered heteroaryl radical which may contain up to two substituents, where the substituents are each independently selected from the following list:

halogen, cyano, nitro, hydroxyl, amino, —SH, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_4$-haloalkynyl, $C_2$-$C_4$-alkoxyalkyl, $C_1$-$C_6$-alkylcarbonyl, $C_1$-$C_6$-haloalkylcarbonyl, $C_1$-$C_6$-alkoxycarbonyl, $C_1$-$C_4$-alkoxy, $C_1$-$C_4$-haloalkoxy, $C_2$-$C_6$-alkenyloxy, $C_2$-$C_6$-alkynyloxy, $C_1$-$C_4$-alkylthio, $C_1$-$C_4$-haloalkylthio, $C_1$-$C_4$-alkylsulphonyl, $C_1$-$C_4$-haloalkylsulphonyl or $C_1$-$C_4$-alkylamino, di($C_1$-$C_4$-alkyl)amino, substituents on nitrogen: hydrogen, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_1$-$C_4$-alkoxy-$C_1$-$C_4$-alkyl, phenyl, benzyl, $C_1$-$C_4$-haloalkylsulphonyl, $C_1$-$C_6$-alkoxycarbonyl, $C_1$-$C_6$-haloalkoxycarbonyl, phenylsulphonyl, $C_1$-$C_4$-alkylsulphonyl, —C(=O)H, or $C_1$-$C_3$-alkylcarbonyl, and $Z^3$ is more preferably a phenyl radical which may contain up to two substituents, where the substituents are each independently selected from the following list:

chlorine, bromine, iodine, fluorine, cyano, nitro, hydroxyl, amino, —SH, methyl, ethyl, n-propyl, 1-methylethyl, 1,1-dimethylethyl, ethenyl, propen-2-yl, ethynyl, propyn-2-yl, trifluoromethyl, difluoromethyl, methoxymethyl, methylcarbonyl, ethylcarbonyl, trifluoromethylcarbonyl, methoxycarbonyl, ethoxycarbonyl, n-propoxycarbonyl, 1-methylethoxycarbonyl, 1,1-dimethylethoxycarbonyl, methoxy, ethoxy, n-propoxy, 1-methylethoxy, 1,1-dimethylethoxy, trifluoromethoxy, ethenyloxy, 2-propenyloxy, ethynyloxy, 2-propynyloxy, methylthio, ethylthio, trifluoromethylthio, methylsulphonyl, ethylsulphonyl, propylthionyl, 1-methylethylthio, trifluoromethylsulphonyl, methylamino, ethylamino, n-propylamino, 1-methylethylamino, 1,1-dimethylethylamino or dimethylamino, or $Z^3$ is more preferably naphthalenyl, $Z^4$ is preferably —SH, —C(=O)H, $C_1$-$C_6$-alkoxy-$C_1$-$C_6$-alkoxy-$C_1$-$C_6$-alkyl, $C_1$-$C_6$-alkylthioalkyl, $C_1$-$C_6$-alkylsulphinyl-$C_1$-$C_6$-alkyl, $C_1$-$C_6$-alkylsulphonyl-$C_1$-$C_6$-alkyl, $C_4$-$C_6$-alkylcarbonyl, $C_1$-$C_6$-haloalkylcarbonyl, $C_3$-$C_6$-cycloalkoxycarbonyl, $C_3$-$C_6$-cycloalkyl-$C_1$-$C_6$-alkoxycarbonyl, $C_3$-$C_6$-cycloalkylaminocarbonyl, $C_1$-$C_6$-haloalkoxy-$C_1$-$C_6$-alkyl, $C_5$-$C_6$-alkoxy, $C_5$-$C_6$-haloalkoxy, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkoxy-$C_1$-$C_6$-alkoxy, $C_1$-$C_6$-haloalkylcarbonyloxy, $C_3$-$C_6$-cycloalkylcarbonyloxy, $C_1$-$C_6$-alkylcarbonyl-$C_1$-$C_6$-alkoxy, $C_5$-$C_6$-alkylthio, $C_5$-$C_6$-haloalkylthio, $C_5$-$C_6$-haloalkylsulphinyl, $C_5$-$C_6$-haloalkylsulphonyl, $C_1$-$C_6$-alkylsulphonylamino, $C_1$-$C_6$-haloalkylsulphonylamino, cyano-$C_1$-$C_6$-alkyl, $C_2$-$C_6$-alkenylcarbonyloxy, $C_2$-$C_6$-alkynylthio, $C_3$-$C_8$-halocycloalkylcarbonyloxy, $C_2$-$C_6$-alkenylamino, $C_2$-$C_6$-alkynyl amino, $C_1$-$C_6$-haloalkylamino, $C_3$-$C_8$-cycloalkyl-$C_1$-$C_6$-alkylamino, $C_1$-$C_6$-alkoxyamino, $C_1$-$C_6$-haloalkoxyamino, $C_1$-$C_6$-alkylcarbonylamino, $C_1$-$C_6$-haloalkylcarbonylamino, $C_1$-$C_6$-alkoxycarbonylamino, $C_1$-$C_6$-alkylcarbonyl($C_1$-$C_6$-alkyl)amino, $C_1$-$C_6$-haloalkylcarbonyl($C_1$-$C_6$-alkyl)amino, $C_1$-$C_6$-alkoxycarbonyl($C_1$-$C_6$-alkyl)amino, $C_2$-$C_6$-alkenylthio, $C_1$-$C_6$-haloalkoxycarbonyl, $C_1$-$C_6$-alkoxy-$C_1$-$C_4$-alkylcarbonyl, —SF$_5$, $C_1$-$C_6$-haloalkoxycarbonylamino, —NHC(=O)H, $C_1$-$C_6$-alkoxy($C_1$-$C_4$-alkyl)aminocarbonyl, $C_1$-$C_6$-alkoxycarbonyl-$C_1$-$C_6$-alkoxy, di($C_1$-$C_6$-alkyl)aminocarbonylamino, di($C_1$-$C_6$-alkyl)aminosulphonyl, di($C_1$-$C_6$-haloalkyl)amino, $C_1$-$C_6$-alkylaminosulphonyl, $C_1$-$C_6$-alkylaminocarbonylamino, tri($C_1$-$C_4$-alkyl)silyloxy, $C_1$-$C_6$-haloalkylsulphonyloxy, $C_1$-$C_6$-alkylsulphonyloxy, tri($C_1$-$C_4$-alkyl)silyl-$C_2$-$C_4$-alkynyloxy, tri($C_1$-$C_4$-alkyl)silyl-$C_2$-$C_4$-alkynyl, $C_2$-$C_4$-alkynylcarbonyloxy, cyano-$C_1$-$C_3$-alkylcarbonyloxy, $C_3$-$C_8$-cycloalkylsulphonyloxy, $C_3$-$C_8$-halocycloalkylsulphonyloxy, $C_2$-$C_4$-alkenylsulphonyloxy, $C_1$-$C_3$-alkylaminocarbonyloxy, $C_2$-$C_4$-alkynyl-$C_3$-$C_8$-cycloalkyloxy, cyanocarbonyloxy, cyano-$C_2$-$C_4$-alkenyloxy, —C(=NOR$^9$)R$^{10}$, —C(=O)OH, —C(=O)NH$_2$, —C(=S)NR$^{11}$R$^{12}$, —NR$^{11}$R$^{12}$, —C(=O)NR$^{11}$R$^{12}$, —SO$_2$NR$^{11}$R$^{12}$, —NR$^{12}$SO$_2$Z$^3$, —O(C=O)H, —SCN, $C_1$-$C_3$-alkoxysulphonyl, $C_3$-$C_8$-cycloalkylsulphinyl, cyano($C_1$-$C_3$-alkoxy)-$C_1$-$C_3$-alkyl or -$L^3Z^3$, or $Z^4$ is preferably $C_1$-$C_3$-alkyl which contains 1 or 2 substituents, where the substituents are each independently selected from the following list:

cyano, —C(=O)H, $C_2$-$C_4$-alkenyloxy, $C_2$-$C_4$-alkynyloxy, $C_2$-$C_4$-alkenylthio, $C_2$-$C_4$-alkynylthio, $C_1$-$C_3$-haloalkylthio, $C_2$-$C_4$-alkenylsulphinyl, $C_2$-$C_4$-alkynylsulphinyl, $C_1$-$C_3$-haloalkylsulphinyl, $C_2$-$C_4$-alkenylsulphonyl, $C_2$-$C_4$-alkynylsulphonyl, $C_1$-$C_3$-haloalkylsulphonyl, $C_1$-$C_3$-alkylcarbonyloxy, $C_1$-$C_3$-haloalkylcarbonyloxy, $C_1$-$C_3$-alkylaminocarbonyloxy, $C_1$-$C_3$-alkylcarbonylamino, $C_1$-$C_3$-alkylaminocarbonylamino, $C_1$-$C_3$-haloalkylcarbonylamino, $C_1$-$C_3$-alkylsulphonylamino, $C_1$-$C_3$-haloalkylsulphonylamino, $C_1$-$C_3$-alkylthiocarbonyloxy, cyano-$C_1$-$C_3$-alkoxy, $C_3$-$C_8$-cycloalkyl-$C_1$-$C_3$-alkoxy, $C_1$-$C_3$- alkoxy-$C_1$-$C_3$-alkylthio, $C_1$-$C_3$-alkoxy-$C_1$-$C_3$-alkylsulphinyl, $C_1$-$C_3$-alkoxy-$C_1$-$C_3$-alkylsulphonyl, $C_1$-$C_3$-haloalkoxy-$C_1$-$C_3$-alkoxy, $C_1$-$C_3$-alkylcarbonyl-$C_1$-$C_3$-alkoxy, $C_2$-$C_4$-alkylthio-$C_1$-$C_3$-alkoxy, di($C_1$-$C_3$-alkyl)aminocarbonylamino, tri($C_1$-$C_4$-alkyl)silyloxy, or $Z^4$ is preferably $C_1$-$C_3$-alkoxy which contains 1 or 2 substituents, where the substituents are each independently selected from the following list:

cyano, $C_1$-$C_3$-alkylcarbonyloxy $C_1$-$C_3$-alkoxycarbonyl, $C_3$-$C_8$-cycloalkoxy, $C_1$-$C_3$-alkylcarbonyloxy, —O(C=O)H, $C_1$-$C_3$-alkylthio, hydroxyl-$C_1$-$C_3$-alkyl, $C_3$-$C_8$-cycloalkylsulphonyl, $C_1$-$C_3$-haloalkylsulphonyl, $C_1$-$C_3$-alkoxy-$C_1$-$C_3$-alkoxy, $C_1$-$C_3$-alkylsulphonyl, or $Z^4$ is preferably $C_2$-$C_4$-alkenyloxy which contains 1 or 2 substituents, where the substituents are each independently selected from the following list:

$C_3$-$C_8$-cycloalkyl, hydroxyl, $C_1$-$C_3$-alkoxy, $C_1$-$C_3$-alkoxycarbonyl, $C_1$-$C_3$-alkylcarbonyl, or $Z^4$ is preferably $C_2$-$C_4$-alkynyloxy which contains 1 or 2 substituents, where the substituents are each independently selected from the following list:

$C_3$-$C_8$-cycloalkyl, —$Z^3$, $Z^4$ is more preferably—formyl, methoxymethoxy, 2-methoxyethoxy, allyloxy, 2-fluoroprop-2-en-1-yloxy, 2-chloroprop-2-en-1-yloxy, 3-chloroprop-2-en-1-yloxy, 2-bromoprop-2-en-1-yloxy, 2-methylprop-2-en-1-yloxy, 3,3-dichloroprop-2-en-1-yloxy, 3,3-dichloro-2-fluoroprop-2-en-1-yloxy, but-2-en-1-yloxy, but-3-en-2-yloxy, but-3-en-1-yloxy, 3-chlorobut-2-en-1-yloxy 3-methylbut-2-en-1-yloxy, 4,4,4-trifluorobut-2-en-1-yloxy, prop-2-yn-1-yloxy, 3-chloroprop-2-yn-1-yloxy, 3-bromoprop-2-yn-1-yloxy, but-2-yn-1-yloxy, pent-2-yn-1-yloxy, 2-fluoro-2-methylpropanoyloxy, 3,3,3-trifluoropropanoyloxy, cyclopropylcarbonyloxy, cyclohexylcarbonyloxy, (1-chlorocyclopropyl)carbonyloxy, but-2-enoyloxy, acryloyloxy, cyanomethoxy, methylsulphonyloxy, ethylsulphonyloxy, trifluoromethylsulphonyloxy, cyclopropylsulphonyloxy, 2-methoxyethoxymethyl, allyloxymethyl, prop-2-yn-1-yloxymethyl, methylsulphonylmethyl, methylcarbonylaminomethyl, methylsulphonylaminomethyl, —C(=NOR$^9$)R$^{10}$, dimethylaminosulphonyl, ethylaminosulphonyl, trimethylsilylethynyl, diethylaminosulphonyl, methylaminosulphonyl, trimethylsilyloxy, trimethylsilylprop-2-yn-1-yloxy, trifluoromethylamino, dimethylaminocarbonylamino, —C(=O)OH, —NHC(=O)H, —C(=O)NH$_2$, —C(=S)NR$^{11}$R$^{12}$ 1,1-dimethylethylcarbonylamino, chloromethylcarbonylamino, trifluoromethylcarbonylamino, 1,1-dimethylethoxycarbonylamino, ethylcarbonylamino, 1-methylethoxycarbonylamino, trifluoromethylcarbonylamino, methylcarbonylamino, methoxycarbonylamino, ethoxycarbonylamino, iso-propoxycarbonylamino, 1-methylethylcarbonylamino, methylsulphonylamino or phenylsulphonylamino, 3-bromoprop-2-en-1-yloxy, or -L$^3$Z$^3$, The piperidinecarboxylic acid derivatives usable in accordance with the invention are defined in general terms by the formula (I). The radical definitions of the radical definitions above and specified below of the formula (I) apply to the end products of the formula (I), and also equally to all intermediates (see also below under "Elucidations of the processes and intermediates").

The radical definitions and elucidations listed above and below, in general terms or in areas of preference, can be combined with one another as desired, i.e. including combinations between the particular areas and areas of preference. They apply both to the end products and correspondingly to precursors and intermediates. Moreover, individual definitions may not apply.

Preference is given to those compounds of the formula (I) in which all radicals have the abovementioned preferred definitions.

Particular preference is given to those compounds of the formula (I) in which all radicals have the abovementioned more preferred definitions.

Very particular preference is given to those compounds of the formula (I) in which all radicals have the abovementioned most preferred definitions.

Preference is additionally given to compounds of the formula (I) and agrochemically active salts, metal complexes and N-oxides thereof, in which:

A is 3,5-bis(difluoromethyl)-1H-pyrazol-1-yl, or
A is 5-methyl-3-(trifluoromethyl)-1H-pyrazol-1-yl, or
A is 3-(difluoromethyl)-5-methyl-1H-pyrazol-1-yl, or
A is 2,5-bis(difluoromethyl)phenyl, or
A is 3-(difluoromethyl)-1-methyl-1H-pyrazol-5-yl, or
A is 1-(difluoromethyl)-3-methyl-1H-pyrazol-4-yl, or
A is 2,5-dimethylphenyl, or
A is phenyl, or
A is 4-fluorophenyl, or
A is 4-chlorophenyl, or
A is 2-(trifluoromethyl)phenyl, or
A is 3-chlorophenyl, or
A is 4-(trifluoromethoxy)phenyl, or
A is 4-chloro-3-(trifluoromethyl)phenyl, or
A is 3-cyanophenyl, or
A is 3-(difluoromethyl)-1-methyl-1H-pyrazol-4-yl, or
A is 5-(difluoromethyl)-3-methyl-1H-pyrazol-1-yl, or
A is 1-methyl-3-(trifluoromethyl)-1H-pyrazol-5-yl, or
A is 5-chloro-2-methylphenyl, or
L$^1$ is —CH$_2$— or —N—, or
L$^2$ is a direct bond, or
p is 0, or
Q is Q$^{24}$-3, or
R$^1$ is 2,6-difluorophenyl, or
R$^1$ is biphenyl-2-yl, or
R$^1$ is 2,3-difluoro-6-(prop-2-yn-1-yloxy)phenyl, or
R$^1$ is 2-(prop-2-yn-1-yloxy)phenyl, or
R$^1$ is phenyl, or
R$^1$ is 2-fluoro-6-(prop-2-yn-1-yloxy)phenyl, or
R$^1$ is 2-chloro-6-(prop-2-yn-1-yloxy)phenyl, or
R$^1$ is 2-fluoro-6-[(methylsulfonyl)oxy]phenyl, or
R$^1$ is 2-chloro-6-[(methylsulfonyl)oxy]phenyl, or
R$^1$ is 2-[(methylsulfonyl)oxy]phenyl, or
R$^2$ is (tetrahydrofuran-3-yloxy)carbonyl, or
R$^2$ is (2-methoxyethoxy)carbonyl, or
R$^2$ is [2-(methylsulfanyl)ethoxy]carbonyl, or
R$^2$ is (prop-2-yn-1-yloxy)carbonyl, or
R$^2$ is (allyloxy)carbonyl, or
R$^2$ is (benzyloxy)carbonyl, or
R$^2$ is methoxycarbonyl, or
R$^2$ is —COOH, or
R$^2$ is isopropoxycarbonyl, or
R$^2$ is ethoxycarbonyl, or
R$^2$ is tert-butoxycarbonyl, or
R$^2$ is sec-butylcarbamoyl, or
R$^2$ is methyl(3-methylbut-2-en-1-yl)carbamoyl, or
R$^2$ is (3-methylbut-2-en-1-yl)carbamoyl, or
R$^2$ is butylcarbamoyl, or
T is hydrogen, or
Y is oxygen or sulfur.

The radical definitions specified above can be combined with one another as desired. Moreover, individual definitions may not apply.

According to the type of substituents defined above, the compounds of the formula (I) have acidic or basic properties and can form salts, possibly also internal salts or adducts, with inorganic or organic acids or with bases or with metal ions. If the compounds of the formula (I) bear amino, alkylamino or other groups which induce basic properties, these compounds can be reacted with acids to give salts, or they are obtained directly as salts by the synthesis. If the compounds of the formula (I) bear hydroxyl, carboxyl or other groups which induce acidic properties, these compounds can be reacted with bases to give salts. Suitable bases are, for example, hydroxides, carbonates, hydrogencarbonates of the alkali metals and alkaline earth metals, especially those of sodium, potassium, magnesium and calcium, and also ammonia, primary, secondary and tertiary amines having $C_1$-$C_4$-alkyl groups, mono-, di- and trialkanolamines of $C_1$-$C_4$-alkanols, choline and chlorocholine.

The salts thus obtainable likewise have fungicidal properties.

The invention also provides compounds of the formula (IV)

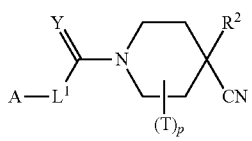

In which the radicals A, $L^1$, Y, p, T and $R^2$ are as defined as the formula (I), and salts, metal complexes and N-oxides of the compounds of the formula (IV).

The compounds of the formula (IV) may be present either in pure form or as mixtures of different possible isomeric forms, especially of stereoisomers, such as E and Z, threo and erythro, and also optical isomers, such as R and S isomers or atropisomers, and, if appropriate, also of tautomers. Both the E and Z isomers, and the threo and erythro isomers, and also the optical isomers, any desired mixtures of these isomers, and the possible tautomeric forms are claimed.

The preferred, more preferred and most preferred radicals A, $L^1$, Y, p, T and $R^2$ are as defined as the formula (I), and salts, metal complexes and N-oxides of the compounds of the formula (IV).

The invention also provides compounds of the formula (VI)

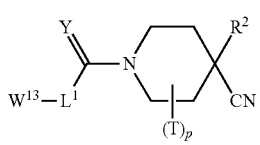

In which the radicals $L^1$, Y, p, T and $R^2$ are as defined as the formula (I), $W^{13}$ is a leaving group or hydroxy, and salts, metal complexes and N-oxides of the compounds of the formula (VI).

The compounds of the formula (VI) may be present either in pure form or as mixtures of different possible isomeric forms, especially of stereoisomers, such as E and Z, threo and erythro, and also optical isomers, such as R and S isomers or atropisomers, and, if appropriate, also of tautomers. Both the E and Z isomers, and the threo and erythro isomers, and also the optical isomers, any desired mixtures of these isomers, and the possible tautomeric forms are claimed.

The preferred, more preferred and most preferred radicals $L^1$, Y, p, T and $R^2$ are as defined as the formula (I), $W^{13}$ is preferably hydroxy, halogen, methylsulfonyloxy, trifluoromethylsulfonyloxy, phenylsulfonyloxy, 4-methylphenylsulfonyloxy, and salts, metal complexes and N-oxides of the compounds of the formula (VI).

The invention also provides compounds of the formula (II)

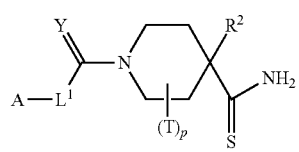

In which the radicals A, $L^1$, Y, p, T and $R^2$ are as defined as the formula (I), and salts, metal complexes and N-oxides of the compounds of the formula (II).

The compounds of the formula (II) may be present either in pure form or as mixtures of different possible isomeric forms, especially of stereoisomers, such as E and Z, threo and erythro, and also optical isomers, such as R and S isomers or atropisomers, and, if appropriate, also of tautomers. Both the E and Z isomers, and the threo and erythro isomers, and also the optical isomers, any desired mixtures of these isomers, and the possible tautomeric forms are claimed.

The preferred, more preferred and most preferred radicals A, $L^1$, Y, p, T and $R^2$ are as defined as the formula (I), and salts, metal complexes and N-oxides of the compounds of the formula (II).

The invention also provides compounds of the formula (XI)

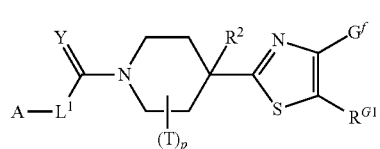

in which the radicals A, $L^1$, Y, T, $R^2$, p and $R^{G1}$ are as defined as the formula (I), and $G^f$ is formyl, cyano, haloalkyl, hydroxyalkyl, —C(=O)$R^{116}$, —CO$_2$$R^{116}$, CH$_2$OR$^{117}$, CH(OR$^{118}$)$_2$, —CH=NOH, —CCl=NOH, $R^{116}$ is hydrogen, alkyl, alkenyl, haloalkyl, haloalkenyl, phenyl, benzyl, $R^{117}$ is hydrogen, alkylsulfonyl, aryl, 4-methylphenyl, $R^{18}$ is alkyl and salts, metal complexes and N-oxides of the compounds of the formula (XI).

The compounds of the formula (XI) may be present either in pure form or as mixtures of different possible isomeric forms, especially of stereoisomers, such as E and Z, threo and erythro, and also optical isomers, such as R and S isomers or atropisomers, and, if appropriate, also of tautomers. Both the E and Z isomers, and the threo and erythro isomers, and also the optical isomers, any desired mixtures of these isomers, and the possible tautomeric forms are claimed.

The radical definitions of the inventive compounds of the formula (XI) preferably, more preferably and most preferably have the following definitions:

The preferred, more preferred and most preferred radicals A, $L^1$, Y, T, $R^2$, p and $R^{G1}$ are as defined as the formula (I), and $G^f$ is preferably formyl, cyano, $C_1$-$C_4$-haloalkyl, hydroxyl-$C_1$-$C_4$-alkyl, —$CO_2R^{116}$, $CH_2OR^{117}$, $CH(OR^{118})_2$, —CH=NOH, —CCl=NOH, $R^{116}$ is preferably hydrogen, $C_1$-$C_4$-alkyl, $C_2$-$C_4$-alkenyl, $C_1$-$C_4$-haloalkyl, $C_1$-$C_4$-haloalkenyl, phenyl, benzyl, $R^{117}$ is preferably hydrogen, $C_1$-$C_4$-alkylsulfonyl, aryl, 4-methylphenyl, $R^{118}$ is preferably $C_1$-$C_4$-alkyl and salts, metal complexes and N-oxides of the compounds of the formula (XI).

The invention also provides compounds of the formula (XIV)

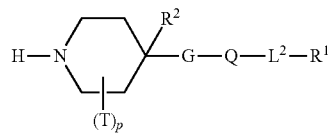

(XIV)

In which the radicals p, T, G, Q, $L^2$, $R^1$ and $R^2$ are as defined as the formula (I), and salts, metal complexes and N-oxides of the compounds of the formula (XIV).

The compounds of the formula (XIV) may be present either in pure form or as mixtures of different possible isomeric forms, especially of stereoisomers, such as E and Z, threo and erythro, and also optical isomers, such as R and S isomers or atropisomers, and, if appropriate, also of tautomers. Both the E and Z isomers, and the threo and erythro isomers, and also the optical isomers, any desired mixtures of these isomers, and the possible tautomeric forms are claimed.

The preferred, more preferred and most preferred radicals p, T, G, Q, $L^2$, $R^1$ and $R^2$ are as defined as the formula (I), and salts, metal complexes and N-oxides of the compounds of the formula (XIV).

The invention also provides compounds of the formula (XV)

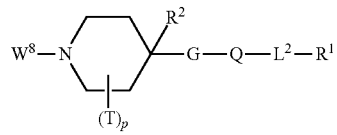

(XV)

In which the radicals p, T, G, Q, $L^2$, $R^1$ and $R^2$ are as defined as the formula (I), $W^8$ is a substituted or unsubstituted $C_1$-$C_4$-alkoxycarbonyl, benzyl, allyl or propargyl, wherein the substituents are selected from phenyl, $C_1$-$C_4$-alkyl, $C_1$-$C_4$-haloalkyl, $C_1$-$C_4$-alkoxy or $C_1$-$C_4$-haloalkoxy, and salts, metal complexes and N-oxides of the compounds of the formula (XV).

The compounds of the formula (XV) may be present either in pure form or as mixtures of different possible isomeric forms, especially of stereoisomers, such as E and Z, threo and erythro, and also optical isomers, such as R and S isomers or atropisomers, and, if appropriate, also of tautomers. Both the E and Z isomers, and the threo and erythro isomers, and also the optical isomers, any desired mixtures of these isomers, and the possible tautomeric forms are claimed.

The preferred, more preferred and most preferred radicals p, T, G, Q, $L^2$, $R^1$ and $R^2$ are as defined as the formula (I), $W^8$ is preferably $C_1$-$C_4$-alkoxycarbonyl, benzyl, allyl or propargyl, and salts, metal complexes and N-oxides of the compounds of the formula (XV).

The invention also provides compounds of the formula (XVI)

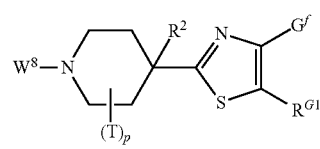

(XVI)

In which the radicals p, T, $R^2$ and $R^{G1}$ are as defined in the formula (I), $W^8$ is as defined in the formula (XV)

G is as defined in the formula (XI)

and salts, metal complexes and N-oxides of the compounds of the formula (XVI).

The compounds of the formula (XVI) may be present either in pure form or as mixtures of different possible isomeric forms, especially of stereoisomers, such as E and Z, threo and erythro, and also optical isomers, such as R and S isomers or atropisomers, and, if appropriate, also of tautomers. Both the E and Z isomers, and the threo and erythro isomers, and also the optical isomers, any desired mixtures of these isomers, and the possible tautomeric forms are claimed.

The preferred, more preferred and most preferred radicals p, T, $R^2$ and $R^{G1}$ are as defined in the formula (I), The preferred, more preferred and most preferred radical $W^8$ is as defined in the formula (XV)

The preferred, more preferred and most preferred radical $G^f$ is as defined in the formula (XI)

and salts, metal complexes and N-oxides of the compounds of the formula (XVI).

The invention also provides compounds of the formula (XVII)

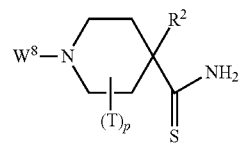

(XVII)

In which the radicals p, T and $R^2$ are as defined in the formula (I),
$W^8$ is as defined in the formula (XV), provided that $W^8$ is not tert-butoxycarbonyl when p is 0 and $R^2$ is benzyloxycarbonyl,
and salts, metal complexes and N-oxides of the compounds of the formula (XVII).

The compounds of the formula (XVII) may be present either in pure form or as mixtures of different possible isomeric forms, especially of stereoisomers, such as E and Z, threo and erythro, and also optical isomers, such as R and S isomers or atropisomers, and, if appropriate, also of tautomers. Both the E and Z isomers, and the threo and erythro isomers, and also the optical isomers, any desired mixtures of these isomers, and the possible tautomeric forms are claimed.

The preferred, more preferred and most preferred radicals p, T and $R^2$ are as defined in the formula (I),
The preferred, more preferred and most preferred radical $W^8$ is as defined in the formula (XV), provided that $W^8$ is not tert-butoxycarbonyl when p is 0 and $R^2$ is benzyloxycarbonyl,
and salts, metal complexes and N-oxides of the compounds of the formula (XVII).

The invention also provides compounds of the formula (XVIII)

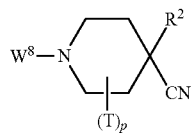

(XVIII)

In which the radicals p, T and $R^2$ are as defined in the formula (I),
$W^8$ is as defined in the formula (XV)
and salts, metal complexes and N-oxides of the compounds of the formula (XVIII).

The compounds of the formula (XVIII) may be present either in pure form or as mixtures of different possible isomeric forms, especially of stereoisomers, such as E and Z, threo and erythro, and also optical isomers, such as R and S isomers or atropisomers, and, if appropriate, also of tautomers. Both the E and Z isomers, and the threo and erythro isomers, and also the optical isomers, any desired mixtures of these isomers, and the possible tautomeric forms are claimed.

The preferred, more preferred and most preferred radicals p, T and $R^2$ are as defined in the formula (I),
The preferred, more preferred and most preferred radical $W^8$ is as defined in the formula (XV)
and salts, metal complexes and N-oxides of the compounds of the formula (XVIII).

Examples of inorganic acids are hydrohalic acids, such as hydrogen fluoride, hydrogen chloride, hydrogen bromide and hydrogen iodide, sulfuric acid, phosphoric acid and nitric acid, and acidic salts, such as $NaHSO_4$ and $KHSO_4$. Useful organic acids include, for example, formic acid, carbonic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, saturated or mono- or diunsaturated $C_6$-$C_{20}$ fatty acids, alkylsulphuric monoesters, alkylsulphonic acids (sulphonic acids having straight-chain or branched alkyl radicals having 1 to 20 carbon atoms), arylsulphonic acids or aryldisulphonic acids (aromatic radicals, such as phenyl and naphthyl, which bear one or two sulphonic acid groups), alkylphosphonic acids (phosphonic acids having straight-chain or branched alkyl radicals having 1 to 20 carbon atoms), arylphosphonic acids or aryldiphosphonic acids (aromatic radicals, such as phenyl and naphthyl, which bear one or two phosphonic acid radicals), where the alkyl and aryl radicals may bear further substituents, for example p-toluenesulphonic acid, salicylic acid, p-aminosalicylic acid, 2-phenoxybenzoic acid, 2-acetoxybenzoic acid, etc.

Useful metal ions are especially the ions of the elements of the second main group, especially calcium and magnesium, of the third and fourth main group, especially aluminium, tin and lead, and also of the first to eighth transition groups, especially chromium, manganese, iron, cobalt, nickel, copper, zinc and others. Particular preference is given to the metal ions of the elements of the fourth period. Here, the metals can be present in the various valencies that they can assume.

Optionally substituted groups may be mono- or polysubstituted, where the substituents in the case of polysubstitutions may be identical or different.

In the definitions of the symbols given in the above formulae, collective terms were used, which are generally representative of the following substituents:

Halogen: fluorine, chlorine, bromine and iodine and preferably fluorine, chlorine, bromine and more preferably fluorine, chlorine.

Alkyl: saturated, straight-chain or branched hydrocarbyl radicals having 1 to 8, preferably 1 to 6 and more preferably 1 to 3 carbon atoms, for example (but not limited to) $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. This definition also applies to alkyl as part of a composite substituent, for example cycloalkylalkyl, hydroxyalkyl etc., unless defined elsewhere like, for example, alkylthio, alkylsufinyl, alkylsulphonyl, haloalkyl or haloalkylthio. If the alkyl is at the end of a composite substituent, as, for example, in alkylcycloalkyl, the part of the composite substituent at the start, for example the cycloalkyl, may be mono- or polysubstituted identically or differently and independently by alkyl. The same also applies to composite substituents in which other radicals, for example alkenyl, alkynyl, hydroxyl, halogen, formyl etc., are at the end.

Alkenyl: unsaturated, straight-chain or branched hydrocarbyl radicals having 2 to 8, preferably 2 to 6, carbon atoms and one double bond in any position, for example (but not limited to) $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-l-pentenyl, 2-methyl-l-pentenyl, 3-methyl-1-pentenyl, 4-methyl-l-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1,-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl. This definition also applies to alkenyl as part of a composite substituent, for example haloalkenyl etc., unless defined elsewhere.

Alkynyl: straight-chain or branched hydrocarbyl groups having 2 to 8, preferably 2 to 6, carbon atoms and one triple bond in any position, for example (but not limited to) $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl. This definition also applies to alkynyl as part of a composite substituent, for example haloalkynyl etc., unless defined elsewhere.

Alkoxy: saturated, straight-chain or branched alkoxy radicals having 1 to 8, preferably 1 to 6 and more preferably 1 to 3 carbon atoms, for example (but not limited to) $C_1$-$C_6$-alkoxy such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy. This definition also applies to alkoxy as part of a composite substituent, for example haloalkoxy, alkynylalkoxy, etc., unless defined elsewhere.

Alkylthio: saturated, straight-chain or branched alkylthio radicals having 1 to 8, preferably 1 to 6 and more preferably 1 to 3 carbon atoms, for example (but not limited to) $C_1$-$C_6$-alkylthio such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio. This definition also applies to alkylthio as part of a composite substituent, for example haloalkylthio etc., unless defined elsewhere.

Alkoxycarbonyl: an alkoxy group which has 1 to 6, preferably 1 to 3, carbon atoms (as specified above) and is bonded to the skeleton via a carbonyl group (—CO—). This definition also applies to alkoxycarbonyl as part of a composite substituent, for example cycloalkylalkoxycarbonyl etc., unless defined elsewhere.

Alkylsulphinyl: saturated, straight-chain or branched alkylsulphinyl radicals having 1 to 8, preferably 1 to 6 and more preferably 1 to 3 carbon atoms, for example (but not limited to) $C_1$-$C_6$-alkylsulphinyl such as methylsulphinyl, ethylsulphinyl, propylsulphinyl, 1-methylethylsulphinyl, butylsulphinyl, 1-methylpropylsulphinyl, 2-methylpropylsulphinyl, 1,1-dimethylethylsulphinyl, pentylsulphinyl, 1-methylbutylsulphinyl, 2-methylbutylsulphinyl, 3-methylbutylsulphinyl, 2,2-dimethylpropylsulphinyl, 1-ethylpropylsulphinyl, hexylsulphinyl, 1,1-dimethylpropylsulphinyl, 1,2-dimethylpropylsulphinyl, 1-methylpentylsulphinyl, 2-methylpentylsulphinyl, 3-methylpentylsulphinyl, 4-methylpentylsulphinyl, 1,1-dimethylbutyl sulphinyl, 1,2-dimethylbutylsulphinyl, 1,3-dimethylbutylsulphinyl, 2,2-dimethylbutylsulphinyl, 2,3-dimethylbutylsulphinyl, 3,3-dimethylbutylsulphinyl, 1-ethylbutylsulphinyl, 2-ethylbutylsulphinyl, 1,1,2-trimethylpropylsulphinyl, 1,2,2-trimethylpropylsulphinyl, 1-ethyl-1-methylpropylsulphinyl and 1-ethyl-2-methylpropylsulphinyl. This definition also applies to alkylsulphinyl as part of a composite substituent, for example haloalkylsulphinyl etc., unless defined elsewhere.

Alkylsulphonyl: saturated, straight-chain or branched alkylsulphonyl radicals having 1 to 8, preferably 1 to 6 and more preferably 1 to 3 carbon atoms, for example (but not limited to) $C_1$-$C_6$-alkylsulphonyl such as methylsulphonyl, ethylsulphonyl, propylsulphonyl, 1-methylethylsulphonyl, butylsulphonyl, 1-methylpropylsulphonyl, 2-methylpropylsulphonyl, 1,1-dimethylethylsulphonyl, pentylsulphonyl, 1-methylbutylsulphonyl, 2-methylbutylsulphonyl, 3-methylbutylsulphonyl, 2,2-dimethylpropylsulphonyl, 1-ethylpropylsulphonyl, hexylsulphonyl, 1,1-dimethylpropylsulphonyl, 1,2-dimethylpropylsulphonyl, 1-methylpentylsulphonyl, 2-methylpentylsulphonyl, 3-methylpentylsulphonyl, 4-methylpentylsulphonyl, 1,1-dimethylbutylsulphonyl, 1,2-dimethylbutylsulphonyl, 1,3-dimethylbutylsulphonyl, 2,2-dimethylbutylsulphonyl, 2,3-dimethylbutylsulphonyl, 3,3-dimethylbutylsulphonyl, 1-ethylbutylsulphonyl, 2-ethylbutylsulphonyl, 1,1,2-trimethylpropylsulphonyl, 1,2,2-trimethylpropylsulphonyl, 1-ethyl-1-methylpropylsulphonyl and 1-ethyl-2-methylpropylsulphonyl. This definition also applies to alkylsulphonyl as part of a composite substituent, for example alkylsulphonylalkyl etc., unless defined elsewhere.

Cycloalkyl: monocyclic, saturated hydrocarbyl groups having 3 to 10, preferably 3 to 8 and more preferably 3 to 6 carbon ring members, for example (but not limited to) cyclopropyl, cyclopentyl and cyclohexyl. This definition also applies to cycloalkyl as part of a composite substituent, for example cycloalkylalkyl etc., unless defined elsewhere.

Cycloalkenyl: monocyclic, partially unsaturated hydrocarbyl groups having 3 to 10, preferably 3 to 8 and more preferably 3 to 6 carbon ring members, for example (but not limited to) cyclopropenyl, cyclopentenyl and cyclohexenyl.

This definition also applies to cycloalkenyl as part of a composite substituent, for example cycloalkenylalkyl etc., unless defined elsewhere.

Cycloalkoxy: monocyclic, saturated cycloalkyloxy radicals having 3 to 10, preferably 3 to 8 and more preferably 3 to 6 carbon ring members, for example (but not limited to) cyclopropyloxy, cyclopentyloxy and cyclohexyloxy. This definition also applies to cycloalkoxy as part of a composite substituent, for example cycloalkoxyalkyl etc., unless defined elsewhere.

Haloalkyl: straight-chain or branched alkyl groups having 1 to 8, preferably 1 to 6 and more preferably 1 to 3 carbon atoms (as specified above), where some or all of the hydrogen atoms in these groups may be replaced by halogen atoms as specified above, for example (but not limited to) $C_1$-$C_3$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 1,1,1-trifluoroprop-2-yl. This definition also applies to haloalkyl as part of a composite substituent, for example haloalkylaminoalkyl etc., unless defined elsewhere.

Haloalkenyl and haloalkynyl are defined analogously to haloalkyl except that, instead of alkyl groups, alkenyl and alkynyl groups are present as part of the substituent.

Haloalkoxy: straight-chain or branched alkoxy groups having 1 to 8, preferably 1 to 6 and more preferably 1 to 3 carbon atoms (as specified above), where some or all of the hydrogen atoms in these groups may be replaced by halogen atoms as specified above, for example (but not limited to) $C_1$-$C_3$-haloalkoxy such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and 1,1,1-trifluoroprop-2-oxy. This definition also applies to haloalkoxy as part of a composite substituent, for example haloalkoxyalkyl etc., unless defined elsewhere.

Haloalkylthio: straight-chain or branched alkylthio groups having 1 to 8, preferably 1 to 6 and more preferably 1 to 3 carbon atoms (as specified above), where some or all of the hydrogen atoms in these groups may be replaced by halogen atoms as specified above, for example (but not limited to) $C_1$-$C_3$-haloalkylthio such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, pentafluoroethylthio and 1,1,1-trifluoroprop-2-ylthio. This definition also applies to haloalkylthio as part of a composite substituent, for example haloalkylthioalkyl etc., unless defined elsewhere.

Heteroaryl: 5 or 6-membered, fully unsaturated monocyclic ring system containing one to four heteroatoms from the group of oxygen, nitrogen and sulphur; if the ring contains more than one oxygen atom, they are not directly adjacent;

5-membered heteroaryl containing one to four nitrogen atoms or one to three nitrogen atoms and one sulphur or oxygen atom: 5-membered heteroaryl groups which, in addition to carbon atoms, may contain one to four nitrogen atoms or one to three nitrogen atoms and one sulphur or oxygen atom as ring members, for example (but not limited thereto) 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl; nitrogen-bonded 5-membered heteroaryl containing one to four nitrogen atoms, or benzofused nitrogen-bonded 5-membered heteroaryl containing one to three nitrogen atoms: 5-membered heteroaryl groups which, in addition to carbon atoms, may contain one to four nitrogen atoms or one to three nitrogen atoms as ring members and in which two adjacent carbon ring members or one nitrogen and one adjacent carbon ring member may be bridged by a buta-1,3-diene-1,4-diyl group in which one or two carbon atoms may be replaced by nitrogen atoms, where these rings are attached to the skeleton via one of the nitrogen ring members, for example (but not limited to) 1-pyrrolyl, 1-pyrazolyl, 1,2,4-triazol-1-yl, 1-imidazolyl, 1,2,3-triazol-1-yl and 1,3,4-triazol-1-yl;

6-membered heteroaryl which contains one to four nitrogen atoms: 6-membered heteroaryl groups which, in addition to carbon atoms, may contain, respectively, one to three and one to four nitrogen atoms as ring members, for example (but not limited thereto) 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl;

benzofused 5-membered heteroaryl containing one to three nitrogen atoms or one nitrogen atom and one oxygen or sulphur atom: for example (but not limited to) indol-1-yl, indol-2-yl, indol-3-yl, indol-4-yl, indol-5-yl, indol-6-yl, indol-7-yl, benzimidazol-1-yl, benzimidazol-2-yl, benzimidazol-4-yl, benzimidazol-5-yl, indazol-1-yl, indazol-3-yl, indazol-4-yl, indazol-5-yl, indazol-6-yl, indazol-7-yl, indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,3-benzoxazol-2-yl, 1,3-benzoxazol-4-yl, 1,3-benzoxazol-5-yl, 1,3-benzoxazol-6-yl and 1,3-benzoxazol-7-yl;

benzofused 6-membered heteroaryl which contains one to three nitrogen atoms: for example (but not limited to) quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl and isoquinolin-8-yl.

This definition also applies to heteroaryl as part of a composite substituent, for example heteroarylalkyl etc., unless defined elsewhere.

Heterocyclyl: three- to fifteen-membered, preferably three- to nine-membered, saturated or partially unsaturated heterocycle containing one to four heteroatoms from the group of oxygen, nitrogen and sulphur: mono, bi- or tricyclic heterocycles which contain, in addition to carbon ring members, one to three nitrogen atoms and/or one oxygen or sulphur atom or one or two oxygen and/or sulphur atoms; if the ring contains more than one oxygen atom, they are not directly adjacent; for example (but not limited to) oxiranyl, aziridinyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl. This definition also applies to heterocyclyl as part of a composite substituent, for example heterocyclylalkyl etc., unless defined elsewhere.

Leaving group: $S_N1$ or $S_N2$ leaving group, for example chlorine, bromine, iodine, alkylsulphonates (—OSO$_2$-alkyl, e.g. —OSO$_2$CH$_3$, —OSO$_2$CF$_3$) or arylsulphonates (—OSO$_2$-aryl, e.g. —OSO$_2$Ph, —OSO$_2$PhMe).

Not included are combinations which are against natural laws and which the person skilled in the art would therefore exclude based on his/her expert knowledge. Ring structures having three or more adjacent oxygen atoms, for example, are excluded.

Elucidation of the Preparation Processes and Intermediates

The piperidinecarboxylic acidderivatives of the formula (I) can be prepared in different ways. First of all, the possible processes are shown schematically below. Unless indicated otherwise, the radicals given have the meanings given above.

The processes according to the invention for preparing compounds of the formula (I) are optionally performed using one or more reaction auxiliaries.

Useful reaction auxiliaries are, as appropriate, inorganic or organic bases or acid acceptors. These preferably include alkali metal or alkaline earth metal acetates, amides, carbonates, hydrogencarbonates, hydrides, hydroxides or alkoxides, for example sodium acetate, potassium acetate or calcium acetate, lithium amide, sodium amide, potassium amide or calcium amide, sodium carbonate, potassium carbonate or calcium carbonate, sodium hydrogencarbonate, potassium hydrogencarbonate or calcium hydrogencarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; and also basic organic nitrogen compounds, for example trimethylamine, triethylamine, tripropylamine, tributylamine, ethyldiisopropylamine, N,N-dimethylcyclohexylamine, dicyclohexylamine, ethyldicyclohexylamine, N,N-dimethylaniline, N,N-dimethylbenzylamine, pyridine, 2-methyl-, 3-methyl-, 4-methyl-, 2,4-dimethyl-, 2,6-dimethyl-, 3,4-dimethyl- and 3,5-dimethylpyridine, 5-ethyl-2-methylpyridine, 4-dimethylaminopyridine, N-methylpiperidine, 1,4-diazabicyclo [2.2.2]-octane (DABCO), 1,5-diazabicyclo [4.3.0]-non-5-ene (DBN) or 1,8-diazabicyclo [5.4.0]-undec-7-ene (DBU).

Useful reaction auxiliaries are, as appropriate, inorganic or organic acids. These preferably include inorganic acids, for example hydrogen fluoride, hydrogen chloride, hydrogen bromide and hydrogen iodide, sulphuric acid, phosphoric acid and nitric acid, and acidic salts such as NaHSO$_4$ and KHSO$_4$, or organic acids, for example, formic acid, carbonic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, saturated or mono- or diunsaturated $C_6$-$C_{20}$ fatty acids, alkylsulphuric monoesters, alkylsulphonic acids (sulphonic acids having straight-chain or branched alkyl radicals having 1 to 20 carbon atoms), arylsulphonic acids or aryldisulphonic acids (aromatic radicals, such as phenyl and naphthyl, which bear one or two sulphonic acid groups), alkylphosphonic acids (phosphonic acids having straight-chain or branched alkyl radicals having 1 to 20 carbon atoms), arylphosphonic acids or aryldiphosphonic acids (aromatic radicals, such as phenyl and naphthyl, which bear one or two phosphonic acid radicals), where the alkyl and aryl radicals may bear further substituents, for example p-toluenesulphonic acid, salicylic acid, p-aminosalicylic acid, 2-phenoxybenzoic acid, 2-acetoxybenzoic acid, etc.

The processes according to the invention are optionally performed using one or more diluents. Useful diluents are virtually all inert organic solvents. These preferably include aliphatic and aromatic, optionally halogenated hydrocarbons, such as pentane, hexane, heptane, cyclohexane, methyl cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether, methyl tert-butyl ether and dibutyl ether, glycol dimethyl ether and diglycol dimethyl ether, methyltetrahydrofuran, tetrahydrofuran and dioxane, ketones such as acetone, methyl ethyl ketone, methyl isopropyl ketone and methyl isobutyl ketone, esters, such as methyl acetate, ethyl acetate and butyl acetate, nitriles, for example acetonitrile, propionitrile and butyronitrile, alcohols, for example methanol, ethanol, propanol, iso-propanol, butanol, tert-butanol, amides, for example dimethylformamide, dimethylacetamide and N-methylpyrrolidone, and also dimethyl sulphoxide, tetramethylenesulphone and hexamethylphosphoramide and DMPU.

In the processes according to the invention, the reaction temperatures can be varied within a relatively wide range. In general, the temperatures employed are between 0° C. and 250° C., preferably temperatures between 10° C. and 185° C.

The reaction time varies as a function of the scale of the reaction and of the reaction temperature, but is generally between a few minutes and 48 hours.

The processes according to the invention are generally performed under standard pressure. However, it is also possible to work under elevated or reduced pressure.

For performance of the processes according to the invention, the starting materials required in each case are generally used in approximately equimolar amounts. However, it is also possible to use one of the components used in each case in a relatively large excess.

Process A

Scheme 1: Process A

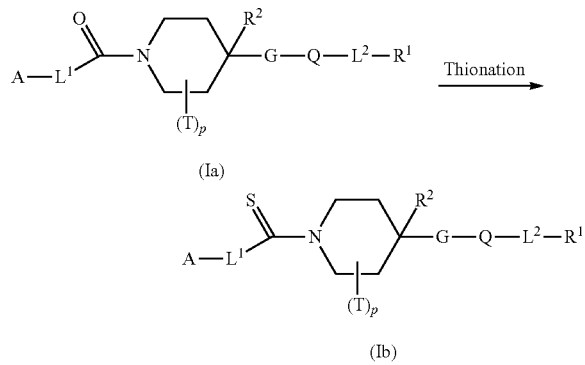

in which the symbols A, $L^1$, T, p, $R^2$, G, Q, $L^2$ and $R^1$ each have the general definitions specified above.

The amides (Ia) can be converted by means of methods described in the literature to the corresponding thioamides (Ib) (e.g. *Bioorganic & Medicinal Chemistry Letters*, 2009, 19(2), 462-468) (Process A, Scheme 1). This involves reacting the compounds of the formula (Ia) typically with phosphorus pentasulphide or 2,4-bis(4-methoxyphenyl)-1,3-dithia-2,4-diphosphetane 2,4-disulphide (Lawesson's reagent).

Process A according to the invention is preferably carried out using one or more diluents. The preferred solvents are toluene, tetrahydrofuran, 1,4-dioxane and 1,2-dimethoxyethane.

After the reaction has ended, the compounds (Ib) are separated from the reaction mixture by one of the customary separation techniques. If necessary, the compounds are purified by recrystallization or chromatography.

Process B

Scheme 2: Process B

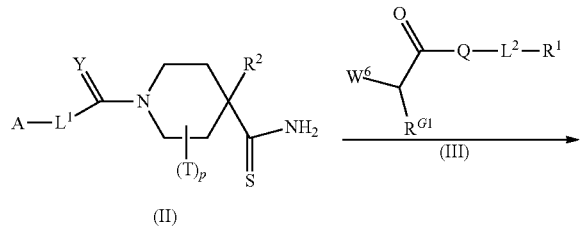

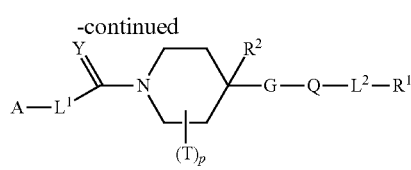

in which the symbols A, $L^1$, Y, T, p, $R^2$, $R^{G1}$, Q, $L^2$ and $R^1$ each have the general definitions specified above, and $W^6$ is a leaving group One means of preparing compounds of the formula (I) from a corresponding thioamide of the formula (II) is shown in Scheme 2 (process B).

A thioamide of the formula (II) is converted in the presence of a compound of the formula (III) to a compound of the formula (I) by Hantzch thiazole synthesis described in the literature (Organic & Biomolecular Chemistry, 2012, 10, 1093-1101; Journal of Medicinal Chemistry, 1991, 34, 600-605).

The compound with the general formula (III) can be synthesized analogously to methods well described in the literature (see, for example WO 2008013925).

After the reaction has ended, the compounds (I) are separated from the reaction mixture by one of the customary separation techniques. If necessary, the compounds are purified by recrystallization or chromatography, or can, if desired, also be used in the next step without prior purification.

Process C

Scheme 3: Process C

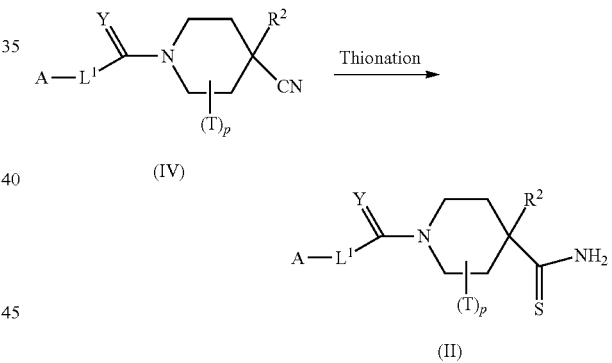

in which the symbols A, $L^1$, T, p, $R^2$ and Y each have the general definitions specified above.

A nitrile of the formula (IV) can be converted to the corresponding thioamides (II) by thionation (Process C, Scheme 3). The reaction can be performed under appropriate reaction conditions described in the literature (for example, see Synlett, 2009, 2338-2340; Synthesis, 2006, 224-226; Synlett, 2011, 2807-2810; EP696581), and it involves reacting the compounds of the formula (IV) in the presence of a thionating reagent, for example, hydrogen sulphide or its bisulfide salt with an alkali metal or ammonia, and if necessary in the presence of an acid or a base.

In addition, a nitrile of the formula (IV) can be hydrolysed first under acidic or basic conditions (for example, with aqueous sodium, potassium or lithium hydroxide solution or with aqueous hydrochloric acid) to a corresponding amide, then converted under an appropriate thionating conditions similar to Process A to a thioamide of the general formula (II).

After the reaction has ended, the compounds (II) are separated from the reaction mixture by one of the customary separation techniques. If necessary, the compounds are purified by recrystallization or chromatography.

Process D

Scheme 4: Process D

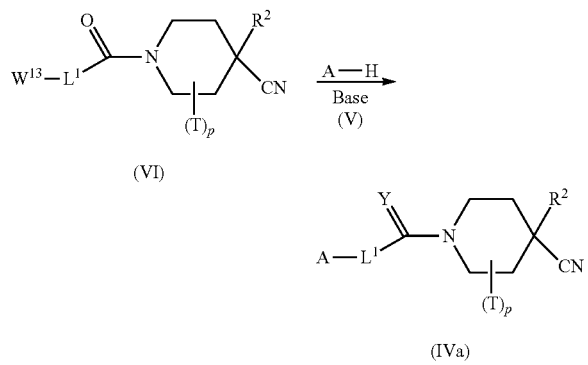

(IVa)

in which the symbols W$^{13}$, A, L$^1$, T, p and R$^2$ each have the general definitions specified above.

In general, it is possible to prepare compounds of the formula (IVa) from corresponding compounds (VI) which bear a suitable leaving group W$^{13}$ for a substitution reaction with a substrate such as A-H (V), where A is defined as above and H is hydrogen (see Scheme 4, Process D).

For the substitution reaction, at least one equivalent of a base (e.g. sodium hydride, potassium carbonate) or an acid scavenger is used in relation to the starting material of the general formula (VI).

After the reaction has ended, the compounds (IVa) are separated from the reaction mixture by one of the customary separation techniques. If necessary, the compounds are purified by recrystallization or chromatography.

Process E

Scheme 5: Process E

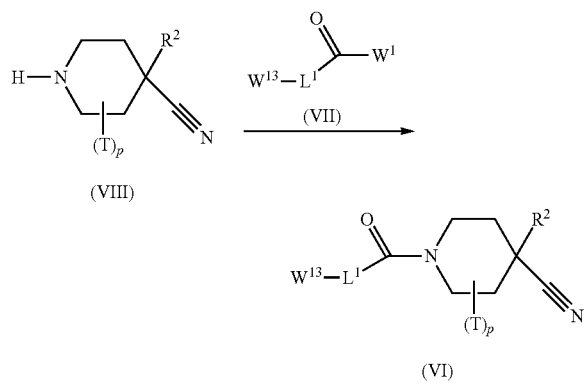

in which the symbols W$^{13}$, L$^1$, T, p and R$^2$ each have the general definitions specified above and W$^1$ is F, Cl or OH One means of preparing compounds of the formula (VI) from corresponding compounds (VIII) with the compounds (VII) is shown in Scheme 5 (process E).

A compound of the formula (VI) is prepared analogously to Process F (Scheme 6) or to a method known in the literature from a commercially available acid chloride or carboxylic acid (for example, with glycolic acid or hydroxyacetyl chloride, see, for example, WO2005082859; WO 2008013925).

Compounds of formula (VIII) are either commercially available or can be synthesized analogously to methods described in the literature (for example, Polish Journal of Chemistry, 1988, 62, 451-5; WO2012045124). Compounds of formula (VII), for example, glycolic acid and chloroacetyl chloride, are either commercially available or can be synthesized analogously to methods described in the literature (for example, Bulletin de la Societe Chimique de France, 1948, 995-1001).

After the reaction has ended, the compounds (VI) are separated from the reaction mixture by one of the customary separation techniques. If necessary, the compounds are purified by recrystallization or chromatography.

Process F

Scheme 6: Process F

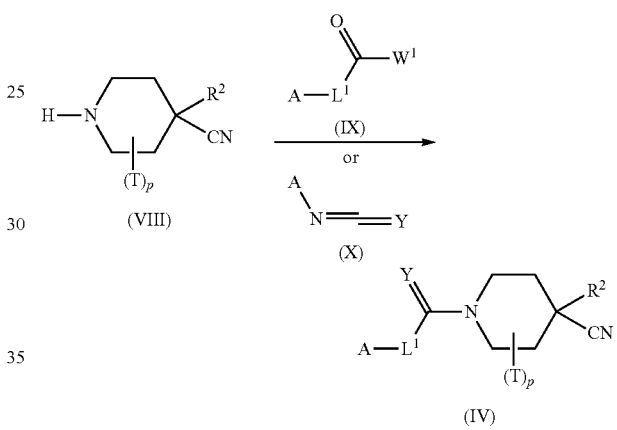

in which the symbols A, L$^1$, T, p and R$^2$ and Y each have the general definitions specified above and W$^1$ is F, Cl or OH or phenoxy, One means of preparing compounds of the formula (IV) from corresponding compounds (VIII) with a comound of the formula (IX) or (X) is shown in Scheme 6 (process F).

Compounds (IX) or (X) are either commercially available or can be prepared by processes described in the literature (see, for example, WO2008091580, WO2007014290 and WO2008091594).

A compound with the general formula (IV) can be synthesized analogously to methods described in the literature (see, for example WO2008091594), by a coupling reaction of a compound with the corresponding general formula (VIII) with a substrate of the general formula (IX) where W$^1$ is chlorine or fluorine, optionally in the presence of an acid scavenger/base.

At least one equivalent of an acid scavenger/a base (for example Htinig's base, triethylamine or commercially available polymeric acid scavengers) is used, in relation to the starting material of the general formula (VIII). If the starting material is a salt, at least two equivalents of the acid scavenger are required.

Alternatively, a compound of the formula (IV) can also be synthesized from the corresponding compound of the formula (VIII) with a substrate of the formula (IX) where W$^1$ is hydroxyl in the presence of a coupling agent, analogously to methods described in the literature (for example Tetrahedron, 2005, 61, 10827-10852, and references cited therein).

Suitable coupling reagents are, for example, peptide coupling reagents (for example N-(3-dimethylaminopropyl)-N'-ethylcarbodiimide mixed with 4-dimethylaminopyridine, N-(3-dimethylaminopropyl)-N'-ethylcarbodiimide mixed with 1-hydroxybenzotriazole, bromotripyrrolidinophosphonium hexafluorophosphate, O-(7-azabenzotriazol-1-yl)-N,N,N',N'-tetramethyluronium hexafluorophosphate, etc.).

In addition, a compound with the general formula (IV) can be synthesized analogously to methods described in the literature (see, for example WO 2009/055514), by a coupling reaction of a compound with the corresponding general formula (VIII) with an isocyanate or isothiocyanate of the general formula (X), optionally in the presence of an acid scavenger/base, for example, triethylamine, 1,8-diazabicyclo[5.4.0]undec-7-ene or Hünig's base.

After the reaction has ended, the compounds (IV) are separated from the reaction mixture by one of the customary separation techniques. If necessary, the compounds are purified by recrystallization or chromatography.

Process G

Scheme 7: Process G

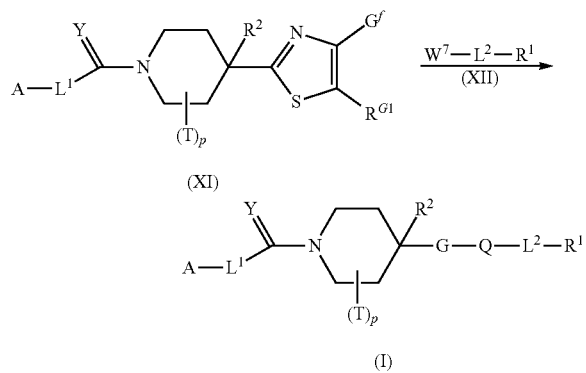

in which the symbols A, $L^1$, Y, T, p, $R^2$, $R^{G1}$ and $G^f$ each have the general definitions specified above, and $W^7$ is a suitable functional group which, together with $G^f$, can form the desired heterocycle Q.

In general, it is also possible to prepare compounds of the formula (I) from corresponding compounds (XI) and (XII) with suitable functional groups $G^f$ and $W^7$ (Scheme 7, Process G). There are numerous literature methods for the preparation of heterocycles (see WO 2008/013622; Comprehensive Heterocyclic Chemistry vol. 4-6, editors: A. R. Katritzky and C. W. Rees, Pergamon Press, New York, 1984; Comprehensive Heterocyclic Chemistry II, vol. 2-4, editors: A. R. Katritzky, C. W. Rees and E. F. Scriven, Pergamon Press, New York, 1996; The Chemistry of Heterocyclic Compounds, editor: E. C. Taylor, Wiley, N.Y.; Rodd's Chemistry of Carbon Compounds, vol. 2-4, Elsevier, New York; Synthesis, 1982, 6, 508-509; Tetrahedron, 2000, 56, 1057-1064).

Compounds with the general formula (XII), for example styrenes, are generally commercially available or can be prepared by methods described in the literature.

After the reaction has ended, the compounds (I) are separated from the reaction mixture by one of the customary separation techniques. If necessary, the compounds are purified by recrystallization or chromatography.

Process H

Scheme 8: Process H

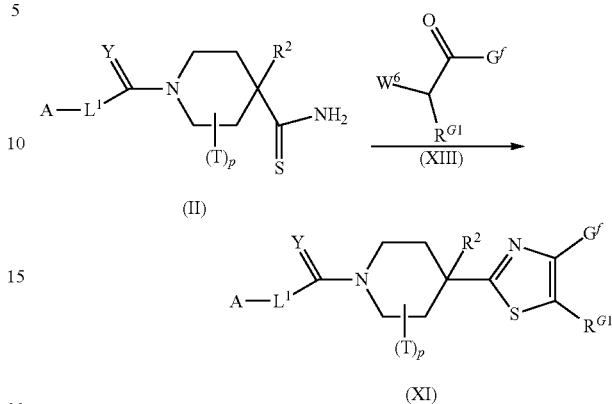

in which the symbols A, $L^1$, Y, T, p, $R^2$, $R^{G1}$ and $G^f$ each have the general definitions specified above, and $W^6$ is a leaving group One means of preparing compounds of the formula (XI) from a corresponding thioamide of the formula (II) is shown in Scheme 8 (process H).

A thioamide of the formula (II) is converted in the presence of a compound of the formula (XIII) to a compound of the formula (XI) by Hantzch thiazole synthesis analogously to Process B (Scheme 2).

The compound with the general formula (XIII) can be synthesized analogously to methods well described in the literature (see, for example WO 2008013925).

After the reaction has ended, the compounds (XI) are separated from the reaction mixture by one of the customary separation techniques. If necessary, the compounds are purified by recrystallization or chromatography, or can, if desired, also be used in the next step without prior purification.

Process I

Scheme 9: Process I

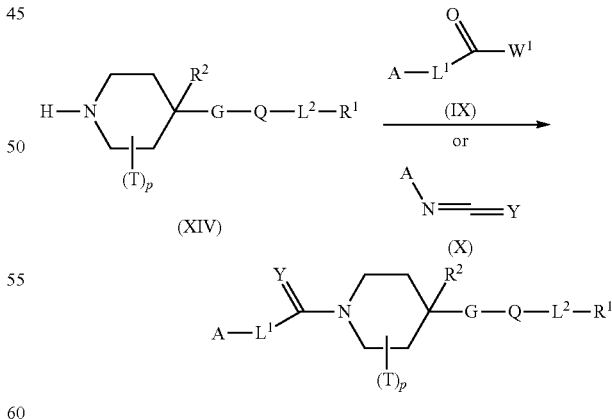

in which the symbols A, $L^1$, Y, T, p, $R^2$, G, Q, $L^2$ and $R^1$ each have the general definitions specified above, and $W^1$ is F, Cl or OH One means of preparing compounds of the formula (I) from corresponding compounds (XIV) with the compounds (IX) or (X) is shown in Scheme 9 (process I).

A compound with the general formula (I) can be synthesized analogously to Process F (Scheme 6), by a coupling reaction of a compound with the corresponding general formula (XIV) with a substrate of the general formula (IX) or (X). If a compound of the general formula (IX) is used in the reaction, the resulting product is of the formula (I) with Y being O (this means it is of the formula (Ia) as in Scheme 1).

After the reaction has ended, the compounds (I) are separated from the reaction mixture by one of the customary separation techniques. If necessary, the compounds are purified by recrystallization or chromatography.

Process J

Scheme 10: Process J

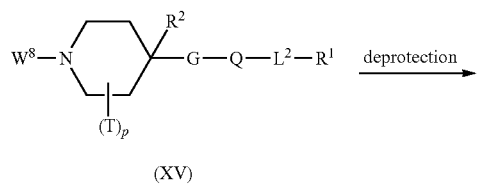

(XV)

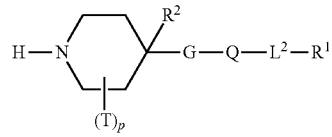

(XIV)

in which the symbols $W^8$, A, $L^1$, T, p, $R^2$, G, Q, $L^2$ and $R^1$ each have the general definitions specified above.

One means of preparing compounds of the formula (I) from corresponding compounds (XIV) with the compounds (IX) or (X) is shown in Scheme 9 (process I).

A compound of the formula (XV) is converted to a compound of the formula (XIV) by suitable methods for removing protecting groups described in the literature ("*Protective Groups in Organic Synthesis*"; Theodora W. Greene, Peter G. M. Wuts; Wiley-Interscience; Third Edition; 1999; 494-653).

For example, tert-Butoxycarbonyl and benzyloxycarbonyl protecting groups can be removed in an acidic medium (for example with hydrochloric acid or trifluoroacetic acid). Acetyl protecting groups can be removed under basic conditions (for example with potassium carbonate or caesium carbonate). Benzylic protecting groups can be removed hydrogenolytically with hydrogen in the presence of a catalyst (for example palladium on activated carbon).

After the reaction has ended, the compounds (XIV) are separated from the reaction mixture by one of the customary separation techniques. If necessary, the compounds are purified by recrystallization or chromatography, or can, if desired, also be used in the next step without prior purification. It is also possible to isolate the compound of the general formula (XIV) as a salt, for example as a salt of hydrochloric acid or of trifluoroacetic acid.

Process K

Scheme 11: Process K

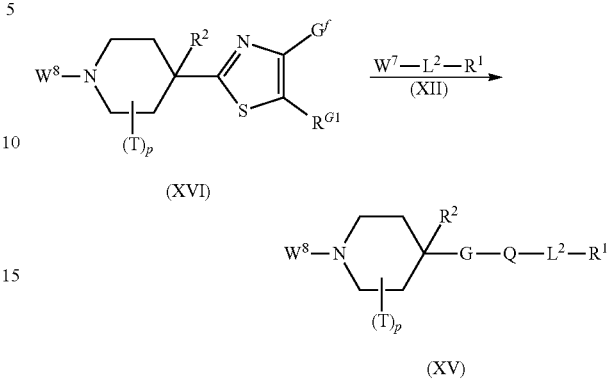

in which the symbols $W^8$, T, p, $R^2$, $R^{G1}$ and $G^f$ each have the general definitions specified above, and $W^7$ is a suitable functional group which, together with $G^f$, can form the desired heterocycle Q.

In general, it is possible to prepare compounds of the formula (XV) from corresponding compounds (XVI) and (XII) with suitable functional groups $G^f$ and $W^7$ (Scheme 11, Process K). A compound with the general formula (XV) can be synthesized from (XVI) with a compound of the general formula (XII), analogously to Process G (Scheme 7).

After the reaction has ended, the compounds (XV) are separated from the reaction mixture by one of the customary separation techniques. If necessary, the compounds are purified by recrystallization or chromatography.

Process L

Scheme 12: Process L

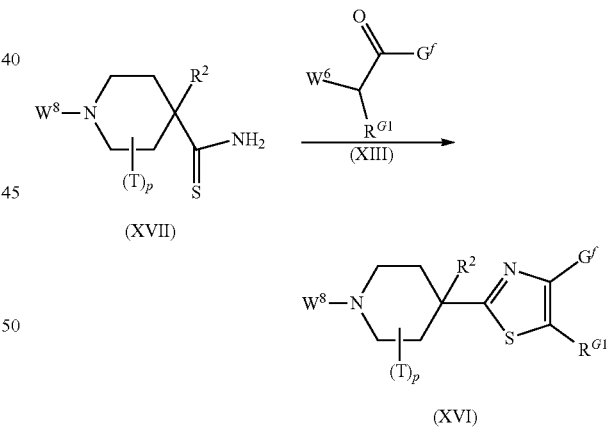

in which the symbols $W^8$, T, p, $R^2$, $R^{G1}$ and $G^f$ each have the general definitions specified above, and $W^6$ is a leaving group In general, it is possible to prepare compounds of the formula (XVI) from corresponding compounds (XVII) and (XIII) (Scheme 12, Process L). A compound with the general formula (XVI) can be synthesized from (XVII) with a compound of the general formula (XIII), analogously to Process B (Scheme 2).

After the reaction has ended, the compounds (XVI) are separated from the reaction mixture by one of the customary separation techniques. If necessary, the compounds are purified by recrystallization or chromatography.

Process M

Scheme 13: Process M

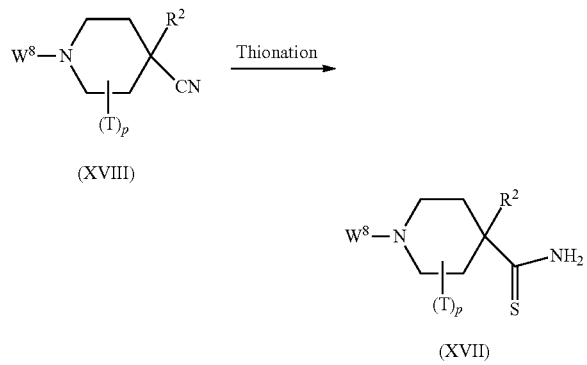

in which the symbols $W^8$, T, p and $R^2$ each have the general definitions specified above.

In general, it is possible to prepare compounds of the formula (XVII) from corresponding compounds (XVIII) (Scheme 13, Process M). A compound with the general formula (XVII) can be synthesized from (XVIII) by thionation analogously to Process C (Scheme 3).

After the reaction has ended, the compounds (XVII) are separated from the reaction mixture by one of the customary separation techniques. If necessary, the compounds are purified by recrystallization or chromatography.

It is recognized that the sustituent $R^2$ can be converted from one substituent definition to another as specified above, at any appropriate stage of the synthesis, in one or more steps, by synthetic methods commonly used by the person skilled in the art of chemical synthesis. For example, an intermediate or a final product that bears an ester as $R^2$ can be saponified in the presence of an aqueous base or an acid to its corresponding carboxylic acid that can be in turn converted to an amide or another ester by amidation or by esterification.

Furthermore, it is also recognized that some reagents and reaction conditions described above for preparation of compounds of the formula (I) may not be compatible with particular functionalities present in the intermediate compounds. In these cases, the introduction of protection/deprotection sequences or of mutual conversions of functional groups into the synthesis helps to obtain the desired products. The use and selection of the protecting groups is obvious to the person skilled in the art of chemical synthesis (see, for example, "Protective Groups in Organic Synthesis"; Third Edition; 494-653, and literature cited therein). The person skilled in the art will recognize that, in some cases, after the introduction of a given reagent as shown in an individual scheme, it may be necessary to perform additional routine synthesis steps not described individually in order to complete the synthesis of compounds of the formula (I). The person skilled in the art will likewise recognize that it may be necessary to perform a combination of the steps illustrated in the above schemes in a sequence other than the implied sequence shown specifically, in order to prepare the compounds of the formula (I).

The workup is carried out by customary methods. If necessary, the compounds are purified by recrystallization or chromatography.

The invention also relates to a method for controlling unwanted microorganisms, characterized in that the inventive piperidinecarboxylic acid derivatives are applied to the microorganisms and/or in their habitat.

The invention further relates to seed which has been treated with at least one inventive piperidinecarboxylic acidderivative.

The invention finally provides a method for protecting seed against unwanted microorganisms by using seed treated with at least one piperidinecarboxylic acidderivative according to the present invention.

The inventive substances have potent microbicidal activity and can be used for control of unwanted microorganisms, such as fungi and bacteria, in crop protection and in the protection of materials.

The inventive piperidinecarboxylic acid derivatives of the formula (I) have very good fungicidal properties and can be used in crop protection, for example for control of *Plasmodiophoromycetes, Oomycetes, Chytridiomycetes, Zygomycetes, Ascomycetes, Basidiomycetes* and *Deuteromycetes*.

Bactericides can be used in crop protection, for example, for control of Pseudomonadaceae, Rhizobiaceae, Enterobacteriaceae, Corynebacteriaceae and Streptomycetaceae.

The inventive fungicidal compositions can be used for curative or protective control of phytopathogenic fungi. The invention therefore also relates to curative and protective methods for controlling phytopathogenic fungi by the use of the inventive active ingredients or compositions, which are applied to the seed, the plant or plant parts, the fruit or the soil in which the plants grow.

The inventive compositions for controlling phytopathogenic fungi in crop protection comprise an effective but non-phytotoxic amount of the inventive active ingredients. An "effective but non-phytotoxic amount" means an amount of the inventive composition which is sufficient to control the fungal disease of the plant in a satisfactory manner or to eradicate the fungal disease completely, and which, at the same time, does not cause any significant symptoms of phytotoxicity. In general, this application rate may vary within a relatively wide range. It depends on several factors, for example on the fungus to be controlled, the plant, the climatic conditions and the ingredients of the inventive compositions.

All plants and plant parts can be treated in accordance with the invention. Plants are understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant cultivars which are protectable and non-protectable by plant breeders' rights. Plant parts are understood to mean all parts and organs of plants above and below the ground, such as shoot, leaf, flower and root, examples of which include leaves, needles, stalks, stems, flowers, fruit bodies, fruits and seeds, and also roots, tubers and rhizomes. The plant parts also include harvested material and vegetative and generative propagation material, for example cuttings, tubers, rhizomes, slips and seeds.

Composition/Formulation

The present invention further relates to a crop protection composition for controlling harmful microorganisms, especially unwanted fungi and bacteria, comprising an effective and non-phytotoxic amount of the inventive active ingredients. These are preferably fungicidal compositions which comprise agriculturally suitable auxiliaries, solvents, carriers, surfactants or extenders.

In the context of the present invention, "control of harmful microorganisms" means a reduction in infestation by harmful microorganisms, compared with the untreated plant measured as fungicidal efficacy, preferably a reduction by 25-50%, compared with the untreated plant (100%), more preferably a reduction by 40-79%, compared with the untreated plant (100%); even more preferably, the infection by harmful microorganisms is entirely suppressed (by 70-100%). The control may be curative, i.e. for treatment of already infected plants, or protective, for protection of plants which have not yet been infected.

An "effective but non-phytotoxic amount" means an amount of the inventive composition which is sufficient to control the fungal disease of the plant in a satisfactory manner or to eradicate the fungal disease completely, and which, at the same time, does not cause any significant symptoms of phytotoxicity. In general, this application rate may vary within a relatively wide range. It depends on several factors, for example on the fungus to be controlled, the plant, the climatic conditions and the ingredients of the inventive compositions.

Suitable organic solvents include all polar and non-polar organic solvents usually employed for formulation purposes. Preferable the solvents are selected from ketones, e.g. methyl-isobutyl-ketone and cyclohexanone, amides, e.g. dimethyl formamide and alkanecarboxylic acid amides, e.g. N,N-dimethyl decaneamide and N,N-dimethyl octanamide, furthermore cyclic solvents, e.g. N-methyl-pyrrolidone, N-octyl-pyrrolidone, N-dodecyl-pyrrolidone, N-octyl-caprolactame, N-dodecyl-caprolactame and butyrolactone, furthermore strong polar solvents, e.g. dimethylsulfoxide, and aromatic hydrocarbons, e.g. xylol, Solvesso™, mineral oils, e.g. white spirit, petroleum, alkyl benzenes and spindle oil, also esters, e.g. propyleneglycol-monomethylether acetate, adipic acid dibutylester, acetic acid hexylester, acetic acid heptylester, citric acid tri-n-butylester and phthalic acid di-n-butylester, and also alcohols, e.g. benzyl alcohol and 1-methoxy-2-propanol.

According to the invention, a carrier is a natural or synthetic, organic or inorganic substance with which the active ingredients are mixed or combined for better applicability, in particular for application to plants or plant parts or seed. The carrier, which may be solid or liquid, is generally inert and should be suitable for use in agriculture.

Useful solid or liquid carriers include: for example ammonium salts and natural rock dusts, such as kaolins, clays, talc, chalk, quartz, attapulgite, montmorillonite or diatomaceous earth, and synthetic rock dusts, such as finely divided silica, alumina and natural or synthetic silicates, resins, waxes, solid fertilizers, water, alcohols, especially butanol, organic solvents, mineral and vegetable oils, and derivatives thereof. Mixtures of such carriers can likewise be used.

Suitable solid filler and carrier include inorganic particles, e.g. carbonates, silikates, sulphates and oxides with an average particle size of between 0.005 and 20 µm, preferably of between 0.02 to 10 µm, for example ammonium sulphate, ammonium phosphate, urea, calcium carbonate, calcium sulphate, magnesium sulphate, magnesium oxide, aluminium oxide, silicium dioxide, so-called fine-particle silica, silica gels, natural or synthetic silicates, and alumosilicates and plant products like cereal flour, wood powder/sawdust and cellulose powder.

Useful solid carriers for granules include: for example crushed and fractionated natural rocks such as calcite, marble, pumice, sepiolite, dolomite, and synthetic granules of inorganic and organic meals, and also granules of organic material such as sawdust, coconut shells, maize cobs and tobacco stalks.

Useful liquefied gaseous extenders or carriers are those liquids which are gaseous at standard temperature and under standard pressure, for example aerosol propellants such as halohydrocarbons, and also butane, propane, nitrogen and carbon dioxide.

In the formulations, it is possible to use tackifiers such as carboxymethylcellulose, and natural and synthetic polymers in the form of powders, granules or latices, such as gum arabic, polyvinyl alcohol and polyvinyl acetate, or else natural phospholipids, such as cephalins and lecithins, and synthetic phospholipids. Further additives may be mineral and vegetable oils.

If the extender used is water, it is also possible to employ, for example, organic solvents as auxiliary solvents. Useful liquid solvents are essentially: aromatics such as xylene, toluene or alkylnaphthalenes, chlorinated aromatics and chlorinated aliphatic hydrocarbons such as chlorobenzenes, chloroethylenes or dichloromethane, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

Suitable surfactants (adjuvants, emulsifiers, dispersants, protective colloids, wetting agent and adhesive) include all common ionic and non-ionic substances, for example ethoxylated nonylphenols, polyalkylene glycolether of linear or branched alcohols, reaction products of alkyl phenols with ethylene oxide and/or propylene oxide, reaction products of fatty acid amines with ethylene oxide and/or propylene oxide, furthermore fattic acid esters, alkyl sulfonates, alkyl sulphates, alkyl ethersulphates, alkyl etherphosphates, arylsulphate, ethoxylated arylalkylphenols, e.g. tristyrylphenol-ethoxylates, furthermore ethoxylated and propoxylated arylalkylphenols like sulphated or phosphated arylalkylphenol-ethoxylates and -ethoxy- and -propoxylates. Further examples are natural and synthetic, water soluble polymers, e.g. lignosulphonates, gelatine, gum arabic, phospholipids, starch, hydrophobic modified starch and cellulose derivatives, in particular cellulose ester and cellulose ether, further polyvinyl alcohol, polyvinyl acetate, polyvinyl pyrrolidone, polyacrylic acid, polymethacrylic acid and co-polymerisates of (meth)acrylic acid and (meth)acrylic acid esters, and further co-polymerisates of methacrylic acid and methacrylic acid esters which are neutralized with alkali-metal hydroxide and also condensation products of optionally substituted naphthalene sulfonic acid salts with formaldehyde. The presence of a surfactant is necessary if one of the active ingredients and/or one of the inert carriers is insoluble in water and when application is effected in water. The proportion of surfactants is between 5 and 40 per cent by weight of the inventive composition.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

Antifoams which may be present in the formulations include e.g. silicone emulsions, longchain alcohols, fattiy acids and their salts as well as fluoroorganic substances and mixtures therof.

Examples of thickeners are polysaccharides, e.g. xanthan gum or veegum, silicates, e.g. attapulgite, bentonite as well as fine-particle silica.

If appropriate, it is also possible for other additional components to be present, for example protective colloids, binders, adhesives, thickeners, thixotropic substances, penetrants, stabilizers, sequestrants, complexing agents. In general, the active ingredients can be combined with any solid or liquid additive commonly used for formulation purposes.

The inventive active ingredients or compositions can be used as such or, depending on their particular physical and/or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, microgranules, microgranules, oil-dispersible powders, oil-miscible flowable concentrates, oil-miscible liquids, gas (under pressure), gas generating product, foams, pastes, pesticide coated seed, suspension concentrates, suspoemulsion concentrates, soluble concentrates, suspensions, wettable powders, soluble powders, dusts and granules, water-soluble and water-dispersible granules or tablets, water-soluble and water-dispersible powders for the treatment of seed, wettable powders, natural products and synthetic substances impregnated with active ingredient, and also microencapsulations in polymeric substances and in coating materials for seed, and also ULV cold-fogging and warm-fogging formulations.

The inventive compositions include not only formulations which are already ready for use and can be applied with a suitable apparatus to the plant or the seed, but also commercial concentrates which have to be diluted with water prior to use. Customary applications are for example dilution in water and subsequent spraying of the resulting spray liquor, application after dilution in oil, direct application without dilution, seed treatment or soil application of granules.

The inventive compositions and formulations generally contain between 0.05 and 99% by weight, 0.01 and 98% by weight, preferably between 0.1 and 95% by weight, more preferably between 0.5 and 90% of active ingredient, most preferably between 10 and 70% by weight. For special applications, e.g. for protection of wood and derived timber products the inventive compositions and formulations generally contain between 0.0001 and 95% by weight, preferably 0.001 to 60% by weight of active ingredient.

The contents of active ingredient in the application forms prepared from the commercial formulations may vary in a broad range. The concentration of the active ingredients in the application forms is generally between 0.000001 to 95% by weight, preferably between 0.0001 and 2% by weight.

The formulations mentioned can be prepared in a manner known per se, for example by mixing the active ingredients with at least one customary extender, solvent or diluent, adjuvant, emulsifier, dispersant, and/or binder or fixative, wetting agent, water repellent, if appropriate desiccants and UV stabilizers and, if appropriate, dyes and pigments, antifoams, preservatives, inorganic and organic thickeners, adhesives, gibberellins and also further processing auxiliaries and also water. Depending on the formulation type to be prepared further processing steps are necessary, e.g. wet grinding, dry grinding and granulation.

The inventive active ingredients may be present as such or in their (commercial) formulations and in the use forms prepared from these formulations as a mixture with other (known) active ingredients, such as insecticides, attractants, sterilants, bactericides, acaricides, nematicides, fungicides, growth regulators, herbicides, fertilizers, safeners and/or semiochemicals.

The inventive treatment of the plants and plant parts with the active ingredients or compositions is effected directly or by action on their surroundings, habitat or storage space by the customary treatment methods, for example by dipping, spraying, atomizing, irrigating, evaporating, dusting, fogging, broadcasting, foaming, painting, spreading-on, watering (drenching), drip irrigating and, in the case of propagation material, especially in the case of seeds, also by dry seed treatment, wet seed treatment, slurry treatment, incrustation, coating with one or more coats, etc. It is also possible to deploy the active ingredients by the ultra-low volume method or to inject the active ingredient preparation or the active ingredient itself into the soil.

Plant/Crop Protection

The inventive active ingredients or compositions have potent microbicidal activity and can be used for control of unwanted microorganisms, such as fungi and bacteria, in crop protection and in the protection of materials.

The invention also relates to a method for controlling unwanted microorganisms, characterized in that the inventive active ingredients are applied to the phytopathogenic fungi, phytopathogenic bacteria and/or their habitat.

Fungicides can be used in crop protection for control of phytopathogenic fungi. They are characterized by an outstanding efficacy against a broad spectrum of phytopathogenic fungi, including soilborne pathogens, which are in particular members of the classes Plasmodiophoromycetes, Peronosporomycetes (Syn. Oomycetes), Chytridiomycetes, Zygomycetes, Ascomycetes, Basidiomycetes and Deuteromycetes (Syn. Fungi imperfecti). Some fungicides are systemically active and ca be used in plant protection as foliar, seed dressing or soil fungicide. Furthermore, they are suitable for combating fungi, which inter alia infest wood or roots of plant.

Bactericides can be used in crop protection for control of Pseudomonadaceae, Rhizobiaceae, Enterobacteriaceae, Corynebacteriaceae and Streptomycetaceae.

Non-limiting examples of pathogens of fungal diseases which can be treated in accordance with the invention include:

diseases caused by powdery mildew pathogens, for example *Blumeria* species, for example *Blumeria graminis*; *Podosphaera* species, for example *Podosphaera leucotricha*; *Sphaerotheca* species, for example *Sphaerotheca fuliginea*; *Uncinula* species, for example *Uncinula necator*;

diseases caused by rust disease pathogens, for example *Gymnosporangium* species, for example *Gymnosporangium sabinae*; *Hemileia* species, for example *Hemileia vastatrix*; *Phakopsora* species, for example *Phakopsora pachyrhizi* and *Phakopsora meibomiae*; *Puccinia* species, for example *Puccinia recondite, P. triticina, P. graminis* or *P. striiformis*; *Uromyces* species, for example *Uromyces appendiculatus*;

diseases caused by pathogens from the group of the Oomycetes, for example *Albugo* species, for example *Algubo candida*; *Bremia* species, for example *Bremia lactucae*; *Peronospora* species, for example *Peronospora pisi* or *P. brassicae*; *Phytophthora* species, for example *Phytophthora infestans*; *Plasmopara* species, for example *Plasmopara viticola*; *Pseudoperonospora* species, for example *Pseudoperonospora humuli* or *Pseudoperonospora cubensis*; *Pythium* species, for example *Pythium ultimum*;

leaf blotch diseases and leaf wilt diseases caused, for example, by *Alternaria* species, for example *Alternaria solani*; *Cercospora* species, for example *Cercospora beticola*; *Cladiosporium* species, for example *Cladiosporium cucumerinum*; *Cochliobolus* species, for example *Cochliobolus sativus* (conidia form: Drechslera, Syn: Helminthosporium), *Cochliobolus miyabeanus*; *Colletotrichum* species, for example *Colletotrichum lindemuthanium*; *Cycloconium* species, for example *Cycloconium oleaginum*; *Diaporthe* species, for example *Diaporthe citri*; *Elsinoe* species, for example *Elsinoe fawcettii*; *Gloeosporium* species, for example *Gloeosporium laeticolor*; *Glomerella* species, for example *Glomerella cingulata*; *Guignardia* species, for example *Guignardia bidwelli*; *Leptosphaeria* species, for example *Leptosphaeria maculans, Leptosphaeria nodorum*; *Magnaporthe* species, for example *Magnaporthe grisea*; *Microdochium* species, for example *Microdochium nivale*; *Mycosphaerella* species, for example *Mycosphaerella graminicola, M. arachidicola* and *M. fijiensis*; *Phaeosphaeria* species, for example *Phaeosphaeria nodorum*; *Pyrenophora* species, for example *Pyrenophora teres, Pyrenophora tritici repentis*; *Ramularia* species, for example *Ramularia collo-cygni, Ramularia areola*; *Rhynchosporium* species, for example *Rhynchosporium secalis*; *Septoria* species, for example *Septoria apii, Septoria lycopersii*; *Typhula* species, for example *Typhula incarnata*; *Venturia* species, for example *Venturia inaequalis*;

root and stem diseases caused, for example, by *Corticium* species, for example *Corticium graminearum*; *Fusarium* species, for example *Fusarium oxysporum*; *Gaeumannomyces* species, for example *Gaeumannomyces graminis*; *Rhizoctonia* species, such as, for example *Rhizoctonia solani*; *Sarocladium* diseases caused for example by *Sarocladium oryzae*; *Sclerotium* diseases caused for example by *Sclerotium oryzae*; *Tapesia* species, for example *Tapesia acuformis*; *Thielaviopsis* species, for example *Thielaviopsis basicola*;

ear and panicle diseases (including corn cobs) caused, for example, by *Alternaria* species, for example *Alternaria* spp.; *Aspergillus* species, for example *Aspergillus flavus*; *Cladosporium* species, for example *Cladosporium cladosporioides*; *Claviceps* species, for example *Claviceps purpurea*; *Fusarium* species, for example *Fusarium culmorum*; *Gibberella* species, for example *Gibberella zeae*; *Monographella* species, for example *Monographella nivalis*; *Septoria* species, for example *Septoria nodorum*; diseases caused by smut fungi, for example *Sphacelotheca* species, for example *Sphacelotheca reiliana*; *Tilletia* species, for example Tilletia *caries, T. controversa*; *Urocystis* species, for example *Urocystis occulta*; *Ustilago* species, for example *Ustilago nuda, U. nuda tritici*;

fruit rot caused, for example, by *Aspergillus* species, for example *Aspergillus flavus*; *Botrytis* species, for example *Botrytis cinerea*; *Penicillium* species, for example *Penicillium expansum* and *P. purpurogenum*; *Sclerotinia* species, for example *Sclerotinia sclerotiorum*; *Verticilium* species, for example *Verticilium alboatrum*;

seed and soilborne decay, mould, wilt, rot and damping-off diseases caused, for example, by *Alternaria* species, caused for example by *Alternaria brassicicola*; *Aphanomyces* species, caused for example by *Aphanomyces euteiches*; *Ascochyta* species, caused for example by *Ascochyta lentis*; *Aspergillus* species, caused for example by *Aspergillus flavus*; *Cladosporium* species, caused for example by *Cladosporium herbarum*; *Cochliobolus* species, caused for example by *Cochliobolus sativus*; (Conidiaform: Drechslera, Bipolaris Syn: Helminthosporium); *Colletotrichum* species, caused for example by *Colletotrichum coccodes*; *Fusarium* species, caused for example by *Fusarium culmorum*; *Gibberella* species, caused for example by *Gibberella zeae*; *Macrophomina* species, caused for example by *Macrophomina phaseolina*; *Monographella* species, caused for example by *Monographella nivalis*; *Penicillium* species, caused for example by *Penicillium expansum*; *Phoma* species, caused for example by *Phoma lingam*; *Phomopsis* species, caused for example by *Phomopsis sojae*; *Phytophthora* species, caused for example by *Phytophthora cactorum*; *Pyrenophora* species, caused for example by *Pyrenophora graminea*; *Pyricularia* species, caused for example by *Pyricularia oryzae*; *Pythium* species, caused for example by *Pythium ultimum*; *Rhizoctonia* species, caused for example by *Rhizoctonia solani*; *Rhizopus* species, caused for example by *Rhizopus oryzae*; *Sclerotium* species, caused for example by *Sclerotium rolfsii*; *Septoria* species, caused for example by *Septoria nodorum*; *Typhula* species, caused for example by *Typhula incarnata*; *Verticillium* species, caused for example by *Verticillium dahliae*;

cancers, galls and witches' broom caused, for example, by *Nectria* species, for example *Nectria galligena*;

wilt diseases caused, for example, by *Monilinia* species, for example *Monilinia laxa*;

leaf blister or leaf curl diseases caused, for example, by *Exobasidium* species, for example *Exobasidium vexans*;

*Taphrina* species, for example *Taphrina deformans*;

decline diseases of wooden plants caused, for example, by Esca disease, caused for example by *Phaemoniella clamydospora, Phaeoacremonium aleophilum* and *Fomitiporia mediterranea*; *Eutypa* dyeback, caused for example by *Eutypa lata*; *Ganoderma* diseases caused for example by *Ganoderma boninense*; *Rigidoporus* diseases caused for example by *Rigidoporus lignosus*;

diseases of flowers and seeds caused, for example, by *Botrytis* species, for example *Botrytis cinerea*; diseases of plant tubers caused, for example, by *Rhizoctonia* species, for example *Rhizoctonia solani*; *Helminthosporium* species, for example *Helminthosporium solani*;

Club root caused, for example, by *Plasmodiophora* species, for example *Plamodiophora brassicae*; diseases caused by bacterial pathogens, for example *Xanthomonas* species, for example *Xanthomonas campestris* pv. *oryzae*; *Pseudomonas* species, for example *Pseudomonas syringae* pv. *lachrymans*; *Erwinia* species, for example *Erwinia amylovora*.

The following diseases of soya beans can be controlled with preference:

Fungal diseases on leaves, stems, pods and seeds caused, for example, by *Alternaria* leaf spot (*Alternaria* spec. *atrans tenuissima*), Anthracnose (*Colletotrichum gloeosporoides dematium* var. *truncaturn*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi, Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megaspenna*), brown stem rot (*Phialophora gregata*), pythium rot (*Pythium aphanidennatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The inventive fungicidal compositions can be used for curative or protective/preventive control of phytopathogenic fungi. The invention therefore also relates to curative and protective methods for controlling phytopathogenic fungi by the use of the inventive active ingredients or compositions, which are applied to the seed, the plant or plant parts, the fruit or the soil in which the plants grow.

The fact that the active ingredients are well tolerated by plants at the concentrations required for controlling plant diseases allows the treatment of above-ground parts of plants, of propagation stock and seeds, and of the soil.

According to the invention all plants and plant parts can be treated. By plants is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. By plant parts is meant all above ground and below ground parts and organs of plants such as shoot, leaf, blossom and root, whereby for example leaves, needles, stems, branches, blossoms, fruiting bodies, fruits and seed as well as roots, corms and rhizomes are listed. Crops and vegetative and generative propagating material, for example cuttings, corms, rhizomes, runners and seeds also belong to plant parts.

The inventive active ingredients, when they are well tolerated by plants, have favourable homeotherm toxicity and are well tolerated by the environment, are suitable for protecting plants and plant organs, for enhancing harvest yields, for improving the quality of the harvested material. They can preferably be used as crop protection compositions. They are active against normally sensitive and resistant species and against all or some stages of development.

Plants which can be treated in accordance with the invention include the following main crop plants: maize, soya bean, alfalfa, cotton, sunflower, *Brassica* oil seeds such as *Brassica napus* (e.g. canola, rapeseed), *Brassica rapa, B. juncea* (e.g. field) mustard) and *Brassica carinata, Arecaceae* sp. (e.g. oilpalm, coconut), rice, wheat, sugar beet, sugar cane, oats, rye, barley, millet and sorghum, triticale, flax, nuts, grapes and vine and various fruit and vegetables from various botanic taxa, e.g. *Rosaceae* sp. (e.g. pome fruits such as apples and pears, but also stone fruits such as apricots, cherries, almonds, plums and peaches, and berry fruits such as strawberries, raspberries, red and black currant and gooseberry), *Ribesioidae* sp., *Juglandaceae* sp., *Betulaceae* sp., *Anacardiaceae* sp., *Fagaceae* sp., *Moraceae* sp., *Oleaceae* sp. (e.g. olive tree), *Actinidaceae* sp., *Lauraceae* sp. (e.g. avocado, cinnamon, camphor), *Musaceae* sp. (e.g. banana trees and plantations), *Rubiaceae* sp. (e.g. coffee), *Theaceae* sp. (e.g. tea), *Sterculiceae* sp., *Rutaceae* sp. (e.g. lemons, oranges, mandarins and grapefruit); *Solanaceae* sp. (e.g. tomatoes, potatoes, peppers, capsicum, aubergines, tobacco), *Liliaceae* sp., *Compositae* sp. (e.g. lettuce, artichokes and chicory—including root chicory, endive or common chicory), *Umbelliferae* sp. (e.g. carrots, parsley, celery and celeriac), *Cucurbitaceae* sp. (e.g. cucumbers—including gherkins, pumpkins, watermelons, calabashes and melons), *Alliaceae* sp. (e.g. leeks and onions), *Cruciferae* sp. (e.g. white cabbage, red cabbage, broccoli, cauliflower, Brussels sprouts, pak choi, kohlrabi, radishes, horseradish, cress and chinese cabbage), *Leguminosae* sp. (e.g. peanuts, peas, lentils and beans—e.g. common beans and broad beans), *Chenopodiaceae* sp. (e.g. Swiss chard, fodder beet, spinach, beetroot), *Linaceae* sp. (e.g. hemp), *Cannabeacea* sp. (e.g. cannabis), *Malvaceae* sp. (e.g. okra, cocoa), *Papaveraceae* (e.g. poppy), *Asparagaceae* (e.g. asparagus); useful plants and ornamental plants in the garden and woods including turf, lawn, grass and Stevia rebaudiana; and in each case genetically modified types of these plants.

Seed Treatment

The invention further comprises a method for treating seed.

The invention further relates to seed which has been treated by one of the methods described in the previous paragraph. The inventive seeds are employed in methods for the protection of seed from harmful microorganisms. In these methods, seed treated with at least one inventive active ingredient is used.

The inventive active ingredients or compositions are also suitable for treating seed. A large part of the damage to crop plants caused by harmful organisms is triggered by the infection of the seed during storage or after sowing, and also during and after germination of the plant. This phase is particularly critical since the roots and shoots of the growing plant are particularly sensitive, and even minor damage may result in the death of the plant. There is therefore a great interest in protecting the seed and the germinating plant by using appropriate compositions.

The control of phytopathogenic fungi by treating the seed of plants has been known for a long time and is the subject of constant improvements. However, the treatment of seed entails a series of problems which cannot always be solved in a satisfactory manner For instance, it is desirable to develop methods for protecting the seed and the germinating plant, which dispense with, or at least significantly reduce, the additional deployment of crop protection compositions after planting or after emergence of the plants. It is also desirable to optimize the amount of the active ingredient used so as to provide the best possible protection for the seed and the germinating plant from attack by phytopathogenic fungi, but without damaging the plant itself by the active ingredient employed. In particular, methods for the treatment of seed should also take account of the intrinsic fungicidal properties of transgenic plants in order to achieve optimal protection of the seed and the germinating plant with a minimum expenditure of crop protection compositions.

The present invention therefore also relates to a method for protection of seed and germinating plants from attack by phytopathogenic fungi, by treating the seed with an inventive composition. The invention likewise relates to the use of the inventive compositions for treatment of seed to protect the seed and the germinating plant from phytopathogenic fungi. The invention further relates to seed which has been treated with an inventive composition for protection from phytopathogenic fungi.

The control of phytopathogenic fungi which damage plants post-emergence is effected primarily by treating the soil and the above-ground parts of plants with crop protection compositions. Owing to the concerns regarding a possible influence of the crop protection compositions on the environment and the health of humans and animals, there are efforts to reduce the amount of active ingredients deployed.

One of the advantages of the present invention is that the particular systemic properties of the inventive active ingredients and compositions mean that treatment of the seed with these active ingredients and compositions not only protects the seed itself, but also the resulting plants after emergence, from phytopathogenic fungi. In this way, the immediate treatment of the crop at the time of sowing or shortly thereafter can be dispensed with.

It is likewise considered to be advantageous that the inventive active ingredients or compositions can especially also be used with transgenic seed, in which case the plant growing from this seed is capable of expressing a protein which acts against pests. By virtue of the treatment of such seed with the inventive active ingredients or compositions, merely the expression of the protein, for example an insecticidal protein, can control certain pests. Surprisingly, a further synergistic effect can be observed in this case, which additionally increases the effectiveness for protection against attack by pests.

The inventive compositions are suitable for protecting seed of any plant variety which is used in agriculture, in greenhouses, in forests or in horticulture and viticulture. In particular, this is the seed of cereals (such as wheat, barley, rye, triticale, sorghum/millet and oats), maize, cotton, soya beans, rice, potatoes, sunflower, bean, coffee, beet (for example sugar beet and fodder beet), peanut, oilseed rape, poppy, olive, coconut, cocoa, sugar cane, tobacco, vegetables (such as tomato, cucumbers, onions and lettuce), turf and ornamentals (see also below). The treatment of the seed of cereals (such as wheat, barley, rye, triticale and oats), maize and rice is of particular significance.

As also described below, the treatment of transgenic seed with the inventive active ingredients or compositions is of particular significance. This relates to the seed of plants containing at least one heterologous gene. Definition and examples of suitable heterologous genes are given below.

In the context of the present invention, the inventive composition is applied to the seed alone or in a suitable formulation. Preferably, the seed is treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content of less than 15% by weight. Alternatively, it is also possible to use seed which, after drying, for example, has been treated with water and then dried again.

When treating the seed, care must generally be taken that the amount of the inventive composition applied to the seed and/or the amount of further additives is selected such that the germination of the seed is not impaired, or that the resulting plant is not damaged. This has to be borne in mind in particular in the case of active ingredients which can have phytotoxic effects at certain application rates.

The inventive compositions can be applied directly, i.e. without containing any other components and without having been diluted. In general, it is preferable to apply the compositions to the seed in the form of a suitable formulation. Suitable formulations and methods for seed treatment are known to those skilled in the art and are described, for example, in the following documents: U.S. Pat. Nos. 4,272,417, 4,245,432, 4,808,430, 5,876,739, US 2003/0176428 A1, WO 2002/080675, WO 2002/028186.

The active ingredients usable in accordance with the invention can be converted to the customary seed dressing formulations, such as solutions, emulsions, suspensions, powders, foams, slurries or other coating compositions for seed, and also ULV formulations.

These formulations are prepared in a known manner, by mixing the active ingredients with customary additives, for example customary extenders and also solvents or diluents, dyes, wetting agents, dispersants, emulsifiers, antifoams, preservatives, secondary thickeners, adhesives, gibberellins and also water.

Useful dyes which may be present in the seed dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are conventionally used for the formulation of active agrochemical ingredients. Preference is given to using alkyl naphthalenesulphonates, such as diisopropyl or diisobutyl naphthalenesulphonates.

Useful dispersants and/or emulsifiers which may be present in the seed dressing formulations usable in accordance with the invention are all nonionic, anionic and cationic dispersants conventionally used for the formulation of active agrochemical ingredients. Usable with preference are nonionic or anionic dispersants or mixtures of nonionic or anionic dispersants. Suitable nonionic dispersants include especially ethylene oxide/propylene oxide block polymers, alkylphenol polyglycol ethers and tristryrylphenol polyglycol ether, and the phosphated or sulphated derivatives thereof. Suitable anionic dispersants are especially lignosulphonates, polyacrylic acid salts and arylsulphonate/formaldehyde condensates.

Antifoams which may be present in the seed dressing formulations usable in accordance with the invention are all foam-inhibiting substances conventionally used for the formulation of active agrochemical ingredients. Silicone antifoams and magnesium stearate can be used with preference.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances usable for such purposes in agrochemical compositions. Preferred examples include cellulose derivatives, acrylic acid derivatives, xanthan, modified clays and finely divided silica.

Adhesives which may be present in the seed dressing formulations usable in accordance with the invention are all customary binders usable in seed dressing products. Preferred examples include polyvinylpyrrolidone, polyvinyl acetate, polyvinyl alcohol and tylose.

The gibberellins which may be present in the seed dressing formulations usable in accordance with the invention may preferably be gibberellins A1, A3 (=gibberellic acid), A4 and A7; particular preference is given to using gibberellic acid. The gibberellins are known (cf. R. Wegler "Chemie der Pflanzenschutz-und Schädlingsbekämpfungsmittel" [Chemistry of the Crop Protection Compositions and Pesticides], vol. 2, Springer Verlag, 1970, p. 401-412).

The seed dressing formulations usable in accordance with the invention can be used, either directly or after previously having been diluted with water, for the treatment of a wide range of different seed, including the seed of transgenic plants. In this case, additional synergistic effects may also occur in interaction with the substances formed by expression.

For treatment of seed with the seed dressing formulations usable in accordance with the invention, or the preparations prepared therefrom by adding water, all mixing units usable customarily for the seed dressing are useful. Specifically, the procedure in the seed dressing is to place the seed into a mixer, to add the particular desired amount of seed dressing formulations, either as such or after prior dilution with water, and to mix everything until the formulation is distributed homogeneously on the seed. If appropriate, this is followed by a drying process.

Mycotoxins

In addition, the inventive treatment can reduce the mycotoxin content in the harvested material and the foods and feeds prepared therefrom. Mycotoxins include particularly, but not exclusively, the following: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaroproliferin, fusarenol, ochratoxins, patulin, ergot alkaloids and aflatoxins which can be produced, for example, by the following fungi: *Fusarium* spec., such as *F. acuminatum, F. asiaticum, F. avenaceum, F. crookwellense, F. culmorum, F. graminearum (Gibberella zeae), F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides* etc., and also by *Aspergillus* spec., such as *A. flavus, A. parasiticus, A. nomius, A. ochraceus, A. clavatus, A. terreus, A. versicolor, Penicillium* spec., such as *P. verrucosum, P. viridicatum, P. citrinum, P. expansum, P. claviforme, P. roqueforti, Claviceps spec.*, such as *C. purpurea, C. fusifomis, C. paspali, C. africana, Stachybotrys* spec. and others.

Material Protection

The inventive active ingredients or compositions can also be used in the protection of materials, for protection of industrial materials against attack and destruction by harmful microorganisms, for example fungi and insects.

In addition, the inventive compounds can be used as antifouling compositions, alone or in combinations with other active ingredients.

Industrial materials in the present context are understood to mean inanimate materials which have been prepared for use in industry. For example, industrial materials which are to be protected by inventive active ingredients from microbial alteration or destruction may be adhesives, glues, paper, wallpaper and board/cardboard, textiles, carpets, leather, wood, fibers and tissues, paints and plastic articles, cooling lubricants and other materials which can be infected with or destroyed by microorganisms. Parts of production plants and buildings, for example cooling-water circuits, cooling and heating systems and ventilation and air-conditioning units, which may be impaired by the proliferation of microorganisms may also be mentioned within the scope of the materials to be protected. Industrial materials within the scope of the present invention preferably include adhesives, sizes, paper and card, leather, wood, paints, cooling lubricants and heat transfer fluids, more preferably wood.

The inventive active ingredients or compositions may prevent adverse effects, such as rotting, decay, discoloration, decoloration or formation of mould.

In the case of treatment of wood the compounds/compositions according to the invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds according to the invention or a composition according to the invention; this includes for example direct application, spraying, dipping, injection or any other suitable means.

In addition, the inventive compounds can be used to protect objects which come into contact with saltwater or brackish water, especially hulls, screens, nets, buildings, moorings and signalling systems, from fouling.

The inventive method for controlling unwanted fungi can also be employed for protecting storage goods. Storage goods are understood to mean natural substances of vegetable or animal origin or processed products thereof which are of natural origin, and for which long-term protection is desired. Storage goods of vegetable origin, for example plants or plant parts, such as stems, leaves, tubers, seeds, fruits, grains, can be protected freshly harvested or after processing by (pre)drying, moistening, comminuting, grinding, pressing or roasting. Storage goods also include timber, both unprocessed, such as construction timber, electricity poles and barriers, or in the form of finished products, such as furniture. Storage goods of animal origin are, for example, hides, leather, furs and hairs. The inventive active ingredients may prevent adverse effects, such as rotting, decay, discoloration, decoloration or formation of mould.

Microorganisms capable of degrading or altering the industrial materials include, for example, bacteria, fungi, yeasts, algae and slime organisms. The inventive active ingredients preferably act against fungi, especially moulds, wood-discoloring and wood-destroying fungi (*Ascomycetes, Basidiomycetes, Deuteromycetes* and *Zygomycetes*), and against slime organisms and algae. Examples include microorganisms of the following genera: *Altemaria*, such as *Altemaria tenuis; Aspergillus*, such as *Aspergillus niger; Chaetomium*, such as *Chaetomium globosum; Coniophora*, such as *Coniophora puetana; Lentinus*, such as *Lentinus tigrinus; Penicillium*, such as *Penicillium glaucum; Polyporus*, such as *Polyporus versicolor; Aureobasidium*, such as *Aureobasidium pullulans; Sclerophoma*, such as *Sclerophoma pityophila; Trichoderma*, such as *Trichoderma viride; Ophiostoma* spp., *Ceratocystis* spp., *Humicola* spp., *Petriella* spp., *Trichurus* spp., *Coriolus* spp., *Gloeophyllum* spp., *Pleurotus* spp., *Poria* spp., *Serpula* spp. and *Tyromyces* spp., *Cladosporium* spp., *Paecilomyces* spp. *Mucor* spp., *Escherichia*, such as *Escherichia coli; Pseudomonas*, such as *Pseudomonas aeruginosa; Staphylococcus*, such as *Staphylococcus aureus, Candida* spp. and *Saccharomyces* spp., such as *Saccharomyces cerevisae*.

Antimycotic Activity

In addition, the inventive active ingredients also have very good antimycotic activity. They have a very broad antimycotic activity spectrum, especially against dermatophytes and yeasts, moulds and diphasic fungi (for example against *Candida* species, such as *C. albicans*, *C. glabrata*), and *Epidermophyton floccosum*, *Aspergillus* species, such as *A. niger* and *A. fumigatus*, *Trichophyton* species, such as *T. mentagrophytes*, Microsporon species such as *M. canis* and *M. audouinii*. The list of these fungi by no means constitutes a restriction of the mycotic spectrum covered, and is merely of illustrative character.

The inventive active ingredients can therefore be used both in medical and in non-medical applications.

Application Rates and Timing

When using the inventive active ingredients as fungicides, the application rates can be varied within a relatively wide range, depending on the kind of application. The application rate of the inventive active ingredients is in the case of treatment of plant parts, for example leaves: from 0.1 to 10 000 g/ha, preferably from 10 to 1000 g/ha, more preferably from 10 to 800 g/ha, even more preferably from 50 to 300 g/ha (in the case of application by watering or dripping, it is even possible to reduce the application rate, especially when inert substrates such as rockwool or perlite are used);

in the case of seed treatment: from 2 to 200 g per 100 kg of seed, preferably from 3 to 150 g per 100 kg of seed, more preferably from 2.5 to 25 g per 100 kg of seed, even more preferably from 2.5 to 12.5 g per 100 kg of seed;

in the case of soil treatment: from 0.1 to 10 000 g/ha, preferably from 1 to 5000 g/ha.

These application rates are merely by way of example and are not limiting for the purposes of the invention.

The inventive active ingredients or compositions comprising a compound according to formula (I) can thus be used to protect plants from attack by the pathogens mentioned for a certain period of time after treatment. The period for which protection is provided extends generally for 1 to 28 days, preferably for 1 to 14 days, more preferably for 1 to 10 days, most preferably for 1 to 7 days, after the treatment of the plants with the active ingredients, or for up to 200 days after a seed treatment.

The plants listed can particularly advantageously be treated in accordance with the invention with the compounds of the general formula (I) and the inventive compositions. The preferred ranges stated above for the active ingredients or compositions also apply to the treatment of these plants. Particular emphasis is given to the treatment of plants with the compounds or compositions specifically mentioned in the present text.

The invention is illustrated by the examples below. However, the invention is not limited to the examples.

PREPARATION EXAMPLES

General notes: Unless stated otherwise, all chromatographic purification and separation steps are carried out on silica gel and using a solvent gradient from 0:100 ethyl acetate/cyclohexane to 100:0 ethyl acetate/cyclohexane.

Preparation of methyl 1-{[3,5-bis(difluoromethyl)-1H-pyrazol-1-yl]acetyl}-4-[4-(5-{2-[(methylsulfonyyl)oxy]phenyl}-4,5-dihydro-1,2-oxazol-3-yl)-1,3-thiazol-2-yl]piperidine-4-carboxylate (I-7)

Step 1

Preparation of 2-[3-(chloroacetyl)-4,5-dihydro-1,2-oxazol-5-yl]phenyl methanesulfonate To a solution of 2-vinylphenyl methanesulfonate (734 mg) in acetonitrile (10 ml) were added sodium hydrogencarbonate (2.40 g) and 3-chloro-N-hydroxy-2-oxopropanimidoyl chloride (566 mg) at room temperature under argon. The reaction mixture was stirred at room temperature until the starting material was completely consumed. The solids were filtered off and the filtrate was concentrated under reduced pressure. The residue was dissolved in acetonitrile and washed with heptane. The acetonitrile phase was concentrated under reduced pressure to obtain 2-[3-(chloroacetyl)-4,5-dihydro-1,2-oxazol-5-yl]phenyl methanesulfonate (1.55 g, 91% pure, quantitative yield).

LogP (pH 2.7): 2.54

Step 2

Preparation of methyl 1-(chloroacetyl)-4-cyanopiperidine-4-carboxylate (VI-1)

To a solution of 4-cyano-4-(methoxycarbonyl)piperidinium chloride (150 mg) and triethylamine (148 mg) in dichloromethane (10 ml) were added chloroacetyl chloride (83 mg) at 0° C. The reaction mixture was stirred at room temperature for an hour. Then water was added to the reaction mixture, and the aqueous phase was separated and extracted with dichloromethane. The combined organic phases were dried over sodium sulphate and concentrated to obtain methyl 1-(chloroacetyl)-4-cyanopiperidine-4-carboxylate (VI-1) (180 mg, 98% pure, 98% yield) as white solid.

Step 3: preparation of methyl 1-{[3,5-bis(difluoromethyl)-1H-pyrazol-1-yl]acetyl}-4-cyanopiperidine-4-carboxylate (IV-13)

A mixture of methyl 1-(chloroacetyl)-4-cyanopiperidine-4-carboxylate (VI-1) (50 mg), 3,5-bis(difluoromethyl)-1H-pyrazole (34 mg), potassium carbonate (56 mg) and potassium iodide (3 mg) in acetonitrile (10 ml) was stirred at 40° C. for an hour. Then water was added to the reaction mixture, and the aqueous phase was separated and extracted with dichloromethane. The combined organic phases were dried over sodium sulphate and concentrated to obtain methyl 1-{[3,5-bis(difluoromethyl)-1H-pyrazol-1-yl]acetyl}-4-cyanopiperidine-4-carboxylate (IV-13) (70 mg, 88% pure, 80% yield) as colorless solid.

Alternative synthesis of methyl 1-{[3,5-bis(difluoromethyl)-1H-pyrazol-1-yl]acetyl}-4-cyanopiperidine-4-carboxylate (IV-13)

To a solution of [3,5-bis(difluoromethyl)-1H-pyrazol-1-yl]acetic acid (5.0 g) in dichloromethane (20 ml) were added drop-wise, at 0° C., oxalyl chloride (3.86 ml) and two drops of N,N-dimethylformamide. The reaction mixture was stirred at room temperature for 2 hours. Then the solvent and the excess reagent were removed under reduced pressure to obtain [3,5-bis(difluoromethyl)-1H-pyrazol-1-yl]acetyl chloride (5.9 g, quantitative yield).

To a solution of [4-cyano-4-(methoxycarbonyl)piperidinium chloride (300 mg) in dichloromethane (5 mL) was added triethylamine (150 mg), followed by drop-wise addition of [3,5-bis(difluoromethyl)-1H-pyrazol-1-yl]acetyl chloride (394 mg) in dichloromethane (1 mL). The reaction mixture was stirred at room temperature for 2 h. Then water was added to the reaction mixture, and the aqueous phase was separated and extracted with dichloromethane. The combined organic phases were dried over magenesium sulphate and concentrated under reduced pressure. Purification by column chromatography gave methyl 1-{[3,5-bis(difluoromethyl)-1H-pyrazol-1-yl]acetyl }-4-cyanopiperidine-4-carboxylate (IV-13) (240 mg, 95% pure, 41% yield).

Step 4

Preparation of methyl 1-{[3,5-bis(difluoromethyl)-1H-pyrazol-1-yl]acetyl}-4-carbamothioylpiperidine-4-carboxylate (II-11)

To a solution of 1-{[3,5-bis(difluoromethyl)-1H-pyrazol-1-yl]acetyl}-4-cyanopiperidine-4-carboxylate (IV-13) (2.30 g) in N,N-dimethylformamide (20 mL) was added a solution of ammonium sulfide in water (1.89 g, 44%). The reaction mixture was stirred ar room temperature for 2 hours. Then water was added and the aqueous layer was extracted twice with ethyl acetate. The combined organic extracts were washed with brine, dried over magnesium sulfate and concentrated under reduced pressure. The residue was then washed with diethylether and heptane to obtain methyl 1-{[3,5-bis(difluoromethyl)-1H-pyrazol-1-yl]acetyl}-4-carbamothioylpiperidine-4-carboxylate (II-11) (2.30 g, 91% pure, 83% yield) as white solid.

Step 5

Preparation of methyl 1-{[3,5-bis(difluoromethyl)-1H-pyrazol-1-yl]acetyl}-4-[4-(5-{2-[(methylsulfonyl)oxy]phenyl}-4,5-dihydro-1,2-oxazol-3-yl)-1,3-thiazol-2-yl]piperidine-4-carboxylate (I-7)

To a solution of 2-[3-(chloroacetyl)-4,5-dihydro-1,2-oxazol-5-yl]phenyl methanesulfonate (116 mg) and 1-{[3,5-bis(difluoromethyl)-1H-pyrazol-1-yl]acetyl}-4-carbamothioylpiperidine-4-carboxyl ate (II-11) (150 mg) in tetrahydrofuran (2 ml) at room temperature was added tetrabutylammonium bromide (12 mg). The reaction mixture was stirred at 70° C. and at room temperature until the reaction was complete. Then water was added, and the aqueous phase was separated and extracted with dichloromethane. The combined organic phases were dried over magnesium sulfate and concentrated under reduced pressure. Purification by column chromatography gave 1-{[3,5-bis(difluoromethyl)-1H-pyrazol-1-yl]acetyl}-4-[4-(5-{2-[methylsulfonyl)oxy]phenyl}-4,5-dihydro-1,2-oxazol-3-yl)-1,3-thiazol-2-yl]piperidine-4-carboxylate (I-7) (183 mg, 99% pure, 74% yield).

Preparation of methyl 1-{[3,5-bis(difluoromethyl)-1H-pyrazol-1-yl]acetyl}-4-[4-(5-{2-chloro-6-[methylsulfonyl)oxy]phenyl}-4,5-dihydro-1,2-oxazol-3-yl)-1,3-thiazol-2-yl]piperidine-4-carboxylate (1-6)

Step 1

Preparation of 2-(3-acetyl-4,5-dihydro-1,2-oxazol-5-yl)-3-chlorophenyl methanesulfonate To a mixture of 1-(hydroxyimino)acetone (430 mg), 3-chloro-2-vinylphenyl methanesulfonate (1.15 g), potassium hydrogen carbonate in ethyl acetate (20 mL) were added N-chlorosuccinimide (989 mg) and 4 drops of water. The reaction mixture was stirred at room temperature for an hour. Then water was added, and the aqueous layer was extracted with ethyl acetate. The combined organic extracts were washed with brine, dried over magnesium sulfate and concentrated under reduced pressure. The residue was then purified by column chromatography to obtain 2-(3-acetyl-4,5-dihydro-1,2-oxazol-5-yl)-3-chlorophenyl methanesulfonate (1.10 g, 87% pure, 63% yield).

LogP (pH 2.7): 2.46

Step 2

Preparation of 2-[3-(bromoacetyl)-4,5-dihydro-1,2-oxazol-5-yl]-3-chlorophenyl methanesulfonate To a solution of 2-(3-acetyl-4,5-dihydro-1,2-oxazol-5-yl)-3-chlorophenyl methanesulfonate (1.80 g) in chloroform was added polymer-supported tribromide (5 g). The reaction mixture was stirred at 40° C. for an hour, and then another portion of polymer-supported tribromide (5 g) was added. Further 2 hours of stirring at 40° C., the solid was filtered off and the filtrate concentrated under reduced pressure to obtain 2-[3-(bromoacetyl)-4,5-dihydro-1,2-oxazol-5-yl]-3-chlorophenyl methanesulfonate (3.40 g, 69% pure, quantitative yield).

LogP (pH 2.7): 2.93

Step 3

Preparation of methyl 1-{[3,5-bis(difluoromethyl)-1H-pyrazol-1-yl]acetyl}-4-[4-(5-{2-chloro-6-[methylsulfonyl)oxy]phenyl}-4,5-dihydro-1,2-oxazol-3-yl)-1,3-thiazol-2-yl]piperidine-4-carboxylate (I-6)

A mixture of 2-[3-(bromoacetyl)-4,5-dihydro-1,2-oxazol-5-yl]-3-chlorophenyl methanesulfonate (1.12 g, 69% pure) and 1-{[3,5-bis(difluoromethyl)-1H-pyrazol-1-yl]acetyl}-4-carbamothioylpiperidine-4-carboxylate (II-11) (800 mg) in tetrahydrofuran (10 ml) was stirred at 60° C. until the reaction was complete. Then water was added. The aqueous phase was separated and extracted with dichloromethane. The combined organic phases were dried over magnesium sulfate and concentrated under reduced pressure. Purification by column chromatography gave methyl 1-{[3,5-bis(difluoromethyl)-1H-pyrazol-1-yl]acetyl}-4-[4-(5-{2-chloro-6-[methylsulfonyl)oxy]phenyl}-4,5-dihydro-1,2- oxazol-3-yl)-1,3-thiazol-2-yl]piperidine-4-carboxylate (I-6) (1.07 g, 97% pure, 83% yield).

Preparation of methyl 4-[4-(5-{2-chloro-6-[(methylsulfonyl)oxy]phenyl}-4,5-dihydro-1,2-oxazol-3-yl)-1,3-thiazol-2-yl]-1-{[3-(difluoromethyl)-1-methyl-1H-pyrazol-5-yl]carbamoyl}piperidine-4-carboxylate (I-12)

Step 1

Preparation of phenyl [3-(difluoromethyl)-1-methyl-1H-pyrazol-5-yl]carbamate

A mixture of 3-(difluoromethyl)-1-methyl-1H-pyrazol-5-amine (500 mg), phenyl chloroformate (532 mg) and pyridine (1.37 mL) in dichloromethane (10 ml) was stirred at room temperature until the reaction was complete. Then 1N HCl solution was added to adjust the pH of the reaction mixture to 2-3. The aqueous phase was separated and extracted with dichloromethane. The combined organic phases were dried over magnesium sulfate and concentrated under reduced pressure, to obtain phenyl [3-(difluoromethyl)-1-methyl-1H-pyrazol-5-yl]carbamate (1.07 g, 90% pure, 100% yield).
LogP (pH 2.7): 2.18

Step 2

Preparation of methyl 4-cyano-1-{[3-(difluoromethyl)-1-methyl-1H-pyrazol-5-yl]carbamoyl}piperidine-4-carboxylate (IV-17)

A mixture of phenyl [3-(difluoromethyl)-1-methyl-1H-pyrazol-5-yl]carbamate (520 mg), 4-cyano-4-(methoxycarbonyl)piperidinium chloride (398 mg) and triethylamine (0.27 mL) in dichloromethane (10 ml) was stirred at room temperature until the reaction was complete. Then water was added. The aqueous phase was separated and extracted with dichloromethane. The combined organic phases were dried over magnesium sulfate and concentrated under reduced pressure. Purification by chromatography gave methyl 4-cyano-1-{[3-(difluoromethyl)-1-methyl-1H-pyrazol-5-yl]carbamoyl}piperidine-4-carboxylate (IV-17) (497 mg, 99% pure, 74% yield).

Step 3

Preparation of methyl 4-carbamothioyl-1-{[3-(difluoromethyl)-1-methyl-1H-pyrazol-5-yl]carbamoyl}piperidine-4-carboxylate (II-12)

To a solution of methyl 4-cyano-1-{[3-(difluoromethyl)-1-methyl-1H-pyrazol-5-yl]carbamoyl}piperidine-4-carboxylate (IV-17) (351 mg) in N,N-dimethylformamide (25 mL) was added a solution of ammonium sulfide in water (772 mg, 44%). The reaction mixture was stirred ar room temperature for 2 hours. Then water was added and the aqueous layer was extracted twice with ethyl acetate. The combined organic extracts were washed with brine, dried over magnesium sulfate and concentrated under reduced pressure. The residue was then purified by column chromatography to obtain 4-carbamothioyl-1-{[3-(difluoromethyl)-1-methyl-1H-pyrazol-5-yl]carbamoyl}piperidine-4-carboxylate (II-12) (1.00 g, 100% pure, 100% yield).

Step 4

Preparation of methyl 4-[4-(5-{2-chloro-6-[(methylsulfonyl)oxy]phenyl}-4,5-dihydro-1,2-oxazol-3-yl)-1,3-thiazol-2-yl]-1-{[3-(difluoromethyl)-1-methyl-1H-pyrazol-5-yl]carbamoyl}piperidine-4-carboxylate (I-12)

A mixture of 2-[3-(bromoacetyl)-4,5-dihydro-1,2-oxazol-5-yl]-3-chlorophenyl methanesulfonate (211 mg) and methyl 4-carbamothioyl-1-{[3-(difluoromethyl)-1-methyl-1H-pyrazol-5-yl]carbamoyl}piperidine-4-carboxylate (II-12) (200 mg) in tetrahydrofuran (10 ml) was stirred at 60° C. until the reaction was complete. Then water was added. The aqueous phase was separated and extracted with dichloromethane. The combined organic phases were dried over magnesium sulfate and concentrated under reduced pressure. Purification by chromatography gave methyl 4-[4-(5-{2-chloro-6-[(methylsulfonyl)oxy]phenyl}-4,5-dihydro-1,2-oxazol-3-yl)-1,3-thiazol-2-yl]-1-{[3-(difluoromethyl)-1-methyl-1H-pyrazol-5-yl]carbamoyl}piperidine-4-carboxylate (I-12) (14 mg, 99% pure, 4% yield).

COMPOUND EXAMPLES

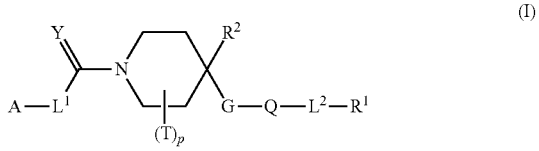

(I)

The structural elements G and Q listed in Table 1 are defined as follows:

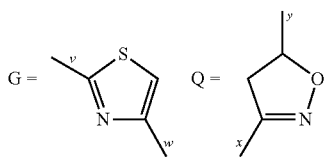

For all compounds listed in Table 1, p=0 and $L^2$=direct bond.

TABLE 1

| Ex. | A | Y | $L^1$ | $R^2$ | $R^1$ | Log p[a] |
|---|---|---|---|---|---|---|
| I-1 | 3,5-bis(difluoromethyl)-1H-pyrazol-1-yl | O | $CH_2$ | methoxycarbonyl | 2,6-difluorophenyl | 3.44 |
| I-2 | 3,5-bis(difluoromethyl)-1H-pyrazol-1-yl | O | $CH_2$ | methoxycarbonyl | biphenyl-2-yl | 4.36 |
| I-3 | 3,5-bis(difluoromethyl)-1H-pyrazol-1-yl | O | $CH_2$ | methoxycarbonyl | 2,3-difluoro-6-(prop-2-yn-1-yloxy)phenyl | 3.61 |
| I-4 | 3,5-bis(difluoromethyl)-1H-pyrazol-1-yl | O | $CH_2$ | methoxycarbonyl | 2-(prop-2-yn-1-yloxy)phenyl | 3.61 |
| I-5 | 3,5-bis(difluoromethyl)-1H-pyrazol-1-yl | O | $CH_2$ | methoxycarbonyl | phenyl | 3.48 |
| I-6 | 3,5-bis(difluoromethyl)-1H-pyrazol-1-yl | O | $CH_2$ | methoxycarbonyl | 2-chloro-6-[(methylsulfonyl)oxy]phenyl | 3.44 |

TABLE 1-continued

| Ex. | A | Y | L¹ | R² | R¹ | Log p[a] |
|---|---|---|---|---|---|---|
| I-7 | 3,5-bis(difluoromethyl)-1H-pyrazol-1-yl | O | CH₂ | methoxycarbonyl | 2-[(methylsulfonyl)oxy]phenyl | 3.27 |
| I-8 | 3-(difluoromethyl)-1-methyl-1H-pyrazol-5-yl | O | N | methoxycarbonyl | 2-[(methylsulfonyl)oxy]phenyl | 2.64 |
| I-9 | 2,5-bis(difluoromethyl)phenyl | O | N | methoxycarbonyl | 2-[(methylsulfonyl)oxy]phenyl | 3.42 |
| I-10 | 1-(fluoromethyl)-3-methyl-1H-pyrazol-4-yl | O | N | methoxycarbonyl | 2-[(methylsulfonyl)oxy]phenyl | 2.64 |
| I-11 | 2,5-dimethylphenyl | O | N | methoxycarbonyl | 2-[(methylsulfonyl)oxy]phenyl | 3.29 |
| I-12 | 3-(difluoromethyl)-1-methyl-1H-pyrazol-5-yl | O | N | methoxycarbonyl | 2-chloro-6-[(methylsulfonyl)oxy]phenyl | 2.84 |
| I-13 | 1-(difluoromethyl)-3-methyl-1H-pyrazol-4-yl | O | N | methoxycarbonyl | 2-chloro-6-[(methylsulfonyl)oxy]phenyl | 2.86 |
| I-14 | 3-(difluoromethyl)-1-methyl-1H-pyrazol-4-yl | O | N | methoxycarbonyl | 2-chloro-6-[(methylsulfonyl)oxy]phenyl | 2.73 |
| I-15 | 3-(difluoromethyl)-1-methyl-1H-pyrazol-5-yl | O | N | methoxycarbonyl | 2-(prop-2-yn-1-yloxy)phenyl | 3.00 |
| I-16 | 3-(difluoromethyl)-1-methyl-1H-pyrazol-5-yl | O | N | methoxycarbonyl | 2,3-difluoro-6-(prop-2-yn-1-yloxy)phenyl | 3.00 |
| I-17 | 1-(difluoromethyl)-3-methyl-1H-pyrazol-4-yl | O | N | methoxycarbonyl | 2-(prop-2-yn-1-yloxy)phenyl | 3.02 |
| I-18 | 1-(difluoromethyl)-3-methyl-1H-pyrazol-4-yl | O | N | methoxycarbonyl | 2,3-difluoro-6-(prop-2-yn-1-yloxy)phenyl | 3.04 |
| I-19 | 3-(difluoromethyl)-1-methyl-1H-pyrazol-4-yl | O | N | methoxycarbonyl | 2-[(methylsulfonyl)oxy]phenyl | 2.53 |
| I-20 | 3-(difluoromethyl)-1-methyl-1H-pyrazol-4-yl | O | N | methoxycarbonyl | 2-(prop-2-yn-1-yloxy)phenyl | 2.88 |
| I-21 | 3-(difluoromethyl)-1-methyl-1H-pyrazol-4-yl | O | N | methoxycarbonyl | 2,3-difluoro-6-(prop-2-yn-1-yloxy)phenyl | 2.88 |
| I-22 | 3,5-bis(difluoromethyl)-1H-pyrazol-1-yl | O | CH₂ | ethoxycarbonyl | 2-chloro-6-[(methylsulfonyl)oxy]phenyl | 3.71 |
| I-23 | 3,5-bis(difluoromethyl)-1H-pyrazol-1-yl | O | CH₂ | ethoxycarbonyl | biphenyl-2-yl | 4.64 |
| I-24 | 3,5-bis(difluoromethyl)-1H-pyrazol-1-yl | O | CH₂ | ethoxycarbonyl | 2,6-difluorophenyl | 3.73 |
| I-25 | 3,5-bis(difluoromethyl)-1H-pyrazol-1-yl | O | CH₂ | ethoxycarbonyl | phenyl | 3.76 |
| I-26 | 3,5-bis(difluoromethyl)-1H-pyrazol-1-yl | O | CH₂ | ethoxycarbonyl | 2-[(methylsulfonyl)oxy]phenyl | 3.51 |
| I-27 | 3,5-bis(difluoromethyl)-1H-pyrazol-1-yl | O | CH₂ | ethoxycarbonyl | 2-(prop-2-yn-1-yloxy)phenyl | 3.87 |
| I-28 | 3,5-bis(difluoromethyl)-1H-pyrazol-1-yl | O | CH₂ | ethoxycarbonyl | 2,3-difluoro-6-(prop-2-yn-1-yloxy)phenyl | 3.85 |
| I-29 | 3,5-bis(difluoromethyl)-1H-pyrazol-1-yl | O | CH₂ | isopropoxycarbonyl | 2-chloro-6-[(methylsulfonyl)oxy]phenyl | 3.96 |
| I-30 | 3,5-bis(difluoromethyl)-1H-pyrazol-1-yl | O | CH₂ | isopropoxycarbonyl | biphenyl-2-yl | 4.92 |
| I-31 | 3,5-bis(difluoromethyl)-1H-pyrazol-1-yl | O | CH₂ | isopropoxycarbonyl | 2,6-difluorophenyl | 3.99 |
| I-32 | 3,5-bis(difluoromethyl)-1H-pyrazol-1-yl | O | CH₂ | isopropoxycarbonyl | phenyl | 4.04 |
| I-33 | 3,5-bis(difluoromethyl)-1H-pyrazol-1-yl | O | CH₂ | isopropoxycarbonyl | 2-(prop-2-yn-1-yloxy)phenyl | 4.14 |
| I-34 | 3,5-bis(difluoromethyl)-1H-pyrazol-1-yl | O | CH₂ | isopropoxycarbonyl | 2,3-difluoro-6-(prop-2-yn-1-yloxy)phenyl | 4.09 |
| I-35 | 3,5-bis(difluoromethyl)-1H-pyrazol-1-yl | O | CH₂ | (benzyloxy)carbonyl | 2-chloro-6-[(methylsulfonyl)oxy]phenyl | 4.19 |
| I-36 | 3,5-bis(difluoromethyl)-1H-pyrazol-1-yl | O | CH₂ | (benzyloxy)carbonyl | biphenyl-2-yl | 5.08 |
| I-37 | 3,5-bis(difluoromethyl)-1H-pyrazol-1-yl | O | CH₂ | (benzyloxy)carbonyl | 2,6-difluorophenyl | 4.21 |
| I-38 | 3,5-bis(difluoromethyl)-1H-pyrazol-1-yl | O | CH₂ | (benzyloxy)carbonyl | phenyl | 4.26 |
| I-39 | 3,5-bis(difluoromethyl)-1H-pyrazol-1-yl | O | CH₂ | (benzyloxy)carbonyl | 2-(prop-2-yn-1-yloxy)phenyl | 4.34 |
| I-40 | 3,5-bis(difluoromethyl)-1H-pyrazol-1-yl | O | CH₂ | (benzyloxy)carbonyl | 2,3-difluoro-6-(prop-2-yn-1-yloxy)phenyl | 4.31 |
| I-41 | 3,5-bis(difluoromethyl)-1H-pyrazol-1-yl | O | CH₂ | (allyloxy)carbonyl | 2-chloro-6-[(methylsulfonyl)oxy]phenyl | 3.80 |
| I-42 | 3,5-bis(difluoromethyl)-1H-pyrazol-1-yl | O | CH₂ | (allyloxy)carbonyl | biphenyl-2-yl | 4.72 |
| I-43 | 3,5-bis(difluoromethyl)-1H-pyrazol-1-yl | O | CH₂ | (allyloxy)carbonyl | 2,6-difluorophenyl | 3.83 |
| I-44 | 3,5-bis(difluoromethyl)-1H-pyrazol-1-yl | O | CH₂ | (allyloxy)carbonyl | phenyl | 3.85 |
| I-45 | 3,5-bis(difluoromethyl)-1H-pyrazol-1-yl | O | CH₂ | (allyloxy)carbonyl | 2-(prop-2-yn-1-yloxy)phenyl | 3.96 |
| I-46 | 3,5-bis(difluoromethyl)-1H-pyrazol-1-yl | O | CH₂ | (allyloxy)carbonyl | 2,3-difluoro-6-(prop-2-yn-1-yloxy)phenyl | 3.94 |
| I-47 | 3,5-bis(difluoromethyl)-1H-pyrazol-1-yl | O | CH₂ | [2-(methylsulfanyl)ethoxy]carbonyl | 2-chloro-6-[(methylsulfonyl)oxy]phenyl | 3.85 |
| I-48 | 3,5-bis(difluoromethyl)-1H-pyrazol-1-yl | O | CH₂ | [2-(methylsulfanyl)ethoxy]carbonyl | biphenyl-2-yl | 4.77 |
| I-49 | 3,5-bis(difluoromethyl)-1H-pyrazol-1-yl | O | CH₂ | [2-(methylsulfanyl)ethoxy]carbonyl | 2,6-difluorophenyl | 3.87 |
| I-50 | 3,5-bis(difluoromethyl)-1H-pyrazol-1-yl | O | CH₂ | [2-(methylsulfanyl)ethoxy]carbonyl | phenyl | 3.89 |
| I-51 | 3,5-bis(difluoromethyl)-1H-pyrazol-1-yl | O | CH₂ | [2-(methylsulfanyl)ethoxy]carbonyl | 2-(prop-2-yn-1-yloxy)phenyl | 4.01 |
| I-52 | 3,5-bis(difluoromethyl)-1H-pyrazol-1-yl | O | CH₂ | [2-(methylsulfanyl)ethoxy]carbonyl | 2,3-difluoro-6-(prop-2-yn-1-yloxy)phenyl | 3.99 |
| I-53 | 3,5-bis(difluoromethyl)-1H-pyrazol-1-yl | O | CH₂ | (tetrahydrofuran-3-yloxy)carbonyl | 2-chloro-6-[(methylsulfonyl)oxy]phenyl | 3.39 |
| I-54 | 3,5-bis(difluoromethyl)-1H-pyrazol-1-yl | O | CH₂ | (tetrahydrofuran-3-yloxy)carbonyl | biphenyl-2-yl | 4.31 |
| I-55 | 3,5-bis(difluoromethyl)-1H-pyrazol-1-yl | O | CH₂ | (tetrahydrofuran-3-yloxy)carbonyl | 2,6-difluorophenyl | 3.39 |
| I-56 | 3,5-bis(difluoromethyl)-1H-pyrazol-1-yl | O | CH₂ | (tetrahydrofuran-3-yloxy)carbonyl | phenyl | 3.39 |
| I-57 | 3,5-bis(difluoromethyl)-1H-pyrazol-1-yl | O | CH₂ | (tetrahydrofuran-3-yloxy)carbonyl | 2-[(methylsulfonyl)oxy]phenyl | 3.21 |
| I-58 | 3,5-bis(difluoromethyl)-1H-pyrazol-1-yl | O | CH₂ | (tetrahydrofuran-3-yloxy)carbonyl | 2-(prop-2-yn-1-yloxy)phenyl | 3.55 |
| I-59 | 3,5-bis(difluoromethyl)-1H-pyrazol-1-yl | O | CH₂ | (tetrahydrofuran-3-yloxy)carbonyl | 2,3-difluoro-6-(prop-2-yn-1-yloxy)phenyl | 3.55 |
| I-60 | 3-(difluoromethyl)-5-methyl-1H-pyrazol-1-yl | O | CH₂ | methoxycarbonyl | 2-chloro-6-[(methylsulfonyl)oxy]phenyl | 3.19 |
| I-61 | 3-(difluoromethyl)-5-methyl-1H-pyrazol-1-yl | O | CH₂ | methoxycarbonyl | biphenyl-2-yl | 4.09 |
| I-62 | 3-(difluoromethyl)-5-methyl-1H-pyrazol-1-yl | O | CH₂ | methoxycarbonyl | 2,6-difluorophenyl | 3.17 |
| I-63 | 3-(difluoromethyl)-5-methyl-1H-pyrazol-1-yl | O | CH₂ | methoxycarbonyl | phenyl | 3.17 |
| I-64 | 3-(difluoromethyl)-5-methyl-1H-pyrazol-1-yl | O | CH₂ | methoxycarbonyl | 2-[(methylsulfonyl)oxy]phenyl | 2.96 |
| I-65 | 3-(difluoromethyl)-5-methyl-1H-pyrazol-1-yl | O | CH₂ | methoxycarbonyl | 2-(prop-2-yn-1-yloxy)phenyl | 3.33 |
| I-66 | 3-(difluoromethyl)-5-methyl-1H-pyrazol-1-yl | O | CH₂ | methoxycarbonyl | 2,3-difluoro-6-(prop-2-yn-1-yloxy)phenyl | 3.33 |
| I-67 | 5-methyl-3-(trifluoromethyl)-1H-pyrazol-1-yl | O | CH₂ | methoxycarbonyl | 2-chloro-6-[(methylsulfonyl)oxy]phenyl | 3.55 |
| I-68 | 5-methyl-3-(trifluoromethyl)-1H-pyrazol-1-yl | O | CH₂ | methoxycarbonyl | biphenyl-2-yl | 4.49 |
| I-69 | 5-methyl-3-(trifluoromethyl)-1H-pyrazol-1-yl | O | CH₂ | methoxycarbonyl | 2,6-difluorophenyl | 3.55 |
| I-70 | 5-methyl-3-(trifluoromethyl)-1H-pyrazol-1-yl | O | CH₂ | methoxycarbonyl | phenyl | 3.55 |
| I-71 | 5-methyl-3-(trifluoromethyl)-1H-pyrazol-1-yl | O | CH₂ | methoxycarbonyl | 2-[(methylsulfonyl)oxy]phenyl | 3.33 |
| I-72 | 5-methyl-3-(trifluoromethyl)-1H-pyrazol-1-yl | O | CH₂ | methoxycarbonyl | 2-(prop-2-yn-1-yloxy)phenyl | 3.71 |
| I-73 | 5-methyl-3-(trifluoromethyl)-1H-pyrazol-1-yl | O | CH₂ | methoxycarbonyl | 2,3-difluoro-6-(prop-2-yn-1-yloxy)phenyl | 3.71 |
| I-74 | 5-(difluoromethyl)-3-methyl-1H-pyrazol-1-yl | O | CH₂ | methoxycarbonyl | 2-chloro-6-[(methylsulfonyl)oxy]phenyl | 3.15 |
| I-75 | 5-(difluoromethyl)-3-methyl-1H-pyrazol-1-yl | O | CH₂ | methoxycarbonyl | 2,6-difluorophenyl | 3.11 |
| I-76 | 5-(difluoromethyl)-3-methyl-1H-pyrazol-1-yl | O | CH₂ | methoxycarbonyl | 2,3-difluoro-6-(prop-2-yn-1-yloxy)phenyl | 3.09 |
| I-77 | 3,5-bis(difluoromethyl)-1H-pyrazol-1-yl | O | CH₂ | (2-methoxyethoxy)carbonyl | 2-chloro-6-[(methylsulfonyl)oxy]phenyl | 3.48 |
| I-78 | 3,5-bis(difluoromethyl)-1H-pyrazol-1-yl | O | CH₂ | (prop-2-yn-1-yloxy)carbonyl | 2-chloro-6-[(methylsulfonyl)oxy]phenyl | 3.58 |
| I-79 | 1-methyl-3-(trifluoromethyl)-1H-pyrazol-5-yl | O | N | methoxycarbonyl | 2-[(methylsulfonyl)oxy]phenyl | 3.00 |
| I-80 | 1-methyl-3-(trifluoromethyl)-1H-pyrazol-5-yl | O | N | methoxycarbonyl | 2-(prop-2-yn-1-yloxy)phenyl | 3.35 |
| I-81 | 1-methyl-3-(trifluoromethyl)-1H-pyrazol-5-yl | O | N | methoxycarbonyl | 2,3-difluoro-6-(prop-2-yn-1-yloxy)phenyl | 3.35 |

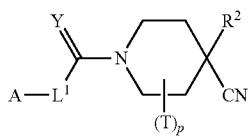

(IV)

For all compounds listed in Table 2, p=0.

For all compounds listed in Table 3, p=0.

TABLE 3

| Ex. | W[13] | Y | L[1] | R[2] | Log P[a] |
|---|---|---|---|---|---|
| VI-1 | chloro | O | CH[2] | methoxycarbonyl | 1.27 |

TABLE 2

| Ex. | A | Y | L[1] | R[2] | Log P[a] |
|---|---|---|---|---|---|
| IV-1 | 3,5-bis(difluoromethyl)-1H-pyrazol-1-yl | O | CH[2] | (tetrahydrofuran-3-yloxy)carbonyl | 2.26 |
| IV-2 | 3,5-bis(difluoromethyl)-1H-pyrazol-1-yl | O | CH[2] | (2-methoxyethoxy)carbonyl | 2.32 |
| IV-3 | 3,5-bis(difluoromethyl)-1H-pyrazol-1-yl | O | CH[2] | [2-(methylsulfanyl)ethoxy]carbonyl | 2.78 |
| IV-4 | 3,5-bis(difluoromethyl)-1H-pyrazol-1-yl | O | CH[2] | (prop-2-yn-1-yloxy)carbonyl | 2.52 |
| IV-5 | 3,5-bis(difluoromethyl)-1H-pyrazol-1-yl | O | CH[2] | (allyloxy)carbonyl | 2.71 |
| IV-6 | 3,5-bis(difluoromethyl)-1H-pyrazol-1-yl | O | CH[2] | (benzyloxy)carbonyl | 3.23 |
| IV-7 | 5-methyl-3-(trifluoromethyl)-1H-pyrazol-1-yl | O | CH[2] | methoxycarbonyl | 2.32 |
| IV-8 | 3-(difluoromethyl)-5-methyl-1H-pyrazol-1-yl | O | CH[2] | COOH | 1.10 |
| IV-9 | 3-(difluoromethyl)-5-methyl-1H-pyrazol-1-yl | O | CH[2] | methoxycarbonyl | 1.89 |
| IV-10 | 3,5-bis(difluoromethyl)-1H-pyrazol-1-yl | O | CH[2] | isopropoxycarbonyl | 2.84 |
| IV-11 | 3,5-bis(difluoromethyl)-1H-pyrazol-1-yl | O | CH[2] | ethoxycarbonyl | 2.55 |
| IV-12 | 3,5-bis(difluoromethyl)-1H-pyrazol-1-yl | O | CH[2] | COOH | 1.44 |
| IV-13 | 3,5-bis(difluoromethyl)-1H-pyrazol-1-yl | O | CH[2] | methoxycarbonyl | 2.26 |
| IV-14 | 5-methyl-3-(trifluoromethyl)-1H-pyrazol-1-yl | O | CH[2] | COOH | 1.50 |
| IV-16 | 2,5-bis(difluoromethyl)phenyl | O | N | methoxycarbonyl | 2.47 |
| IV-17 | 3-(difluoromethyl)-1-methyl-1H-pyrazol-5-yl | O | N | methoxycarbonyl | 1.53 |
| IV-18 | 1-(difluoromethyl)-3-methyl-1H-pyrazol-4-yl | O | N | methoxycarbonyl | 1.51 |
| IV-19 | 2,5-dimethylphenyl | O | N | methoxycarbonyl | 2.26 |
| IV-20 | phenyl | O | N | tert-butoxycarbonyl | 2.82 |
| IV-21 | phenyl | O | N | COOH | 1.16 |
| IV-22 | 4-fluorophenyl | O | N | tert-butoxycarbonyl | 2.96 |
| IV-23 | phenyl | O | CH[2] | tert-butoxycarbonyl | 2.96 |
| IV-24 | 4-chlorophenyl | O | CH[2] | tert-butoxycarbonyl | 3.37 |
| IV-25 | 2-(trifluoromethyl)phenyl | S | N | tert-butoxycarbonyl | 3.50 |
| IV-26 | 3-chlorophenyl | S | N | tert-butoxycarbonyl | 3.72 |
| IV-27 | 4-(trifluoromethoxy)phenyl | S | N | tert-butoxycarbonyl | 4.01 |
| IV-28 | 4-chloro-3-(trifluoromethyl)phenyl | O | N | tert-butoxycarbonyl | 4.06 |
| IV-29 | 3-cyanophenyl | O | N | tert-butoxycarbonyl | 2.88 |
| IV-30 | 4-chloro-3-(trifluoromethyl)phenyl | O | N | COOH | 2.42 |
| IV-31 | 3-cyanophenyl | O | N | COOH | 1.29 |
| IV-32 | 3-chlorophenyl | S | N | COOH | 2.01 |
| IV-33 | 4-(trifluoromethoxy)phenyl | S | N | COOH | 2.33 |
| IV-34 | 3-(difluoromethyl)-1-methyl-1H-pyrazol-4-yl | O | N | methoxycarbonyl | 1.40 |
| IV-35 | 3-chlorophenyl | S | N | sec-butylcarbamoyl | 2.69 |
| IV-36 | 3-cyanophenyl | O | N | sec-butylcarbamoyl | 1.28 |
| IV-37 | 4-chlorophenyl | O | CH[2] | sec-butylcarbamoyl | 2.46 |
| IV-38 | phenyl | O | CH[2] | sec-butylcarbamoyl | 2.08 |
| IV-39 | 4-chloro-3-(trifluoromethyl)phenyl | O | N | sec-butylcarbamoyl | 3.15 |
| IV-40 | 4-fluorophenyl | O | N | methyl(3-methylbut-2-en-1-yl)carbamoyl | 2.71 |
| IV-41 | phenyl | O | N | methyl(3-methylbut-2-en-1-yl)carbamoyl | 2.61 |
| IV-42 | phenyl | O | N | (3-methylbut-2-en-1-yl)carbamoyl | 2.26 |
| IV-43 | 4-chlorophenyl | O | N | (3-methylbut-2-en-1-yl)carbamoyl | 2.68 |
| IV-44 | 4-fluorophenyl | O | N | (3-methylbut-2-en-1-yl)carbamoyl | 2.16 |
| IV-45 | phenyl | O | N | sec-butylcarbamoyl | 2.13 |
| IV-46 | 4-chlorophenyl | O | N | methyl(3-methylbut-2-en-1-yl)carbamoyl | 3.03 |
| IV-48 | phenyl | O | N | butylcarbamoyl | 2.20 |

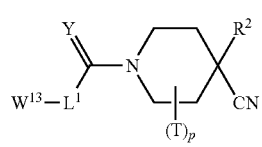

(VI)

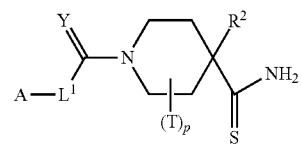

(II)

For all compounds listed in Table 4, p=0.

TABLE 4

| Ex. | A | Y | L¹ | R² | Log P[a] |
|---|---|---|---|---|---|
| II-1 | 3,5-bis(difluoromethyl)-1H-pyrazol-1-yl | O | $CH_2$ | (tetrahydrofuran-3-yloxy)carbonyl | 2.02 |
| II-2 | 3,5-bis(difluoromethyl)-1H-pyrazol-1-yl | O | $CH_2$ | [2-(methylsulfanyl)ethoxy]carbonyl | 2.49 |
| II-3 | 3,5-bis(difluoromethyl)-1H-pyrazol-1-yl | O | $CH_2$ | (allyloxy)carbonyl | 2.42 |
| II-4 | 3,5-bis(difluoromethyl)-1H-pyrazol-1-yl | O | $CH_2$ | (benzyloxy)carbonyl | 2.90 |
| II-5 | 5-(difluoromethyl)-3-methyl-1H-pyrazol-1-yl | O | $CH_2$ | methoxycarbonyl | 1.75 |
| II-6 | 5-methyl-3-(trifluoromethyl)-1H-pyrazol-1-yl | O | $CH_2$ | methoxycarbonyl | 2.08 |
| II-7 | 3-(difluoromethyl)-5-methyl-1H-pyrazol-1-yl | O | $CH_2$ | methoxycarbonyl | 1.68 |
| II-9 | 3,5-bis(difluoromethyl)-1H-pyrazol-1-yl | O | $CH_2$ | isopropoxycarbonyl | 2.52 |
| II-10 | 3,5-bis(difluoromethyl)-1H-pyrazol-1-yl | O | $CH_2$ | ethoxycarbonyl | 2.26 |
| II-11 | 3,5-bis(difluoromethyl)-1H-pyrazol-1-yl | O | $CH_2$ | methoxycarbonyl | 1.98 |
| II-12 | 3-(difluoromethyl)-1-methyl-1H-pyrazol-5-yl | O | N | methoxycarbonyl | 1.33 |
| II-13 | 2,5-bis(difluoromethyl)phenyl | O | N | methoxycarbonyl | 2.23 |
| II-14 | 1-(difluoromethyl)-3-methyl-1H-pyrazol-4-yl | O | N | methoxycarbonyl | 1.30 |
| II-15 | 2,5-dimethylphenyl | O | N | methoxycarbonyl | 2.02 |
| II-16 | 3-(difluoromethyl)-1-methyl-1H-pyrazol-4-yl | O | N | methoxycarbonyl | 1.22 |
| II-17 | 3,5-bis(difluoromethyl)-1H-pyrazol-1-yl | O | $CH_2$ | (prop-2-yn-1-yloxy)carbonyl | 2.27 |
| II-18 | 3,5-bis(difluoromethyl)-1H-pyrazol-1-yl | O | $CH_2$ | (2-methoxyethoxy)carbonyl | 2.10 |
| II-19 | 1-methyl-3-(trifluoromethyl)-1H-pyrazol-5-yl | O | N | methoxycarbonyl | 1.74 |

Measurement of LogP values was performed according to EEC directive 79/831 Annex V.A8 by HPLC (High Performance Liquid Chromatography) on reversed phase columns with the following methods:
[a]LogP value is determined by measurement of LC-UV, in an acidic range, with 0.1% formic acid in water and acetonitrile as eluent (linear gradient from 10% acetonitrile to 95% acetonitrile).

Calibration was done with straight-chain alkan2-ones (with 3 to 16 carbon atoms) with known LogP values (measurement of LogP values using retention times with linear interpolation between successive alkanones). Lambda-max-values were determined using UV-spectra from 200 nm to 400 nm and the peak values of the chromatographic signals.

NMR Data of Selected Examples

¹H-NMR data of selected examples are written in form of ¹H-NMR-peak lists. To each signal peak are listed the δ-value in ppm and the signal intensity in round brackets. Between the δ-value—signal intensity pairs are semicolons as delimiters.

The peak list of an example has therefore the form:

$\delta_1$ (intensity$_1$); $\delta_2$ (intensity$_2$); ... ; $\delta_i$ (intensity$_i$); ... ; $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown The ¹H-NMR peak lists are similar to classical ¹H-NMR prints and contain therefore usually all peaks, which are listed at classical NMR-interpretation.

Additionally they can show like classical 1H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-d$_6$ and the peak of water are shown in our ¹H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical ¹H-NMR interpretation.

Further details of NMR-data description with peak lists you find in the publication "Citation of NMR Peaklist Data within Patent Applications" of the Research Disclosure Database Number 564025.

Example I-1, Solvent: $CDCl_3$, Spectrometer: 300.16 MHz
7.8376 (4.99); 7.3401 (0.62); 7.3327 (0.53); 7.3189 (0.40); 7.3120 (1.22); 7.3051 (0.48); 7.2903 (0.58); 7.2840 (0.78); 7.2622 (11.39); 7.0351 (1.04); 6.9543 (1.86); 6.9384 (0.37); 6.9267 (3.28); 6.9156 (0.42); 6.9106 (0.38); 6.8990 (1.55); 6.8513 (2.18); 6.8348 (1.08); 6.7471 (2.15); 6.6676 (1.11); 6.6517 (2.20); 6.4686 (1.06); 6.1118 (0.70); 6.0805 (0.87); 6.0721 (0.85); 6.0407 (0.75); 5.3006 (9.16); 5.1178 (4.86); 3.8794 (0.74); 3.8399 (0.92); 3.8220 (1.32); 3.7763 (16.00); 3.6772 (1.24); 3.6458 (1.36); 3.6199 (1.10); 3.5881 (0.98); 3.5739 (0.80); 3.5606 (0.79); 3.5455 (0.84); 3.5316 (0.66); 3.5148 (0.48); 3.4990 (0.47); 2.5621 (0.39); 2.5395 (0.61); 2.5287 (0.59); 2.4911 (0.39); 2.4808 (0.41); 2.4689 (0.40); 2.4085 (0.36); 2.3834 (0.40); 2.3150 (0.40); 2.3015 (0.37); 2.2855 (0.41); 2.2745 (0.36); 1.5727 (6.15); 1.2549 (0.47); −0.0002 (8.86); −0.0111 (0.35)

Example I-2, Solvent: $CDCl_3$, Spectrometer: 300.16 MHz
7.7611 (4.23); 7.6197 (0.99); 7.6143 (1.10); 7.5899 (1.32); 7.4830 (0.54); 7.4771 (0.87); 7.4718 (0.44); 7.4547 (2.49); 7.4490 (1.95); 7.4421 (0.89); 7.4305 (2.96); 7.4233 (1.91); 7.4174 (1.66); 7.4086 (1.70); 7.4031 (1.55); 7.3983 (2.05); 7.3917 (2.17); 7.3854 (1.75); 7.3732 (1.85); 7.3677 (1.73); 7.3558 (3.08); 7.3499 (3.55); 7.3434 (1.37); 7.3338 (1.24); 7.3286 (2.16); 7.3241 (1.49); 7.2982 (1.68); 7.2936 (1.40); 7.2913 (1.20); 7.2742 (1.23); 7.2676 (1.12); 7.2600 (7.25); 7.0304 (0.91); 6.8466 (1.94); 6.8328 (1.01); 7.4760 (2.21); 6.6629 (1.01); 6.6497 (2.03); 6.4666 (0.97); 5.7840 (0.75); 5.7532 (1.00); 5.7473 (0.97); 5.7164 (0.78); 5.2982 (7.78); 5.1119 (4.69); 3.8419 (0.35); 3.8159 (0.43); 3.8082 (0.43); 3.7962 (0.42); 3.7567 (16.00); 3.6728 (0.73); 3.6356 (0.85); 3.6150 (1.45); 3.5776 (1.40); 3.5630 (0.78); 3.5471 (0.81);

3.5357 (0.91); 3.5073 (0.59); 3.4897 (0.50); 3.4253 (1.23); 3.3949 (1.20); 3.3675 (0.82); 3.3371 (0.79); 2.5484 (0.41); 2.5241 (0.64); 2.5137 (0.60); 2.4771 (0.42); 2.4657 (0.44); 2.4545 (0.42); 2.3947 (0.37); 2.3816 (0.40); 2.3669 (0.41); 2.2961 (0.37); 2.2844 (0.42); 2.2683 (0.40); 2.2537 (0.47); 1.5800 (3.61); 1.2552 (0.33); −0.0002 (6.02)

Example I-3, Solvent: $CDCl_3$, Spectrometer: 300.16 MHz
7.8125 (5.10); 7.2622 (14.05); 7.1712 (0.58); 7.1404 (1.34); 7.1098 (1.32); 7.0790 (0.62); 7.0351 (1.01); 6.8514 (2.14); 6.8344 (1.09); 6.7997 (0.67); 6.7930 (0.77); 6.7878 (0.75); 6.7811 (0.73); 6.7688 (0.62); 6.7620 (0.74); 6.7477 (2.33); 6.6677 (1.09); 6.6513 (2.24); 6.4683 (1.08); 6.2049 (0.75); 6.1743 (0.92); 6.1648 (0.87); 6.1341 (0.79); 5.3006 (12.04); 5.1181 (4.70); 4.6705 (5.27); 4.6626 (5.35); 3.8451 (0.34); 3.8227 (0.82); 3.7994 (0.45); 3.7759 (16.00); 3.7664 (1.59); 3.7244 (1.01); 3.6800 (1.33); 3.6494 (1.45); 3.6228 (1.03); 3.6082 (0.45); 3.5914 (1.07); 3.5783 (0.88); 3.5625 (0.79); 3.5506 (0.86); 3.5320 (0.49); 3.5157 (0.47); 3.5050 (0.45); 2.5620 (1.07); 2.5362 (0.60); 2.4894 (0.39); 2.4686 (1.57); 2.4607 (2.84); 2.4528 (1.56); 2.4265 (0.35); 2.4128 (0.37); 2.4001 (0.41); 2.3850 (0.36); 2.3220 (0.37); 2.3069 (0.39); 2.2921 (0.41); 2.2767 (0.35); 1.5734 (1.82); −0.0002 (9.79); −0.0111 (0.40)

Example I-4, Solvent: $CDCl_3$, Spectrometer: 300.16 MHz
7.7619 (6.53); 7.4971 (1.09); 7.4928 (1.15); 7.4708 (1.32); 7.4674 (1.29); 7.3278 (0.74); 7.3224 (0.72); 7.3020 (1.46); 7.2760 (1.19); 7.2701 (1.29); 7.2611 (21.14); 7.0486 (1.36); 7.0383 (2.12); 7.0350 (2.29); 7.0264 (2.42); 7.0108 (1.63); 7.0076 (1.67); 7.0013 (1.03); 6.8456 (2.36); 6.8323 (1.08); 6.7447 (2.39); 6.6617 (1.25); 6.6491 (2.19); 6.4661 (1.05); 6.0344 (0.92); 6.0094 (1.01); 5.9973 (0.98); 5.9725 (0.89); 5.3000 (8.74); 5.1088 (4.43); 4.7715 (5.75); 4.7636 (5.76); 3.9342 (1.06); 3.8968 (1.14); 3.8762 (1.39); 3.8389 (1.67); 3.8154 (0.40); 3.8044 (0.44); 3.7916 (0.50); 3.7800 (0.55); 3.7527 (16.00); 3.6210 (0.50); 3.5980 (0.70); 3.5835 (0.97); 3.5776 (1.07); 3.5647 (0.95); 3.5563 (0.85); 3.5480 (0.97); 3.5384 (1.02); 3.5183 (0.45); 3.5033 (0.57); 3.3444 (1.14); 3.3194 (1.10); 3.2864 (0.96); 3.2615 (0.91); 2.5372 (1.39); 2.5286 (2.07); 2.5207 (3.79); 2.5128 (2.11); 2.4683 (0.47); 2.4571 (0.49); 2.4447 (0.51); 2.4336 (0.52); 2.4172 (0.45); 2.4048 (0.48); 2.3916 (0.44); 2.2973 (0.42); 2.2812 (0.42); 2.2672 (0.47); 1.5637 (7.98); 1.2549 (0.44); 0.0106 (0.51); −0.0002 (15.05); −0.0111 (0.57)

Example I-5, Solvent: $CDCl_3$, Spectrometer: 300.16 MHz
7.8024 (4.42); 7.4159 (0.43); 7.3989 (4.30); 7.3881 (4.72); 7.3848 (5.18); 7.3660 (0.75); 7.3592 (0.66); 7.3533 (1.11); 7.3396 (0.92); 7.3314 (0.57); 7.3246 (0.82); 7.3153 (0.43); 7.3101 (0.41); 7.2615 (10.74); 7.0297 (0.88); 6.8944 (0.36); 6.8628 (0.54); 6.8458 (1.99); 6.8329 (0.99); 6.7451 (2.12); 6.6609 (1.43); 6.6498 (1.96); 6.4765 (0.40); 6.4667 (0.96); 5.7855 (0.94); 5.7576 (1.12); 5.7486 (1.12); 5.7207 (0.99); 5.2992 (16.00); 5.1358 (1.08); 5.1262 (1.29); 5.1121 (4.26); 3.9158 (0.85); 3.8788 (0.97); 3.8581 (1.34); 3.8378 (3.19); 3.8212 (1.34); 3.8084 (0.46); 3.7959 (0.40); 3.7617 (15.49); 3.7428 (3.20); 3.6675 (0.37); 3.6473 (0.39); 3.6220 (0.59); 3.6085 (0.65); 3.6017 (0.59); 3.5778 (0.65); 3.5595 (0.88); 3.5407 (0.96); 3.5128 (0.59); 3.4947 (0.48); 3.4841 (0.47); 3.4741 (1.29); 3.4462 (1.11); 3.4164 (0.85); 3.3886 (0.82); 2.5509 (0.41); 2.5284 (0.66); 2.5177 (0.68); 2.4701 (0.60); 2.4559 (0.67); 2.4031 (0.62); 2.3850 (0.50); 2.3700 (0.41); 2.3024 (0.38); 2.2903 (0.43); 2.2741 (0.43); 2.2607 (0.48); −0.0002 (7.54)

Example I-6, Solvent: $CDCl_3$, Spectrometer: 300.16 MHz
7.8147 (5.21); 7.5182 (1.14); 7.5128 (1.19); 7.4919 (1.60); 7.4866 (1.63); 7.4146 (0.69); 7.4092 (0.96); 7.3876 (2.54); 7.3822 (1.93); 7.3664 (2.48); 7.3400 (2.29); 7.3131 (0.76); 7.2712 (1.90); 7.0317 (0.94); 6.8481 (2.01); 6.8345 (1.04); 6.7431 (2.25); 6.6645 (1.06); 6.6513 (2.09); 6.4683 (1.00); 6.3153 (0.89); 6.2798 (1.32); 6.2748 (1.17); 6.2393 (0.94); 5.1185 (4.17); 4.1542 (0.80); 4.1303 (2.45); 4.1065 (2.51); 4.0827 (0.86); 3.9192 (0.74); 3.8783 (0.88); 3.8608 (1.51); 3.8202 (1.47); 3.7996 (0.54); 3.7870 (0.83); 3.7704 (14.63); 3.6842 (1.33); 3.6489 (1.39); 3.6259 (1.23); 3.6087 (0.53); 3.5906 (1.07); 3.5672 (0.84); 3.5524 (0.83); 3.5385 (0.90); 3.5217 (0.64); 3.5060 (0.50); 3.4933 (0.46); 3.2214 (16.00); 2.5297 (0.68); 2.5194 (0.64); 2.4832 (0.42); 2.4723 (0.44); 2.4609 (0.43); 2.4205 (0.35); 2.4088 (0.40); 2.3958 (0.40); 2.3799 (0.44); 2.3099 (0.37); 2.2984 (0.43); 2.2827 (0.42); 2.2684 (0.47); 2.2561 (0.34); 2.0426 (11.21); 1.7127 (1.81); 1.2807 (3.40); 1.2569 (6.80); 1.2331 (3.05); 0.9030 (0.46); 0.8812 (1.41); 0.8580 (0.54); −0.0002 (1.25)

Example I-7, Solvent: $DMSO-d_6$, Spectrometer: 300.16 MHz 8.2082 (5.49); 7.5372 (0.74); 7.5318 (0.80); 7.5099 (1.43); 7.4847 (0.33); 7.4786 (0.69); 7.4721 (0.99); 7.4582 (2.90); 7.4539 (3.55); 7.4365 (1.79); 7.4269 (0.79); 7.4120 (0.90); 7.4066 (0.61); 7.4022 (0.59); 7.3926 (0.42); 7.3828 (0.37); 7.3241 (0.79); 7.2021 (0.93); 7.1466 (1.77); 7.0208 (2.27); 6.9694 (0.87); 6.9034 (2.05); 6.8399 (1.04); 6.0301 (0.70); 6.0037 (0.89); 5.9931 (0.85); 5.9665 (0.74); 5.7584 (1.61); 5.3797 (3.30); 4.0408 (0.85); 4.0170 (1.23); 3.9934 (0.34); 3.9798 (0.44); 3.9747 (0.44); 3.9591 (0.52); 3.9543 (0.52); 3.9177 (0.47); 3.7026 (12.44); 3.6825 (1.06); 3.6269 (0.70); 3.6242 (0.69); 3.5566 (16.00); 3.5093 (0.42); 3.4894 (0.43); 3.4795 (0.44); 3.3823 (0.75); 3.3589 (0.86); 3.3264 (16.50); 3.2994 (0.80); 2.5138 (2.24); 2.5078 (4.64); 2.5017 (6.28); 2.4956 (4.64); 2.4896 (2.34); 2.4561 (0.53); 2.4133 (0.36); 2.3928 (0.33); 2.3549 (0.48); 2.3452 (0.50); 2.3013 (0.41); 2.1454 (0.35); 2.1138 (0.44); 1.9891 (3.80); 1.1981 (1.06); 1.1744 (2.10); 1.1506 (1.04); −0.0002 (7.23)

Example I-8, Solvent: $CDCl_3$, Spectrometer: 300.16 MHz
7.7306 (5.18); 7.5381 (1.01); 7.5331 (0.67); 7.5157 (1.36); 7.4331 (0.47); 7.4274 (0.76); 7.4256 (0.76); 7.4133 (1.46); 7.4054 (0.95); 7.3986 (0.57); 7.3914 (0.75); 7.3841 (1.87); 7.3807 (1.98); 7.3721 (4.61); 7.3682 (4.05); 7.3609 (2.18); 7.3537 (0.96); 7.3413 (0.78); 7.3373 (1.00); 7.3294 (0.48); 7.3234 (0.63); 7.2720 (2.02); 6.9891 (1.87); 6.7324 (0.77); 6.5480 (1.84); 6.3639 (0.86); 6.1868 (2.66); 6.0370 (0.86); 6.0094 (1.10); 5.9995 (0.95); 5.9715 (0.82); 4.7302 (2.64); 3.9767 (0.77); 3.9389 (0.85); 3.9181 (1.05); 3.8805 (0.92); 3.7362 (12.55); 3.6936 (0.47); 3.6731 (0.72); 3.6489 (8.57); 3.6340 (1.34); 3.6133 (0.90); 3.5994 (0.97); 3.5924 (0.97); 3.4554 (1.20); 3.4278 (1.57); 3.3971 (1.54); 3.3692 (1.35); 3.2553 (16.00); 3.2448 (1.09); 3.2402 (0.80); 3.2245 (4.12); 3.2106 (0.49); 3.1798 (0.32); 2.5034 (0.64); 2.4932 (0.60); 2.4809 (0.61); 2.4678 (0.81); 2.4574 (0.89); 2.4479 (0.89); 2.2961 (0.77); 2.2793 (0.76); 2.2654 (0.90); 2.2338 (0.54); 2.2245 (0.45); 1.9998 (4.58); 1.2573 (0.60); −0.0002 (1.08)

Example I-9, Solvent: $CDCl_3$, Spectrometer: 300.16 MHz
8.1644 (1.71); 7.7858 (4.98); 7.5826 (0.93); 7.5765 (0.54); 7.5624 (1.14); 7.5551 (0.99); 7.4527 (0.95); 7.4261 (1.33); 7.4125 (0.48); 7.4013 (1.36); 7.3958 (2.07); 7.3883 (2.13); 7.3864 (2.14); 7.3820 (2.31); 7.3758 (1.77); 7.3677 (1.34); 7.3580 (0.77); 7.3545 (0.77); 7.3490 (0.84); 7.3437 (0.91); 7.3340 (0.64); 7.3236 (0.41); 7.2871 (1.01); 7.2670 (2.89); 7.1004 (0.99); 6.8644 (0.74); 6.8108 (0.73); 6.6819 (1.53); 6.6238 (1.48); 6.4995 (0.77); 6.4369 (0.74); 6.0493 (0.75); 6.0214 (0.92); 6.0117 (0.88); 5.9839 (0.78); 4.1541 (0.40); 4.1303 (1.20); 4.1065 (1.22); 4.0827 (0.42); 3.9981 (0.82); 3.9603 (0.87); 3.9393 (1.09); 3.9016 (0.94); 3.7567 (13.54); 3.7124 (0.45); 3.7005 (0.57); 3.6903 (0.54); 3.6673 (0.73); 3.6538 (0.83); 3.6452 (0.84); 3.6328 (0.64); 3.5240 (0.71); 3.5072 (0.73); 3.4854 (1.62); 3.4575 (1.43); 3.4266 (0.89); 3.3989 (0.85); 3.2609 (16.00); 2.5934 (0.45); 2.5824 (0.58); 2.5714 (0.53); 2.5592 (0.54); 2.5477 (0.74); 2.5367 (0.81);

2.5258 (0.81); 2.5151 (0.62); 2.3892 (0.66); 2.3771 (0.78); 2.3616 (0.77); 2.3475 (0.87); 2.3312 (0.53); 2.3156 (0.54); 2.3033 (0.42); 2.0428 (5.50); 1.6761 (0.91); 1.2808 (1.81); 1.2570 (3.95); 1.2331 (1.56); 0.9029 (0.34); 0.8812 (1.04); 0.8578 (0.40); −0.0002 (1.49)

Example I-10, Solvent: CDCl$_3$, Spectrometer: 300.16 MHz 8.0185 (3.55); 7.7549 (5.22); 7.5655 (1.17); 7.5604 (0.81); 7.5453 (1.27); 7.5406 (1.17); 7.3858 (2.33); 7.3736 (4.49); 7.3693 (3.25); 7.3628 (2.22); 7.3503 (0.88); 7.3465 (1.08); 7.3425 (0.89); 7.3387 (1.17); 7.3305 (0.52); 7.3250 (0.70); 7.3221 (0.71); 7.3087 (0.38); 7.2775 (1.82); 7.2178 (0.93); 7.0156 (2.03); 6.8132 (1.00); 6.2968 (2.18); 6.0424 (0.84); 6.0146 (1.02); 6.0051 (1.03); 5.9771 (0.86); 5.2985 (1.62); 3.9825 (0.88); 3.9447 (0.94); 3.9238 (1.15); 3.8861 (1.00); 3.7400 (13.43); 3.6797 (0.64); 3.6679 (0.86); 3.6593 (0.84); 3.6447 (0.85); 3.6353 (1.01); 3.6220 (1.12); 3.6136 (1.17); 3.6013 (0.89); 3.4633 (1.90); 3.4356 (2.09); 3.4045 (1.49); 3.3770 (1.03); 3.2609 (16.00); 3.2357 (0.39); 3.2312 (0.44); 3.2275 (0.39); 2.5349 (0.79); 2.5244 (0.75); 2.5123 (0.76); 2.4999 (0.98); 2.4891 (1.08); 2.4791 (1.09); 2.3243 (0.98); 2.3070 (1.02); 2.2936 (1.15); 2.2619 (0.76); 2.2008 (8.43); 2.1646 (0.92); 1.9997 (0.88); 1.3699 (0.32); 1.2581 (0.34); −0.0002 (0.53)

Example I-11, Solvent: CDCl$_3$, Spectrometer: 300.16 MHz 7.7723 (5.03); 7.5798 (0.90); 7.5734 (0.50); 7.5599 (1.10); 7.5524 (0.94); 7.4066 (0.53); 7.3956 (1.76); 7.3907 (3.65); 7.3830 (3.22); 7.3807 (2.72); 7.3775 (2.71); 7.3713 (1.91); 7.3648 (1.45); 7.3536 (0.74); 7.3507 (0.72); 7.3453 (0.79); 7.3409 (0.93); 7.3307 (0.61); 7.3211 (0.40); 7.2649 (2.17); 7.0337 (1.16); 7.0081 (1.47); 6.8335 (0.95); 6.8306 (0.93); 6.8080 (0.76); 6.1902 (1.65); 6.0437 (0.73); 6.0158 (0.89); 6.0061 (0.86); 5.9783 (0.77); 5.2917 (3.22); 3.9896 (0.82); 3.9519 (0.85); 3.9309 (1.06); 3.8932 (0.92); 3.7452 (13.53); 3.6856 (0.42); 3.6829 (0.41); 3.6736 (0.56); 3.6639 (0.52); 3.6504 (0.54); 3.6405 (0.68); 3.6273 (0.78); 3.6184 (0.81); 3.6061 (0.62); 3.4873 (0.69); 3.4760 (1.45); 3.4594 (0.78); 3.4483 (1.56); 3.4171 (1.28); 3.3895 (0.88); 3.2510 (16.00); 3.2359 (0.97); 2.5681 (0.40); 2.5574 (0.53); 2.5462 (0.48); 2.5343 (0.49); 2.5228 (0.68); 2.5119 (0.75); 2.5012 (0.77); 2.4900 (0.62); 2.3583 (0.59); 2.3462 (0.72); 2.3306 (0.71); 2.3161 (0.85); 2.3004 (0.57); 2.2779 (7.80); 2.1741 (7.75); 1.2575 (0.39); −0.0002 (0.69)

Example I-12, Solvent: CDCl$_3$, Spectrometer: 300.2 MHz 7.754 (5.6); 7.486 (1.1); 7.481 (1.3); 7.460 (1.6); 7.455 (1.8); 7.414 (0.7); 7.409 (1.1); 7.387 (2.6); 7.382 (2.0); 7.367 (2.6); 7.341 (2.2); 7.314 (0.7); 7.270 (3.4); 6.887 (2.2); 6.740 (0.9); 6.556 (2.1); 6.372 (1.0); 6.293 (0.9); 6.258 (1.3); 6.253 (1.2); 6.217 (1.0); 6.197 (2.9); 5.301 (2.4); 4.126 (0.5); 4.103 (0.6); 3.895 (0.7); 3.854 (0.9); 3.837 (1.3); 3.796 (1.2); 3.752 (13.3); 3.682 (2.0); 3.667 (9.3); 3.647 (2.2); 3.636 (1.2); 3.624 (1.7); 3.600 (0.9); 3.589 (1.0); 3.455 (0.8); 3.421 (1.0); 3.387 (0.6); 3.213 (16.0); 2.522 (0.7); 2.511 (0.6); 2.499 (0.6); 2.486 (0.9); 2.476 (0.9); 2.466 (0.9); 2.318 (0.8); 2.301 (0.8); 2.287 (1.0); 2.256 (0.6); 2.042 (2.4); 1.814 (0.5); 1.280 (0.8); 1.256 (2.0); 1.232 (0.8); 0.000 (1.6)

Example I-13, Solvent: CDCl$_3$, Spectrometer: 300.2 MHz 8.011 (3.4); 7.774 (5.7); 7.489 (1.1); 7.484 (1.2); 7.463 (1.7); 7.457 (1.8); 7.408 (0.7); 7.402 (1.1); 7.381 (2.8); 7.375 (2.1); 7.360 (2.6); 7.346 (0.3); 7.333 (2.2); 7.306 (0.8); 7.282 (1.5); 7.220 (0.9); 7.018 (2.1); 6.816 (1.0); 6.321 (1.9); 6.294 (0.9); 6.258 (1.2); 6.253 (1.1); 6.218 (0.9); 5.300 (8.6); 3.901 (0.6); 3.860 (0.8); 3.843 (1.2); 3.802 (1.0); 3.750 (13.5); 3.678 (1.6); 3.643 (1.8); 3.632 (0.9); 3.620 (1.4); 3.584 (1.0); 3.490 (0.4); 3.471 (0.7); 3.468 (0.6); 3.462 (0.6); 3.454 (0.8); 3.444 (0.8); 3.435 (0.7); 3.432 (0.7); 3.417 (0.4); 3.408 (0.4); 3.399 (0.5); 3.246 (2.3); 3.217 (16.0); 2.551 (0.4); 2.541 (0.5); 2.531 (0.5); 2.519 (0.5); 2.506 (0.7); 2.496 (0.8); 2.485 (0.8); 2.337 (0.5); 2.326 (0.7); 2.310 (0.7); 2.296 (0.8); 2.282 (0.5); 2.264 (0.5); 2.254 (0.4); 2.195 (7.5); 1.961 (0.7); 0.000 (1.0)

Example I-14, Solvent: CDCl$_3$, Spectrometer: 300.2 MHz 7.903 (3.4); 7.805 (5.6); 7.511 (1.1); 7.505 (1.2); 7.485 (1.5); 7.479 (1.6); 7.406 (0.7); 7.401 (1.0); 7.379 (2.6); 7.374 (1.9); 7.359 (2.5); 7.333 (2.2); 7.306 (0.8); 7.286 (1.5); 6.912 (0.9); 6.730 (1.9); 6.696 (1.0); 6.547 (0.9); 6.305 (0.8); 6.270 (1.2); 6.265 (1.1); 6.229 (0.9); 5.302 (9.4); 3.922 (0.7); 3.881 (0.8); 3.863 (1.3); 3.840 (7.1); 3.823 (1.2); 3.756 (14.1); 3.680 (1.4); 3.669 (0.6); 3.658 (0.6); 3.644 (1.5); 3.636 (0.8); 3.621 (1.4); 3.613 (0.9); 3.603 (0.8); 3.586 (1.0); 3.475 (0.7); 3.466 (0.6); 3.447 (0.8); 3.439 (0.8); 3.420 (0.4); 3.411 (0.4); 3.402 (0.5); 3.221 (16.0); 3.191 (1.0); 2.581 (0.4); 2.569 (0.6); 2.563 (1.5); 2.548 (0.5); 2.536 (0.7); 2.525 (0.8); 2.515 (0.8); 2.505 (0.6); 2.368 (0.7); 2.356 (0.8); 2.341 (0.8); 2.326 (0.9); 2.310 (0.6); 2.295 (0.7); 2.282 (0.5); 0.000 (0.9)

Example I-15, Solvent: CDCl$_3$, Spectrometer: 300.2 MHz 7.704 (6.2); 7.464 (1.0); 7.460 (1.1); 7.438 (1.2); 7.434 (1.2); 7.329 (0.6); 7.323 (0.6); 7.303 (1.2); 7.298 (1.0); 7.276 (0.9); 7.270 (1.1); 7.263 (15.1); 7.255 (0.4); 7.041 (1.2); 7.034 (1.9); 7.031 (1.7); 7.019 (1.7); 7.007 (1.5); 7.004 (1.4); 6.994 (0.9); 6.751 (1.0); 6.567 (2.4); 6.549 (2.0); 6.383 (1.1); 6.246 (2.7); 6.023 (0.7); 5.998 (0.9); 5.986 (0.9); 5.961 (0.8); 4.762 (5.2); 4.754 (5.4); 3.919 (0.9); 3.881 (1.0); 3.861 (1.2); 3.824 (1.1); 3.743 (16.0); 3.708 (9.3); 3.682 (0.8); 3.679 (0.8); 3.635 (0.9); 3.494 (0.8); 3.485 (0.6); 3.476 (0.6); 3.468 (0.8); 3.458 (0.8); 3.431 (0.5); 3.421 (0.5); 3.339 (1.2); 3.314 (1.2); 3.281 (1.0); 3.256 (1.0); 2.547 (0.6); 2.536 (0.7); 2.526 (2.1); 2.518 (3.9); 2.510 (2.3); 2.503 (1.0); 2.490 (0.9); 2.360 (0.7); 2.345 (0.8); 2.331 (0.8); 2.315 (0.7); 2.299 (0.5); 2.285 (0.5); 2.007 (2.0); 1.255 (0.4); 0.000 (8.1); −0.011 (0.4)

Example I-16, Solvent: CDCl$_3$, Spectrometer: 300.2 MHz 7.761 (5.9); 7.263 (25.1); 7.180 (0.4); 7.174 (0.6); 7.144 (1.3); 7.113 (1.3); 7.082 (0.6); 6.797 (0.7); 6.790 (0.8); 6.785 (0.8); 6.779 (0.8); 6.766 (0.7); 6.755 (1.7); 6.717 (0.4); 6.571 (2.3); 6.533 (0.5); 6.444 (2.0); 6.387 (1.1); 6.259 (2.8); 6.203 (0.8); 6.172 (0.9); 6.163 (0.9); 6.132 (0.8); 5.709 (0.6); 4.667 (5.2); 4.659 (5.3); 4.646 (1.5); 4.638 (1.3); 4.572 (0.3); 4.553 (0.4); 4.537 (0.4); 4.520 (0.4); 3.811 (0.6); 3.768 (16.0); 3.756 (1.6); 3.720 (10.2); 3.682 (1.1); 3.670 (1.9); 3.640 (1.8); 3.613 (0.6); 3.583 (0.6); 3.509 (0.9); 3.492 (1.0); 3.478 (1.0); 3.461 (0.6); 3.452 (0.6); 3.444 (0.6); 3.433 (0.5); 3.417 (0.4); 3.387 (0.4); 2.567 (0.8); 2.537 (0.9); 2.527 (0.9); 2.515 (0.9); 2.504 (1.0); 2.496 (1.0); 2.488 (0.5); 2.469 (1.5); 2.461 (3.1); 2.453 (1.5); 2.397 (0.4); 2.384 (0.8); 2.370 (0.8); 2.355 (0.9); 2.339 (0.8); 2.324 (0.6); 2.310 (0.5); 2.009 (4.2); 1.680 (0.7); 1.255 (0.5); 0.011 (0.5); 0.000 (15.9); −0.011 (0.7)

Example I-17, Solvent: CDCl$_3$, Spectrometer: 300.2 MHz 8.043 (3.6); 7.719 (6.1); 7.480 (0.9); 7.479 (0.9); 7.474 (1.0); 7.454 (1.1); 7.452 (1.1); 7.449 (1.2); 7.322 (0.6); 7.316 (0.6); 7.295 (1.2); 7.292 (0.9); 7.267 (4.5); 7.217 (1.0); 7.038 (1.2); 7.032 (1.9); 7.028 (1.7); 7.015 (3.9); 7.004 (1.6); 7.001 (1.4); 6.991 (0.8); 6.812 (1.1); 6.153 (1.9); 6.022 (0.7); 5.997 (0.9); 5.985 (0.9); 5.960 (0.8); 4.763 (5.2); 4.755 (5.2); 3.923 (0.9); 3.885 (1.0); 3.865 (1.2); 3.827 (1.1); 3.736 (16.0); 3.680 (0.4); 3.667 (0.6); 3.658 (0.5); 3.634 (0.7); 3.621 (0.8); 3.612 (0.9); 3.600 (0.7); 3.487 (0.8); 3.476 (0.6); 3.470 (0.6); 3.459 (0.9); 3.450 (0.7); 3.430 (0.4); 3.424 (0.4); 3.413 (0.6); 3.338 (1.2); 3.313 (1.2); 3.281 (1.0); 3.256 (1.0); 2.555 (0.4); 2.544 (0.6); 2.530 (1.9); 2.522 (3.7); 2.514 (2.0); 2.498

(0.9); 2.487 (0.9); 2.477 (0.7); 2.350 (0.7); 2.338 (0.7); 2.324 (0.9); 2.314 (0.7); 2.290 (0.5); 2.277 (0.5); 2.215 (8.3); 2.004 (5.3); 1.797 (0.4); 0.000 (2.4)

Example I-18, Solvent: CDCl$_3$, Spectrometer: 300.2 MHz
8.039 (3.5); 7.761 (6.0); 7.272 (3.4); 7.218 (1.0); 7.165 (0.5); 7.135 (1.2); 7.104 (1.2); 7.073 (0.6); 7.016 (2.3); 6.813 (1.1); 6.791 (0.6); 6.784 (0.7); 6.779 (0.7); 6.772 (0.7); 6.760 (0.5); 6.753 (0.6); 6.748 (0.6); 6.742 (0.5); 6.223 (2.0); 6.193 (0.7); 6.162 (0.9); 6.153 (0.8); 6.122 (0.7); 4.663 (4.9); 4.655 (5.0); 3.811 (0.4); 3.769 (0.6); 3.756 (16.0); 3.713 (1.0); 3.703 (0.5); 3.689 (0.6); 3.670 (1.5); 3.657 (0.8); 3.639 (1.8); 3.622 (0.7); 3.614 (0.7); 3.582 (0.5); 3.487 (0.7); 3.467 (0.7); 3.455 (0.8); 3.442 (0.5); 3.421 (0.5); 3.413 (0.4); 2.567 (0.4); 2.557 (0.6); 2.545 (0.5); 2.533 (0.5); 2.522 (0.7); 2.511 (0.8); 2.500 (0.8); 2.468 (1.4); 2.461 (3.1); 2.453 (1.4); 2.369 (0.4); 2.358 (0.7); 2.344 (0.8); 2.329 (0.9); 2.314 (0.7); 2.298 (0.5); 2.284 (0.5); 2.213 (8.0); 2.006 (8.0); 2.000 (0.4); 1.826 (0.3); 0.000 (1.9)

Example I-19, Solvent: CDCl$_3$, Spectrometer: 300.2 MHz
7.911 (3.0); 7.786 (4.9); 7.583 (0.8); 7.577 (0.5); 7.575 (0.4); 7.563 (1.0); 7.556 (0.9); 7.416 (0.4); 7.404 (1.3); 7.399 (1.8); 7.392 (1.9); 7.390 (1.8); 7.384 (2.0); 7.378 (1.5); 7.369 (1.2); 7.360 (0.7); 7.357 (0.7); 7.351 (0.7); 7.345 (0.8); 7.336 (0.6); 7.325 (0.3); 7.269 (4.0); 6.907 (0.8); 6.724 (1.6); 6.639 (1.0); 6.542 (0.8); 6.048 (0.7); 6.020 (0.8); 6.010 (0.8); 5.983 (0.7); 4.734 (0.4); 3.995 (0.8); 3.957 (0.8); 3.936 (1.0); 3.899 (0.9); 3.841 (6.2); 3.749 (13.4); 3.648 (0.5); 3.615 (0.6); 3.601 (0.7); 3.594 (0.7); 3.581 (0.5); 3.484 (1.3); 3.473 (0.6); 3.466 (0.6); 3.456 (1.5); 3.438 (0.7); 3.425 (1.2); 3.397 (1.1); 3.264 (16.0); 3.233 (0.7); 2.579 (0.4); 2.568 (0.5); 2.557 (0.4); 2.545 (0.4); 2.533 (0.6); 2.522 (0.7); 2.512 (0.7); 2.501 (0.5); 2.369 (0.6); 2.356 (0.7); 2.341 (0.7); 2.326 (0.8); 2.310 (0.5); 2.295 (0.5); 2.282 (0.4); 2.006 (3.4); 1.743 (0.4); 0.000 (2.5)

Example I-20, Solvent: CDCl$_3$, Spectrometer: 300.2 MHz
7.910 (3.5); 7.756 (5.8); 7.493 (0.8); 7.491 (0.9); 7.486 (0.9); 7.466 (1.0); 7.464 (1.1); 7.461 (1.0); 7.317 (0.5); 7.311 (0.5); 7.291 (1.1); 7.287 (0.9); 7.284 (0.8); 7.267 (3.7); 7.259 (0.8); 7.038 (1.1); 7.030 (1.7); 7.027 (1.6); 7.015 (1.6); 7.002 (1.3); 6.999 (1.3); 6.991 (0.8); 6.905 (0.9); 6.722 (1.9); 6.635 (1.1); 6.540 (0.9); 6.022 (0.7); 5.997 (0.8); 5.984 (0.8); 5.959 (0.7); 4.767 (4.9); 4.759 (5.0); 3.935 (0.9); 3.898 (1.0); 3.877 (1.2); 3.839 (8.0); 3.735 (16.0); 3.647 (0.4); 3.634 (0.6); 3.624 (0.5); 3.610 (0.6); 3.602 (0.8); 3.588 (0.8); 3.579 (0.9); 3.566 (0.7); 3.486 (0.5); 3.474 (0.7); 3.466 (0.6); 3.457 (0.6); 3.449 (0.7); 3.439 (0.7); 3.421 (0.4); 3.412 (0.4); 3.404 (0.5); 3.347 (1.2); 3.322 (1.1); 3.289 (1.0); 3.264 (1.0); 2.564 (0.4); 2.553 (0.5); 2.542 (0.5); 2.535 (0.7); 2.529 (1.9); 2.521 (3.8); 2.513 (2.0); 2.496 (0.8); 2.485 (0.6); 2.366 (0.6); 2.358 (0.6); 2.339 (0.6); 2.326 (0.8); 2.313 (0.4); 2.293 (0.4); 2.285 (0.4); 1.724 (0.5); 0.000 (2.3)

Example I-21, Solvent: CDCl$_3$, Spectrometer: 300.2 MHz
7.910 (3.8); 7.805 (5.9); 7.277 (2.4); 7.162 (0.5); 7.132 (1.3); 7.123 (0.4); 7.101 (1.3); 7.070 (0.6); 6.908 (1.0); 6.792 (0.7); 6.785 (0.8); 6.780 (0.7); 6.774 (0.7); 6.761 (0.7); 6.754 (0.8); 6.749 (0.7); 6.743 (0.7); 6.726 (2.1); 6.657 (1.3); 6.543 (1.0); 6.190 (0.8); 6.160 (0.9); 6.150 (0.9); 6.120 (0.8); 4.663 (5.3); 4.655 (5.4); 3.842 (7.8); 3.827 (0.7); 3.784 (0.6); 3.758 (16.0); 3.728 (1.1); 3.683 (1.2); 3.652 (1.6); 3.625 (1.2); 3.606 (0.9); 3.595 (1.1); 3.486 (0.9); 3.478 (0.7); 3.469 (0.7); 3.460 (0.8); 3.450 (0.8); 3.430 (0.6); 3.415 (0.5); 2.581 (0.5); 2.564 (3.9); 2.545 (0.8); 2.537 (1.3); 2.529 (1.0); 2.515 (0.9); 2.504 (0.7); 2.467 (1.5); 2.459 (3.1); 2.451 (1.4); 2.391 (0.4); 2.378 (0.8); 2.364 (0.9); 2.349 (0.9); 2.334 (0.8); 2.318 (0.6); 2.304 (0.5); 2.006 (11.4); 0.000 (1.3)

Example I-22, Solvent: CDCl$_3$, Spectrometer: 300.2 MHz
7.809 (5.0); 7.510 (0.9); 7.505 (1.0); 7.484 (1.3); 7.479 (1.4); 7.414 (0.6); 7.408 (0.9); 7.387 (2.2); 7.381 (1.7); 7.365 (2.3); 7.339 (2.0); 7.312 (0.7); 7.278 (1.3); 7.032 (0.7); 6.848 (1.6); 6.837 (0.8); 6.742 (1.7); 6.665 (0.8); 6.654 (1.8); 6.471 (0.8); 6.312 (0.7); 6.277 (1.0); 6.272 (1.0); 6.236 (0.8); 5.124 (3.2); 4.271 (0.9); 4.247 (3.0); 4.224 (3.1); 4.200 (1.0); 3.916 (0.6); 3.875 (0.9); 3.858 (1.3); 3.828 (0.3); 3.817 (1.1); 3.686 (1.1); 3.651 (1.1); 3.640 (0.4); 3.628 (1.0); 3.592 (0.7); 3.560 (0.3); 3.539 (0.6); 3.510 (0.4); 3.497 (0.4); 3.221 (14.2); 2.529 (0.5); 2.519 (0.5); 2.252 (0.4); 1.998 (16.0); 1.990 (0.5); 1.989 (0.3); 1.284 (3.4); 1.260 (7.3); 1.236 (3.3); 0.000 (0.6)

Example I-23, Solvent: CDCl$_3$, Spectrometer: 300.2 MHz
7.745 (3.7); 7.613 (0.9); 7.608 (1.0); 7.587 (1.0); 7.583 (1.2); 7.473 (0.5); 7.467 (0.9); 7.462 (0.4); 7.451 (0.6); 7.445 (2.3); 7.439 (1.6); 7.429 (0.8); 7.425 (1.3); 7.421 (2.8); 7.418 (2.1); 7.411 (1.5); 7.404 (1.8); 7.398 (1.6); 7.393 (1.3); 7.386 (2.0); 7.380 (2.2); 7.375 (1.8); 7.362 (1.7); 7.356 (1.8); 7.348 (2.9); 7.342 (3.1); 7.338 (1.4); 7.334 (1.0); 7.332 (1.0); 7.326 (1.2); 7.320 (2.1); 7.316 (1.4); 7.288 (1.6); 7.284 (1.3); 7.281 (1.1); 7.265 (1.3); 7.261 (1.6); 7.259 (1.0); 7.023 (1.8); 6.840 (1.3); 6.829 (1.0); 6.737 (2.0); 6.656 (1.0); 6.646 (2.0); 6.463 (0.9); 5.775 (0.7); 5.744 (0.9); 5.738 (0.9); 5.707 (0.7); 5.117 (4.1); 4.252 (1.1); 4.228 (3.7); 4.205 (3.8); 4.181 (1.2); 3.846 (0.3); 3.835 (0.4); 3.824 (0.3); 3.671 (0.7); 3.634 (0.9); 3.613 (1.4); 3.576 (1.0); 3.556 (0.4); 3.545 (0.4); 3.527 (0.5); 3.512 (0.6); 3.497 (0.5); 3.481 (0.6); 3.469 (0.5); 3.426 (1.1); 3.396 (1.0); 3.369 (0.7); 3.338 (0.6); 2.537 (0.4); 2.517 (0.6); 2.507 (0.6); 2.470 (0.4); 2.460 (0.4); 2.449 (0.4); 2.335 (0.4); 2.259 (0.4); 2.243 (0.4); 2.228 (0.4); 1.977 (16.0); 1.969 (0.5); 1.968 (0.3); 1.265 (4.0); 1.241 (8.7); 1.218 (3.9); 0.000 (0.5)

Example I-24, Solvent: CDCl$_3$, Spectrometer: 300.2 MHz
7.823 (6.9); 7.357 (0.4); 7.335 (0.9); 7.328 (0.8); 7.314 (0.6); 7.307 (1.7); 7.301 (0.7); 7.286 (0.9); 7.280 (2.2); 7.258 (0.5); 7.031 (1.4); 6.959 (0.4); 6.947 (2.6); 6.935 (0.5); 6.931 (0.5); 6.919 (4.7); 6.908 (0.6); 6.903 (0.5); 6.892 (2.2); 6.880 (0.4); 6.847 (3.1); 6.835 (1.6); 6.738 (3.2); 6.664 (1.6); 6.651 (3.2); 6.468 (1.5); 6.103 (1.0); 6.071 (1.3); 6.063 (1.2); 6.032 (1.1); 5.128 (6.8); 4.272 (1.6); 4.248 (5.0); 4.225 (5.1); 4.201 (1.7); 3.894 (0.5); 3.877 (1.1); 3.838 (1.2); 3.820 (1.4); 3.780 (1.2); 3.675 (1.7); 3.662 (0.5); 3.644 (1.9); 3.617 (1.3); 3.586 (0.9); 3.573 (0.6); 3.563 (0.6); 3.534 (1.0); 3.495 (0.9); 3.461 (0.5); 3.451 (0.4); 2.589 (0.4); 2.580 (0.4); 2.567 (0.4); 2.554 (0.6); 2.533 (0.9); 2.523 (0.9); 2.499 (0.5); 2.486 (0.6); 2.475 (0.6); 2.465 (0.6); 2.396 (0.5); 2.363 (0.6); 2.335 (0.4); 2.328 (0.4); 2.290 (0.5); 2.278 (0.5); 2.261 (0.6); 2.249 (0.5); 2.230 (0.3); 2.217 (0.4); 1.992 (16.0); 1.284 (5.2); 1.261 (10.9); 1.237 (5.1); 0.000 (0.7)

Example I-25, Solvent: CDCl$_3$, Spectrometer: 300.2 MHz
7.791 (7.9); 7.410 (0.8); 7.393 (8.4); 7.383 (8.4); 7.378 (8.3); 7.377 (8.0); 7.367 (1.0); 7.359 (1.4); 7.353 (1.6); 7.346 (2.1); 7.336 (1.7); 7.332 (1.4); 7.324 (1.2); 7.318 (1.5); 7.312 (0.5); 7.310 (0.5); 7.307 (0.6); 7.303 (0.6); 7.297 (0.4); 7.266 (3.3); 7.027 (1.7); 6.843 (3.7); 6.832 (1.9); 6.739 (3.9); 6.660 (1.9); 6.649 (3.8); 6.466 (1.8); 5.776 (1.8); 5.748 (2.2); 5.739 (2.1); 5.711 (1.9); 5.115 (8.1); 4.261 (2.2); 4.237 (7.1); 4.213 (7.3); 4.189 (2.4); 3.910 (1.7); 3.873 (2.3); 3.853 (2.9); 3.831 (0.8); 3.816 (2.6); 3.674 (2.4); 3.664 (0.4); 3.653 (0.4); 3.640 (0.6); 3.628 (0.8); 3.617 (0.8); 3.608 (0.8); 3.565 (0.7); 3.554 (0.9); 3.536 (1.1); 3.525 (1.4); 3.507 (0.9); 3.490 (1.1); 3.471

(2.8); 3.443 (2.5); 3.413 (1.8); 3.385 (1.8); 2.578 (0.5); 2.569 (0.5); 2.556 (0.5); 2.544 (0.7); 2.523 (1.2); 2.512 (1.1); 2.487 (0.6); 2.476 (0.7); 2.464 (0.7); 2.454 (0.7); 2.394 (0.6); 2.382 (0.7); 2.367 (0.7); 2.352 (0.8); 2.337 (0.5); 2.321 (0.5); 2.309 (0.4); 2.280 (0.6); 2.268 (0.7); 2.252 (0.7); 2.238 (0.9); 2.223 (0.5); 2.215 (0.4); 2.206 (0.5); 2.194 (0.4); 1.991 (15.7); 1.985 (0.6); 1.983 (0.4); 1.762 (0.4); 1.274 (7.5); 1.250 (16.0); 1.227 (7.3); 0.000 (1.7)

Example I-26, Solvent: CDCl$_3$, Spectrometer: 300.2 MHz
7.791 (4.2); 7.587 (0.9); 7.581 (0.5); 7.566 (1.1); 7.559 (0.9); 7.406 (1.1); 7.401 (2.0); 7.392 (2.2); 7.388 (2.9); 7.382 (2.0); 7.375 (1.4); 7.364 (0.7); 7.360 (0.7); 7.356 (0.7); 7.351 (0.9); 7.340 (0.5); 7.332 (0.4); 7.268 (2.8); 7.031 (0.7); 6.848 (1.5); 6.835 (0.7); 6.744 (1.8); 6.664 (0.8); 6.652 (1.4); 6.469 (0.7); 6.056 (0.7); 6.028 (0.9); 6.018 (0.8); 5.990 (0.7); 5.118 (3.3); 4.266 (0.9); 4.242 (2.9); 4.218 (3.0); 4.194 (1.0); 3.995 (0.7); 3.957 (0.7); 3.936 (0.9); 3.899 (0.9); 3.824 (0.4); 3.627 (0.4); 3.563 (0.4); 3.545 (0.5); 3.534 (0.7); 3.516 (0.4); 3.497 (0.6); 3.482 (1.3); 3.455 (1.2); 3.424 (0.8); 3.396 (0.8); 3.265 (16.0); 2.528 (0.6); 2.517 (0.5); 2.482 (0.3); 2.470 (0.4); 2.460 (0.4); 2.372 (0.4); 2.270 (0.3); 2.254 (0.3); 2.240 (0.4); 2.003 (9.1); 1.280 (3.0); 1.256 (6.4); 1.232 (3.0); 0.000 (1.4)

Example I-27, Solvent: CDCl$_3$, Spectrometer: 300.2 MHz
7.752 (6.6); 7.488 (1.0); 7.483 (1.2); 7.462 (1.3); 7.458 (1.3); 7.322 (0.6); 7.317 (0.6); 7.296 (1.3); 7.292 (1.0); 7.290 (1.0); 7.269 (2.6); 7.265 (1.0); 7.040 (1.6); 7.035 (2.2); 7.032 (2.1); 7.028 (1.5); 7.018 (1.9); 7.015 (1.8); 7.008 (1.7); 7.005 (1.6); 6.993 (0.9); 6.843 (2.3); 6.833 (1.1); 6.740 (2.4); 6.660 (1.2); 6.650 (2.2); 6.467 (1.0); 6.024 (0.8); 5.999 (1.0); 5.987 (1.0); 5.962 (0.9); 5.114 (4.4); 4.765 (5.3); 4.757 (5.4); 4.252 (1.1); 4.228 (3.5); 4.205 (3.6); 4.181 (1.2); 3.931 (1.0); 3.893 (1.1); 3.873 (1.5); 3.856 (0.4); 3.835 (1.5); 3.822 (0.4); 3.810 (0.5); 3.800 (0.4); 3.628 (0.4); 3.608 (0.6); 3.595 (0.4); 3.553 (0.6); 3.538 (0.8); 3.527 (0.8); 3.509 (0.7); 3.493 (0.6); 3.481 (0.5); 3.464 (0.3); 3.346 (1.2); 3.321 (1.2); 3.288 (1.0); 3.263 (1.0); 2.535 (1.8); 2.528 (3.5); 2.520 (2.0); 2.502 (0.7); 2.476 (0.4); 2.464 (0.5); 2.453 (0.5); 2.443 (0.5); 2.432 (0.4); 2.396 (0.4); 2.383 (0.4); 2.368 (0.4); 2.276 (0.4); 2.257 (0.4); 2.244 (0.5); 1.994 (16.0); 1.985 (0.4); 1.267 (3.9); 1.243 (8.1); 1.220 (3.8); 0.000 (0.9)

Example I-28, Solvent: CDCl$_3$, Spectrometer: 300.2 MHz
7.801 (5.1); 7.277 (1.6); 7.168 (0.5); 7.137 (1.3); 7.106 (1.3); 7.075 (0.6); 7.032 (1.0); 6.849 (2.1); 6.835 (1.1); 6.798 (0.6); 6.791 (0.8); 6.786 (0.7); 6.779 (0.7); 6.767 (0.6); 6.760 (0.7); 6.755 (0.7); 6.742 (2.3); 6.665 (1.1); 6.652 (2.3); 6.469 (1.1); 6.198 (0.7); 6.168 (0.9); 6.158 (0.9); 6.127 (0.8); 5.126 (4.7); 4.665 (4.8); 4.657 (4.9); 4.273 (1.1); 4.250 (3.6); 4.226 (3.7); 4.202 (1.2); 3.860 (0.3); 3.848 (0.4); 3.837 (0.4); 3.821 (0.7); 3.779 (0.5); 3.762 (1.0); 3.723 (1.0); 3.679 (1.3); 3.649 (1.5); 3.622 (0.9); 3.591 (0.6); 3.580 (0.4); 3.569 (0.5); 3.552 (0.7); 3.541 (0.8); 3.521 (0.6); 3.508 (0.6); 2.532 (0.6); 2.522 (0.6); 2.497 (0.3); 2.476 (1.6); 2.468 (3.0); 2.460 (1.7); 2.396 (0.4); 2.381 (0.4); 2.366 (0.4); 2.300 (0.4); 2.285 (0.4); 2.270 (0.4); 2.255 (0.4); 2.223 (0.3); 1.999 (16.0); 1.287 (3.5); 1.263 (7.3); 1.239 (3.4); 0.000 (0.8)

Example I-29, Solvent: CDCl$_3$, Spectrometer: 300.2 MHz
7.803 (5.6); 7.512 (1.0); 7.506 (1.2); 7.485 (1.5); 7.480 (1.6); 7.412 (0.6); 7.406 (1.0); 7.385 (2.4); 7.379 (1.9); 7.363 (2.5); 7.337 (2.3); 7.310 (0.8); 7.275 (1.4); 7.034 (0.9); 6.851 (1.9); 6.836 (1.0); 6.742 (2.0); 6.667 (1.0); 6.653 (2.1); 6.470 (1.0); 6.312 (0.8); 6.277 (1.0); 6.272 (1.1); 6.236 (0.9); 5.124 (4.0); 5.112 (1.4); 5.091 (1.3); 5.070 (1.0); 5.050 (0.4); 3.912 (1.0); 3.900 (0.4); 3.889 (0.4); 3.871 (1.0); 3.854 (1.3); 3.813 (1.1); 3.686 (1.3); 3.650 (1.4); 3.627 (0.9); 3.592 (0.7); 3.551 (0.4); 3.516 (0.4); 3.495 (0.3); 3.482 (0.5); 3.469 (0.5); 3.449 (0.5); 3.438 (0.4); 3.217 (16.0); 2.524 (0.6); 2.514 (0.6); 2.478 (0.4); 2.467 (0.4); 2.458 (0.4); 2.342 (0.4); 2.251 (0.4); 2.233 (0.4); 2.220 (0.5); 1.996 (1.6); 1.781 (0.4); 1.258 (4.5); 1.247 (5.0); 1.237 (4.9); 1.227 (4.7); 0.000 (0.7)

Example I-30, Solvent: CDCl$_3$, Spectrometer: 300.2 MHz
7.744 (4.9); 7.616 (1.5); 7.611 (1.7); 7.590 (1.8); 7.586 (2.0); 7.474 (0.8); 7.468 (1.4); 7.463 (0.7); 7.452 (1.0); 7.446 (3.9); 7.440 (2.9); 7.432 (1.3); 7.426 (2.1); 7.422 (4.6); 7.414 (2.9); 7.407 (2.6); 7.400 (2.7); 7.394 (2.3); 7.389 (3.3); 7.382 (3.5); 7.376 (2.9); 7.364 (2.9); 7.358 (2.9); 7.349 (4.9); 7.343 (5.3); 7.335 (1.9); 7.327 (2.0); 7.322 (3.6); 7.317 (2.5); 7.310 (0.5); 7.290 (2.6); 7.286 (2.2); 7.283 (1.9); 7.266 (1.9); 7.260 (3.4); 7.028 (1.4); 6.844 (3.1); 6.830 (1.6); 6.739 (3.4); 6.661 (1.6); 6.647 (3.3); 6.464 (1.6); 5.775 (1.1); 5.744 (1.6); 5.738 (1.5); 5.707 (1.2); 5.118 (7.4); 5.102 (2.1); 5.081 (2.4); 5.060 (1.8); 5.039 (0.7); 3.954 (0.5); 3.944 (0.5); 3.934 (0.5); 3.921 (0.5); 3.908 (0.6); 3.898 (0.6); 3.888 (0.6); 3.667 (1.5); 3.629 (2.0); 3.609 (2.4); 3.572 (1.8); 3.540 (0.5); 3.530 (0.7); 3.511 (0.7); 3.499 (0.8); 3.483 (0.5); 3.463 (0.6); 3.450 (0.8); 3.423 (1.8); 3.393 (1.7); 3.366 (1.2); 3.335 (0.9); 2.570 (0.5); 2.550 (0.5); 2.514 (1.0); 2.504 (0.9); 2.481 (0.5); 2.465 (0.6); 2.454 (0.7); 2.447 (0.7); 2.346 (0.5); 2.336 (0.5); 2.318 (0.5); 2.304 (0.7); 2.272 (0.4); 2.261 (0.4); 2.239 (0.5); 2.227 (0.6); 2.206 (0.6); 2.195 (0.8); 2.182 (0.5); 2.164 (0.4); 2.151 (0.3); 1.982 (16.0); 1.792 (0.3); 1.245 (7.0); 1.232 (8.4); 1.225 (8.0); 1.212 (7.5); 0.000 (0.9)

Example I-31, Solvent: CDCl$_3$, Spectrometer: 300.2 MHz
7.827 (12.8); 7.358 (0.9); 7.337 (1.8); 7.329 (1.5); 7.316 (1.2); 7.309 (3.6); 7.302 (1.4); 7.287 (1.6); 7.281 (2.3); 7.275 (0.5); 7.269 (7.3); 7.260 (1.2); 7.037 (3.0); 6.967 (0.6); 6.962 (0.9); 6.950 (5.4); 6.939 (0.9); 6.934 (1.0); 6.922 (9.6); 6.911 (1.2); 6.906 (0.9); 6.895 (4.6); 6.883 (0.8); 6.879 (0.6); 6.853 (6.3); 6.835 (3.2); 6.744 (6.3); 6.669 (3.2); 6.652 (6.6); 6.469 (3.2); 6.108 (2.1); 6.076 (2.5); 6.068 (2.4); 6.037 (2.2); 5.139 (1.7); 5.125 (14.9); 5.098 (4.3); 5.077 (3.1); 5.056 (1.2); 3.974 (0.7); 3.960 (1.0); 3.954 (1.0); 3.940 (0.9); 3.929 (1.0); 3.908 (1.2); 3.895 (0.9); 3.874 (1.6); 3.834 (1.5); 3.816 (2.7); 3.777 (2.5); 3.717 (0.6); 3.703 (0.9); 3.676 (3.5); 3.645 (3.7); 3.618 (1.7); 3.587 (1.6); 3.552 (1.1); 3.531 (1.1); 3.520 (1.3); 3.478 (1.4); 3.469 (1.4); 3.449 (1.1); 3.436 (1.4); 3.422 (0.9); 3.403 (0.9); 3.393 (0.8); 2.588 (0.9); 2.568 (0.8); 2.554 (1.1); 2.532 (1.8); 2.523 (1.7); 2.498 (0.9); 2.484 (1.1); 2.472 (1.2); 2.464 (1.2); 2.372 (1.0); 2.361 (0.9); 2.355 (0.9); 2.341 (1.1); 2.331 (1.1); 2.316 (0.7); 2.309 (0.7); 2.298 (0.7); 2.274 (0.7); 2.262 (1.1); 2.248 (1.0); 2.231 (1.3); 2.217 (1.2); 2.201 (0.7); 2.186 (0.7); 2.173 (0.4); 2.001 (16.0); 1.701 (1.2); 1.262 (14.6); 1.252 (13.8); 1.242 (15.7); 1.231 (13.2); 0.000 (3.7)

Example I-32, Solvent: CDCl$_3$, Spectrometer: 300.2 MHz
7.781 (5.1); 7.405 (0.6); 7.387 (6.3); 7.378 (5.5); 7.370 (5.5); 7.353 (1.0); 7.347 (1.2); 7.340 (1.6); 7.331 (1.3); 7.325 (1.0); 7.318 (0.8); 7.311 (1.1); 7.298 (0.4); 7.272 (1.3); 7.026 (1.2); 6.842 (2.6); 6.833 (1.4); 6.735 (2.8); 6.659 (1.4); 6.650 (2.8); 6.467 (1.3); 5.767 (1.3); 5.739 (1.5); 5.730 (1.5); 5.702 (1.3); 5.119 (6.0); 5.101 (1.6); 5.081 (1.9); 5.060 (1.4); 5.039 (0.6); 3.929 (0.4); 3.904 (1.6); 3.879 (0.6); 3.867 (1.7); 3.846 (1.8); 3.809 (1.5); 3.676 (0.3); 3.666 (0.3); 3.653 (0.4); 3.630 (0.6); 3.540 (0.4); 3.530 (0.5); 3.511 (0.6); 3.499 (0.6); 3.483 (0.4); 3.467 (2.3); 3.439 (2.1); 3.422 (0.7); 3.409 (1.7); 3.381 (1.6); 2.568 (0.4); 2.549 (0.4); 2.513 (0.8); 2.503 (0.8); 2.480 (0.4); 2.465 (0.5); 2.454 (0.5); 2.445 (0.5); 2.362 (0.4); 2.350 (0.5);

2.333 (0.5); 2.319 (0.6); 2.304 (0.4); 2.287 (0.4); 2.244 (0.4); 2.232 (0.5); 2.214 (0.5); 2.201 (0.7); 2.186 (0.4); 2.168 (0.4); 1.976 (16.0); 1.247 (6.7); 1.236 (6.2); 1.226 (7.2); 1.216 (5.9); 0.000 (0.6)

Example I-33, Solvent: CDCl₃, Spectrometer: 300.2 MHz
7.749 (7.3); 7.490 (1.1); 7.489 (1.1); 7.484 (1.3); 7.464 (1.3); 7.462 (1.4); 7.459 (1.4); 7.322 (0.7); 7.317 (0.7); 7.296 (1.5); 7.292 (1.1); 7.270 (2.9); 7.265 (1.0); 7.040 (1.7); 7.035 (2.6); 7.031 (2.9); 7.017 (2.1); 7.007 (1.9); 7.004 (1.7); 6.993 (1.0); 6.846 (2.4); 6.834 (1.2); 6.741 (2.6); 6.663 (1.3); 6.651 (2.4); 6.468 (1.1); 6.022 (0.9); 5.997 (1.1); 5.985 (1.0); 5.960 (1.0); 5.117 (5.4); 5.098 (1.3); 5.077 (1.5); 5.056 (1.1); 5.035 (0.4); 4.763 (6.0); 4.755 (6.0); 3.929 (1.3); 3.915 (0.4); 3.892 (1.6); 3.871 (1.9); 3.834 (1.3); 3.679 (0.3); 3.647 (0.4); 3.631 (0.6); 3.615 (0.4); 3.548 (0.4); 3.538 (0.5); 3.520 (0.5); 3.508 (0.6); 3.473 (0.7); 3.439 (0.5); 3.403 (0.4); 3.346 (1.4); 3.321 (1.4); 3.288 (1.2); 3.263 (1.2); 2.565 (0.3); 2.535 (1.9); 2.527 (3.7); 2.519 (2.1); 2.507 (0.8); 2.472 (0.4); 2.458 (0.5); 2.445 (0.5); 2.438 (0.5); 2.364 (0.4); 2.331 (0.5); 2.254 (0.4); 2.242 (0.4); 2.224 (0.4); 2.217 (0.5); 2.211 (0.6); 2.197 (0.3); 1.993 (16.0); 1.984 (0.4); 1.244 (6.1); 1.234 (4.9); 1.230 (4.8); 1.223 (6.7); 1.214 (4.7); 0.000 (1.0)

Example I-34, Solvent: CDCl₃, Spectrometer: 300.2 MHz
7.803 (10.1); 7.269 (5.6); 7.169 (1.1); 7.138 (2.6); 7.107 (2.6); 7.076 (1.2); 7.037 (1.9); 6.853 (4.1); 6.836 (2.1); 6.798 (1.3); 6.791 (1.5); 6.786 (1.4); 6.779 (1.4); 6.767 (1.2); 6.760 (1.4); 6.746 (4.8); 6.670 (2.1); 6.653 (4.4); 6.470 (2.1); 6.201 (1.5); 6.170 (1.9); 6.161 (1.7); 6.130 (1.6); 5.138 (1.3); 5.126 (9.8); 5.097 (2.9); 5.076 (2.1); 5.055 (0.8); 4.665 (9.4); 4.657 (9.6); 3.953 (0.5); 3.932 (0.6); 3.920 (0.6); 3.907 (0.7); 3.887 (0.7); 3.873 (0.4); 3.817 (0.9); 3.777 (0.9); 3.760 (2.1); 3.720 (2.2); 3.703 (0.6); 3.679 (2.7); 3.649 (3.1); 3.622 (1.2); 3.591 (1.0); 3.566 (0.7); 3.556 (0.8); 3.538 (0.8); 3.526 (0.9); 3.509 (0.6); 3.490 (1.1); 3.481 (1.0); 3.469 (0.7); 3.453 (0.9); 3.416 (0.6); 2.587 (0.6); 2.567 (0.5); 2.530 (1.2); 2.520 (1.1); 2.496 (0.6); 2.472 (3.2); 2.464 (5.9); 2.456 (3.1); 2.399 (0.4); 2.381 (0.6); 2.369 (0.7); 2.354 (0.7); 2.337 (0.7); 2.324 (0.5); 2.306 (0.4); 2.283 (0.5); 2.270 (0.7); 2.255 (0.7); 2.239 (0.9); 2.225 (0.8); 2.209 (0.5); 2.194 (0.5); 2.004 (16.0); 1.698 (1.1); 1.262 (9.0); 1.253 (10.1); 1.242 (9.6); 1.232 (9.7); 0.000 (3.2)

Example I-35, Solvent: CDCl₃, Spectrometer: 300.2 MHz
7.801 (8.1); 7.528 (2.0); 7.523 (2.2); 7.502 (2.7); 7.496 (2.9); 7.418 (1.1); 7.413 (1.7); 7.391 (4.3); 7.386 (3.5); 7.370 (4.5); 7.361 (1.0); 7.355 (0.8); 7.343 (6.4); 7.320 (7.1); 7.277 (4.7); 7.268 (3.7); 7.262 (10.9); 7.252 (2.7); 7.246 (2.1); 7.023 (1.6); 6.840 (3.5); 6.827 (1.9); 6.738 (3.9); 6.656 (1.8); 6.644 (3.9); 6.461 (1.8); 6.308 (1.6); 6.273 (2.3); 6.268 (2.1); 6.233 (1.7); 5.194 (13.1); 5.100 (7.8); 3.868 (1.2); 3.826 (1.4); 3.814 (1.8); 3.809 (1.7); 3.773 (1.1); 3.768 (1.1); 3.661 (0.4); 3.637 (1.8); 3.602 (2.1); 3.580 (1.2); 3.542 (1.4); 3.512 (1.1); 3.501 (1.4); 3.487 (1.1); 3.469 (1.1); 3.458 (1.0); 3.440 (0.6); 3.426 (0.6); 3.196 (16.0); 2.602 (0.5); 2.546 (1.2); 2.505 (0.7); 2.493 (0.8); 2.483 (0.7); 2.398 (0.6); 2.365 (0.7); 2.329 (0.5); 2.300 (0.6); 2.288 (0.7); 2.272 (0.7); 2.258 (0.8); 2.243 (0.6); 2.227 (0.5); 2.213 (0.4); 2.003 (2.3); 1.625 (7.8); 0.000 (5.3)

Example I-36, Solvent: CDCl₃, Spectrometer: 300.2 MHz
7.749 (10.4); 7.611 (2.1); 7.606 (2.4); 7.585 (2.4); 7.581 (2.8); 7.479 (1.1); 7.473 (1.8); 7.468 (0.9); 7.450 (5.3); 7.445 (3.9); 7.426 (6.5); 7.424 (6.4); 7.417 (3.6); 7.411 (2.2); 7.406 (3.6); 7.399 (5.2); 7.392 (5.1); 7.383 (3.5); 7.374 (3.6); 7.368 (3.5); 7.363 (1.2); 7.358 (1.5); 7.349 (7.6); 7.343 (7.8); 7.336 (2.1); 7.327 (3.0); 7.322 (5.5); 7.317 (3.8); 7.298 (5.7); 7.291 (8.2); 7.284 (7.9); 7.275 (5.1); 7.269 (3.8); 7.262 (2.0); 7.256 (10.4); 7.252 (6.4); 7.242 (3.8); 7.237 (2.4); 7.226 (2.7); 7.219 (2.0); 7.017 (1.9); 6.833 (4.1); 6.822 (2.2); 6.735 (4.6); 6.650 (2.2); 6.639 (4.5); 6.456 (2.1); 5.773 (1.6); 5.743 (2.2); 5.736 (2.1); 5.706 (1.7); 5.175 (16.0); 5.094 (10.0); 3.881 (0.6); 3.863 (0.6); 3.835 (0.8); 3.824 (0.7); 3.633 (2.0); 3.595 (2.6); 3.575 (3.4); 3.537 (2.6); 3.518 (1.0); 3.499 (1.0); 3.487 (1.3); 3.471 (1.1); 3.454 (1.2); 3.441 (1.2); 3.427 (0.9); 3.409 (0.7); 3.389 (1.6); 3.384 (1.5); 3.359 (1.3); 3.354 (1.2); 3.331 (0.8); 3.326 (0.8); 3.301 (0.8); 3.295 (0.8); 2.597 (0.6); 2.541 (1.3); 2.532 (1.3); 2.509 (0.7); 2.496 (0.8); 2.484 (0.9); 2.474 (0.9); 2.367 (0.7); 2.353 (0.7); 2.338 (0.9); 2.324 (0.8); 2.307 (0.6); 2.292 (0.6); 2.278 (0.9); 2.266 (0.9); 2.248 (0.8); 2.234 (1.0); 2.219 (0.7); 2.202 (0.6); 2.191 (0.5); 1.995 (11.0); 1.646 (2.2); 0.000 (4.6)

Example I-37, Solvent: CDCl₃, Spectrometer: 300.2 MHz
7.820 (13.3); 7.360 (0.9); 7.354 (0.8); 7.349 (0.8); 7.339 (4.1); 7.333 (4.0); 7.315 (8.3); 7.305 (3.1); 7.291 (1.9); 7.283 (2.6); 7.272 (5.4); 7.262 (12.4); 7.247 (3.0); 7.240 (2.3); 7.022 (2.2); 6.970 (0.5); 6.965 (0.6); 6.953 (4.2); 6.942 (0.7); 6.937 (0.8); 6.926 (7.3); 6.915 (0.9); 6.909 (0.7); 6.898 (3.5); 6.886 (0.6); 6.882 (0.5); 6.838 (4.7); 6.825 (2.4); 6.736 (4.7); 6.655 (2.4); 6.642 (5.0); 6.459 (2.4); 6.097 (1.5); 6.066 (1.8); 6.058 (1.8); 6.026 (1.6); 5.195 (16.0); 5.101 (10.6); 3.891 (0.7); 3.882 (0.6); 3.866 (0.6); 3.857 (0.7); 3.824 (1.4); 3.784 (0.8); 3.767 (1.5); 3.727 (1.4); 3.672 (0.4); 3.658 (0.6); 3.627 (2.3); 3.596 (2.3); 3.570 (1.1); 3.539 (1.6); 3.512 (1.0); 3.497 (1.4); 3.484 (1.3); 3.466 (1.3); 3.454 (1.4); 3.439 (0.8); 3.420 (0.7); 3.410 (0.6); 2.610 (0.6); 2.601 (0.6); 2.588 (0.6); 2.555 (1.4); 2.544 (1.3); 2.523 (0.7); 2.508 (0.8); 2.497 (0.9); 2.488 (0.9); 2.387 (0.7); 2.371 (0.8); 2.357 (0.9); 2.324 (0.6); 2.307 (0.7); 2.295 (0.8); 2.259 (0.9); 2.231 (0.5); 2.223 (0.6); 1.999 (7.6); 1.668 (0.7); 0.000 (4.5)

Example I-38, Solvent: CDCl₃, Spectrometer: 300.2 MHz
7.782 (10.5); 7.394 (8.4); 7.379 (16.9); 7.362 (1.9); 7.350 (2.9); 7.338 (2.7); 7.331 (1.5); 7.322 (2.9); 7.310 (3.3); 7.305 (4.8); 7.296 (6.9); 7.289 (4.9); 7.258 (8.7); 7.246 (3.4); 7.233 (2.2); 7.226 (1.6); 7.013 (1.8); 6.830 (4.0); 6.821 (2.2); 6.731 (4.3); 6.646 (2.2); 6.638 (4.2); 6.455 (2.0); 5.768 (1.9); 5.740 (2.3); 5.731 (2.3); 5.703 (2.0); 5.179 (14.4); 5.092 (9.1); 3.867 (2.2); 3.843 (0.7); 3.830 (2.4); 3.810 (2.9); 3.773 (2.0); 3.637 (0.5); 3.591 (1.0); 3.516 (0.9); 3.497 (1.0); 3.487 (1.3); 3.479 (1.2); 3.466 (1.0); 3.448 (1.3); 3.429 (2.7); 3.401 (2.5); 3.371 (1.7); 3.343 (1.6); 2.597 (0.6); 2.541 (1.3); 2.532 (1.2); 2.509 (0.7); 2.496 (0.8); 2.484 (0.8); 2.475 (0.8); 2.376 (0.7); 2.367 (0.6); 2.361 (0.6); 2.339 (0.8); 2.314 (0.5); 2.305 (0.5); 2.281 (0.7); 2.269 (0.8); 2.252 (0.8); 2.238 (0.9); 2.223 (0.6); 2.212 (0.5); 2.206 (0.6); 2.194 (0.5); 1.988 (16.0); 1.710 (0.9); 0.000 (2.3)

Example I-39, Solvent: CDCl₃, Spectrometer: 300.2 MHz
7.749 (9.8); 7.493 (1.7); 7.489 (1.8); 7.469 (1.8); 7.467 (2.0); 7.463 (2.1); 7.330 (1.3); 7.324 (1.4); 7.301 (5.1); 7.294 (4.9); 7.281 (4.2); 7.272 (2.8); 7.260 (9.0); 7.251 (3.3); 7.241 (2.7); 7.229 (1.6); 7.049 (2.0); 7.039 (3.1); 7.036 (3.2); 7.027 (3.1); 7.016 (2.4); 7.012 (2.9); 7.009 (2.7); 7.002 (1.7); 6.832 (3.7); 6.823 (1.8); 6.735 (3.7); 6.649 (2.0); 6.640 (3.5); 6.457 (1.7); 6.028 (1.3); 6.003 (1.5); 5.991 (1.5); 5.966 (1.4); 5.172 (11.2); 5.091 (7.2); 4.763 (8.9); 4.755 (9.1); 3.902 (1.2); 3.865 (1.5); 3.844 (2.1); 3.807 (2.0); 3.637 (0.4); 3.604 (0.7); 3.590 (0.8); 3.583 (0.8); 3.569 (0.7); 3.521 (0.8); 3.495 (1.3); 3.483 (1.0); 3.466 (1.0); 3.452 (0.9); 3.436 (0.6); 3.420 (0.5); 3.315 (1.8); 3.290 (1.8); 3.257 (1.5); 3.232 (1.5); 2.586

(0.5); 2.520 (2.9); 2.512 (4.8); 2.504 (2.6); 2.487 (0.7); 2.475 (0.8); 2.465 (0.7); 2.390 (0.6); 2.377 (0.6); 2.362 (0.7); 2.347 (0.6); 2.331 (0.5); 2.317 (0.5); 2.280 (0.6); 2.248 (0.7); 2.223 (0.4); 2.214 (0.4); 1.999 (16.0); 1.652 (1.6); 0.000 (4.1)

Example I-40, Solvent: CDCl$_3$, Spectrometer: 300.2 MHz
7.798 (6.9); 7.359 (0.7); 7.354 (0.7); 7.344 (2.5); 7.339 (2.6); 7.327 (5.5); 7.321 (6.2); 7.297 (0.7); 7.288 (1.1); 7.279 (4.4); 7.268 (3.7); 7.263 (11.8); 7.254 (2.5); 7.246 (1.9); 7.172 (1.0); 7.141 (2.3); 7.110 (2.3); 7.079 (1.1); 7.023 (1.8); 6.840 (3.8); 6.826 (1.9); 6.796 (1.2); 6.789 (1.4); 6.784 (1.3); 6.777 (1.2); 6.765 (1.1); 6.758 (1.3); 6.752 (1.4); 6.739 (4.0); 6.656 (2.0); 6.643 (4.0); 6.460 (1.9); 6.194 (1.3); 6.164 (1.6); 6.155 (1.5); 6.124 (1.4); 5.196 (13.4); 5.103 (8.5); 4.655 (9.0); 4.647 (9.0); 4.518 (0.4); 4.515 (0.4); 3.882 (0.5); 3.871 (0.5); 3.860 (0.6); 3.848 (0.6); 3.836 (0.7); 3.825 (0.7); 3.814 (0.6); 3.776 (0.6); 3.735 (0.6); 3.718 (1.4); 3.678 (1.5); 3.662 (0.6); 3.638 (2.3); 3.607 (2.7); 3.581 (1.0); 3.550 (1.3); 3.536 (0.9); 3.517 (1.2); 3.507 (1.4); 3.488 (1.0); 3.471 (1.3); 3.438 (0.6); 2.609 (0.5); 2.554 (1.1); 2.544 (1.1); 2.519 (0.6); 2.508 (0.7); 2.496 (0.7); 2.486 (0.7); 2.453 (2.2); 2.445 (4.5); 2.437 (2.2); 2.422 (0.4); 2.408 (0.6); 2.394 (0.7); 2.380 (0.8); 2.364 (0.7); 2.348 (0.5); 2.335 (0.5); 2.319 (0.6); 2.307 (0.7); 2.294 (0.6); 2.277 (0.7); 2.263 (0.7); 2.247 (0.4); 2.232 (0.5); 2.228 (0.4); 2.003 (16.0); 1.640 (2.1); 0.000 (5.2)

Example I-41, Solvent: CDCl$_3$, Spectrometer: 300.2 MHz
7.820 (5.0); 7.521 (1.1); 7.515 (1.1); 7.494 (1.5); 7.489 (1.6); 7.417 (0.7); 7.411 (1.0); 7.390 (2.4); 7.384 (1.9); 7.368 (2.5); 7.342 (2.3); 7.315 (0.8); 7.267 (3.2); 7.033 (0.9); 6.850 (1.8); 6.836 (1.0); 6.745 (2.0); 6.666 (1.0); 6.652 (2.0); 6.469 (1.0); 6.319 (0.8); 6.283 (1.2); 6.278 (1.1); 6.243 (0.9); 5.917 (0.6); 5.901 (0.4); 5.898 (0.3); 5.882 (0.7); 5.879 (0.4); 5.863 (0.4); 5.859 (0.8); 5.844 (0.4); 5.840 (0.4); 5.825 (0.8); 5.806 (0.4); 5.311 (0.5); 5.306 (1.2); 5.302 (1.3); 5.297 (0.5); 5.269 (1.3); 5.265 (1.1); 5.254 (0.4); 5.249 (1.0); 5.244 (1.2); 5.239 (0.9); 5.234 (1.2); 5.230 (1.0); 5.120 (3.7); 5.306 (1.2); 5.302 (1.3); 5.297 (0.5); 5.269 (1.3); 5.265 (1.1); 5.254 (0.4); 5.249 (1.0); 5.244 (1.2); 5.239 (0.9); 5.234 (1.2); 5.230 (1.0); 5.120 (3.7); 4.675 (1.7); 4.671 (2.6); 4.667 (1.6); 4.656 (1.7); 4.652 (2.5); 4.647 (1.6); 3.917 (0.7); 3.876 (1.0); 3.859 (1.5); 3.842 (0.3); 3.818 (1.4); 3.686 (1.3); 3.651 (1.4); 3.628 (1.2); 3.592 (1.1); 3.576 (0.7); 3.561 (0.7); 3.547 (0.7); 3.532 (0.5); 3.514 (0.4); 3.501 (0.4); 3.218 (16.0); 2.550 (0.6); 2.504 (0.4); 2.493 (0.4); 2.482 (0.4); 2.414 (0.3); 2.391 (0.3); 2.310 (0.4); 2.294 (0.3); 2.280 (0.4); 2.004 (3.6); 1.673 (1.0); 0.000 (1.7)

Example I-42, Solvent: CDCl$_3$, Spectrometer: 300.2 MHz
7.765 (4.7); 7.616 (1.2); 7.611 (1.4); 7.586 (1.7); 7.482 (0.7); 7.476 (1.2); 7.470 (0.6); 7.460 (0.8); 7.453 (3.2); 7.448 (2.5); 7.440 (1.1); 7.434 (1.7); 7.429 (3.8); 7.427 (3.1); 7.422 (2.4); 7.415 (2.1); 7.407 (2.2); 7.402 (1.9); 7.397 (2.7); 7.390 (2.9); 7.384 (2.3); 7.372 (2.4); 7.366 (2.3); 7.355 (3.9); 7.349 (4.6); 7.342 (1.8); 7.333 (1.5); 7.328 (2.8); 7.323 (2.0); 7.297 (2.1); 7.293 (1.8); 7.290 (1.6); 7.273 (1.6); 7.267 (1.3); 7.261 (6.1); 7.029 (1.2); 6.845 (2.5); 6.832 (1.3); 6.745 (2.8); 6.662 (1.3); 6.649 (2.7); 6.466 (1.3); 5.921 (0.4); 5.902 (0.9); 5.886 (0.5); 5.883 (0.5); 5.867 (1.0); 5.864 (0.7); 5.848 (0.6); 5.845 (1.2); 5.829 (0.6); 5.826 (0.6); 5.810 (1.2); 5.791 (0.6); 5.782 (1.0); 5.752 (1.3); 5.746 (1.2); 5.715 (1.0); 5.303 (0.6); 5.298 (1.5); 5.294 (1.9); 5.289 (0.8); 5.250 (1.8); 5.246 (2.1); 5.241 (1.5); 5.236 (1.7); 5.232 (0.8); 5.216 (1.5); 5.212 (1.5); 5.114 (6.0); 4.660 (2.4); 4.655 (3.8); 4.651 (2.6); 4.641 (2.4); 4.636 (3.7); 4.632 (2.5); 3.881 (0.4); 3.869 (0.4); 3.859 (0.4); 3.847 (0.4); 3.835 (0.5); 3.823 (0.5); 3.813 (0.5); 3.671 (1.1); 3.633 (1.3); 3.613 (2.1); 3.576 (1.8); 3.550 (1.0); 3.535 (1.0); 3.518 (0.8); 3.504 (0.8); 3.488 (0.5); 3.472 (0.4); 3.426 (1.5); 3.395 (1.5); 3.368 (1.0); 3.337 (1.0); 2.595 (0.4); 2.540 (0.7); 2.530 (0.8); 2.506 (0.4); 2.493 (0.5); 2.482 (0.5); 2.472 (0.5); 2.398 (0.4); 2.386 (0.5); 2.363 (0.5); 2.339 (0.3); 2.328 (0.3); 2.301 (0.5); 2.289 (0.5); 2.273 (0.5); 2.258 (0.6); 2.242 (0.4); 2.226 (0.4); 2.001 (16.0); 1.639 (1.1); 0.000 (3.3)

Example I-43, Solvent: CDCl$_3$, Spectrometer: 300.2 MHz
7.841 (7.6); 7.360 (0.5); 7.339 (1.0); 7.333 (0.8); 7.318 (0.6); 7.311 (1.9); 7.304 (0.7); 7.289 (0.8); 7.283 (1.2); 7.267 (5.8); 7.034 (1.6); 6.970 (0.3); 6.964 (0.5); 6.953 (2.8); 6.941 (0.5); 6.937 (0.5); 6.925 (5.0); 6.914 (0.7); 6.908 (0.5); 6.897 (2.4); 6.885 (0.4); 6.850 (3.3); 6.834 (1.7); 6.745 (3.3); 6.667 (1.7); 6.651 (3.4); 6.468 (1.7); 6.111 (1.1); 6.080 (1.3); 6.071 (1.3); 6.040 (1.1); 5.938 (0.4); 5.919 (0.8); 5.903 (0.5); 5.900 (0.5); 5.884 (1.1); 5.881 (0.7); 5.861 (1.1); 5.846 (0.7); 5.842 (0.6); 5.827 (1.1); 5.808 (0.6); 5.310 (1.6); 5.305 (1.8); 5.267 (1.8); 5.263 (1.7); 5.252 (1.5); 5.248 (1.5); 5.232 (1.6); 5.229 (1.5); 5.122 (7.4); 4.677 (2.7); 4.673 (4.3); 4.669 (2.8); 4.658 (2.8); 4.654 (4.2); 4.650 (2.6); 3.972 (0.7); 3.899 (0.3); 3.877 (1.2); 3.864 (0.5); 3.854 (0.6); 3.837 (1.3); 3.819 (1.9); 3.779 (1.3); 3.677 (1.8); 3.646 (2.0); 3.619 (1.4); 3.588 (1.5); 3.562 (1.2); 3.545 (1.1); 3.532 (1.0); 3.515 (0.8); 3.498 (0.6); 3.487 (0.4); 2.610 (0.4); 2.602 (0.4); 2.577 (0.6); 2.555 (1.0); 2.544 (0.9); 2.520 (0.5); 2.509 (0.6); 2.497 (0.6); 2.486 (0.6); 2.425 (0.5); 2.412 (0.6); 2.398 (0.6); 2.365 (0.4); 2.352 (0.4); 2.333 (0.4); 2.320 (0.6); 2.307 (0.6); 2.292 (0.6); 2.277 (0.5); 2.260 (0.4); 2.247 (0.4); 2.004 (16.0); 1.997 (0.5); 1.995 (0.3); 1.661 (1.1); 0.000 (3.2)

Example I-44, Solvent: CDCl$_3$, Spectrometer: 300.2 MHz
7.805 (10.2); 7.413 (0.9); 7.396 (10.5); 7.385 (12.5); 7.382 (13.5); 7.363 (2.0); 7.357 (1.8); 7.351 (3.0); 7.337 (2.4); 7.329 (1.5); 7.323 (2.0); 7.313 (0.9); 7.308 (0.9); 7.302 (0.5); 7.294 (0.4); 7.263 (9.2); 7.028 (2.3); 6.844 (4.8); 6.832 (2.5); 6.743 (5.0); 6.661 (2.5); 6.649 (5.0); 6.466 (2.4); 5.925 (0.6); 5.906 (1.4); 5.890 (0.9); 5.887 (0.8); 5.871 (1.7); 5.868 (1.1); 5.852 (1.1); 5.849 (1.9); 5.833 (1.1); 5.830 (1.0); 5.814 (1.9); 5.795 (1.0); 5.782 (2.5); 5.754 (3.0); 5.745 (2.9); 5.717 (2.6); 5.307 (1.2); 5.302 (3.1); 5.297 (3.3); 5.293 (1.4); 5.250 (3.2); 5.245 (3.4); 5.240 (3.0); 5.235 (1.3); 5.217 (2.4); 5.114 (10.6); 4.664 (4.4); 4.660 (6.8); 4.655 (4.4); 4.645 (4.5); 4.640 (6.7); 4.636 (4.2); 3.970 (0.5); 3.912 (2.3); 3.875 (3.0); 3.854 (3.8); 3.832 (0.9); 3.817 (3.6); 3.675 (0.4); 3.664 (0.5); 3.652 (0.5); 3.640 (0.8); 3.628 (1.1); 3.617 (1.2); 3.607 (1.1); 3.594 (0.7); 3.580 (1.0); 3.569 (1.5); 3.555 (1.9); 3.542 (1.9); 3.527 (1.5); 3.509 (1.3); 3.495 (1.1); 3.474 (3.4); 3.446 (3.0); 3.416 (2.4); 3.388 (2.4); 2.599 (0.6); 2.564 (0.9); 2.544 (1.5); 2.533 (1.5); 2.510 (0.8); 2.498 (0.9); 2.486 (1.0); 2.474 (1.0); 2.395 (0.8); 2.374 (0.9); 2.348 (0.6); 2.341 (0.6); 2.306 (0.8); 2.295 (1.0); 2.278 (0.9); 2.265 (1.1); 2.248 (0.7); 2.232 (0.7); 2.224 (0.5); 2.221 (0.5); 2.000 (16.0); 1.993 (0.5); 1.991 (0.4); 1.659 (2.3); 0.000 (5.2)

Example I-45, Solvent: CDCl$_3$, Spectrometer: 300.2 MHz
7.765 (12.9); 7.491 (2.0); 7.487 (2.2); 7.465 (2.4); 7.461 (2.5); 7.326 (1.2); 7.321 (1.2); 7.300 (2.5); 7.296 (2.0); 7.274 (1.9); 7.267 (2.2); 7.264 (8.4); 7.045 (2.5); 7.037 (4.0); 7.034 (3.9); 7.028 (3.1); 7.023 (4.0); 7.009 (3.2); 7.006 (3.0); 6.998 (1.9); 6.844 (4.4); 6.832 (2.1); 6.743 (4.5); 6.660 (2.3); 6.649 (4.1); 6.466 (2.0); 6.030 (1.6); 6.005 (1.9); 5.993 (1.9); 5.968 (1.7); 5.919 (0.5); 5.900 (1.0); 5.884 (0.7); 5.881 (0.6); 5.865 (1.3); 5.842 (1.4);

5.826 (0.8); 5.824 (0.8); 5.808 (1.4); 5.788 (0.7); 5.297 (2.4); 5.292 (2.6); 5.288 (1.2); 5.247 (2.6); 5.240 (2.7); 5.235 (2.4); 5.230 (1.1); 5.212 (2.1); 5.112 (8.4); 4.768 (10.7); 4.760 (11.0); 4.651 (5.4); 4.632 (5.3); 3.931 (2.0); 3.893 (2.2); 3.873 (2.9); 3.855 (0.6); 3.835 (2.9); 3.821 (0.8); 3.809 (0.8); 3.798 (0.9); 3.787 (0.8); 3.660 (0.4); 3.628 (0.8); 3.607 (1.1); 3.581 (1.4); 3.569 (1.8); 3.555 (1.7); 3.541 (1.9); 3.524 (1.2); 3.507 (1.0); 3.495 (1.0); 3.346 (2.4); 3.321 (2.3); 3.288 (2.0); 3.263 (2.0); 2.585 (0.5); 2.530 (4.0); 2.522 (7.0); 2.515 (3.7); 2.497 (0.8); 2.485 (0.9); 2.474 (0.9); 2.462 (0.9); 2.451 (0.7); 2.431 (0.5); 2.419 (0.8); 2.406 (0.9); 2.393 (0.9); 2.379 (0.7); 2.360 (0.6); 2.347 (0.5); 2.302 (0.7); 2.269 (0.9); 2.237 (0.5); 2.226 (0.5); 2.002 (16.0); 1.990 (0.4); 1.667 (1.3); 0.000 (4.7)

Example I-46, Solvent: CDCl$_3$, Spectrometer: 300.2 MHz
7.819 (10.0); 7.264 (22.8); 7.172 (1.3); 7.141 (3.1); 7.110 (3.1); 7.080 (1.4); 7.036 (2.3); 6.852 (4.9); 6.835 (2.5); 6.799 (1.5); 6.793 (1.8); 6.788 (1.7); 6.781 (1.7); 6.768 (1.4); 6.762 (1.7); 6.749 (5.8); 6.668 (2.5); 6.652 (5.2); 6.469 (2.5); 6.206 (1.7); 6.176 (2.2); 6.166 (2.0); 6.136 (1.8); 5.939 (0.6); 5.920 (1.3); 5.904 (0.8); 5.901 (0.8); 5.885 (1.6); 5.863 (1.7); 5.847 (1.0); 5.844 (1.0); 5.828 (1.7); 5.809 (1.0); 5.313 (2.5); 5.308 (2.7); 5.271 (2.5); 5.267 (2.6); 5.255 (2.2); 5.251 (2.4); 5.246 (1.3); 5.236 (2.5); 5.233 (2.3); 5.121 (10.9); 4.678 (4.5); 4.674 (7.6); 4.668 (14.3); 4.659 (16.0); 4.655 (8.3); 4.650 (4.9); 3.880 (0.6); 3.857 (0.7); 3.834 (0.9); 3.820 (1.8); 3.780 (1.1); 3.762 (2.4); 3.722 (2.3); 3.681 (3.1); 3.650 (3.6); 3.624 (2.2); 3.593 (2.5); 3.587 (2.1); 3.571 (1.8); 3.558 (2.0); 3.523 (1.1); 3.512 (1.1); 2.605 (0.6); 2.554 (1.4); 2.544 (1.4); 2.508 (0.9); 2.496 (1.0); 2.485 (1.0); 2.468 (3.2); 2.460 (5.9); 2.452 (3.2); 2.441 (0.8); 2.408 (0.9); 2.393 (0.8); 2.345 (0.7); 2.331 (0.9); 2.316 (0.9); 2.302 (1.0); 2.287 (0.8); 2.270 (0.7); 2.256 (0.6); 2.008 (13.9); 1.599 (9.0); 0.011 (0.4); 0.000 (13.0); -0.011 (0.6)

Example I-47, Solvent: CDCl$_3$, Spectrometer: 300.2 MHz
7.819 (4.5); 7.523 (1.0); 7.518 (1.1); 7.497 (1.4); 7.492 (1.5); 7.418 (0.6); 7.413 (0.9); 7.391 (2.4); 7.385 (1.8); 7.370 (2.4); 7.343 (2.2); 7.316 (0.8); 7.267 (4.0); 7.037 (0.8); 6.854 (1.8); 6.837 (0.9); 6.747 (1.9); 6.670 (0.9); 6.654 (1.9); 6.471 (0.9); 6.318 (0.8); 6.283 (1.2); 6.278 (1.0); 6.242 (0.9); 5.123 (3.5); 4.367 (1.9); 4.345 (4.3); 4.323 (2.0); 3.917 (0.8); 3.876 (1.0); 3.859 (1.5); 3.818 (1.0); 3.686 (1.2); 3.650 (1.4); 3.627 (1.3); 3.614 (0.6); 3.592 (1.2); 3.578 (0.7); 3.564 (0.4); 3.547 (0.5); 3.534 (0.4); 3.223 (16.0); 2.737 (2.0); 2.716 (4.3); 2.694 (1.9); 2.585 (0.4); 2.563 (0.6); 2.552 (0.5); 2.505 (0.3); 2.496 (0.3); 2.367 (0.4); 2.289 (0.3); 2.258 (0.4); 2.103 (15.1); 2.085 (0.4); 2.005 (2.3); 1.647 (1.6); 0.000 (2.3)

Example I-48, Solvent: CDCl$_3$, Spectrometer: 300.2 MHz
7.758 (3.6); 7.612 (1.0); 7.606 (1.1); 7.586 (1.1); 7.582 (1.3); 7.481 (0.5); 7.475 (0.9); 7.470 (0.4); 7.453 (2.5); 7.447 (1.8); 7.433 (1.4); 7.429 (2.9); 7.418 (1.6); 7.412 (2.0); 7.406 (1.8); 7.401 (1.4); 7.394 (2.2); 7.387 (2.4); 7.383 (2.0); 7.369 (1.8); 7.364 (1.9); 7.353 (3.1); 7.348 (3.4); 7.340 (1.4); 7.331 (1.2); 7.326 (2.2); 7.321 (1.6); 7.295 (1.7); 7.290 (1.4); 7.288 (1.3); 7.271 (1.2); 7.262 (3.0); 7.030 (0.9); 6.846 (2.0); 6.833 (1.0); 6.744 (2.3); 6.663 (1.0); 6.649 (2.1); 6.466 (1.0); 5.780 (0.7); 5.750 (1.0); 5.743 (1.0); 5.713 (0.8); 5.118 (4.6); 4.348 (2.1); 4.326 (4.6); 4.304 (2.2); 3.895 (0.3); 3.882 (0.3); 3.870 (0.4); 3.864 (0.4); 3.849 (0.4); 3.670 (0.8); 3.633 (1.0); 3.612 (1.6); 3.575 (1.4); 3.564 (0.7); 3.550 (0.5); 3.531 (0.5); 3.518 (0.6); 3.505 (0.5); 3.488 (0.3); 3.425 (1.2); 3.395 (1.2); 3.367 (0.8); 3.337 (0.8); 2.720 (2.1); 2.698 (4.6); 2.676 (2.0); 2.575 (0.6); 2.552 (0.7); 2.541 (0.6); 2.520 (0.4); 2.504 (0.4); 2.493 (0.4); 2.484 (0.4); 2.357 (0.4); 2.350 (0.4); 2.338 (0.4); 2.317 (0.4); 2.278 (0.4); 2.266 (0.4); 2.249 (0.4); 2.235 (0.5); 2.220 (0.4); 2.149 (0.4); 2.087 (16.0); 1.996 (13.3); 1.271 (0.3); 1.247 (0.7); 0.000 (1.6)

Example I-49, Solvent: CDCl$_3$, Spectrometer: 300.2 MHz
7.834 (5.2); 7.339 (0.6); 7.332 (0.5); 7.318 (0.4); 7.311 (1.1); 7.304 (0.4); 7.290 (0.5); 7.283 (0.7); 7.270 (2.5); 7.262 (0.4); 7.036 (0.9); 6.952 (1.7); 6.936 (0.3); 6.925 (3.0); 6.914 (0.4); 6.897 (1.4); 6.852 (2.0); 6.836 (1.0); 6.745 (2.0); 6.668 (1.0); 6.653 (2.1); 6.470 (1.0); 6.110 (0.6); 6.078 (0.8); 6.070 (0.8); 6.039 (0.7); 5.125 (4.3); 4.368 (1.9); 4.346 (4.2); 4.324 (2.1); 3.875 (0.8); 3.835 (0.5); 3.817 (0.8); 3.778 (0.7); 3.675 (1.0); 3.643 (1.4); 3.617 (1.1); 3.586 (1.0); 3.576 (0.7); 3.564 (0.5); 3.545 (0.5); 3.533 (0.6); 3.517 (0.3); 2.738 (2.0); 2.716 (4.1); 2.694 (1.9); 2.566 (0.6); 2.555 (0.6); 2.518 (0.4); 2.506 (0.4); 2.497 (0.4); 2.364 (0.4); 2.330 (0.3); 2.298 (0.3); 2.267 (0.4); 2.101 (16.0); 2.003 (11.2); 1.994 (0.4); 1.703 (0.5); 0.000 (1.4)

Example I-50, Solvent: CDCl$_3$, Spectrometer: 300.2 MHz
7.802 (4.8); 7.413 (0.4); 7.397 (4.8); 7.385 (6.0); 7.382 (6.6); 7.364 (0.9); 7.357 (0.8); 7.352 (1.4); 7.338 (1.2); 7.330 (1.0); 7.323 (1.0); 7.314 (0.5); 7.309 (0.4); 7.264 (4.9); 7.032 (1.0); 6.848 (2.2); 6.835 (1.1); 6.745 (2.3); 6.665 (1.1); 6.651 (2.2); 6.468 (1.1); 5.784 (1.1); 5.756 (1.3); 5.747 (1.3); 5.719 (1.2); 5.117 (4.8); 4.355 (2.4); 4.333 (5.4); 4.311 (2.6); 3.912 (1.3); 3.874 (1.3); 3.854 (1.7); 3.817 (1.2); 3.612 (0.8); 3.601 (0.7); 3.583 (0.6); 3.570 (0.8); 3.551 (0.5); 3.531 (0.6); 3.484 (0.4); 3.473 (1.4); 3.445 (1.2); 3.415 (0.9); 3.388 (0.9); 2.727 (2.5); 2.705 (5.3); 2.683 (2.4); 2.610 (0.3); 2.557 (0.7); 2.546 (0.7); 2.525 (0.4); 2.510 (0.4); 2.499 (0.5); 2.490 (0.5); 2.380 (0.4); 2.367 (0.4); 2.351 (0.5); 2.321 (0.4); 2.286 (0.4); 2.274 (0.4); 2.257 (0.4); 2.243 (0.5); 2.227 (0.4); 2.091 (16.0); 2.002 (6.8); 1.647 (1.3); 0.000 (2.7)

Example I-51, Solvent: CDCl$_3$, Spectrometer: 300.2 MHz
7.784 (0.4); 7.763 (8.8); 7.755 (0.4); 7.494 (1.4); 7.492 (1.4); 7.488 (1.6); 7.468 (1.5); 7.466 (1.6); 7.462 (1.6); 7.327 (1.0); 7.322 (1.0); 7.301 (1.8); 7.297 (1.4); 7.295 (1.4); 7.286 (0.7); 7.275 (1.5); 7.270 (1.6); 7.264 (10.8); 7.047 (2.1); 7.038 (3.0); 7.034 (3.5); 7.024 (2.7); 7.011 (2.1); 7.008 (2.0); 6.999 (1.3); 6.849 (3.0); 6.834 (1.3); 6.746 (3.1); 6.665 (1.1); 6.651 (2.7); 6.468 (1.3); 6.032 (1.1); 6.007 (1.3); 5.995 (1.3); 5.970 (1.1); 5.115 (5.5); 4.910 (0.3); 4.772 (7.5); 4.764 (7.4); 4.498 (0.4); 4.347 (3.1); 4.325 (6.1); 4.303 (2.9); 3.930 (1.4); 3.893 (1.9); 3.883 (0.7); 3.872 (2.2); 3.857 (0.7); 3.835 (2.1); 3.670 (0.4); 3.636 (0.8); 3.611 (1.3); 3.601 (1.3); 3.583 (1.1); 3.572 (1.3); 3.554 (0.8); 3.544 (0.8); 3.537 (0.8); 3.509 (0.4); 3.500 (0.4); 3.343 (1.6); 3.318 (1.5); 3.285 (1.3); 3.260 (1.3); 2.720 (3.2); 2.698 (6.1); 2.676 (2.7); 2.601 (0.5); 2.569 (0.8); 2.535 (3.0); 2.527 (4.9); 2.519 (2.5); 2.499 (0.7); 2.488 (0.7); 2.478 (0.6); 2.467 (0.5); 2.383 (0.6); 2.361 (0.6); 2.337 (0.4); 2.317 (0.4); 2.293 (0.5); 2.280 (0.6); 2.264 (0.6); 2.250 (0.7); 2.234 (0.4); 2.218 (0.4); 2.109 (1.1); 2.088 (16.0); 2.028 (0.4); 2.022 (0.3); 2.016 (0.3); 2.015 (0.4); 2.013 (0.4); 2.006 (9.9); 1.628 (1.9); 0.000 (6.0)

Example I-52, Solvent: CDCl$_3$, Spectrometer: 300.2 MHz
7.815 (4.5); 7.265 (8.6); 7.172 (0.5); 7.142 (1.2); 7.111 (1.2); 7.080 (0.6); 7.039 (1.0); 6.855 (2.0); 6.837 (1.0); 6.801 (0.6); 6.795 (0.7); 6.789 (0.7); 6.783 (0.7); 6.770 (0.6); 6.764 (0.7); 6.750 (2.4); 6.671 (1.0); 6.654 (2.1); 6.471 (1.0); 6.206 (0.7); 6.176 (0.9); 6.166 (0.8); 6.135 (0.7); 5.125 (4.6); 4.672 (4.9); 4.664 (4.9); 4.370 (2.0); 4.348 (4.4); 4.326 (2.1); 3.913 (0.4); 3.875 (0.4); 3.865 (0.4); 3.857 (0.4); 3.819 (0.4); 3.778 (0.4); 3.761 (1.0); 3.721

(0.9); 3.678 (1.2); 3.647 (1.6); 3.621 (1.1); 3.589 (1.1); 3.548 (0.6); 2.741 (2.0); 2.719 (4.1); 2.697 (1.9); 2.597 (0.5); 2.567 (0.6); 2.557 (0.6); 2.519 (0.4); 2.508 (0.4); 2.498 (0.4); 2.479 (1.3); 2.472 (2.6); 2.464 (1.3); 2.398 (0.4); 2.384 (0.4); 2.368 (0.4); 2.337 (0.3); 2.307 (0.4); 2.293 (0.4); 2.277 (0.4); 2.263 (0.4); 2.153 (0.4); 2.107 (16.0); 2.008 (7.4); 1.615 (1.1); 0.000 (4.9)

Example I-53, Solvent: CDCl$_3$, Spectrometer: 300.2 MHz
7.821 (4.7); 7.523 (1.0); 7.518 (1.1); 7.497 (1.4); 7.492 (1.5); 7.419 (0.6); 7.414 (1.0); 7.392 (2.3); 7.387 (1.8); 7.371 (2.5); 7.344 (2.2); 7.318 (0.8); 7.268 (4.1); 7.035 (0.8); 6.852 (1.8); 6.838 (1.0); 6.749 (2.0); 6.668 (0.9); 6.662 (0.6); 6.655 (2.0); 6.472 (1.0); 6.321 (0.8); 6.286 (1.1); 6.281 (1.0); 6.246 (0.9); 5.396 (0.5); 5.379 (0.7); 5.362 (0.5); 5.123 (3.8); 3.931 (0.3); 3.924 (0.4); 3.908 (0.9); 3.904 (0.8); 3.895 (0.9); 3.888 (1.0); 3.880 (0.9); 3.873 (1.0); 3.867 (1.1); 3.862 (1.3); 3.849 (1.7); 3.845 (1.9); 3.831 (1.5); 3.808 (1.8); 3.805 (1.8); 3.764 (0.5); 3.687 (0.9); 3.680 (0.8); 3.652 (1.0); 3.645 (0.9); 3.629 (0.8); 3.622 (0.6); 3.594 (0.6); 3.586 (0.5); 3.562 (0.5); 3.537 (0.6); 3.517 (0.5); 3.504 (0.5); 3.220 (16.0); 2.519 (0.6); 2.460 (0.4); 2.399 (0.4); 2.385 (0.4); 2.371 (0.4); 2.293 (0.3); 2.279 (0.4); 2.265 (0.4); 2.248 (0.4); 2.229 (0.4); 2.218 (0.5); 2.198 (0.4); 2.192 (0.4); 2.171 (0.5); 2.151 (0.4); 2.145 (0.4); 2.005 (9.7); 1.996 (0.4); 1.994 (0.4); 1.993 (0.4); 1.991 (0.5); 1.988 (0.5); 1.974 (0.4); 1.677 (1.0); 0.000 (2.4)

Example I-54, Solvent: CDCl$_3$, Spectrometer: 300.2 MHz
7.761 (2.9); 7.614 (0.8); 7.609 (0.9); 7.588 (1.0); 7.585 (1.1); 7.482 (0.5); 7.476 (0.8); 7.470 (0.4); 7.460 (0.6); 7.453 (2.1); 7.447 (1.7); 7.440 (0.8); 7.433 (1.2); 7.429 (2.6); 7.427 (2.0); 7.422 (1.7); 7.416 (1.5); 7.407 (1.5); 7.401 (1.3); 7.397 (1.9); 7.390 (1.9); 7.383 (1.6); 7.372 (1.6); 7.367 (1.5); 7.355 (2.5); 7.349 (2.9); 7.342 (1.2); 7.333 (1.0); 7.328 (1.8); 7.323 (1.3); 7.297 (1.5); 7.293 (1.2); 7.290 (1.1); 7.273 (1.1); 7.266 (1.0); 7.263 (3.3); 7.030 (0.8); 6.846 (1.7); 6.833 (0.9); 6.746 (1.9); 6.663 (0.9); 6.650 (1.8); 6.467 (0.9); 5.783 (0.7); 5.753 (0.9); 5.746 (0.8); 5.716 (0.7); 5.381 (0.4); 5.365 (0.7); 5.349 (0.5); 5.117 (4.0); 3.912 (0.5); 3.905 (0.5); 3.898 (0.6); 3.883 (0.7); 3.876 (0.9); 3.862 (0.9); 3.847 (0.9); 3.832 (1.0); 3.820 (1.1); 3.811 (0.9); 3.797 (1.2); 3.783 (0.9); 3.757 (0.4); 3.745 (0.4); 3.666 (0.5); 3.655 (0.6); 3.629 (0.7); 3.618 (0.8); 3.608 (0.7); 3.597 (0.8); 3.570 (0.5); 3.560 (0.8); 3.526 (0.4); 3.512 (0.5); 3.499 (0.4); 3.481 (0.5); 3.470 (0.4); 3.419 (0.9); 3.388 (0.8); 3.361 (0.5); 3.330 (0.5); 2.510 (0.5); 2.449 (0.3); 2.338 (0.3); 2.237 (0.4); 2.223 (0.5); 2.208 (0.4); 2.189 (0.4); 2.181 (0.4); 2.162 (0.4); 2.154 (0.3); 2.134 (0.3); 1.998 (16.0); 1.989 (0.4); 1.988 (0.4); 1.986 (0.3); 1.985 (0.3); 1.982 (0.5); 1.979 (0.4); 1.977 (0.4); 1.976 (0.4); 1.975 (0.4); 1.961 (0.4); 1.960 (0.4); 1.958 (0.4); 1.699 (0.5); 0.000 (1.8)

Example I-55, Solvent: CDCl$_3$, Spectrometer: 300.2 MHz
7.841 (4.1); 7.838 (3.9); 7.362 (0.4); 7.341 (0.8); 7.334 (0.7); 7.320 (0.5); 7.313 (1.6); 7.306 (0.6); 7.291 (0.7); 7.285 (1.0); 7.267 (6.2); 7.036 (1.3); 6.965 (0.4); 6.954 (2.5); 6.942 (0.4); 6.937 (0.5); 6.926 (4.4); 6.915 (0.6); 6.909 (0.4); 6.898 (2.1); 6.886 (0.4); 6.852 (2.8); 6.837 (1.5); 6.749 (2.8); 6.669 (1.4); 6.654 (3.0); 6.471 (1.5); 6.115 (0.9); 6.084 (1.1); 6.075 (1.1); 6.044 (1.0); 5.402 (0.6); 5.386 (1.0); 5.382 (1.1); 5.367 (0.7); 5.124 (6.4); 3.932 (0.8); 3.917 (0.8); 3.896 (1.3); 3.886 (1.3); 3.881 (1.4); 3.864 (2.0); 3.846 (1.5); 3.835 (1.7); 3.825 (1.8); 3.811 (2.8); 3.770 (1.5); 3.694 (0.3); 3.671 (1.2); 3.641 (1.4); 3.614 (0.6); 3.583 (0.8); 3.578 (0.8); 3.557 (0.7); 3.534 (0.9); 3.493 (0.7); 3.458 (0.4); 2.585 (0.4); 2.576 (0.3); 2.550 (0.5); 2.529 (0.8); 2.467 (0.5); 2.393 (0.5); 2.379 (0.5); 2.364 (0.6); 2.348 (0.4); 2.332 (0.4); 2.318 (0.4); 2.298 (0.4); 2.287 (0.4); 2.270 (0.5); 2.258 (0.5); 2.249 (0.5); 2.244 (0.5); 2.229 (0.5); 2.221 (0.6); 2.200 (0.6); 2.174 (0.6); 2.154 (0.4); 2.148 (0.5); 2.005 (16.0); 1.992 (0.7); 1.990 (0.7); 1.988 (0.7); 1.984 (0.6); 1.983 (0.6); 1.981 (0.6); 1.939 (0.4); 1.670 (1.8); 0.000 (3.4)

Example I-56, Solvent: CDCl$_3$, Spectrometer: 300.2 MHz
7.806 (6.0); 7.399 (7.7); 7.384 (11.1); 7.366 (1.4); 7.359 (1.2); 7.354 (2.3); 7.340 (1.9); 7.332 (0.9); 7.325 (1.5); 7.316 (0.7); 7.311 (0.7); 7.305 (0.4); 7.264 (10.6); 7.031 (1.6); 6.847 (3.5); 6.835 (1.9); 6.747 (3.9); 6.664 (1.9); 6.652 (3.8); 6.469 (1.8); 5.786 (1.8); 5.758 (2.2); 5.749 (2.1); 5.721 (1.9); 5.389 (0.9); 5.370 (1.5); 5.354 (1.0); 5.117 (8.0); 3.906 (2.1); 3.901 (2.0); 3.889 (1.8); 3.885 (1.8); 3.869 (2.8); 3.864 (2.5); 3.849 (3.4); 3.843 (3.1); 3.835 (2.6); 3.827 (2.5); 3.822 (2.4); 3.811 (3.1); 3.806 (3.9); 3.761 (1.0); 3.686 (0.5); 3.674 (0.5); 3.638 (0.8); 3.562 (0.8); 3.525 (1.1); 3.490 (1.0); 3.472 (1.8); 3.464 (1.8); 3.444 (1.5); 3.436 (1.6); 3.414 (0.9); 3.407 (1.0); 3.387 (0.9); 3.379 (1.0); 2.568 (0.5); 2.511 (1.1); 2.453 (0.8); 2.383 (0.7); 2.368 (0.6); 2.353 (0.7); 2.322 (0.5); 2.312 (0.4); 2.277 (0.7); 2.263 (0.7); 2.245 (0.8); 2.232 (0.8); 2.228 (0.8); 2.214 (0.8); 2.193 (0.9); 2.166 (0.9); 2.144 (0.7); 2.003 (16.0); 1.994 (0.7); 1.993 (0.7); 1.991 (0.7); 1.985 (0.9); 1.984 (0.9); 1.982 (0.9); 1.965 (0.8); 1.940 (0.6); 1.935 (0.6); 1.921 (0.5); 1.659 (2.1); 0.000 (6.0)

Example I-57, Solvent: CDCl$_3$, Spectrometer: 300.2 MHz
7.800 (4.0); 7.584 (0.9); 7.578 (0.5); 7.564 (1.1); 7.557 (0.9); 7.409 (1.1); 7.404 (2.0); 7.395 (2.2); 7.391 (3.2); 7.385 (2.1); 7.378 (1.4); 7.367 (0.7); 7.363 (0.7); 7.359 (0.7); 7.354 (0.9); 7.343 (0.5); 7.335 (0.4); 7.268 (4.3); 7.032 (0.7); 6.848 (1.6); 6.836 (0.8); 6.747 (1.8); 6.665 (0.8); 6.653 (1.5); 6.470 (0.7); 6.056 (0.7); 6.028 (0.9); 6.018 (0.9); 5.990 (0.8); 5.390 (0.4); 5.371 (0.7); 5.356 (0.5); 5.120 (3.3); 4.098 (1.2); 3.989 (0.4); 3.983 (0.5); 3.951 (0.5); 3.946 (0.5); 3.930 (0.7); 3.925 (1.0); 3.910 (0.5); 3.892 (1.1); 3.887 (1.3); 3.874 (0.9); 3.852 (1.0); 3.836 (1.2); 3.830 (1.3); 3.802 (1.1); 3.761 (0.5); 3.645 (0.4); 3.562 (0.3); 3.526 (0.5); 3.510 (0.5); 3.498 (0.5); 3.490 (0.5); 3.480 (1.0); 3.474 (0.8); 3.452 (0.8); 3.446 (0.7); 3.421 (0.5); 3.415 (0.4); 3.393 (0.5); 3.387 (0.4); 3.267 (16.0); 2.515 (0.5); 2.455 (0.3); 2.361 (0.3); 2.242 (0.4); 2.229 (0.4); 2.214 (0.4); 2.195 (0.5); 2.168 (0.5); 2.147 (0.3); 2.004 (15.2); 1.997 (0.7); 1.995 (0.7); 1.994 (0.6); 1.992 (0.6); 1.991 (0.6); 1.989 (0.6); 1.981 (0.4); 1.975 (0.4); 1.687 (0.7); 0.000 (2.7)

Example I-58, Solvent: CDCl$_3$, Spectrometer: 300.2 MHz
7.766 (4.8); 7.490 (1.1); 7.485 (1.2); 7.463 (1.3); 7.459 (1.3); 7.328 (0.6); 7.322 (0.6); 7.302 (1.4); 7.298 (1.1); 7.276 (1.0); 7.270 (1.3); 7.265 (5.7); 7.047 (1.4); 7.038 (2.1); 7.035 (2.2); 7.030 (1.6); 7.024 (2.1); 7.011 (1.7); 7.008 (1.6); 6.999 (1.0); 6.846 (2.4); 6.834 (1.1); 6.746 (2.5); 6.663 (1.2); 6.651 (2.3); 6.468 (1.1); 6.030 (0.9); 6.005 (1.0); 5.993 (1.0); 5.968 (0.9); 5.382 (0.5); 5.367 (0.9); 5.362 (1.0); 5.347 (0.6); 5.115 (4.6); 4.769 (6.0); 4.761 (6.0); 3.925 (0.9); 3.921 (1.0); 3.915 (0.9); 3.904 (0.6); 3.897 (0.5); 3.887 (1.5); 3.883 (1.7); 3.867 (1.9); 3.863 (1.6); 3.844 (1.2); 3.829 (2.2); 3.816 (1.7); 3.799 (1.6); 3.793 (1.6); 3.754 (0.6); 3.626 (0.5); 3.561 (0.5); 3.547 (0.6); 3.533 (0.8); 3.521 (0.8); 3.503 (0.7); 3.490 (0.7); 3.474 (0.5); 3.458 (0.3); 3.341 (0.8); 3.337 (0.7); 3.316 (0.8); 3.312 (0.7); 3.283 (0.7); 3.279 (0.6); 3.258 (0.7); 3.254 (0.6); 2.537 (1.8); 2.529 (3.6); 2.521 (2.0); 2.502 (0.7); 2.453 (0.5); 2.441 (0.5); 2.390 (0.4); 2.375 (0.5); 2.360 (0.5); 2.345 (0.4); 2.280 (0.4); 2.265 (0.4); 2.249 (0.5); 2.234 (0.5); 2.228 (0.4); 2.217 (0.4); 2.205 (0.5); 2.187 (0.5); 2.169 (0.4); 2.159 (0.5); 2.137 (0.4); 2.004 (16.0);

1.993 (0.5); 1.990 (0.4); 1.987 (0.5); 1.980 (0.6); 1.978 (0.6); 1.977 (0.6); 1.961 (0.5); 1.933 (0.4); 1.671 (1.2); 0.000 (3.4)

Example I-59, Solvent: CDCl$_3$, Spectrometer: 300.2 MHz
7.816 (4.3); 7.269 (4.0); 7.172 (0.5); 7.141 (1.3); 7.110 (1.3); 7.080 (0.6); 7.035 (0.9); 6.852 (1.9); 6.837 (1.1); 6.800 (0.6); 6.793 (0.7); 6.788 (0.7); 6.781 (0.7); 6.769 (0.6); 6.762 (0.7); 6.749 (2.5); 6.668 (1.0); 6.654 (2.2); 6.471 (1.0); 6.207 (0.7); 6.176 (0.9); 6.167 (0.8); 6.136 (0.7); 5.400 (0.5); 5.381 (0.8); 5.365 (0.5); 5.125 (4.5); 4.669 (4.8); 4.661 (4.9); 3.927 (0.5); 3.916 (0.9); 3.892 (1.0); 3.882 (1.0); 3.877 (1.0); 3.862 (1.2); 3.844 (1.3); 3.835 (1.4); 3.810 (1.8); 3.770 (0.8); 3.752 (1.0); 3.712 (0.9); 3.673 (1.0); 3.643 (1.1); 3.617 (0.4); 3.581 (0.5); 3.557 (0.5); 3.545 (0.6); 3.532 (0.6); 3.512 (0.5); 3.500 (0.6); 2.525 (0.6); 2.485 (1.4); 2.477 (2.7); 2.469 (1.5); 2.393 (0.3); 2.377 (0.4); 2.278 (0.4); 2.265 (0.4); 2.248 (0.4); 2.230 (0.4); 2.220 (0.4); 2.199 (0.4); 2.173 (0.5); 2.149 (0.4); 2.005 (16.0); 1.995 (0.7); 1.993 (0.6); 1.992 (0.6); 1.990 (0.6); 1.989 (0.6); 1.986 (0.5); 1.984 (0.5); 1.983 (0.5); 1.981 (0.5); 1.980 (0.5); 1.971 (0.4); 1.970 (0.4); 1.968 (0.4); 1.967 (0.4); 1.964 (0.3); 1.961 (0.3); 1.959 (0.3); 1.697 (0.7); 0.000 (2.3)

Example I-60, Solvent: CDCl$_3$, Spectrometer: 300.2 MHz
7.806 (5.5); 7.517 (1.0); 7.512 (1.1); 7.491 (1.4); 7.485 (1.5); 7.415 (0.6); 7.410 (1.0); 7.388 (2.5); 7.383 (1.9); 7.367 (2.6); 7.341 (2.3); 7.314 (0.8); 7.274 (2.3); 6.787 (0.8); 6.603 (1.6); 6.418 (0.8); 6.312 (0.8); 6.276 (3.0); 6.272 (2.7); 6.236 (0.9); 4.923 (3.7); 3.914 (0.7); 3.874 (0.9); 3.856 (1.4); 3.815 (1.3); 3.800 (0.4); 3.788 (0.3); 3.761 (14.7); 3.679 (1.4); 3.644 (1.1); 3.621 (0.8); 3.586 (0.9); 3.562 (0.5); 3.549 (0.5); 3.534 (0.5); 3.520 (0.5); 3.513 (0.4); 3.221 (16.0); 2.471 (0.6); 2.448 (0.4); 2.319 (0.3); 2.310 (0.4); 2.275 (9.0); 2.244 (0.5); 2.226 (0.4); 2.002 (13.8); 0.000 (1.1)

Example I-61, Solvent: CDCl$_3$, Spectrometer: 300.2 MHz
7.743 (5.3); 7.611 (0.9); 7.606 (1.0); 7.585 (1.0); 7.581 (1.2); 7.478 (0.5); 7.472 (0.9); 7.466 (0.4); 7.456 (0.6); 7.449 (2.4); 7.444 (1.7); 7.438 (0.7); 7.430 (1.4); 7.425 (2.9); 7.423 (2.1); 7.414 (1.7); 7.408 (2.1); 7.402 (1.7); 7.397 (1.4); 7.390 (2.1); 7.383 (2.2); 7.379 (1.9); 7.365 (1.6); 7.359 (1.8); 7.349 (2.9); 7.343 (3.2); 7.335 (1.3); 7.327 (1.2); 7.322 (2.1); 7.317 (1.5); 7.297 (0.4); 7.291 (1.7); 7.286 (1.4); 7.284 (1.2); 7.267 (1.8); 7.263 (2.3); 6.781 (0.8); 6.597 (1.7); 6.412 (0.8); 6.267 (2.2); 5.773 (0.7); 5.742 (1.0); 5.736 (0.9); 5.705 (0.8); 4.911 (4.6); 3.817 (0.4); 3.806 (0.4); 3.795 (0.4); 3.739 (16.0); 3.721 (0.4); 3.720 (0.4); 3.718 (0.4); 3.708 (0.3); 3.707 (0.3); 3.669 (1.0); 3.651 (0.4); 3.632 (0.8); 3.611 (1.0); 3.574 (1.2); 3.561 (0.5); 3.549 (0.5); 3.532 (0.4); 3.515 (0.5); 3.505 (0.5); 3.490 (0.5); 3.476 (0.4); 3.422 (1.3); 3.392 (1.2); 3.364 (0.8); 3.334 (0.8); 2.501 (0.5); 2.489 (0.6); 2.478 (0.7); 2.467 (0.7); 2.457 (0.7); 2.435 (0.4); 2.319 (0.3); 2.305 (0.4); 2.290 (0.5); 2.265 (9.8); 2.237 (0.6); 2.221 (0.5); 2.210 (0.4); 1.986 (9.7); 0.000 (0.9)

Example I-62, Solvent: CDCl$_3$, Spectrometer: 300.2 MHz
7.818 (6.1); 7.336 (0.6); 7.329 (0.6); 7.315 (0.4); 7.308 (1.3); 7.301 (0.5); 7.287 (0.6); 7.280 (1.0); 7.276 (1.7); 7.259 (0.4); 6.948 (2.0); 6.937 (0.3); 6.932 (0.4); 6.920 (3.5); 6.909 (0.4); 6.904 (0.3); 6.893 (1.6); 6.784 (0.9); 6.600 (1.9); 6.415 (0.9); 6.268 (2.5); 6.100 (0.8); 6.068 (0.9); 6.060 (0.9); 6.029 (0.8); 4.922 (5.7); 3.872 (0.8); 3.851 (0.3); 3.832 (0.9); 3.815 (1.4); 3.774 (1.1); 3.761 (16.0); 3.731 (0.4); 3.696 (0.4); 3.670 (1.5); 3.639 (1.1); 3.612 (0.7); 3.602 (0.4); 3.581 (0.9); 3.562 (0.5); 3.544 (0.6); 3.531 (0.6); 3.515 (0.6); 3.503 (0.5); 3.488 (0.3); 2.503 (0.7); 2.492 (0.7); 2.482 (0.8); 2.471 (0.8); 2.449 (0.5); 2.343 (0.4); 2.334 (0.4); 2.327 (0.4); 2.308 (0.5); 2.270 (11.8); 1.995 (3.1); 0.000 (0.9)

Example I-63, Solvent: CDCl$_3$, Spectrometer: 300.2 MHz
7.784 (5.0); 7.408 (0.5); 7.392 (4.7); 7.381 (5.2); 7.377 (5.5); 7.366 (0.9); 7.358 (0.9); 7.352 (1.0); 7.346 (1.3); 7.335 (1.0); 7.332 (1.0); 7.324 (0.7); 7.317 (1.1); 7.308 (0.7); 7.302 (0.5); 7.297 (0.3); 7.289 (0.4); 7.267 (2.0); 6.787 (0.8); 6.603 (1.7); 6.418 (0.9); 6.272 (2.2); 5.773 (1.0); 5.745 (1.2); 5.736 (1.2); 5.708 (1.0); 4.926 (4.6); 4.486 (1.4); 3.907 (0.8); 3.870 (1.0); 3.849 (1.4); 3.812 (1.4); 3.793 (0.4); 3.785 (0.4); 3.746 (16.0); 3.716 (0.4); 3.704 (0.3); 3.690 (0.4); 3.680 (0.4); 3.677 (0.4); 3.667 (0.5); 3.657 (0.4); 3.650 (0.5); 3.591 (0.6); 3.585 (0.5); 3.569 (0.5); 3.552 (0.7); 3.539 (0.5); 3.529 (0.5); 3.520 (0.6); 3.511 (0.5); 3.501 (0.5); 3.497 (0.5); 3.464 (1.4); 3.436 (1.2); 3.407 (0.9); 3.379 (0.9); 2.527 (0.3); 2.494 (0.7); 2.482 (0.8); 2.471 (0.8); 2.461 (0.8); 2.439 (0.5); 2.333 (0.4); 2.296 (0.5); 2.270 (10.3); 2.244 (0.6); 2.228 (0.6); 2.215 (0.4); 2.212 (0.4); 2.196 (0.3); 1.997 (0.4); 1.991 (5.9); 0.000 (1.0)

Example I-64, Solvent: CDCl$_3$, Spectrometer: 300.2 MHz
7.784 (5.1); 7.582 (0.9); 7.576 (0.5); 7.562 (1.1); 7.555 (0.9); 7.404 (1.2); 7.398 (1.9); 7.390 (2.0); 7.385 (2.5); 7.379 (1.9); 7.371 (1.3); 7.361 (0.7); 7.357 (0.7); 7.353 (0.8); 7.347 (0.9); 7.337 (0.5); 7.328 (0.7); 7.270 (2.0); 6.784 (0.6); 6.600 (1.1); 6.415 (0.6); 6.271 (1.9); 6.052 (0.7); 6.024 (0.8); 6.014 (0.8); 5.986 (0.7); 5.298 (2.2); 4.916 (3.4); 3.989 (0.6); 3.952 (0.6); 3.931 (0.7); 3.893 (0.7); 3.816 (0.3); 3.804 (0.3); 3.793 (0.4); 3.782 (0.3); 3.750 (11.6); 3.726 (0.4); 3.682 (0.4); 3.672 (0.4); 3.662 (0.4); 3.588 (0.4); 3.571 (0.4); 3.558 (0.4); 3.538 (0.5); 3.525 (0.5); 3.509 (0.5); 3.501 (0.4); 3.495 (0.4); 3.475 (1.1); 3.447 (1.0); 3.416 (0.7); 3.388 (0.7); 3.264 (16.0); 2.486 (0.6); 2.476 (0.6); 2.466 (0.6); 2.317 (0.3); 2.309 (0.3); 2.298 (0.3); 2.272 (7.6); 2.239 (0.4); 2.225 (0.4); 0.000 (1.2)

Example I-65, Solvent: CDCl$_3$, Spectrometer: 300.2 MHz
7.749 (6.0); 7.489 (1.0); 7.484 (1.1); 7.463 (1.2); 7.459 (1.2); 7.324 (0.6); 7.319 (0.6); 7.298 (1.3); 7.294 (1.0); 7.272 (1.1); 7.267 (3.7); 7.042 (1.3); 7.036 (2.0); 7.033 (1.7); 7.020 (1.7); 7.009 (1.6); 7.006 (1.4); 6.995 (0.8); 6.784 (0.8); 6.599 (1.6); 6.415 (0.8); 6.271 (2.3); 6.026 (0.8); 6.001 (0.9); 5.989 (0.9); 5.964 (0.8); 4.913 (4.7); 4.768 (5.2); 4.761 (5.3); 3.928 (0.9); 3.891 (1.0); 3.870 (1.2); 3.833 (1.3); 3.816 (0.3); 3.804 (0.4); 3.793 (0.4); 3.781 (0.5); 3.770 (0.4); 3.740 (16.0); 3.710 (0.3); 3.676 (0.4); 3.671 (0.4); 3.662 (0.5); 3.654 (0.5); 3.641 (0.4); 3.599 (0.4); 3.589 (0.5); 3.573 (0.5); 3.559 (0.6); 3.547 (0.6); 3.519 (0.6); 3.490 (0.3); 3.340 (1.0); 3.315 (0.9); 3.282 (0.8); 3.257 (0.8); 2.536 (1.5); 2.528 (3.2); 2.520 (1.6); 2.483 (0.7); 2.459 (0.7); 2.452 (0.8); 2.428 (0.5); 2.339 (0.4); 2.327 (0.4); 2.312 (0.5); 2.272 (11.0); 2.236 (0.5); 2.224 (0.4); 1.999 (12.9); 1.992 (0.3); 0.000 (1.7)

Example I-66, Solvent: CDCl$_3$, Spectrometer: 300.2 MHz
7.797 (4.5); 7.274 (2.3); 7.169 (0.5); 7.138 (1.2); 7.107 (1.2); 7.076 (0.5); 6.797 (0.6); 6.790 (0.8); 6.785 (1.4); 6.779 (0.8); 6.767 (0.5); 6.760 (0.6); 6.755 (0.6); 6.748 (0.5); 6.600 (1.6); 6.416 (0.8); 6.273 (2.0); 6.196 (0.7); 6.166 (0.8); 6.156 (0.8); 6.126 (0.7); 4.923 (4.7); 4.666 (4.7); 4.658 (4.8); 3.831 (0.3); 3.817 (0.7); 3.798 (0.4); 3.774 (0.7); 3.762 (13.9); 3.718 (1.1); 3.698 (0.4); 3.674 (1.4); 3.644 (1.1); 3.616 (0.7); 3.600 (0.4); 3.586 (0.8); 3.571 (0.5); 3.563 (0.5); 3.552 (0.5); 3.534 (0.5); 3.527 (0.5); 2.503 (0.6); 2.490 (0.7); 2.475 (1.4); 2.467 (2.3); 2.460 (1.4); 2.341 (0.3); 2.325 (0.4); 2.306 (0.5); 2.276 (9.6); 2.226 (0.3); 2.002 (16.0); 1.994 (0.6); 1.993 (0.5); 1.991 (0.4); 0.000 (1.3)

Example I-67, Solvent: CDCl$_3$, Spectrometer: 300.2 MHz
7.811 (5.5); 7.524 (1.1); 7.519 (1.1); 7.498 (1.5); 7.493 (1.5); 7.421 (0.3); 7.416 (0.8); 7.413 (0.6); 7.410 (1.0); 7.389 (2.6); 7.383 (1.9); 7.367 (2.5); 7.341 (2.3); 7.314 (0.8); 7.267 (4.1); 6.894 (0.4); 6.320 (2.5); 6.281 (1.2); 6.276 (1.1); 6.240 (0.9); 4.960 (4.0); 3.918 (0.7); 3.877 (0.8); 3.860 (1.4); 3.832 (0.4); 3.819 (1.3); 3.804 (0.4); 3.766 (15.0); 3.744 (0.4); 3.733 (0.3); 3.708 (0.4); 3.697 (0.5); 3.681 (1.5); 3.645 (1.1); 3.622 (0.9); 3.606 (0.4); 3.595 (0.5); 3.587 (1.1); 3.571 (0.4); 3.564 (0.4); 3.551 (0.5); 3.536 (0.5); 3.522 (0.5); 3.507 (0.4); 3.221 (16.0); 3.214 (1.8); 2.506 (0.6); 2.493 (0.6); 2.482 (0.6); 2.472 (0.6); 2.459 (0.4); 2.448 (0.4); 2.359 (0.4); 2.344 (0.3); 2.330 (0.4); 2.319 (0.4); 2.294 (9.0); 2.274 (0.6); 2.257 (0.4); 2.243 (0.5); 2.005 (1.6); 1.656 (1.0); 0.000 (2.5)

Example I-68, Solvent: CDCl$_3$, Spectrometer: 300.2 MHz
7.754 (5.4); 7.615 (0.8); 7.610 (1.0); 7.585 (1.1); 7.482 (0.5); 7.476 (0.8); 7.470 (0.4); 7.460 (0.6); 7.453 (2.3); 7.448 (1.6); 7.434 (1.2); 7.429 (2.7); 7.419 (1.4); 7.412 (1.7); 7.406 (1.6); 7.401 (1.2); 7.394 (1.9); 7.387 (2.0); 7.383 (1.7); 7.369 (1.6); 7.364 (1.7); 7.353 (2.9); 7.348 (3.2); 7.340 (1.2); 7.331 (1.1); 7.326 (2.1); 7.321 (1.4); 7.295 (1.6); 7.290 (1.3); 7.288 (1.1); 7.271 (1.2); 7.262 (3.6); 6.316 (2.4); 5.776 (0.7); 5.746 (0.9); 5.739 (0.9); 5.709 (0.8); 4.952 (4.9); 3.818 (0.4); 3.807 (0.4); 3.796 (0.4); 3.746 (16.0); 3.698 (0.3); 3.673 (0.9); 3.635 (0.6); 3.615 (0.9); 3.602 (0.4); 3.590 (0.4); 3.577 (1.1); 3.562 (0.5); 3.524 (0.5); 3.508 (0.4); 3.491 (0.4); 3.478 (0.4); 3.425 (1.2); 3.395 (1.1); 3.367 (0.8); 3.337 (0.7); 2.481 (0.6); 2.448 (0.4); 2.437 (0.4); 2.332 (0.3); 2.319 (0.4); 2.289 (9.4); 2.261 (0.6); 2.250 (0.5); 2.234 (0.4); 2.220 (0.5); 1.999 (9.3); 1.683 (0.4); 0.000 (1.9)

Example I-69, Solvent: CDCl$_3$, Spectrometer: 300.2 MHz
7.830 (5.4); 7.338 (0.6); 7.330 (0.5); 7.317 (0.4); 7.310 (1.2); 7.303 (0.5); 7.288 (0.5); 7.282 (0.8); 7.265 (5.5); 6.952 (1.8); 6.936 (0.3); 6.924 (3.2); 6.914 (0.4); 6.897 (1.5); 6.320 (2.4); 6.107 (0.7); 6.076 (0.8); 6.067 (0.8); 6.036 (0.7); 4.959 (5.7); 3.875 (0.7); 3.836 (0.8); 3.818 (1.2); 3.767 (16.0); 3.713 (0.4); 3.691 (0.5); 3.675 (1.3); 3.644 (1.0); 3.617 (0.9); 3.606 (0.5); 3.586 (0.9); 3.544 (0.5); 3.535 (0.5); 3.518 (0.5); 3.505 (0.5); 2.511 (0.7); 2.500 (0.7); 2.494 (0.6); 2.462 (0.4); 2.451 (0.4); 2.356 (0.3); 2.341 (0.3); 2.297 (10.6); 2.295 (10.9); 2.271 (0.6); 2.253 (0.5); 2.237 (0.4); 2.006 (0.3); 1.637 (2.3); 0.000 (3.3)

Example I-70, Solvent: CDCl$_3$, Spectrometer: 300.2 MHz
7.796 (4.9); 7.414 (0.4); 7.397 (4.3); 7.387 (4.5); 7.383 (4.7); 7.364 (0.8); 7.357 (0.7); 7.353 (0.9); 7.350 (1.1); 7.340 (0.8); 7.337 (0.8); 7.328 (0.6); 7.322 (0.9); 7.312 (0.4); 7.307 (0.4); 7.263 (5.3); 6.317 (2.1); 5.782 (1.0); 5.754 (1.2); 5.745 (1.1); 5.717 (1.0); 4.952 (5.0); 3.913 (0.6); 3.875 (0.7); 3.855 (1.1); 3.819 (1.1); 3.796 (0.4); 3.753 (16.0); 3.706 (0.4); 3.695 (0.4); 3.685 (0.5); 3.674 (0.4); 3.608 (0.4); 3.598 (0.4); 3.581 (0.4); 3.569 (0.4); 3.532 (0.5); 3.521 (0.5); 3.503 (0.5); 3.485 (0.4); 3.472 (1.2); 3.457 (0.3); 3.444 (1.1); 3.414 (0.8); 3.386 (0.7); 2.501 (0.6); 2.489 (0.6); 2.467 (0.6); 2.453 (0.4); 2.441 (0.4); 2.341 (0.3); 2.326 (0.3); 2.292 (9.5); 2.270 (0.6); 2.257 (0.6); 2.240 (0.4); 2.226 (0.5); 2.003 (1.2); 1.641 (1.3); 0.000 (3.2)

Example I-71, Solvent: CDCl$_3$, Spectrometer: 300.2 MHz
7.791 (4.9); 7.586 (0.9); 7.579 (0.5); 7.565 (1.1); 7.558 (1.0); 7.408 (1.2); 7.402 (1.9); 7.394 (2.0); 7.392 (2.0); 7.389 (2.4); 7.383 (1.8); 7.375 (1.4); 7.365 (0.7); 7.361 (0.7); 7.356 (0.8); 7.351 (0.9); 7.341 (0.6); 7.331 (0.7); 7.267 (3.6); 6.319 (2.5); 6.054 (0.7); 6.026 (0.9); 6.017 (0.9); 5.989 (0.8); 4.956 (3.5); 3.993 (0.5); 3.955 (0.5); 3.934 (0.7); 3.896 (0.6); 3.805 (0.3); 3.793 (0.4); 3.783 (0.4); 3.756 (11.7); 3.705 (0.3); 3.691 (0.4); 3.683 (0.4); 3.673 (0.4); 3.597 (0.4); 3.579 (0.4); 3.567 (0.4); 3.549 (0.4); 3.537 (0.5); 3.522 (0.4); 3.507 (0.4); 3.499 (0.4); 3.481 (1.1); 3.464 (0.3); 3.453 (1.1); 3.422 (0.8); 3.394 (0.8); 3.268 (16.0); 2.503 (0.6); 2.492 (0.6); 2.469 (0.6); 2.456 (0.4); 2.445 (0.4); 2.360 (0.3); 2.331 (0.3); 2.323 (0.3); 2.291 (7.8); 2.257 (0.5); 2.241 (0.4); 2.226 (0.5); 2.005 (3.5); 0.000 (2.0)

Example I-72, Solvent: CDCl$_3$, Spectrometer: 300.2 MHz
7.755 (6.2); 7.492 (1.1); 7.487 (1.2); 7.465 (1.3); 7.462 (1.3); 7.325 (0.7); 7.319 (0.7); 7.299 (1.4); 7.295 (1.1); 7.272 (1.0); 7.264 (5.0); 7.044 (1.4); 7.037 (2.1); 7.034 (2.0); 7.021 (1.9); 7.009 (1.7); 7.006 (1.6); 6.996 (1.0); 6.316 (2.9); 6.029 (0.9); 6.004 (1.1); 5.991 (1.0); 5.966 (0.9); 4.951 (5.1); 4.904 (0.3); 4.770 (5.7); 4.762 (5.8); 3.930 (0.9); 3.893 (1.0); 3.872 (1.2); 3.835 (1.3); 3.823 (0.6); 3.801 (0.4); 3.790 (0.4); 3.779 (0.5); 3.768 (0.5); 3.743 (16.0); 3.684 (0.5); 3.671 (0.6); 3.663 (0.6); 3.649 (0.5); 3.597 (0.5); 3.577 (0.6); 3.566 (0.6); 3.548 (0.6); 3.537 (0.7); 3.520 (0.6); 3.494 (0.4); 3.474 (0.3); 3.342 (0.9); 3.317 (0.9); 3.284 (0.7); 3.259 (0.7); 2.536 (1.3); 2.532 (1.8); 2.524 (3.4); 2.516 (1.8); 2.487 (0.8); 2.476 (0.8); 2.454 (0.8); 2.440 (0.6); 2.428 (0.5); 2.350 (0.4); 2.337 (0.5); 2.319 (0.6); 2.304 (0.7); 2.288 (11.9); 2.250 (0.5); 2.235 (0.5); 2.003 (0.8); 1.670 (0.7); 0.000 (2.5)

Example I-73, Solvent: CDCl$_3$, Spectrometer: 300.2 MHz
7.805 (5.5); 7.266 (5.5); 7.169 (0.6); 7.138 (1.4); 7.108 (1.3); 7.077 (0.6); 6.797 (0.7); 6.791 (0.8); 6.785 (0.8); 6.779 (0.7); 6.766 (0.6); 6.760 (0.7); 6.755 (0.6); 6.748 (0.6); 6.320 (2.6); 6.200 (0.8); 6.170 (1.0); 6.160 (0.9); 6.130 (0.8); 4.960 (5.9); 4.668 (5.5); 4.660 (5.5); 3.856 (0.3); 3.844 (0.3); 3.832 (0.4); 3.819 (0.8); 3.798 (0.5); 3.767 (16.0); 3.732 (0.5); 3.721 (1.3); 3.678 (1.5); 3.647 (1.2); 3.620 (0.9); 3.590 (0.9); 3.562 (0.5); 3.549 (0.6); 3.534 (0.5); 3.518 (0.5); 2.561 (0.5); 2.508 (0.7); 2.494 (0.7); 2.469 (1.4); 2.461 (2.1); 2.454 (1.3); 2.351 (0.4); 2.337 (0.4); 2.321 (0.5); 2.297 (11.0); 2.277 (0.7); 2.261 (0.5); 2.246 (0.4); 2.006 (0.6); 1.648 (1.2); 0.000 (3.2)

Example I-74, Solvent: CDCl$_3$, Spectrometer: 300.2 MHz
7.814 (4.7); 7.522 (1.0); 7.517 (1.1); 7.496 (1.4); 7.490 (1.5); 7.414 (0.6); 7.409 (0.9); 7.387 (2.3); 7.382 (1.8); 7.366 (2.4); 7.339 (2.2); 7.312 (0.8); 7.272 (2.4); 6.969 (0.9); 6.784 (1.8); 6.600 (0.9); 6.310 (2.1); 6.279 (1.1); 6.274 (1.1); 6.239 (0.9); 5.023 (3.6); 3.921 (0.7); 3.881 (0.9); 3.863 (1.4); 3.822 (1.3); 3.809 (0.4); 3.765 (14.1); 3.682 (1.2); 3.647 (1.3); 3.624 (1.0); 3.609 (0.4); 3.588 (0.9); 3.554 (0.5); 3.541 (0.6); 3.528 (0.6); 3.515 (0.6); 3.497 (0.5); 3.483 (0.4); 3.222 (16.0); 2.519 (0.5); 2.509 (0.6); 2.499 (0.5); 2.474 (0.3); 2.465 (0.4); 2.452 (0.3); 2.342 (0.4); 2.293 (0.4); 2.280 (0.4); 2.255 (9.9); 2.003 (4.8); 0.000 (1.3)

Example I-75, Solvent: CDCl$_3$, Spectrometer: 300.2 MHz
7.835 (5.7); 7.377 (0.4); 7.371 (0.3); 7.370 (0.3); 7.358 (0.4); 7.356 (0.4); 7.349 (0.9); 7.342 (0.4); 7.337 (0.7); 7.329 (0.8); 7.321 (0.6); 7.316 (0.5); 7.309 (1.2); 7.302 (0.5); 7.287 (0.6); 7.278 (2.2); 7.260 (0.4); 6.968 (2.1); 6.950 (2.0); 6.939 (2.4); 6.923 (3.4); 6.911 (1.4); 6.895 (1.6); 6.785 (2.2); 6.601 (1.1); 6.309 (2.3); 6.169 (0.4); 6.139 (0.5); 6.128 (0.5); 6.103 (0.8); 6.072 (0.9); 6.064 (0.8); 6.033 (0.7); 5.027 (5.1); 4.750 (8.6); 3.882 (0.7); 3.842 (0.8); 3.824 (1.2); 3.805 (0.4); 3.784 (1.0); 3.765 (16.0); 3.677 (1.2); 3.645 (1.2); 3.619 (1.2); 3.617 (1.2); 3.588 (0.7); 3.578 (0.5); 3.575 (0.7); 3.572 (0.6); 3.561 (0.8); 3.558 (1.1); 3.555 (0.8); 3.545 (0.7); 3.533 (0.8); 3.516 (1.2); 3.501 (0.6); 3.488 (0.5); 3.471 (0.3); 3.387 (0.7); 3.357 (0.7); 3.328 (0.4); 3.298 (0.4); 2.522 (0.6); 2.513 (0.6); 2.475 (0.4); 2.464 (0.4); 2.453 (0.4); 2.345 (0.4);

2.304 (0.4); 2.295 (0.5); 2.278 (0.4); 2.253 (11.6); 2.225 (0.3); 2.001 (10.5); 0.000 (1.1)

Example I-76, Solvent: CDCl₃, Spectrometer: 300.2 MHz 7.815 (5.1); 7.263 (27.9); 7.170 (0.6); 7.139 (1.4); 7.108 (1.4); 7.077 (0.6); 6.977 (0.9); 6.792 (2.6); 6.786 (0.9); 6.779 (0.7); 6.766 (0.6); 6.760 (0.7); 6.755 (0.7); 6.748 (0.6); 6.608 (1.0); 6.324 (2.2); 6.202 (0.8); 6.171 (0.9); 6.162 (0.9); 6.131 (0.8); 5.056 (3.8); 4.669 (5.3); 4.661 (5.3); 4.545 (0.7); 4.529 (0.7); 3.857 (0.3); 3.823 (0.9); 3.798 (0.5); 3.782 (0.9); 3.769 (16.0); 3.726 (1.1); 3.682 (1.3); 3.652 (1.4); 3.625 (1.0); 3.595 (0.7); 3.567 (0.7); 3.553 (0.8); 3.539 (0.8); 3.520 (0.7); 3.482 (0.5); 2.557 (0.5); 2.549 (0.7); 2.541 (0.6); 2.523 (0.7); 2.469 (1.4); 2.462 (2.3); 2.454 (1.4); 2.379 (0.4); 2.370 (0.4); 2.354 (0.4); 2.337 (0.3); 2.305 (0.5); 2.271 (9.9); 2.009 (1.9); 1.693 (1.1); 0.011 (0.6); 0.000 (15.6); −0.011 (0.5)

Example I-77, Solvent: CDCl₃, Spectrometer: 300.2 MHz 7.816 (3.9); 7.528 (1.0); 7.523 (1.1); 7.502 (1.5); 7.496 (1.6); 7.423 (0.4); 7.416 (0.9); 7.412 (1.0); 7.391 (2.4); 7.385 (1.8); 7.369 (2.3); 7.343 (2.1); 7.316 (0.7); 7.263 (10.1); 7.039 (0.9); 6.894 (0.6); 6.855 (1.9); 6.837 (1.0); 6.748 (2.1); 6.671 (0.9); 6.654 (2.0); 6.471 (1.0); 6.320 (0.9); 6.284 (1.2); 6.279 (1.1); 6.244 (0.9); 5.121 (4.2); 4.355 (1.3); 4.342 (1.8); 4.335 (1.6); 4.324 (1.7); 3.947 (0.3); 3.921 (1.0); 3.902 (0.4); 3.880 (1.0); 3.862 (1.3); 3.821 (1.1); 3.699 (0.3); 3.684 (1.4); 3.670 (0.4); 3.649 (1.6); 3.639 (0.7); 3.626 (1.0); 3.590 (3.2); 3.574 (2.6); 3.559 (2.4); 3.531 (0.4); 3.517 (0.5); 3.502 (0.5); 3.485 (0.5); 3.470 (0.5); 3.454 (0.4); 3.435 (0.4); 3.320 (16.0); 3.222 (15.3); 3.214 (2.5); 2.578 (0.6); 2.569 (0.6); 2.530 (0.4); 2.510 (0.4); 2.362 (0.4); 2.291 (0.3); 2.278 (0.4); 2.261 (0.4); 2.246 (0.5); 2.008 (2.6); 1.590 (9.3); 0.000 (7.5); −0.011 (0.4)

Example I-78, Solvent: CDCl₃, Spectrometer: 300.2 MHz 7.828 (4.4); 7.527 (1.1); 7.521 (1.2); 7.500 (1.5); 7.495 (1.6); 7.419 (0.7); 7.414 (1.0); 7.392 (2.5); 7.387 (1.9); 7.371 (2.4); 7.345 (2.2); 7.318 (0.7); 7.263 (16.6); 7.038 (0.9); 6.855 (2.0); 6.838 (1.0); 6.750 (2.1); 6.671 (1.0); 6.655 (2.1); 6.471 (1.0); 6.322 (0.9); 6.286 (1.3); 6.281 (1.1); 6.246 (0.9); 5.124 (4.4); 4.767 (5.1); 4.759 (5.0); 3.955 (0.3); 3.922 (1.0); 3.906 (0.4); 3.881 (1.0); 3.863 (1.3); 3.823 (1.1); 3.687 (1.4); 3.652 (1.6); 3.628 (0.9); 3.593 (1.1); 3.556 (0.5); 3.528 (0.5); 3.512 (0.5); 3.497 (0.5); 3.483 (0.4); 3.453 (0.4); 3.222 (16.0); 2.587 (0.7); 2.512 (1.5); 2.504 (2.6); 2.496 (1.3); 2.403 (0.3); 2.390 (0.3); 2.375 (0.4); 2.307 (0.4); 2.294 (0.4); 2.279 (0.4); 2.265 (0.5); 1.587 (5.2); 1.255 (1.5); 0.000 (8.3); −0.011 (0.4)

Example I-79, Solvent: CDCl₃, Spectrometer: 300.2 MHz 7.732 (5.2); 7.535 (0.8); 7.533 (0.9); 7.515 (1.2); 7.389 (0.7); 7.385 (1.1); 7.382 (1.2); 7.380 (1.4); 7.374 (3.2); 7.372 (3.5); 7.362 (0.6); 7.358 (1.1); 7.350 (0.6); 7.343 (0.4); 7.339 (0.8); 7.336 (0.4); 7.330 (0.5); 7.326 (0.4); 7.317 (0.3); 7.266 (3.0); 6.861 (2.0); 6.277 (3.1); 6.029 (0.7); 6.008 (0.9); 6.001 (0.8); 5.980 (0.8); 3.962 (0.8); 3.934 (0.9); 3.918 (1.0); 3.890 (0.9); 3.742 (12.8); 3.703 (9.0); 3.667 (0.4); 3.658 (0.6); 3.652 (0.5); 3.641 (0.5); 3.633 (0.6); 3.623 (0.7); 3.617 (0.7); 3.608 (0.6); 3.457 (0.6); 3.446 (1.4); 3.436 (0.7); 3.429 (0.9); 3.425 (1.5); 3.402 (1.3); 3.381 (0.9); 3.257 (16.0); 2.522 (0.4); 2.514 (0.5); 2.506 (0.5); 2.497 (0.5); 2.487 (0.6); 2.479 (0.7); 2.471 (0.7); 2.463 (0.5); 2.315 (0.6); 2.305 (0.5); 2.293 (0.6); 2.287 (0.6); 2.268 (0.4); 2.260 (0.4); 1.999 (7.8); 0.000 (1.6)

Example I-80, Solvent: CDCl₃, Spectrometer: 300.2 MHz 7.673 (5.4); 7.429 (0.8); 7.426 (1.1); 7.409 (1.0); 7.407 (1.0); 7.329 (0.3); 7.317 (0.6); 7.312 (0.6); 7.304 (0.3); 7.297 (1.1); 7.294 (0.9); 7.277 (0.7); 7.273 (0.7); 7.262 (5.0); 7.026 (3.1); 7.018 (0.5); 7.006 (2.8); 6.990 (0.8); 6.839 (2.0); 6.293 (3.2); 6.004 (0.7); 5.985 (0.8); 5.976 (0.8); 5.957 (0.7); 4.751 (4.6); 4.746 (4.6); 4.719 (0.9); 4.713 (0.9); 4.500 (2.2); 3.891 (0.8); 3.863 (0.9); 3.848 (1.1); 3.820 (0.9); 3.734 (14.1); 3.723 (9.6); 3.683 (0.6); 3.673 (0.5); 3.661 (0.7); 3.656 (0.6); 3.648 (0.7); 3.471 (0.7); 3.463 (0.5); 3.456 (0.6); 3.450 (0.8); 3.446 (0.8); 3.443 (0.8); 3.440 (0.9); 3.430 (0.5); 3.428 (0.5); 3.425 (0.5); 3.416 (0.5); 3.324 (1.0); 3.305 (1.0); 3.281 (0.9); 3.262 (0.9); 2.534 (0.8); 2.525 (0.7); 2.519 (1.2); 2.516 (1.9); 2.514 (1.2); 2.510 (3.3); 2.504 (1.8); 2.495 (0.7); 2.487 (0.7); 2.479 (0.7); 2.326 (0.6); 2.315 (0.7); 2.303 (0.8); 2.292 (0.7); 2.280 (0.5); 2.269 (0.4); 2.034 (0.4); 2.000 (16.0); 0.000 (2.8)

Example I-81, Solvent: CDCl₃, Spectrometer: 300.2 MHz 7.698 (4.6); 7.268 (2.7); 7.158 (0.4); 7.135 (0.9); 7.112 (0.9); 7.089 (0.4); 7.042 (1.6); 6.782 (0.4); 6.777 (0.5); 6.773 (0.5); 6.769 (0.5); 6.759 (0.4); 6.754 (0.5); 6.750 (0.5); 6.746 (0.4); 6.278 (2.7); 6.182 (0.6); 6.160 (0.7); 6.152 (0.6); 6.129 (0.6); 4.662 (0.5); 4.652 (3.7); 4.646 (3.6); 4.534 (0.5); 4.518 (0.5); 3.779 (0.4); 3.748 (11.6); 3.737 (0.9); 3.708 (8.5); 3.671 (0.5); 3.649 (1.3); 3.626 (0.8); 3.606 (0.5); 3.583 (0.4); 3.464 (0.5); 3.457 (0.6); 3.442 (0.8); 3.434 (0.7); 3.426 (0.5); 3.422 (0.4); 3.409 (0.5); 3.401 (0.4); 2.568 (0.6); 2.519 (0.4); 2.515 (0.4); 2.503 (0.4); 2.480 (0.6); 2.459 (1.2); 2.453 (2.4); 2.447 (1.1); 2.317 (0.5); 2.306 (0.6); 2.294 (0.6); 2.283 (0.6); 2.271 (0.4); 2.260 (0.4); 2.001 (16.0); 0.000 (1.5)

Example II-1, Solvent: CDCl₃, Spectrometer: 400.13 MHz 8.0182 (1.70); 7.2612 (24.87); 6.9891 (0.44); 6.8518 (0.88); 6.8221 (0.58); 6.7998 (0.49); 6.7950 (0.86); 6.7616 (0.66); 6.7503 (0.98); 6.7149 (0.44); 6.6860 (0.55); 6.6628 (0.72); 6.6578 (1.05); 6.5255 (0.36); 6.5204 (0.52); 5.2991 (1.75); 5.1521 (0.44); 5.1231 (0.83); 5.1078 (1.16); 5.0630 (0.35); 4.9647 (1.08); 4.1484 (0.55); 4.1305 (1.69); 4.1127 (1.69); 4.1006 (1.80); 4.0948 (0.61); 4.0537 (2.15); 3.9739 (0.53); 3.9694 (0.34); 3.9268 (0.38); 3.9182 (0.95); 3.9082 (0.52); 3.8971 (0.65); 3.8864 (0.36); 3.8761 (0.49); 3.8652 (0.60); 3.8584 (0.41); 3.8418 (0.35); 3.8377 (0.38); 3.8273 (0.40); 3.7874 (0.39); 3.7776 (0.33); 3.3123 (0.67); 3.2938 (0.53); 3.2919 (0.49); 2.9562 (16.00); 2.8839 (13.78); 2.8826 (13.02); 2.2081 (0.36); 2.1080 (0.34); 2.0964 (0.33); 2.0890 (0.38); 2.0788 (0.43); 2.0746 (0.48); 2.0678 (0.44); 2.0437 (7.99); 2.0346 (0.46); 1.5705 (5.11); 1.4319 (0.75); 1.2766 (2.16); 1.2588 (4.48); 1.2409 (2.17); -0.0002 (3.21)

Example II-2, Solvent: CDCl₃, Spectrometer: 400.13 MHz 8.0181 (1.55); 7.5402 (0.39); 7.5196 (0.47); 7.5061 (0.42); 7.2608 (38.06); 6.9968 (0.34); 6.9917 (1.01); 6.8537 (2.22); 6.8212 (0.46); 6.7998 (0.95); 6.7960 (1.28); 6.7619 (1.24); 6.7496 (1.82); 6.7159 (1.21); 6.6858 (0.59); 6.6627 (1.45); 6.6588 (2.12); 6.5254 (0.71); 6.5214 (1.05); 5.2990 (5.77); 5.1540 (0.81); 5.1298 (0.95); 5.1219 (2.06); 5.1112 (2.11); 5.0804 (0.46); 4.9641 (1.05); 4.4626 (0.48); 4.4468 (0.91); 4.4307 (0.60); 4.4244 (0.47); 4.4088 (0.90); 4.3934 (0.73); 4.3807 (0.60); 4.3636 (0.64); 4.3533 (0.39); 4.3465 (0.39); 4.1483 (0.78); 4.1305 (2.38); 4.1126 (2.41); 4.1005 (1.28); 4.0948 (0.84); 4.0536 (1.58); 3.9737 (0.37); 3.9280 (0.35); 3.9182 (0.60); 3.8428 (0.37); 3.8304 (0.34); 3.7944 (0.37); 3.7508 (0.69); 3.7363 (0.71); 3.3618 (0.42); 2.9829 (0.32); 2.9559 (14.71); 2.8838 (12.16); 2.8827 (11.93); 2.8122 (1.91); 2.7965 (3.86); 2.7808 (1.91); 2.7286 (1.35); 2.7137 (1.75); 2.6991 (0.99); 2.4671 (0.41); 2.3952 (0.39); 2.2951 (0.35); 2.2766 (0.37); 2.2705 (0.44); 2.2420 (0.32); 2.1647 (0.67); 2.1540 (16.00); 2.1238 (1.85); 2.1092 (7.45); 2.0950 (0.57); 2.0806 (1.03); 2.0515 (0.50); 2.0437 (11.23);

1.5618 (6.98); 1.4319 (0.84); 1.3230 (0.52); 1.2766 (3.06); 1.2587 (6.22); 1.2409 (2.98); −0.0002 (4.88)

Example II-3, Solvent: CDCl$_3$, Spectrometer: 400.13 MHz 8.0179 (1.68); 7.6378 (0.45); 7.5418 (0.51); 7.5196 (0.45); 7.3212 (0.56); 7.2608 (43.02); 6.9967 (0.33); 6.9884 (1.71); 6.9553 (0.40); 6.8508 (3.39); 6.8209 (0.99); 6.7998 (1.06); 6.7937 (2.14); 6.7615 (1.40); 6.7484 (2.70); 6.7130 (1.57); 6.6855 (1.24); 6.6627 (1.63); 6.6564 (3.23); 6.5487 (0.41); 6.5254 (0.81); 6.5191 (1.59); 5.9657 (0.33); 5.9508 (0.70); 5.9397 (0.42); 5.9360 (0.39); 5.9248 (0.85); 5.9079 (0.93); 5.8967 (0.46); 5.8930 (0.46); 5.8819 (0.89); 5.8671 (0.46); 5.4047 (0.53); 5.4013 (1.34); 5.3979 (1.42); 5.3945 (0.58); 5.3617 (0.46); 5.3583 (1.17); 5.3550 (1.24); 5.3515 (0.54); 5.3399 (0.64); 5.3372 (1.50); 5.3345 (1.47); 5.3113 (1.37); 5.3085 (1.36); 5.2990 (1.29); 5.1574 (1.14); 5.1300 (1.08); 5.1190 (2.81); 5.1076 (3.40); 5.0818 (0.34); 4.9638 (2.28); 4.7323 (1.86); 4.7292 (2.89); 4.7263 (1.89); 4.7174 (1.77); 4.7144 (2.77); 4.7115 (1.76); 4.3595 (0.47); 4.3262 (0.54); 4.3107 (0.44); 4.1482 (0.69); 4.1304 (2.16); 4.1125 (2.14); 4.1005 (1.77); 4.0947 (0.79); 4.0536 (2.09); 3.9737 (0.47); 3.9693 (0.39); 3.9600 (0.34); 3.9182 (0.80); 3.8286 (0.47); 3.7944 (0.51); 3.4922 (0.33); 3.3396 (0.37); 3.3112 (0.69); 3.2828 (0.33); 2.9714 (0.37); 2.9558 (16.00); 2.9364 (0.65); 2.9074 (0.39); 2.9013 (0.38); 2.8835 (12.75); 2.8826 (13.45); 2.5108 (0.38); 2.4769 (0.52); 2.4293 (0.42); 2.3945 (0.53); 2.2937 (0.50); 2.2833 (0.51); 2.2650 (0.54); 2.2548 (0.61); 2.2304 (0.43); 2.2198 (0.51); 2.1098 (0.78); 2.0999 (0.78); 2.0798 (1.22); 2.0437 (10.08); 1.5631 (9.04); 1.4319 (1.15); 1.3407 (0.38); 1.3229 (0.77); 1.3051 (0.43); 1.2766 (2.69); 1.2587 (5.55); 1.2409 (2.70); −0.0002 (5.45)

Example II-4, Solvent: CDCl$_3$, Spectrometer: 400.13 MHz 8.0128 (1.74); 7.5290 (0.36); 7.5195 (0.38); 7.4042 (0.35); 7.3982 (0.36); 7.3918 (1.24); 7.3890 (0.97); 7.3869 (1.13); 7.3747 (9.48); 7.3634 (6.19); 7.3520 (2.09); 7.3448 (1.47); 7.3327 (0.95); 7.3278 (1.05); 7.3169 (0.85); 7.3089 (0.84); 7.3071 (0.86); 7.3056 (0.93); 7.3021 (0.64); 7.2987 (0.48); 7.2952 (0.96); 7.2900 (0.41); 7.2872 (0.37); 7.2842 (0.53); 7.2812 (0.40); 7.2733 (0.38); 7.2606 (18.87); 7.2430 (0.45); 6.9857 (0.51); 6.9726 (0.71); 6.8483 (1.09); 6.8348 (1.54); 6.8204 (0.76); 6.7979 (0.69); 6.7912 (0.57); 6.7852 (1.08); 6.7593 (0.99); 6.7397 (1.44); 6.7110 (0.55); 6.6971 (0.89); 6.6834 (0.60); 6.6607 (1.15); 6.6539 (0.41); 6.6478 (1.76); 6.5234 (0.59); 6.5104 (0.89); 5.2978 (1.92); 5.2585 (1.91); 5.2447 (1.92); 5.2172 (0.47); 5.1645 (0.61); 5.1286 (0.67); 5.1076 (0.80); 5.0954 (1.59); 5.0768 (1.44); 4.9590 (1.47); 4.7025 (2.09); 4.2893 (0.33); 4.2829 (0.32); 4.1293 (0.81); 4.1115 (0.82); 4.0990 (0.99); 4.0521 (1.24); 3.9168 (0.64); 3.7449 (0.35); 3.2337 (0.38); 2.9537 (16.00); 2.8810 (13.08); 2.8799 (13.66); 2.8645 (0.47); 2.4646 (0.35); 2.3824 (0.36); 2.2696 (0.35); 2.2398 (0.36); 2.2299 (0.41); 2.2231 (0.37); 2.2059 (0.38); 2.0987 (0.39); 2.0888 (0.55); 2.0731 (0.73); 2.0621 (0.65); 2.0504 (0.45); 2.0426 (4.00); 1.7004 (0.43); 1.5924 (1.37); 1.4316 (0.77); 1.3208 (0.37); 1.2758 (1.04); 1.2580 (2.19); 1.2401 (1.07); −0.0002 (2.36)

Example II-5, Solvent: CDCl$_3$, Spectrometer: 300.16 MHz 7.310 (2.6); 6.955 (1.1); 6.771 (2.2); 6.588 (1.1); 6.328 (2.3); 5.099 (0.4); 5.044 (2.3); 5.013 (2.4); 4.958 (0.5); 4.319 (0.5); 4.273 (0.5); 4.159 (0.5); 4.135 (1.6); 4.111 (1.7); 4.087 (0.6); 3.816 (16.0); 3.787 (0.5); 3.774 (0.6); 3.346 (0.3); 3.337 (0.4); 3.308 (0.4); 3.299 (0.7); 3.291 (0.4); 3.262 (0.4); 2.954 (0.4); 2.917 (0.7); 2.880 (0.4); 2.870 (0.3); 2.670 (7.8); 2.504 (0.4); 2.458 (0.6); 2.417 (0.5); 2.371 (0.6); 2.266 (12.4); 2.206 (0.4); 2.192 (0.4); 2.168 (0.4); 2.156 (0.5); 2.147 (0.4); 2.123 (0.3); 2.075 (0.4); 2.061 (0.6); 2.052 (7.5); 2.039 (0.6); 2.029 (0.6); 2.024 (0.6); 2.017 (0.5); 1.992 (0.4); 1.287 (2.0); 1.263 (4.2); 1.239 (2.0); 0.000 (1.7)

Example II-6, Solvent: CDCl$_3$, Spectrometer: 300.16 MHz 8.0231 (2.18); 7.7402 (0.45); 7.4838 (0.44); 7.2763 (1.13); 7.2658 (6.29); 6.3317 (1.76); 6.3091 (1.19); 5.3018 (1.19); 5.1083 (0.39); 5.0541 (1.19); 4.9873 (1.26); 4.9337 (0.40); 4.3723 (0.36); 4.3256 (0.39); 3.9331 (0.33); 3.8863 (0.39); 3.8277 (9.27); 3.2705 (0.47); 2.9706 (3.39); 2.9613 (16.00); 2.9314 (0.37); 2.9225 (0.34); 2.8874 (15.19); 2.8475 (0.36); 2.4620 (0.32); 2.4188 (0.78); 2.3597 (5.77); 2.3213 (0.39); 2.2923 (7.45); 2.2819 (1.08); 2.1169 (0.40); 2.0935 (0.34); 2.0814 (0.47); 2.0682 (0.45); 2.0469 (0.60); 2.0378 (0.42); 1.6880 (0.95); 0.0106 (1.02); −0.0002 (5.79)

Example II-7, Solvent: DMSO-d6, Spectrometer: 499.93 MHz 9.8966 (0.89); 8.9839 (0.90); 6.9499 (1.03); 6.8401 (2.41); 6.7303 (1.15); 6.2788 (2.61); 5.1425 (2.26); 5.1280 (2.20); 3.9278 (0.47); 3.9186 (0.32); 3.9088 (0.33); 3.9007 (0.50); 3.7552 (0.45); 3.7271 (0.50); 3.6728 (16.00); 3.2983 (0.48); 3.2818 (27.14); 3.2559 (0.33); 2.9712 (0.33); 2.9497 (0.57); 2.9286 (0.33); 2.5054 (2.12); 2.5019 (4.33); 2.4982 (5.91); 2.4946 (4.18); 2.4910 (1.94); 2.3051 (0.40); 2.2775 (0.51); 2.1978 (0.43); 2.1647 (11.96); 2.1020 (0.35); 2.0887 (0.37); 2.0817 (0.54); 2.0070 (0.37); 1.9936 (0.39); 1.9863 (0.55); −0.0002 (3.06)

Example II-9, Solvent: CDCl$_3$, Spectrometer: 300.16 MHz 7.6072 (0.47); 7.4962 (1.33); 7.3689 (1.46); 7.2912 (0.36); 7.2613 (74.48); 7.0380 (2.91); 6.9103 (0.47); 6.8543 (6.11); 6.8427 (3.56); 6.7514 (5.59); 6.6706 (3.17); 6.6596 (7.19); 6.4764 (3.53); 5.1946 (1.23); 5.1738 (3.24); 5.1529 (4.13); 5.1320 (3.57); 5.1189 (8.73); 5.1123 (8.91); 4.3980 (1.27); 4.3893 (0.79); 4.3530 (1.31); 3.8333 (1.14); 3.7859 (1.33); 3.3343 (0.84); 3.3249 (0.97); 3.2958 (1.22); 3.2875 (1.72); 3.2493 (0.92); 3.2396 (0.80); 2.9299 (0.77); 2.9224 (0.93); 2.8847 (1.66); 2.8460 (0.90); 2.8370 (0.88); 2.4953 (1.03); 2.4485 (1.53); 2.4352 (1.22); 2.4207 (1.20); 2.3743 (1.36); 2.2740 (0.97); 2.2602 (1.06); 2.2352 (1.15); 2.2215 (1.26); 2.1895 (0.84); 2.1751 (0.76); 2.0947 (0.97); 2.0804 (1.04); 2.0498 (1.20); 2.0412 (1.26); 2.0095 (0.85); 1.9956 (0.78); 1.5545 (16.00); 1.3366 (1.30); 1.3149 (15.82); 1.3087 (15.50); 1.2940 (15.21); 1.2878 (14.98); 1.2572 (2.32); 0.0107 (1.94); −0.0002 (65.21); −0.0111 (2.63)

Example II-10, Solvent: CDCl$_3$, Spectrometer: 300.16 MHz 7.5068 (0.75); 7.3572 (0.83); 7.3279 (0.35); 7.2764 (0.34); 7.2749 (0.40); 7.2734 (0.45); 7.2719 (0.52); 7.2705 (0.65); 7.2689 (0.92); 7.2614 (41.15); 7.2538 (1.07); 7.2523 (0.79); 7.2508 (0.62); 7.2493 (0.53); 7.2478 (0.46); 7.2464 (0.39); 7.2449 (0.32); 7.0363 (1.76); 6.8526 (3.69); 6.8429 (2.25); 6.7513 (3.37); 6.6688 (1.91); 6.6599 (4.40); 6.4767 (2.11); 5.3010 (0.36); 5.1198 (4.80); 5.1127 (4.79); 4.3849 (0.75); 4.3703 (0.49); 4.3387 (2.59); 4.3307 (1.05); 4.3150 (6.14); 4.2913 (6.38); 4.2676 (2.20); 3.8367 (0.68); 3.7895 (0.80); 3.3473 (0.49); 3.3382 (0.59); 3.3093 (0.68); 3.3009 (0.99); 3.2625 (0.50); 3.2539 (0.49); 2.9581 (0.55); 2.9489 (0.54); 2.9114 (0.95); 2.8739 (0.56); 2.8643 (0.50); 2.5028 (0.56); 2.4568 (0.91); 2.4317 (0.73); 2.3812 (0.85); 2.2886 (0.58); 2.2745 (0.64); 2.2505 (0.67); 2.2368 (0.76); 2.2042 (0.47); 2.1904 (0.46); 2.1081 (0.56); 2.0944 (0.64); 2.0678 (0.70); 2.0621 (0.71); 2.0559 (0.76); 2.0236 (0.51); 2.0103 (0.44); 1.5562 (4.71); 1.3761 (0.37); 1.3482 (7.69); 1.3245 (16.00); 1.3007 (7.48); 1.2550 (0.85); 0.0106 (0.98); 0.0074 (0.53); −0.0002 (36.26); −0.0078 (1.48); −0.0093 (1.20); −0.0110 (1.60); −0.0182 (0.44)

Example II-11, Solvent: DMSO-d$_6$, Spectrometer: 300.16 MHz 9.9489 (0.60); 9.0233 (0.61); 7.3190 (0.57); 7.2009 (0.68); 7.1414 (1.32); 7.0199 (1.58); 6.9641 (0.62); 6.8992 (1.26); 6.8389 (0.75); 5.7572 (0.42); 5.3542 (1.31); 5.3408 (1.33); 3.6949 (0.39); 3.6730 (9.00); 3.3195 (16.00); 3.2793 (0.38); 2.9596 (0.38); 2.8904 (0.73); 2.7296 (0.63); 2.5131 (4.25); 2.5071 (9.41); 2.5010 (13.13); 2.4948 (9.66); 2.4889

(4.67); 2.2782 (0.45); 2.1647 (0.36); 2.0906 (0.34); 1.9829 (0.35); 1.2611 (0.65); 0.0107 (0.51); −0.0002 (18.20); −0.0112 (0.77)

Example II-12, Solvent: CDCl$_3$, Spectrometer: 300.16 MHz 11.0477 (0.93); 10.5262 (0.58); 10.5141 (1.36); 10.5042 (3.91); 9.8376 (1.17); 9.6746 (0.43); 9.6535 (2.49); 9.4696 (1.24); 9.3468 (3.50); 7.2787 (22.31); 7.0601 (1.86); 7.0468 (1.18); 7.0134 (2.05); 6.9635 (0.70); 6.9050 (2.44); 6.8928 (5.95); 6.8832 (16.00); 6.7820 (11.38); 6.4694 (0.59); 6.4362 (1.88); 6.4318 (1.93); 6.2665 (1.28); 6.2583 (1.20); 6.2298 (1.93); 6.2212 (2.15); 6.1839 (1.32); 6.1004 (0.84); 6.0871 (2.04); 6.0784 (5.78); 5.9877 (0.80); 5.9738 (1.91); 5.9659 (5.25); 5.5406 (1.65); 5.4955 (2.11); 5.2363 (1.40); 5.2229 (1.43); 5.1989 (1.83); 5.1893 (1.98); 5.1538 (1.10); 5.1409 (0.81); 4.3610 (0.32); 4.3411 (0.64); 3.0826 (0.78); 3.0724 (2.29)

Example II-13, Solvent: CDCl$_3$, Spectrometer: 300.16 MHz 8.1727 (1.73); 7.6261 (0.61); 7.4557 (0.97); 7.4292 (1.35); 7.3860 (0.59); 7.2955 (1.02); 7.2642 (7.28); 7.0672 (0.88); 6.8647 (0.82); 6.8188 (0.76); 6.6823 (1.65); 6.6319 (1.54); 6.4998 (0.82); 6.4450 (0.77); 4.0076 (0.52); 3.9951 (1.06); 3.9829 (0.59); 3.9608 (0.63); 3.9487 (1.16); 3.9365 (0.61); 3.8756 (0.98); 3.8317 (16.00); 3.8179 (0.71); 3.4923 (0.91); 3.4689 (0.92); 3.1662 (0.68); 3.1573 (0.76); 3.1282 (0.87); 3.1198 (1.42); 3.1120 (0.83); 3.0826 (0.75); 3.0735 (0.72); 2.4828 (0.88); 2.4372 (1.23); 2.2633 (0.33); 2.2371 (0.79); 2.2231 (0.84); 2.1991 (0.85); 2.1857 (1.03); 2.1773 (0.85); 2.1534 (0.64); 2.1393 (0.58); 1.6319 (1.09); 1.3013 (0.38); 1.2665 (0.65); 1.2319 (1.03); 1.2086 (1.96); 1.1852 (0.94); 0.8818 (0.72); −0.0002 (3.86)

Example II-14, Solvent: CDCl$_3$, Spectrometer: 300.16 MHz 8.0352 (3.65); 7.6985 (0.62); 7.4181 (0.64); 7.2686 (5.09); 7.2374 (0.34); 7.2297 (1.06); 7.0354 (0.64); 7.0273 (2.27); 6.8331 (0.32); 6.8250 (1.13); 6.0973 (0.35); 6.0648 (1.41); 4.0377 (0.33); 3.9677 (0.59); 3.9556 (1.18); 3.9431 (0.70); 3.9213 (0.75); 3.9096 (1.30); 3.8970 (0.73); 3.8718 (3.41); 3.8460 (0.58); 3.8236 (16.00); 3.7051 (0.47); 3.4932 (0.39); 3.4698 (0.39); 3.1343 (0.68); 3.1258 (0.76); 3.0884 (1.42); 3.0512 (0.77); 3.0426 (0.70); 2.4574 (1.00); 2.4119 (1.37); 2.2210 (9.31); 2.2075 (1.65); 2.1931 (1.18); 2.1689 (1.01); 2.1545 (1.50); 2.1483 (1.48); 2.1236 (0.94); 2.1097 (0.86); 1.3401 (0.37); 1.3147 (0.44); 1.2640 (0.58); 1.2317 (0.48); 1.2083 (0.84); 1.1849 (0.41); −0.0002 (2.96)

Example II-15, Solvent: CDCl$_3$, Spectrometer: 300.16 MHz 7.5274 (0.44); 7.4102 (1.79); 7.3585 (0.35); 7.2614 (20.92); 7.0532 (1.17); 7.0278 (1.49); 6.8529 (1.00); 6.8273 (0.73); 6.0969 (1.06); 4.0035 (0.50); 3.9907 (1.03); 3.9790 (0.56); 3.9569 (0.61); 3.9448 (1.14); 3.9329 (0.57); 3.8726 (1.73); 3.8261 (16.00); 3.8122 (0.48); 3.7727 (0.34); 3.4917 (0.47); 3.4683 (0.45); 3.1325 (0.69); 3.1234 (0.73); 3.0942 (0.84); 3.0860 (1.37); 3.0489 (0.73); 3.0398 (0.69); 2.4655 (0.86); 2.4205 (1.14); 2.3269 (0.39); 2.2990 (7.81); 2.2277 (0.84); 2.2139 (1.13); 2.1936 (8.50); 2.1429 (0.88); 2.1303 (0.75); 1.6553 (0.57); 1.3513 (0.49); 1.2651 (0.44); 1.2326 (0.54); 1.2092 (0.98); 1.1858 (0.48); 0.8820 (0.47); 0.0106 (0.47); −0.0002 (14.16); −0.0111 (0.53)

Example II-16, Solvent: CDCl$_3$, Spectrometer: 300.16 MHz 8.019 (2.0); 7.913 (2.1); 7.690 (0.3); 7.430 (0.3); 7.270 (4.2); 6.912 (0.6); 6.729 (1.2); 6.639 (0.7); 6.547 (0.6); 3.948 (0.4); 3.936 (0.8); 3.923 (0.5); 3.901 (0.5); 3.889 (0.9); 3.876 (0.5); 3.867 (0.4); 3.847 (5.1); 3.844 (3.7); 3.831 (0.5); 3.820 (10.4); 3.122 (0.5); 3.113 (0.6); 3.084 (0.6); 3.076 (1.0); 3.038 (0.6); 3.029 (0.6); 2.959 (16.0); 2.885 (12.8); 2.884 (14.5); 2.466 (0.6); 2.421 (0.9); 2.218 (0.5); 2.204 (0.6); 2.179 (0.6); 2.166 (0.7); 2.159 (0.5); 2.134 (0.4); 2.120 (0.4); 1.711 (2.5); 0.000 (3.2)

Example II-17, Solvent: CDCl$_3$, Spectrometer: 300.16 MHz 8.017 (2.5); 7.762 (2.5); 7.438 (1.5); 7.376 (2.3); 7.268 (11.4); 7.025 (3.9); 6.849 (6.2); 6.842 (8.6); 6.753 (11.0); 6.667 (9.8); 6.484 (4.5); 5.231 (1.5); 5.214 (1.1); 5.177 (5.8); 5.158 (4.2); 5.128 (9.1); 5.073 (2.1); 4.822 (10.8); 4.817 (10.8); 4.398 (1.7); 4.385 (1.4); 4.366 (2.0); 4.353 (2.3); 4.332 (2.8); 4.309 (5.9); 4.285 (5.5); 4.261 (1.9); 4.138 (0.4); 3.832 (2.0); 3.785 (2.5); 3.729 (0.5); 3.706 (0.5); 3.481 (0.6); 3.366 (1.2); 3.334 (2.2); 3.328 (2.3); 3.289 (1.8); 3.260 (0.7); 2.960 (16.0); 2.912 (3.0); 2.883 (13.9); 2.558 (3.5); 2.550 (7.1); 2.542 (4.5); 2.491 (2.6); 2.454 (2.8); 2.411 (2.6); 2.374 (1.3); 2.247 (1.6); 2.235 (1.6); 2.203 (2.5); 2.164 (1.4); 2.091 (2.0); 2.052 (2.8); 2.019 (1.3); 1.700 (3.5); 1.343 (5.5); 1.320 (11.4); 1.296 (5.7); 1.255 (1.4); 1.240 (1.0); 1.216 (0.6); 0.000 (6.7)

Example II-18, Solvent: DMSO-d$_6$, Spectrometer: 300.16 MHz 15.438 (0.6); 9.901 (7.2); 8.934 (7.1); 7.267 (6.3); 7.147 (6.7); 7.089 (14.2); 6.965 (16.0); 6.912 (6.6); 6.845 (15.1); 6.784 (7.3); 5.703 (2.4); 5.360 (1.5); 5.303 (15.4); 5.292 (15.4); 5.237 (1.6); 4.197 (9.9); 4.185 (13.1); 4.166 (12.2); 3.908 (3.4); 3.865 (3.8); 3.829 (0.8); 3.714 (3.3); 3.668 (3.8); 3.499 (12.8); 3.483 (15.6); 3.468 (12.4); 3.437 (1.1); 3.269 (128.4); 3.203 (121.5); 3.169 (3.2); 3.120 (0.9); 3.102 (1.2); 2.966 (0.7); 2.901 (2.4); 2.867 (4.2); 2.830 (2.9); 2.670 (2.6); 2.485 (0.9); 2.457 (32.0); 2.451 (67.2); 2.445 (92.1); 2.439 (69.1); 2.433 (34.8); 2.285 (3.2); 2.241 (4.3); 2.182 (3.1); 2.133 (4.1); 2.052 (2.7); 2.017 (3.8); 1.982 (2.2); 1.934 (2.7); 1.899 (3.9); 1.866 (2.0); 1.854 (1.8); 1.832 (0.6); −0.057 (112.6); −0.067 (5.7); −0.095 (0.9); −0.254 (0.7)

Example II-19, Solvent: DMSO-d$_6$, Spectrometer: 300.16 MHz 9.919 (0.7); 8.995 (0.7); 8.796 (1.2); 6.448 (3.1); 5.758 (10.2); 3.829 (0.9); 3.817 (0.5); 3.804 (0.6); 3.794 (1.0); 3.679 (16.0); 3.362 (0.4); 3.312 (51.5); 3.126 (0.5); 3.120 (0.6); 3.093 (1.0); 3.067 (0.6); 2.898 (0.6); 2.739 (0.5); 2.517 (13.8); 2.512 (27.7); 2.508 (37.1); 2.504 (26.5); 2.499 (12.7); 2.261 (0.8); 2.227 (1.0); 2.052 (0.6); 2.042 (0.7); 2.026 (0.7); 2.017 (1.0); 1.992 (0.5); 1.983 (0.4); 0.867 (0.4)

Example IV-1, Solvent: DMSO-d$_6$, Spectrometer: 400.13 MHz 7.3010 (0.38); 7.1678 (0.87); 7.1643 (0.57); 7.0349 (0.43); 7.0280 (1.00); 6.9147 (0.87); 6.8921 (0.47); 5.7584 (16.00); 5.4632 (0.47); 5.3899 (0.33); 5.3859 (0.34); 5.3679 (0.54); 5.2883 (0.42); 4.2727 (0.37); 3.8265 (0.81); 3.8152 (0.60); 3.8102 (0.49); 3.7896 (0.78); 3.7812 (0.44); 3.7693 (0.41); 3.7605 (0.71); 3.7491 (0.45); 3.7394 (0.37); 3.6419 (0.37); 2.8972 (0.82); 2.7381 (0.49); 2.5164 (2.98); 2.5120 (6.18); 2.5075 (8.42); 2.5031 (6.03); 2.4987 (2.88); 2.2193 (0.36); 2.1996 (0.35); 2.1842 (0.55); 2.1797 (0.50); 2.1647 (0.32); 2.1362 (0.42); 1.8706 (0.33)

Example IV-2, Solvent: DMSO-d$_6$, Spectrometer: 400.13 MHz 7.3016 (1.07); 7.1688 (2.00); 7.0596 (0.43); 7.0360 (0.92); 7.0294 (2.02); 6.9671 (0.40); 6.9156 (1.62); 6.8936 (0.94); 5.7595 (16.00); 5.5115 (0.42); 5.4688 (0.93); 5.3674 (0.97); 5.3247 (0.45); 5.3065 (0.96); 4.3610 (1.53); 4.3540 (1.44); 4.3498 (1.64); 4.3452 (1.35); 4.3383 (1.64); 4.2942 (0.36); 4.2719 (0.33); 4.2569 (0.72); 4.2499 (0.47); 4.2457 (0.51); 4.2340 (0.40); 3.9780 (0.33); 3.9417 (0.36); 3.6077 (1.82); 3.6003 (1.29); 3.5963 (1.84); 3.5927 (1.40); 3.5849 (1.76); 3.5480 (0.60); 3.5410 (0.48); 3.5365 (0.60); 3.5324 (0.44); 3.5251 (0.54); 3.4894 (0.42); 3.3424 (0.54); 3.3097 (0.49); 3.2939 (15.89); 3.2895 (1.87); 3.2806 (0.37); 3.2693 (0.46); 3.2532 (3.23); 3.2509 (1.87); 2.9214 (0.41); 2.8972 (1.47); 2.7387 (1.06); 2.7377 (1.07); 2.5592 (0.32); 2.5453 (0.65); 2.5311 (0.52); 2.5165 (7.22); 2.5120 (14.65); 2.5075 (19.78); 2.5030 (13.86); 2.4985 (6.41); 2.1702 (0.85); 2.1485 (0.52); 2.1293 (0.75); 1.8774 (0.33); 1.8696 (0.35); 1.3631 (0.37)

Example IV-3, Solvent: DMSO-$d_6$, Spectrometer: 400.13 MHz 7.3073 (0.40); 7.3032 (0.82); 7.1702 (1.87); 7.1646 (1.04); 7.0594 (0.34); 7.0373 (0.95); 7.0286 (2.12); 6.9156 (1.76); 6.8928 (0.99); 5.7583 (15.07); 5.5115 (0.43); 5.4688 (0.95); 5.3689 (1.03); 5.3263 (0.46); 5.3032 (0.72); 4.4036 (1.54); 4.3875 (3.46); 4.3715 (1.66); 4.3027 (0.60); 4.2860 (0.74); 4.2719 (0.64); 4.2697 (0.70); 3.9895 (0.33); 3.9541 (0.37); 3.7682 (0.32); 3.3114 (0.43); 2.9220 (0.42); 2.8970 (1.71); 2.8301 (0.33); 2.8114 (2.04); 2.7953 (3.84); 2.7792 (1.73); 2.7389 (1.28); 2.7378 (1.30); 2.7330 (0.35); 2.7163 (0.61); 2.5547 (0.51); 2.5408 (1.06); 2.5268 (0.68); 2.5165 (3.94); 2.5121 (8.07); 2.5076 (10.90); 2.5030 (7.69); 2.4986 (3.58); 2.1723 (0.98); 2.1277 (16.00); 2.1217 (2.47); 2.0752 (2.32); 1.8947 (0.34); 1.8874 (0.35); 1.3634 (0.38); 1.2648 (0.43)

Example IV-4, Solvent: DMSO-$d_6$, Spectrometer: 400.13 MHz 7.3056 (0.67); 7.3019 (1.06); 7.1688 (2.44); 7.1651 (1.50); 7.0672 (0.65); 7.0359 (1.21); 7.0289 (2.71); 6.9773 (0.43); 6.9317 (0.40); 6.9155 (2.25); 6.8931 (1.29); 5.7588 (16.00); 5.5089 (0.55); 5.4663 (1.25); 5.3729 (1.40); 5.3590 (1.37); 5.3304 (0.60); 4.9149 (5.27); 4.9088 (5.22); 4.8194 (1.10); 4.8133 (1.10); 4.3171 (0.46); 4.2896 (0.42); 4.2819 (0.51); 4.2722 (0.51); 4.0457 (1.27); 4.0397 (1.28); 3.9872 (0.45); 3.9787 (0.36); 3.9523 (0.49); 3.7278 (0.35); 3.7119 (1.43); 3.7058 (3.00); 3.6998 (1.38); 3.6414 (0.39); 3.6352 (0.68); 3.6290 (0.34); 3.3111 (0.68); 3.3036 (0.55); 3.2395 (0.58); 2.9346 (0.32); 2.8971 (2.58); 2.7386 (1.83); 2.7377 (1.80); 2.5425 (0.37); 2.5287 (0.46); 2.5164 (8.21); 2.5120 (16.72); 2.5075 (22.59); 2.5030 (15.98); 2.4986 (7.47); 2.2224 (0.38); 2.1887 (1.19); 2.1669 (0.71); 2.1573 (0.92); 2.1401 (0.69); 2.1297 (0.59); 1.8964 (0.34); 1.8733 (0.46); 1.8661 (0.48); 1.3630 (0.50); 1.2644 (0.52)

Example IV-5, Solvent: DMSO-$d_6$, Spectrometer: 400.13 MHz 7.9595 (0.35); 7.6895 (0.38); 7.4443 (0.35); 7.3116 (0.80); 7.3011 (1.71); 7.1994 (0.46); 7.1790 (0.55); 7.1679 (4.22); 7.0639 (0.93); 7.0351 (2.12); 7.0292 (4.33); 6.9721 (0.71); 6.9282 (0.63); 6.9157 (3.69); 6.8933 (2.03); 6.0217 (0.48); 6.0082 (1.03); 5.9951 (0.99); 5.9819 (1.27); 5.9788 (0.78); 5.9683 (0.71); 5.9651 (1.36); 5.9520 (1.23); 5.9388 (1.46); 5.9255 (0.76); 5.7595 (16.00); 5.5070 (0.98); 5.4642 (2.24); 5.4195 (0.94); 5.4158 (2.26); 5.4119 (2.26); 5.4080 (0.87); 5.3726 (4.18); 5.3690 (3.29); 5.3385 (2.38); 5.3288 (1.53); 5.3246 (1.19); 5.3207 (1.42); 5.3175 (2.35); 5.3140 (2.15); 5.2911 (2.09); 5.2877 (2.06); 5.2542 (0.43); 5.2506 (0.41); 5.2279 (0.39); 5.2243 (0.40); 4.7590 (3.08); 4.7555 (4.97); 4.7520 (3.13); 4.7456 (3.11); 4.7421 (4.80); 4.7386 (2.84); 4.6650 (0.56); 4.6614 (0.92); 4.6578 (0.57); 4.6515 (0.57); 4.6479 (0.91); 4.6444 (0.52); 4.3249 (0.79); 4.2899 (0.94); 4.2722 (0.53); 4.2543 (0.39); 3.9915 (0.75); 3.9547 (0.97); 3.9502 (0.91); 3.9457 (0.66); 3.9386 (0.48); 3.4565 (0.32); 3.4391 (0.48); 3.4056 (0.72); 3.3319 (0.62); 3.3020 (0.98); 3.2735 (0.55); 3.2664 (0.48); 2.9306 (0.54); 2.8971 (3.54); 2.8711 (0.56); 2.7381 (2.21); 2.5599 (0.56); 2.5460 (1.10); 2.5315 (1.03); 2.5163 (14.43); 2.5119 (28.70); 2.5074 (38.35); 2.5029 (27.04); 2.4986 (12.68); 2.3390 (0.33); 2.3343 (0.33); 2.2287 (0.65); 2.1925 (2.09); 2.1607 (1.70); 2.1438 (1.05); 2.1333 (0.89); 2.1088 (0.42); 2.0981 (0.33); 1.9166 (0.48); 1.9061 (0.57); 1.8837 (0.77); 1.8746 (0.80); 1.8524 (0.47); 1.8420 (0.39); 1.3631 (0.77); 1.2822 (0.38); 1.2644 (0.80); 1.2466 (0.41)

Example IV-6, Solvent: DMSO-$d_6$, Spectrometer: 400.13 MHz 7.9598 (0.38); 7.7185 (0.35); 7.4446 (0.80); 7.4321 (8.24); 7.4234 (9.45); 7.4214 (10.23); 7.4075 (1.44); 7.4025 (1.38); 7.3986 (2.11); 7.3903 (2.16); 7.3884 (2.29); 7.3817 (1.17); 7.3762 (2.51); 7.3667 (2.70); 7.3560 (0.68); 7.3492 (0.62); 7.3275 (1.20); 7.3153 (3.25); 7.3031 (0.37); 7.2941 (1.64); 7.1994 (0.46); 7.1821 (0.41); 7.1609 (5.12); 7.0639 (0.90); 7.0248 (4.38); 6.9744 (0.70); 6.9283 (0.50); 6.9121 (3.54); 6.8890 (1.91); 5.7598 (16.00); 5.5019 (0.95); 5.4592 (2.13); 5.3636 (3.98); 5.3202 (1.00); 5.2906 (13.23); 5.2029 (2.33); 4.7669 (0.68); 4.4979 (1.79); 4.3206 (0.76); 4.2858 (0.82); 4.2723 (0.59); 3.9852 (0.71); 3.9494 (0.79); 3.4400 (0.43); 3.4226 (0.39); 3.4034 (0.49); 3.3256 (0.59); 3.2954 (0.95); 3.2673 (0.55); 2.9245 (0.51); 2.8966 (3.88); 2.8646 (0.53); 2.7386 (2.43); 2.7377 (2.39); 2.5599 (0.57); 2.5460 (1.15); 2.5319 (0.73); 2.5251 (0.82); 2.5165 (13.09); 2.5120 (27.13); 2.5075 (36.96); 2.5030 (26.27); 2.4986 (12.41); 2.2299 (0.64); 2.1975 (2.07); 2.1616 (1.64); 2.1411 (0.79); 2.1324 (0.83); 2.1074 (0.38); 2.0975 (0.33); 1.9230 (0.45); 1.9128 (0.54); 1.8897 (0.74); 1.8813 (0.76); 1.8585 (0.45); 1.8487 (0.36); 1.3639 (0.76); 1.2645 (0.63)

Example IV-7, Solvent: CDCl$_3$, Spectrometer: 300.16 MHz 7.2644 (7.85); 6.3619 (0.36); 6.3419 (2.49); 6.3257 (1.83); 5.1147 (0.49); 5.0617 (1.33); 4.9514 (1.32); 4.8983 (0.56); 4.8928 (0.59); 4.5633 (0.45); 4.5165 (0.42); 4.1589 (0.40); 4.1351 (1.21); 4.1113 (1.44); 4.0875 (0.68); 4.0485 (0.42); 3.8731 (1.74); 3.8661 (16.00); 3.7907 (0.37); 3.5491 (0.32); 3.5096 (0.57); 3.4703 (0.32); 3.0858 (0.50); 2.3624 (6.95); 2.3604 (7.29); 2.3218 (9.20); 2.3199 (9.77); 2.3114 (2.19); 2.2896 (1.76); 2.1835 (0.72); 2.1759 (0.75); 2.1406 (1.11); 2.1302 (1.19); 2.1126 (0.52); 2.1019 (13.97); 2.0678 (0.49); 2.0478 (5.88); 2.0296 (0.59); 2.0110 (0.74); 1.9965 (0.57); 1.9836 (0.46); 1.9700 (0.65); 1.9563 (0.52); 1.2872 (0.58); 1.2839 (1.62); 1.2601 (3.22); 1.2362 (1.55); -0.0002 (6.43)

Example IV-8, Solvent: CDCl$_3$, Spectrometer: 300.16 MHz 7.3117 (5.40); 7.3097 (4.68); 6.9556 (0.52); 6.7940 (1.43); 6.7725 (1.04); 6.6101 (2.85); 6.5897 (0.61); 6.4260 (1.43); 6.3435 (1.31); 6.3042 (3.70); 5.3141 (0.46); 5.1274 (0.78); 5.0723 (1.05); 5.0375 (1.12); 5.0185 (2.56); 4.9831 (0.45); 4.9227 (2.53); 4.8683 (1.01); 4.5293 (1.18); 4.4831 (1.26); 4.0239 (0.84); 3.9760 (1.01); 3.8653 (0.36); 3.5373 (0.82); 3.4976 (1.34); 3.4602 (0.81); 3.4506 (0.76); 3.4323 (1.89); 3.4304 (1.68); 3.3949 (0.75); 3.3927 (0.71); 3.1741 (10.19); 3.1519 (3.76); 3.0976 (1.72); 3.0584 (0.94); 2.2930 (16.00); 2.2728 (6.37); 2.1776 (1.99); 2.1415 (3.53); 2.1057 (1.24); 2.0772 (1.16); 2.0674 (1.16); 2.0334 (1.33); 2.0225 (1.32); 1.9955 (1.27); 1.9502 (0.64); 1.9379 (0.54); 1.2569 (0.85); -0.0002 (3.89); -0.0022 (3.49)

Example IV-9, Solvent: CDCl$_3$, Spectrometer: 300.16 MHz 7.2704 (2.65); 6.8392 (0.65); 6.7912 (0.77); 6.7837 (0.51); 6.6556 (1.34); 6.6071 (1.56); 6.6007 (0.35); 6.4720 (0.67); 6.4230 (0.76); 6.3289 (0.48); 6.2931 (1.41); 6.2787 (1.17); 5.0735 (0.58); 5.0186 (0.92); 4.9287 (0.85); 4.8753 (0.36); 4.5621 (0.34); 4.5153 (0.32); 4.1983 (0.32); 4.1581 (0.53); 4.1343 (1.60); 4.1105 (1.67); 4.0867 (0.62); 3.8676 (5.48); 3.8636 (11.30); 3.8500 (0.34); 3.4908 (0.46); 3.0804 (0.39); 2.3405 (5.43); 2.2980 (6.24); 2.2782 (1.00); 2.2644 (2.91); 2.1738 (0.72); 2.1286 (1.35); 2.1065 (0.36); 2.1049 (0.34); 2.1019 (0.42); 2.1003 (0.41); 2.0913 (16.00); 2.0807 (0.59); 2.0748 (0.38); 2.0733 (0.37); 2.0719 (0.35); 2.0703 (0.34); 2.0688 (0.34); 2.0673 (0.36); 2.0660 (0.36); 2.0630 (0.33); 2.0473 (7.83); 2.0249 (0.38); 2.0116 (0.60); 1.9984 (0.57); 1.9692 (0.52); 1.9559 (0.45); 1.2831 (2.13); 1.2593 (4.20); 1.2355 (2.03); -0.0002 (2.26)

Example IV-10, Solvent: CDCl$_3$, Spectrometer: 300.16 MHz 7.2650 (11.15); 7.0381 (1.71); 6.9679 (0.75); 6.8551 (3.68); 6.8451 (2.21); 6.7868 (1.56); 6.7633 (3.77); 6.6760 (2.07); 6.6721 (2.10); 6.6622 (4.38); 6.6059 (0.75); 6.4934 (0.85); 6.4792 (2.10); 5.1916 (0.78); 5.1755 (0.38); 5.1707 (0.94); 5.1600 (1.00); 5.1442 (3.66); 5.1394 (3.53); 5.1253 (3.76); 5.1183 (3.75); 5.0972 (2.53); 5.0758 (1.44); 5.0543 (0.44); 5.0096 (4.10); 4.5401 (0.64); 4.4937 (0.71); 4.3839 (0.72); 4.3601 (2.25); 4.3363 (2.28); 4.3125 (0.75); 4.0297

(0.39); 3.8989 (0.57); 3.8516 (0.73); 3.6252 (0.80); 3.5787 (0.46); 3.5700 (0.49); 3.5306 (0.83); 3.4922 (0.41); 3.4840 (0.39); 3.1847 (1.39); 3.1732 (0.48); 3.1642 (0.47); 3.1242 (0.82); 3.0847 (0.44); 3.0771 (0.42); 2.9657 (0.58); 2.8911 (0.51); 2.8894 (0.49); 2.2141 (0.57); 2.1721 (1.54); 2.1437 (1.17); 2.1089 (0.64); 2.0958 (0.72); 2.0561 (0.87); 2.0459 (0.72); 2.0192 (0.85); 2.0062 (0.85); 1.9768 (0.72); 1.9651 (0.73); 1.9326 (0.37); 1.9191 (0.33); 1.5709 (0.94); 1.5507 (0.97); 1.4321 (0.85); 1.4018 (2.34); 1.3780 (5.49); 1.3719 (10.02); 1.3669 (3.65); 1.3540 (4.07); 1.3509 (10.41); 1.3459 (4.45); 1.3359 (16.00); 1.3150 (15.99); 1.2778 (12.40); 1.2569 (12.54); 1.2398 (0.57); 1.2207 (4.78); 1.2003 (4.78); −0.0002 (9.42); −0.0111 (0.42)

Example IV-11, Solvent: CDCl$_3$, Spectrometer: 300.16 MHz 7.2628 (13.86); 7.0356 (1.87); 6.8525 (4.01); 6.8452 (2.42); 6.7640 (3.74); 6.6693 (2.32); 6.6622 (4.59); 6.4792 (2.20); 5.1408 (3.88); 5.1223 (3.96); 5.0445 (0.63); 4.5569 (0.75); 4.5108 (0.81); 4.3531 (2.32); 4.3293 (7.36); 4.3055 (7.50); 4.2930 (0.38); 4.2817 (2.49); 4.2692 (0.46); 4.2453 (0.39); 3.9032 (0.66); 3.8562 (0.86); 3.5825 (0.53); 3.5753 (0.57); 3.5357 (0.95); 3.4968 (0.49); 3.4880 (0.45); 3.1604 (0.50); 3.1220 (0.94); 3.0826 (0.51); 2.2273 (0.69); 2.1872 (1.49); 2.1697 (1.30); 2.1593 (1.31); 2.1235 (0.65); 2.1103 (0.70); 2.0712 (0.82); 2.0339 (0.87); 2.0216 (0.85); 1.9921 (0.78); 1.9791 (0.78); 1.9462 (0.39); 1.9327 (0.34); 1.5766 (1.45); 1.3752 (7.72); 1.3514 (16.00); 1.3276 (7.62); 1.3141 (0.70); 1.2903 (1.00); 1.2664 (0.74); 1.2550 (0.92); −0.0002 (8.64); −0.0111 (0.38)

Example IV-12, Solvent: CDCl$_3$, Spectrometer: 300.16 MHz 7.2910 (24.21); 7.0367 (1.46); 6.8534 (3.64); 6.7690 (2.89); 6.6791 (0.41); 6.6684 (3.97); 6.4853 (1.70); 5.1608 (2.94); 5.1391 (2.97); 5.0338 (0.50); 4.5224 (0.59); 4.4753 (0.62); 3.9035 (0.52); 3.8566 (0.68); 3.5697 (0.45); 3.5298 (0.77); 3.5033 (0.48); 3.4922 (0.41); 3.4800 (0.63); 3.4253 (0.35); 3.4200 (0.68); 3.4145 (0.95); 3.4091 (0.66); 3.4036 (0.34); 3.1835 (0.38); 3.1772 (0.41); 3.1364 (0.76); 3.0977 (0.41); 3.0919 (0.38); 2.3585 (16.00); 2.2373 (0.47); 2.1932 (1.27); 2.1587 (1.04); 2.1511 (1.05); 2.1356 (0.69); 2.1088 (0.63); 2.0964 (0.65); 2.0554 (0.66); 2.0407 (0.95); 2.0153 (0.60); 2.0019 (0.63); 1.9703 (0.34); 1.2541 (6.11); 1.2346 (0.87); 1.2113 (1.02); 1.1878 (0.50); 0.8822 (0.76); 0.8591 (0.35); 0.0719 (0.46); 0.0107 (0.46); −0.0002 (14.06); −0.0111 (0.57)

Example IV-13, Solvent: DMSO-d$_6$, Spectrometer: 300.16 MHz 7.3390 (1.04); 7.2086 (1.17); 7.1619 (2.33); 7.0275 (2.68); 6.9848 (1.15); 6.9140 (2.18); 6.8465 (1.29); 5.7579 (0.33); 5.5080 (0.56); 5.4512 (1.56); 5.3701 (1.55); 5.3132 (0.58); 4.3291 (0.38); 4.3184 (0.52); 4.3057 (0.53); 4.2817 (0.61); 4.2716 (0.58); 3.9867 (0.48); 3.9379 (0.55); 3.8042 (16.00); 3.7920 (1.42); 3.3244 (6.95); 3.2933 (0.48); 3.2813 (0.60); 3.2446 (0.35); 2.9188 (0.35); 2.8808 (0.63); 2.8404 (0.36); 2.5132 (1.60); 2.5072 (3.44); 2.5011 (4.75); 2.4951 (3.49); 2.4891 (1.70); 2.1633 (1.53); 2.1186 (1.10); 1.9024 (0.37); 1.8890 (0.42); 1.8615 (0.49); 1.8470 (0.52); 1.2697 (0.51); −0.0002 (4.77)

Example IV-14, Solvent: CDCl$_3$, Spectrometer: 300.16 MHz 7.3036 (11.72); 6.3502 (2.78); 5.0895 (0.65); 5.0361 (1.97); 4.9469 (1.84); 4.8934 (0.64); 4.5203 (0.50); 4.4750 (0.54); 4.0419 (0.45); 3.9958 (0.52); 3.5594 (0.32); 3.5498 (0.38); 3.5116 (0.65); 3.4736 (0.35); 3.4396 (0.42); 3.4130 (0.33); 3.4076 (0.61); 3.4021 (0.91); 3.3967 (0.61); 3.3913 (0.33); 3.1570 (0.32); 3.1489 (0.36); 3.1097 (0.64); 3.0712 (0.36); 3.0625 (0.32); 2.7770 (16.00); 2.3126 (11.67); 2.3107 (11.39); 2.2928 (1.25); 2.1611 (0.99); 2.1542 (0.98); 2.1440 (0.96); 2.1187 (0.53); 2.1045 (0.53); 2.0784 (0.49); 2.0662 (0.53); 2.0391 (0.52); 2.0255 (0.58); 1.9993 (0.52); 1.9855 (0.51); 1.2570 (0.35); −0.0002 (10.48); −0.0111 (0.46)

Example IV-16, Solvent: CDCl$_3$, Spectrometer: 300.16 MHz 8.1511 (1.63); 7.4677 (0.86); 7.4411 (1.22); 7.3185 (0.93); 7.2922 (0.67); 7.2659 (2.75); 7.0995 (0.77); 6.8710 (0.80); 6.8293 (0.71); 6.6887 (1.63); 6.6424 (1.45); 6.5063 (0.82); 6.4556 (0.72); 4.1295 (0.45); 4.1054 (1.17); 4.1022 (1.09); 4.0918 (0.62); 4.0642 (0.67); 4.0544 (1.16); 4.0446 (0.64); 3.8725 (16.00); 3.3746 (0.71); 3.3640 (0.74); 3.3362 (0.89); 3.3264 (1.36); 3.3169 (0.73); 3.2891 (0.76); 3.2784 (0.68); 2.2040 (0.62); 2.1956 (0.41); 2.1667 (1.08); 2.1582 (1.72); 2.1350 (1.21); 2.1213 (1.14); 2.0967 (0.99); 2.0831 (1.09); 2.0506 (0.48); 2.0420 (2.03); 1.6180 (1.22); 1.2806 (0.65); 1.2660 (0.56); 1.2569 (1.34); 1.2331 (0.52); 0.8816 (0.53); −0.0002 (1.53)

Example IV-17, Solvent: CDCl$_3$, Spectrometer: 300.16 MHz 7.3065 (3.64); 6.7678 (1.07); 6.5839 (2.31); 6.3998 (1.15); 6.2569 (2.88); 4.1439 (1.15); 4.1341 (0.72); 4.0964 (1.32); 3.8800 (16.00); 3.6979 (9.38); 3.3046 (0.75); 3.2945 (0.84); 3.2657 (0.97); 3.2564 (1.56); 3.2473 (0.91); 3.2185 (0.87); 3.2083 (0.80); 2.6116 (4.72); 2.1737 (0.73); 2.1280 (1.97); 2.1004 (1.22); 2.0866 (1.29); 2.0617 (1.12); 2.0482 (1.35); 2.0159 (0.55); 2.0021 (0.51); 1.2574 (0.43); −0.0002 (2.10)

Example IV-18, Solvent: CDCl$_3$, Spectrometer: 300.16 MHz 8.0440 (2.96); 7.2678 (4.01); 7.2340 (0.98); 7.0318 (2.12); 6.8295 (1.05); 6.0478 (1.12); 4.1534 (0.33); 4.1296 (1.01); 4.1058 (1.06); 4.0900 (0.53); 4.0816 (1.22); 4.0696 (0.56); 4.0434 (0.61); 4.0329 (1.10); 4.0229 (0.58); 3.8721 (16.00); 3.3488 (0.67); 3.3380 (0.71); 3.3102 (0.82); 3.3006 (1.25); 3.2912 (0.70); 3.2635 (0.71); 3.2527 (0.65); 2.2277 (7.27); 2.1999 (0.37); 2.1903 (0.63); 2.1821 (0.41); 2.1533 (0.97); 2.1447 (1.61); 2.1226 (1.13); 2.1088 (1.07); 2.0844 (0.93); 2.0706 (1.05); 2.0431 (4.81); 2.0248 (0.43); 1.6529 (1.40); 1.2818 (1.51); 1.2641 (1.00); 1.2580 (3.19); 1.2341 (1.33); 0.9037 (0.32); 0.8818 (1.11); 0.8586 (0.40); −0.0002 (2.48)

Example IV-19, Solvent: CDCl$_3$, Spectrometer: 300.16 MHz 7.3610 (1.48); 7.2613 (10.51); 7.0681 (1.05); 7.0425 (1.35); 6.8773 (0.87); 6.8519 (0.67); 6.0817 (0.89); 5.3003 (2.74); 4.4333 (0.43); 4.1111 (0.52); 4.1009 (0.99); 4.0906 (0.53); 4.0640 (0.60); 4.0538 (1.09); 4.0438 (0.57); 3.8725 (16.00); 3.8411 (2.05); 3.3450 (0.67); 3.3326 (0.65); 3.3081 (0.78); 3.2969 (1.22); 3.2853 (0.60); 3.2615 (0.67); 3.2489 (0.64); 2.3065 (7.14); 2.2148 (0.54); 2.1998 (7.49); 2.1797 (0.55); 2.1692 (0.36); 2.1442 (1.16); 2.1341 (2.97); 2.1206 (1.83); 2.0973 (1.11); 2.0837 (1.12); 2.0519 (0.54); 2.0446 (0.38); 2.0380 (0.43); 1.6123 (0.48); 1.2549 (0.43); −0.0002 (5.86)

Example IV-21, Solvent: DMSO-d$_6$, Spectrometer: 250.1 MHz 8.644 (10.7); 8.325 (0.6); 7.470 (9.5); 7.465 (11.8); 7.435 (16.0); 7.361 (0.5); 7.325 (0.5); 7.272 (9.6); 7.242 (13.8); 7.209 (8.6); 6.976 (4.8); 6.947 (7.8); 6.918 (3.4); 4.183 (5.9); 4.126 (6.4); 4.048 (1.0); 3.704 (0.4); 3.691 (0.3); 3.575 (0.6); 3.496 (0.3); 3.484 (0.4); 3.199 (0.3); 3.178 (0.3); 3.148 (0.4); 3.078 (4.0); 3.030 (7.2); 2.984 (4.1); 2.790 (0.3); 2.745 (0.4); 2.518 (5.0); 2.511 (6.7); 2.503 (5.0); 2.172 (0.8); 2.122 (5.1); 2.081 (5.8); 2.067 (8.4); 1.957 (3.8); 1.942 (4.6); 1.903 (4.9); 1.894 (5.3); 1.855 (2.6); 1.840 (2.1)

Example IV-23, Solvent: DMSO-d$_6$, Spectrometer: 400.1 MHz 7.335 (0.3); 7.316 (0.8); 7.298 (0.7); 7.248 (0.4); 7.235 (1.3); 7.215 (0.8); 5.763 (1.3); 3.754 (1.9); 3.326 (3.1); 2.516 (1.9); 2.512 (4.0); 2.507 (5.5); 2.503 (4.1); 2.498 (2.0); 1.458 (0.8); 1.444 (16.0)

Example IV-24, Solvent: DMSO-d$_6$, Spectrometer: 400.1 MHz 7.379 (1.1); 7.374 (0.4); 7.362 (0.5); 7.358 (1.5); 7.255 (1.3); 7.234 (0.9); 5.762 (2.1); 3.765 (0.9); 3.757 (0.9); 3.325 (2.5); 2.516 (1.7); 2.511 (3.4); 2.507 (4.6); 2.502 (3.2); 2.498 (1.5); 2.043 (0.3); 1.451 (16.0)

Example IV-25, Solvent: DMSO-d$_6$, Spectrometer: 250.1 MHz 9.443 (0.6); 7.746 (0.5); 7.716 (0.7); 7.694 (0.5); 7.663 (0.3); 7.535 (0.3); 7.504 (0.5); 7.411 (0.6); 7.379 (0.5); 4.783 (0.4); 4.726 (0.5); 3.376 (0.5); 3.341 (1.7); 3.330 (0.4); 2.514 (0.4); 2.200 (0.4); 2.144 (0.6); 2.017 (0.4); 1.970 (0.4); 1.490 (16.0)

Example IV-26, Solvent: DMSO-d$_6$, Spectrometer: 250.1 MHz 9.566 (0.7); 7.460 (0.5); 7.452 (0.8); 7.446 (0.5); 7.341 (0.6); 7.310 (0.9); 7.299 (0.8); 7.293 (0.5); 7.193 (0.4); 7.185 (0.6); 7.178 (0.3); 7.156 (0.4); 4.743 (0.4); 4.686 (0.4); 3.350 (0.5); 3.336 (2.1); 2.521 (0.6); 2.514 (0.8); 2.507 (0.6); 2.155 (0.6); 2.086 (1.0); 2.045 (0.3); 1.999 (0.4); 1.489 (16.0)

Example IV-27, Solvent: DMSO-d$_6$, Spectrometer: 400.1 MHz 9.548 (0.7); 7.436 (1.1); 7.431 (0.4); 7.419 (0.5); 7.414 (1.6); 7.309 (1.0); 7.289 (0.7); 4.733 (0.4); 4.697 (0.4); 3.381 (0.3); 3.351 (0.7); 3.324 (25.7); 2.516 (1.4); 2.511 (2.8); 2.507 (3.7); 2.502 (2.7); 2.498 (1.3); 2.192 (0.4); 2.157 (0.5); 1.993 (0.4); 1.482 (16.0)

Example IV-28, Solvent: DMSO-d$_6$, Spectrometer: 250.1 MHz 9.067 (0.9); 8.042 (0.8); 8.033 (0.9); 7.807 (0.4); 7.797 (0.4); 7.771 (0.5); 7.762 (0.5); 7.606 (0.9); 7.570 (0.6); 4.176 (0.5); 4.120 (0.6); 3.440 (0.5); 3.352 (22.9); 3.350 (25.2); 3.118 (0.4); 3.071 (0.7); 3.023 (0.4); 2.520 (1.0); 2.513 (1.2); 2.508 (0.9); 2.148 (0.5); 2.093 (0.7); 1.963 (0.4); 1.948 (0.4); 1.901 (0.5); 1.565 (0.4); 1.475 (16.0)

Example IV-29, Solvent: DMSO-d$_6$, Spectrometer: 250.1 MHz 8.979 (1.1); 7.938 (1.1); 7.934 (1.1); 7.761 (0.5); 7.757 (0.5); 7.738 (0.4); 7.729 (0.7); 7.724 (0.7); 7.499 (0.3); 7.468 (0.9); 7.437 (0.7); 7.410 (1.0); 7.405 (1.0); 7.385 (0.4); 7.380 (0.5); 7.374 (0.5); 4.183 (0.7); 4.127 (0.8); 3.353 (0.8); 3.348 (0.6); 3.124 (0.5); 3.076 (0.8); 3.023 (0.5); 2.512 (0.3); 2.148 (0.6); 2.087 (6.5); 2.082 (4.6); 2.047 (0.5); 1.955 (0.6); 1.909 (0.7); 1.869 (0.3); 1.483 (16.0); 1.478 (12.5); 1.443 (1.3)

Example IV-30, Solvent: DMSO-d$_6$, Spectrometer: 250.1 MHz 9.076 (2.5); 8.049 (2.1); 8.039 (2.5); 7.815 (0.9); 7.806 (1.0); 7.780 (1.2); 7.771 (1.3); 7.604 (2.2); 7.569 (1.6); 4.194 (1.4); 4.137 (1.5); 4.083 (1.2); 4.054 (3.8); 4.026 (3.8); 3.997 (1.2); 3.119 (1.0); 3.071 (1.7); 3.023 (0.9); 2.523 (1.9); 2.516 (2.8); 2.510 (2.4); 2.153 (1.2); 2.098 (2.0); 2.000 (16.0); 1.965 (1.1); 1.917 (1.3); 1.878 (0.6); 1.863 (0.5); 1.319 (0.4); 1.251 (5.5); 1.214 (4.5); 1.185 (8.6); 1.157 (4.0); 1.121 (0.8); 0.888 (1.3); 0.866 (3.8); 0.838 (1.4)

Example IV-31, Solvent: DMSO-d$_6$, Spectrometer: 250.1 MHz 9.284 (0.4); 8.989 (5.8); 8.780 (0.8); 7.991 (0.5); 7.939 (3.6); 7.933 (5.8); 7.778 (1.0); 7.765 (2.0); 7.758 (2.6); 7.751 (2.0); 7.732 (2.5); 7.725 (3.3); 7.718 (2.5); 7.670 (0.9); 7.649 (0.5); 7.610 (0.5); 7.525 (0.5); 7.502 (2.4); 7.471 (5.7); 7.439 (4.3); 7.421 (3.4); 7.416 (5.9); 7.410 (3.5); 7.391 (1.7); 7.385 (2.5); 7.338 (0.8); 7.312 (0.7); 7.281 (0.8); 5.770 (1.5); 5.421 (0.3); 4.190 (3.1); 4.133 (3.4); 3.808 (0.9); 3.112 (2.0); 3.065 (3.7); 3.018 (2.1); 2.528 (5.0); 2.521 (11.0); 2.514 (15.1); 2.506 (10.9); 2.500 (5.0); 2.151 (2.7); 2.096 (4.5); 2.086 (7.0); 1.977 (2.1); 1.961 (2.7); 1.920 (2.9); 1.912 (2.9); 1.874 (1.4); 1.860 (1.2); 1.748 (2.0); 1.478 (2.0); 1.377 (16.0); 1.269 (2.7); 1.237 (5.7); 1.186 (0.3)

Example IV-33, Solvent: DMSO-d$_6$, Spectrometer: 250.1 MHz 9.530 (2.2); 7.449 (2.3); 7.414 (4.1); 7.307 (3.0); 7.272 (1.9); 4.561 (1.2); 4.506 (1.3); 3.482 (0.6); 3.463 (0.9); 3.447 (0.8); 3.427 (1.3); 3.407 (0.9); 3.393 (0.9); 3.372 (0.7); 3.112 (2.1); 3.083 (6.7); 3.054 (7.1); 3.024 (2.5); 2.515 (2.4); 2.509 (2.1); 2.088 (4.6); 2.036 (0.3); 1.978 (2.2); 1.959 (3.6); 1.215 (7.8); 1.186 (16.0); 1.156 (7.6)

Example IV-34, Solvent: CDCl$_3$, Spectrometer: 300.2 MHz 7.916 (2.8); 7.267 (3.3); 6.917 (0.8); 6.735 (1.7); 6.629 (0.7); 6.552 (0.9); 4.050 (0.5); 4.040 (0.9); 4.030 (0.5); 4.003 (0.6); 3.993 (1.0); 3.983 (0.6); 3.867 (16.0); 3.861 (4.8); 3.857 (7.1); 3.853 (4.2); 3.348 (0.6); 3.338 (0.7); 3.310 (0.8); 3.300 (1.2); 3.291 (0.7); 3.263 (0.7); 3.252 (0.6); 2.194 (0.5); 2.186 (0.4); 2.157 (0.9); 2.149 (1.4); 2.141 (0.8); 2.124 (1.0); 2.110 (1.0); 2.085 (0.9); 2.078 (0.6); 2.071 (1.0); 2.045 (0.7); 2.040 (0.4); 2.025 (0.4); 1.631 (2.1); 1.259 (0.4); 0.000 (2.8)

Example IV-40, Solvent: DMSO-d$_6$, Spectrometer: 250.1 MHz δ=8.701 (1.3); 8.676 (6.9); 7.479 (5.6); 7.469 (3.0); 7.458 (6.4); 7.451 (4.7); 7.442 (7.4); 7.431 (3.6); 7.422 (6.5); 7.408 (0.8); 7.335 (0.4); 7.316 (1.2); 7.160 (1.1); 7.118 (7.1); 7.109 (2.3); 7.083 (11.0); 7.055 (1.8); 7.047 (5.4); 5.123 (1.2); 4.175 (3.8); 4.119 (4.0); 3.960 (1.5); 3.520 (0.7); 3.345 (28.1); 3.166 (2.7); 3.119 (3.3); 3.070 (4.7); 3.022 (2.7); 2.779 (1.1); 2.525 (3.1); 2.518 (6.8); 2.511 (9.6); 2.504 (7.0); 2.159 (2.7); 2.105 (4.3); 2.017 (0.5); 1.952 (2.4); 1.903 (2.9); 1.862 (1.4); 1.733 (13.2); 1.698 (16.0); 1.473 (0.4); 1.243 (2.5); 1.179 (0.6); 1.098 (0.4); 1.059 (0.4); 1.034 (0.3); 0.883 (0.6); 0.862 (0.5)

Example IV-41, Solvent: CDCl$_3$, Spectrometer: 250.1 MHz δ=7.835 (0.6); 7.248 (5.1); 7.219 (9.5); 7.191 (6.7); 7.162 (8.7); 7.136 (7.2); 7.085 (0.6); 6.963 (2.4); 6.935 (3.1); 6.907 (1.6); 6.882 (0.6); 5.200 (1.4); 5.037 (1.9); 4.036 (3.8); 3.981 (4.1); 3.913 (1.9); 3.473 (0.5); 3.172 (2.0); 3.150 (3.0); 3.115 (4.8); 3.094 (5.1); 2.775 (1.9); 1.958 (7.8); 1.941 (8.9); 1.682 (10.9); 1.623 (16.0); 1.182 (2.5); 0.833 (0.4); 0.802 (0.6); 0.779 (0.4); −0.001 (5.4)

Example IV-43, Solvent: CDCl$_3$, Spectrometer: 250.1 MHz δ=7.458 (0.4); 7.307 (0.4); 7.285 (0.4); 7.273 (0.4); 7.249 (1.1); 7.238 (0.6); 7.220 (1.3); 7.210 (2.2); 7.198 (3.9); 7.173 (14.0); 7.161 (14.2); 7.136 (1.3); 7.125 (1.9); 7.113 (1.6); 6.742 (3.9); 6.250 (1.1); 6.231 (1.9); 6.211 (1.1); 5.227 (0.8); 5.130 (1.0); 5.125 (0.9); 5.106 (1.6); 5.101 (2.0); 5.096 (1.7); 5.078 (1.0); 5.073 (1.1); 4.104 (2.4); 4.048 (2.6); 3.817 (2.6); 3.793 (4.0); 3.769 (2.5); 3.122 (1.5); 3.113 (1.8); 3.064 (3.1); 3.017 (1.7); 3.008 (1.6); 2.127 (1.1); 2.110 (1.2); 2.072 (2.4); 2.058 (2.4); 2.022 (1.9); 2.006 (1.7); 1.906 (3.8); 1.851 (2.4); 1.813 (1.8); 1.673 (14.9); 1.612 (16.0); 1.247 (0.5); 1.221 (0.7); 1.182 (1.6); 0.843 (0.4); 0.821 (0.3); 0.807 (0.4); −0.001 (4.2); −0.073 (2.2)

Example IV-44, Solvent: CDCl$_3$, Spectrometer: 250.1 MHz δ=7.295 (3.8); 7.276 (5.4); 7.264 (8.0); 7.240 (3.5); 7.021 (4.0); 7.012 (1.8); 6.987 (5.8); 6.952 (2.7); 6.455 (3.4); 6.214 (1.7); 5.299 (16.0); 5.215 (1.2); 5.192 (2.0); 5.187 (2.0); 5.163 (1.0); 4.188 (2.8); 4.132 (3.0); 3.904 (3.2); 3.882 (4.4); 3.857 (2.5); 3.245 (2.0); 3.236 (1.8); 3.188 (3.5); 3.139 (2.0); 2.254 (1.5); 2.238 (1.4); 2.200 (3.1); 2.186 (2.7); 2.149 (2.2); 2.134 (1.7); 2.012 (4.3); 1.959 (2.6); 1.753 (14.9); 1.696 (15.6); 1.646 (9.9); 1.305 (0.8); 1.255 (2.0); 0.880 (0.4); 0.070 (2.8); −0.001 (3.0)

Example VI-1, Solvent: CDCl$_3$, Spectrometer: 300.16 MHz 7.2656 (4.34); 5.3027 (2.47); 4.5819 (0.38); 4.5350 (0.40); 4.1363 (0.35); 4.0961 (2.35); 4.0651 (2.40); 4.0593 (0.94); 4.0250 (0.36); 3.9612 (0.36); 3.9157 (0.45); 3.8726 (16.00); 3.5171 (0.32); 3.5049 (0.49); 3.0915 (0.50); 2.1797 (1.21); 2.1665 (1.14); 2.1515 (0.84); 2.1452 (0.91); 2.1316 (0.54); 2.0513 (0.33); 2.0372 (0.36); 2.0108 (0.38); 1.9971 (0.39); 1.5904 (2.85); 1.3124 (0.44); −0.0002 (2.86)

USE EXAMPLES

Phytophthora Test (Tomatoes)/Preventive
Solvent: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of *Phytophthora infestans*. The plants are then placed in an incubation cabinet at approximately 20° C. and a relative atmospheric humidity of 100%.

The test is evaluated 3 days after the inoculation. 0% means an efficacy which corresponds to that of the untreated control, while an efficacy of 100% means that no disease is observed.

In this test the following compounds according to the invention showed efficacy of 70% or even higher at a concentration of 100 ppm of active ingredient.

| Example | Efficacy % |
|---------|------------|
| I-7     | 95         |
| I-9     | 91         |
| I-10    | 94         |
| I-11    | 100        |

Plasmopara Test (Grapevines)/Preventive
Solvent: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of *Plasmopara viticola* and then remain for 1 day in an incubation cabinet at approximately 20° C. and a relative atmospheric humidity of 100%. The plant is subsequently placed for 4 days in a greenhouse at approximately 21° C. and a relative atmospheric humidity of approximately 90%. The plants are then misted and placed for 1 day in an incubation cabinet.

The test is evaluated 6 days after the inoculation. 0% means an efficacy which corresponds to that of the untreated control, while an efficacy of 100% means that no disease is observed.

In this test the following compounds according to the invention showed efficacy of 70% or even higher at a concentration of 100 ppm of active ingredient.

| Example | Efficacy % |
|---------|------------|
| I-7     | 100        |
| I-9     | 100        |
| I-10    | 96         |
| I-11    | 100        |

In this test the following compounds according to the invention showed efficacy of 70% or even higher at a concentration of 1 ppm of active ingredient.

| Example | Efficacy % |
|---------|------------|
| I-3     | 93         |
| I-66    | 76         |

The invention claimed is:
1. Compound of formula (I)

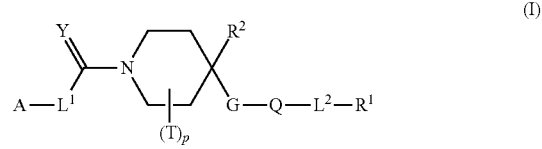

in which the radicals are each defined as follows:
A is phenyl which may contain up to two substituents, where the substituents are each independently selected from the following list:
fluorine, bromine, iodine, chlorine, cyano, nitro, methyl, ethyl, n-propyl, 1-methylethyl, 1,1-dimethylethyl, chlorofluoromethyl, dichloromethyl, dichlorofluoromethyl, difluoromethyl, trichloromethyl, trifluoromethyl, cyclopropyl, ethoxy, 1-methylethoxy, n-propoxy, methoxy, trifluoromethoxy, difluoromethoxy, 1-methylethylthio, methylthio, ethylthio, n-propylthio, difluoromethylthio or trifluoromethylthio, or A is a heteroaromatic radical selected from the following group: pyrazol-1-yl, pyrazol-3-yl, pyrazol-4-yl, or pyrazol-5-yl, which may contain up to two substituents, where the substituents are the same or different and are each independently selected from the following list:
substituents on carbon:
fluorine, chlorine, bromine, iodine, cyano, nitro, methyl, ethyl, n-propyl, 1-methylethyl, 1,1-dimethylethyl, chlorofluoromethyl, dichloromethyl, dichlorofluoromethyl, difluoromethyl, trichloromethyl, trifluoromethyl, cyclopropyl, ethoxy, 1-methylethoxy, n-propoxy, methoxy, trifluoromethoxy, difluoromethoxy, 1-methylethylthio, methylthio, ethylthio, n-propylthio, difluoromethylthio, trifluoromethylthio or phenyl, $R^{G1}$ is hydrogen,
$L^1$ is $CH_2$ or NH,
$L^3$ is a direct bond, $-OCH_2C\equiv C-$ or $-C(=O)O-$,
p is 0,
G is

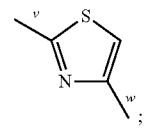

where the bond identified by "v" is bonded directly to dihydropyridine ring and where the bond identified by "w" is bonded directly to Q, Q is $Q^{24}$ =

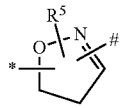

where the bond identified by "*" is bonded directly to G or $L^2$, and where the bond identified by "#" is bonded directly to $L^2$ or G, or where the bond identified by "*" is bonded directly to
$L^2$, and the bond identified by "#" is at the same time bonded directly to G,
$L^2$ is a direct bond,
$R^1$ is phenyl which may contain 0, 1, 2 or 3 substituents, where the substituents are each independently selected from $Z^4$ and from the following list: fluorine, chlorine, bromine, iodine, cyano, nitro, hydroxyl, amino, methyl, ethyl, n-propyl, 1-methylethyl, n-butyl, 1,1-dimethylethyl, 1,2-dimethylethyl, ethenyl, ethynyl, trifluoromethyl, difluoromethyl, trichloromethyl, dichloromethyl, cyclopropyl, methoxy, ethoxy, n-propoxy, 1-methylethoxy, 1,1-dimethylethoxy, methylcarbonyl, ethylcarbonyl, methoxycarbonyl, ethoxycarbonyl, n-propoxycarbonyl, 1-methylethoxycarbonyl, 1,1-dimethylethoxycarbonyl, 1-methylcarbonyl-oxy, methylthio, ethylthio, methylsulphonyl or -$L^3R^3$,
$R^2$ is —$COO^O$, $C_1$-$C_4$-alkylaminocarbonyl or $C_3$-$C_4$-alkenylaminocarbonyl,
$R^3$ is hydrogen, methyl, ethyl, n-propyl, 1-methylethyl, n-butyl or 1,1-dimethylethyl,
$R^5$ is hydrogen,
$R^9$ is hydrogen, methyl, ethyl, n-propyl, 1-methylethyl, n-butyl, 1,1-dimethylethyl or 2-methylpropyl,
$R^{10}$ is hydrogen, methyl, ethyl, n-propyl, 1-methylethyl, n-butyl, 1,1-dimethylethyl or 2-methylpropyl,
$R^{11}$ and $R^{12}$ are the same or different and are each independently hydrogen, alkyl, alkenyl, alkynyl, haloalkyl, cycloalkyl, alkoxyalkyl, cyanoalkyl, formyl, haloalkyl, phenyl, alkylcarbonyl, cycloalkoxycarbonyl, alkoxycarbonyl, alkenyloxycarbonyl, alkynyloxycarbonyl, haloalkylcarbonyl, halocycloalkylcarbonyl, cycloalkoxycarbonyl, cycloalkylcarbonyl, dialkylaminocarbonyl, dialkylaminothiocarbonyl, benzyl or phenyl,
$R^O$ is hydrogen, methyl, ethyl, n-propyl, iso-propyl, n-butyl, iso-butyl, tent-butyl, n-octyl, 2-ethylhexyl, cyclopropyl, cyclobutyl, cyclopentyl, cyclohexyl, prop-2-enyl, 3-methylbut-2-enyl, prop-2-ynyl, phenyl, 2,6-dimethylphenyl, 2,6-diisopropylphenyl, 2,6-di-tert-butylphenyl, benzyl, 4-methoxybenzyl, 3,4-dimethoxybenzyl, tetrahydrofuran, methoxyethyl, ethoxyethyl, methylsulfanylethyl, ethylsulfanylethyl, cyclopropylmethyl, cyanomethyl, cyanoethyl,
Y is oxygen,
$Z^3$ is a phenyl radical which may contain up to two substituents, where the substituents are each independently selected from the following list:
chlorine, bromine, iodine, fluorine, cyano, nitro, hydroxyl, amino, —SH, methyl, ethyl, n-propyl, 1-methylethyl, 1,1-dimethylethyl, ethenyl, propen-2-yl, ethynyl, propyn-2-yl, trifluoromethyl, difluoromethyl, methoxymethyl, methylcarbonyl, ethylcarbonyl, trifluoromethyl carbonyl, methoxycarbonyl, ethoxycarbonyl, n-propoxycarbonyl, 1-methylethoxycarbonyl, 1,1-dimethylethoxycarbonyl, methoxy, ethoxy, n-propoxy, 1-methylethoxy, 1,1-dimethylethoxy, trifluoromethoxy, ethenyloxy, 2-propenyloxy, ethynyloxy, 2-propynyloxy, methylthio, ethylthio, trifluoromethylthio, methylsulphonyl, ethylsulphonyl, propylthionyl, 1-methylethylthio, trifluoromethylsulphonyl, methylamino, ethylamino, n-propylamino, 1-methylethylamino, 1,1-dimethylethylamino or dimethylamino, or
$Z^3$ is naphthalenyl,
$Z^4$ is -formyl, methoxymethoxy, 2-methoxyethoxy, allyloxy, 2-fluoroprop-2-en-1-yloxy, 2-chloroprop-2-en-1-yloxy, 3-chloroprop-2-en-1-yloxy, 2-bromoprop-2-en-1-yloxy, 2-methylprop-2-en-1-yloxy, 3,3-dichloroprop-2-en-1-yloxy, 3,3-dichloro-2-fluoroprop-2-en-1-yloxy, but-2-en-1-yloxy, but-3-en-2-yloxy, but-3-en-1-yloxy, 3-chlorobut-2-en-1-yloxy 3-methylbut-2-en-1-yloxy, 4,4,4-trifluorobut-2-en-1-yloxy, prop-2-yn-1-yloxy, 3-chloroprop-2-yn-1-yloxy, 3-bromoprop-2-yn-1-yloxy, but-2-yn-1-yloxy, pent-2-yn-1-yloxy, 2-fluoro-2-methylpropanoyloxy, 3,3,3-trifluoropropanoyloxy, cyclopropylcarbonyloxy, cyclohexyl-carbonyloxy, (1-chlorocyclopropyl)carbonyloxy, but-2-enoyloxy, acryloyloxy, cyanomethoxy, methylsulphonyloxy, ethylsulphonyloxy, trifluoromethylsulphonyloxy, cyclopropylsulphonyloxy, 2-methoxyethoxymethyl, allyloxymethyl, prop-2-yn-1-yloxymethyl, methylsulphonylmethyl, methylcarbonylaminomethyl, methylsulphonylaminomethyl, —$C(=NOR^9)R^{10}$, dimethylaminosulphonyl, ethylaminosulphonyl, trimethylsilylethynyl, diethylaminosulphonyl, methylaminosulphonyl, trimethylsilyloxy, trimethylsilylprop-2-yn-1-yloxy, trifluoromethylamino, dimethylaminocarbonylamino, —C(=O)OH, —NHC(=O)H, —C(=O)$NH_2$, —C(=S)$NR^{11}R^{12}$ 1,1-dimethylethylcarbonylamino, chloromethylcarbonylamino, trifluoromethylcarbonylamino, 1,1-dimethylethoxy-carbonylamino, ethylcarbonylamino, 1-methylethoxycarbonylamino, trifluoromethylcarbonylamino, methylcarbonylamino, methoxycarbonylamino, ethoxycarbonylamino, iso-propoxycarbonylamino, 1-methylethylcarbonylamino, methylsulphonylamino or phenylsulphonylamino, 3-bromoprop-2-en-1-yloxy, or -$L^3Z^3$,
and/or a salt, metal complex and/or N-oxide thereof.

2. Compound of formula (I) and/or salt, metal complex and/or N-oxide according to claim 1, in which
$R^1$ is phenyl which contains 0, 1, 2 or 3 substituents, where the substituents are each independently selected from the following list:
formyl, methoxymethoxy, 2-methoxyethoxy, allyloxy, 2-fluoroprop-2-en-1-yloxy, 2-chloroprop-2-en-1-yloxy, 3-chloroprop-2-en-1-yloxy, 2-bromoprop-2-en-1-yloxy, 2-methylprop-2-en-1-yloxy, 3,3-dichloroprop-2-en-1-yloxy, 3,3-dichloro-2-fluoroprop-2-en-1-yloxy, but-2-en-1-yloxy, but-3-en-2-yloxy, but-3-en-1-yloxy, 3-chlorobut-2-en-1-yloxy, 3-methylbut-2-en-1-yloxy, 4,4,4-trifluorobut-2-en-1-yloxy, prop-2-yn-1-yloxy, 3-chloroprop-2-yn-1-yloxy, 3-bromoprop-2-yn-1-yloxy, but-2-yn-1-yloxy, pent-2-yn-1-yloxy, 2-fluoro-2-methylpropanoyloxy, 3,3,3-trifluoropropanoyloxy, cyclopropylcarbonyloxy, cyclohexylcarbonyloxy, (1-chlorocyclopropyl)carbonyloxy, but-2-enoyloxy, acryloyloxy, benzoyloxy, 2-fluorobenzoyloxy, 3-fluorobenzoyloxy, 4-fluorobenzoyloxy, cyanomethoxy, methylsulphonyloxy, ethylsulphonyloxy, trifluoromethylsulphonyloxy, cyclopropylsulphonyloxy, 2-methoxyethoxymethyl, allyloxymethyl, prop-2-yn-1- yloxymethyl, methylsulphonylmethyl, methylcarbonylaminomethyl, methylsulphonylaminomethyl, —C(=NOH)H, —C(=NOCH₃)H, —C(=NOCH₂CH₃)H, —C(=NOCH(CH₃)CH₃)H, —C(=NOH)CH₃, —C(=NOCH₃)CH₃, —C(=NOCH₂CH₃)CH₃, —C(=NOCH(CH₃)CH₃)CH₃, dimethylaminosulphonyl, C(=O)NH₂, ethylaminosulphonyl, trimethylsilylethynyl, diethylaminosulphonyl, methylaminosulphonyl, trimethylsilyloxy, trimethylsilylprop-2-yn-1-yloxy, trifluoromethylamino, dimethylaminocarbonylamino, —C(=O)OH, 1,1-dimethylethylcarbonylamino, chloromethylcarbonylamino, trifluoromethylcarbonylamino, 1,1-dimethylethoxycarbonylamino, ethylcarbonyamino, 1-methylethoxycarbonylamino, trifluoromethylcarbonylamino, methylcarbonylamino, methoxycarbonylamino, ethoxycarbonylamino, iso-propoxycarbonylamino, 1-methylethylcarbonylamino, methylsulphonylamino or phenylsulphonylamino, 3-bromoprop-2-en-1-yloxy, fluorine, chlorine, methyl, trifluoromethyl, methoxy.

3. A compound according to claim 1, wherein A is phenyl which may contain up to two substituents.

4. A compound according to claim 1, wherein A is pyrazol-1-yl, pyrazol-3-yl, pyrazol-4-yl, or pyrazol-5-yl, which may contain up to two substituents.

5. A compound according to claim 1, wherein L¹ is CH₂.

6. A compound according to claim 1, wherein L¹ is NH.

7. A compound according to claim 2, wherein R¹ is phenyl which contains 0 substituents.

8. A compound according to claim 2, wherein R¹ is phenyl which contains 1, 2, or 3 substituents.

9. The compound of formula (I) and/or salt, metal complex and/or N-oxide according to claim 1, wherein G is

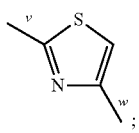

Q is

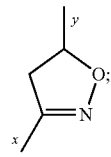

p is 0;
L² is direct bond;
A is 3,5-bis(difluoromethyl)-1H-pyrazol-1-yl;
Y is O;
L¹ is CH₂;
R² is methoxycarbonyl; and
R¹ is 2-[(methylsulfonyl)oxy]phenyl,
wherein the bond identified by "x" is bonded directly to G and where the bond identified as "y" is bonded directly to L².

10. Method for controlling phytopathogenic harmful fungi, comprising applying a compound of formula (I) and/or salt, metal complex and/or N-oxide according to claim 1 to the phytopathogenic harmful fungi and/or a habitat thereof.

11. Composition for controlling phytopathogenic harmful fungi, comprising a content of at least one compound of formula (I) and/or salt, metal complex and/or N-oxide according to claim 1 in addition to one or more extenders and/or surfactants.

12. Compound of formula (I) according to claim 1 capable of being used for controlling phytopathogenic harmful fungi.

13. Process for producing a composition for controlling phytopathogenic harmful fungi, comprising mixing a compound of formula (I) and/or salt, metal complex and/or N-oxide according to claim 1 with one or more extenders and/or surfactants.

14. A method according to claim 10, comprising treatment of one or more transgenic plants.

15. A method according to claim 10, comprising treatment of seed and/or seed of transgenic plants.

* * * * *